US006274322B1

(12) United States Patent
Curiel et al.

(10) Patent No.: US 6,274,322 B1
(45) Date of Patent: Aug. 14, 2001

(54) COMPOSITION FOR INTRODUCING NUCLEIC ACID COMPLEXES INTO HIGHER EUCARYOTIC CELLS

(75) Inventors: David T. Curiel, Chapel Hill, NC (US); Max L. Birnstiel; Matthew Cotten, both of Vienna (AT); Ernst Wagner, Langenzersdorf (AT); Kurt Zatloukal, Vienna (AT); Christian Plank, Vienna (AT); Berndt Oberhauser, Vienna (AT); Walter G. M. Schmidt, Vienna (AT)

(73) Assignees: Boehringer Ingelheim International GmbH (DE); Genentech, Inc., South San Francisco, CA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/465,646

(22) Filed: Dec. 16, 1999

Related U.S. Application Data

(60) Division of application No. 08/449,754, filed on May 25, 1995, now Pat. No. 6,077,663, which is a continuation-in-part of application No. 07/937,788, filed on Sep. 2, 1992, now abandoned, which is a continuation-in-part of application No. 07/864,759, filed on Apr. 7, 1992, which is a continuation-in-part of application No. 07/827,102, filed on Jan. 30, 1992, now abandoned, which is a continuation-in-part of application No. 07/767,788, filed on Sep. 30, 1991, now abandoned, application No. 09/465,646, which is a continuation-in-part of application No. 07/827,103, filed on Jan. 30, 1992, now abandoned, and a continuation-in-part of application No. 07/768,039, filed on Sep. 30, 1991, now abandoned.

(51) Int. Cl.$^7$ .................................................. C12Q 1/68
(52) U.S. Cl. ..................... 435/6; 435/69.1; 435/91.4; 435/240.2; 435/252.3; 435/267; 536/23.5; 536/24.5; 424/93.1; 424/93.2; 424/93.6; 424/520; 935/32; 935/57; 935/71
(58) Field of Search .................. 435/6, 69.1, 91.4, 435/91.41, 240.2, 252.3, 267, 23.5, 7.21, 7.23, 7.24; 536/23.1, 23.5, 24.5; 424/93.1, 93.2, 93.6; 935/32, 57, 71

(56) References Cited

U.S. PATENT DOCUMENTS

| | | | | |
|---|---|---|---|---|
| 5,087,616 | * | 2/1992 | Myers et al. | 514/21 |
| 5,108,921 | * | 4/1992 | Curiel et al. | 435/240.1 |
| 5,166,320 | * | 11/1992 | Wu et al. | 530/395 |
| 5,192,553 | * | 3/1993 | Boyse et al. | 424/529 |
| 5,225,182 | * | 7/1993 | Sharma | 424/9 |

(List continued on next page.)

FOREIGN PATENT DOCUMENTS

| | | | |
|---|---|---|---|
| 2012311 | * | 3/1990 | (CA) . |
| WO 90/01951 | * | 3/1990 | (WO) . |
| WO 92/06180 | * | 4/1992 | (WO) . |
| WO 92/19749 | * | 11/1992 | (WO) . |
| WO 92/20316 | * | 11/1992 | (WO) . |
| WO 92/22635 | | 12/1992 | (WO) . |
| WO 93/04701 | | 3/1993 | (WO) . |
| WO 94/17832 | | 8/1994 | (WO) . |

OTHER PUBLICATIONS

Abrahamson and Rodewald, "Evidence for the Sorting of Endocytic Vesicle Contents During the Receptor–Mediated Transport of IgG across the Newborn Rat Intestine", *J. Cell Biol.* 91:270–280 (Oct., 1981).*

Akopian et al., "Sequence of an Avian Adenovirus (CELO) DNA fragment (0–11.2%)", *Nucl. Acids Res.* 19:424 (May 11, 1990).*

American Type Culture Collection, "Catalogue of Animal Viruses and Antisera, Chlamydiae and Rickettsiae", Buck, C. and Paulino, G. (eds.), *Sixth Ed.:* 1–17 (1990).*

Anderson et al., "Specific binding of $^{125}$I–Human Interferon–γ to High Affinity Receptors on Human Fibroblasts", *J. Biol. Chem.* 257:11301–11304 (Oct. 10, 1982).

Ansardi et al., "Coinfection with Recombinant Vaccinia Viruses Expressing Poliovirus P1 and P3 Proteins Results in Polyprotein Processing and Formation of Empty Capsid Structures", *J. Virol.* 65:1647–1650 (May, 1987).

Armentano et al., "Effect of Internal Viral Sequences on the Utility of Retroviral Vectors", *J. Virol.* 61:6141–6145 (Aug., 1990).

Armentano et al., "Expression of Human Factor IX in Rabbit hepatocytes by Retrovirus–Mediated Gene Transfer: Potential for Gene Therapy of Hemophilia B", *Proc. Natl. Acad. Sci. USA* 87:6141–6145 (Aug., 1990).

Asada–Kubota et al., "Binding and Internalization of $^{125}$I–glucagon in Hepatocytes of Intact Mouse Liver. An Autoradiographic Study", *Exp. Path.* 23:95–101 (1983).

Ascoli and Puett, "Inhibition of the Degradation of Receptor–bound Human Choriogonadrotropin by Lysosomotropic Agents, Protease Inhibitors, and Metabolic Inhibitors", *J. Biol. Chem.* 253:7832–7838 (Nov. 10, 1978).

(List continued on next page.)

Primary Examiner—W. Gary Jones
Assistant Examiner—Janell E. Taylor
(74) Attorney, Agent, or Firm—Sterne, Kessler, Goldstein & Fox P.L.L.C.

(57) ABSTRACT

A composition for the transfection of higher eucaryotic cells, comprising complexes of nucleic acid, a substance having an affinity for nucleic acid and optionally an internalizing factor, contains an endosomolytic agent, e.g. a virus or virus component, which may be conjugated. The endosomolytic agent, which is optionally part of the nucleic acid complex, is internalized into the cells together with the complex and releases the contents of the endosomes into the cytoplasm, thereby increasing the gene transfer capacity. Pharmaceutical preparations, transfection kits and methods for introducing nucleic acid into higher eucaryotic cells by treating the cells with the composition are also disclosed.

5 Claims, 65 Drawing Sheets

U.S. PATENT DOCUMENTS

| | | | |
|---|---|---|---|
| 5,240,846 | * | 8/1993 | Collins et al. ............... 435/240.1 |
| 5,354,844 | * | 10/1994 | Beug et al. ...................... 530/345 |
| 5,428,132 | * | 6/1995 | Hirsch et al. ................. 530/387.1 |
| 5,521,291 | * | 5/1996 | Curiel et al. ................. 530/391.7 |
| 5,547,932 | * | 8/1996 | Curiel et al. ...................... 435/65 |
| 5,583,020 | * | 12/1996 | Sullivan ....................... 435/172.3 |
| 5,693,509 | | 12/1997 | Cotten et al. ................ 435/172.3 |
| 5,789,230 | | 8/1998 | Cotten et al. ................. 435/235.1 |
| 5,792,645 | | 8/1998 | Beug et al. ................... 435/240.2 |
| 5,922,859 | | 7/1999 | Birnstiel et al. ................ 536/24.5 |
| 5,928,944 | | 7/1999 | Seth et al. ....................... 435/375 |
| 5,981,273 | | 11/1999 | Curiel et al. ................. 435/320.1 |
| 6,022,735 | | 2/2000 | Curiel et al. ................. 435/320.1 |

OTHER PUBLICATIONS

Ashwell and Harford, "Carbohydrate–Specific Receptors of the Liver", *Ann. Rev. Biochem. 51:*531–554 (1982).

Barr and Leiden, "Systemic Delivery of Recombinant Proteins by Genetically Modified Myoblasts", *Science 254:*1507–1509 (Dec. 6, 1991).

Baum and Paulson, "Sialyloligosaccharides of the Respiratory Epithelium in the Selection of Human Influenza Virus Receptor Specificity", *Acta Histochem. Suppl. 40:*35–38 (1990).

Berkner and Sharp, "Generation of Adenovirus by Transfection of Plasmids", *Nucl. Acids Res. 11:*6003–6020 (1983).

Berkner, K., "Development of Adenovirus Vectors for the Expression of Heterologous Genes", *BioTechniques 6:*616–629 (1988).

Berns, K., "Parvoviridae and Their Replication", in: *Virology*, 2nd ed., Fields, B.N. et al. (eds.), New York: Raven Press, Ltd., pp. 1743–1763 (1990).

Bragg et al., "Isolation and Identification of Adenovirus 127, the Causative Agent of Egg Drop Syndrome (EDS) from Commercial Laying Hens in South Africa", *Onderstepoort J. Vet. Res. 58:*309–310 (Dec., 1991).

Carpenter, G., "Properties of the Receptor for Epidermal Growth Fctor", *Cell 37:*357–358 (Jun., 1984).

Chardonnet and Dales, "Early Events in the Interaction of Adenoviruses with HeLa Cells", *Virology 40:*462–477 (1970).

Cheng et al., "Receptor–Mediated Uptake of 3,3',5–triiodo–L–thyronine by Cultured Fibroblasts", *Proc. Natl. Acad. Sci. USA 77:*3425–3429 (1980).

Ciliberto et al., "Cell–Specific Expression of a Transfected Human $\alpha_1$–Antitrypsin Gene", *Cell 41:*531–540 (1985).

Clarke, D.D. et al., "The Incorporation of Amines into Protein", *Arch. Biochem. Biophys. 79:*338–354 (1959).

Clarke, L.L. et al., "Defective Epithelial Chloride Transport in a Gene–Targeted Mouse Model of Cystic Fibrosis", *Science 257:*1125–1128 (Aug. 21, 1992).

Collis et al., "Definition of the Minimal Requirements within the Human β–globin Gene and the Dominant Control Region for High Level Expression", *EMBO J. 9:*233–240 (Jan., 1990).

Cotten et al., "High–efficiency Receptor–mediated Delivery of Small and Large (48 kilobase) Gene Constructs Using the Endosome–disruption Activity of Defective or Chemically Inactivated Adenovirus Particles", *Proc. Natl. Acad. Sci. USA 89:*6094–6098 (Jul., 1992).

Cotten et al., "Transferrin–Polycation–Mediated Introduction of DNA into Human Leukemic Cells: Stimulation by Agents that Affect the Survival of Transfected DNA or Modulate Transferrin Receptor Levels", *Proc. Natl. Acad. Sci. USA 87:*4033–4037 (Jun., 1990).

Curiel, D. et al., "Adenovirus Enhancement of Transferrin–Polylysine–Mediated Gene Delivery", *Proc. Natl. Acad. Sci. USA 88:*8850–8854 (Oct., 1991).

Curiel, D. et al., "Gene Transfer to Respiratory Epithelial Cells via the Receptor–Mediated Endocytosis Pathway", *Am. J. Resp. Cell. Mol. Biol. 6:*247–252 (Mar., 1992).

Curiel, D. et al., "High–Efficiency Gene Transfer Mediated by Adenovirus Coupled to DNA–Polylysin Complexes", *Human Gene Therapy 3:*147–154 (Apr., 1992).

Curiel, D. et al., "In vivo Gene Transfer to Airway Epithelium Employing Molecular Conjugate Vectors", *Cold Spring Harbor Gene Therapy Conference* (Jul., 1992).

Curiel, T. et al., "Foreign Gene Expression in EBV–Transformed B–Cells: Potential for the Development of Novel CTL Target Cells", *J. Cell. Biochem. Suppl. 60:*Q407 (1992).

Davidson and Hassell, "Overproduction of Polyomavirus Middle T Antigen in Mammalian Cells Through the Use of an Adenovirus Vector", *J. Virol. 61:*1226–1239 (Apr., 1987).

De Wet et al., "Firefly Luciferase Gene: Structure and Expression in Mammalian Cells", *Mol. Cell. Biol. 7:*725–737 (Feb., 1987).

Defer et al., "Human Adenovirus–Host Cell Interactions: Comparative Study with Members of Subgroups B and C", *J. Virol. 64:*3661–3673 (Aug., 1990).

Dhawan et al., "Systemic Delivery of Human Growth Hormone by Injection of Genetically Engineered Myoblasts", *Science 254:*1509–1512 (Dec. 6, 1991).

Eaton et al., "Construction and Characterization of an Active Factor VIII Variant Lacking the Central One–Third of the Molecule", *Biochem. 25:*8343–8347 (Dec. 30, 1986).

Fernandez–Puentes and Carrasco, "Viral Infection Permeabilizes Mammalian Cells to Protein Toxins", *Cell 20:*769–775 (Jul., 1980).

FitzGerald et al., "Adenovirus–Induced Release of Epidermal Growth Factor and Pseudomonas Toxin into the Cytosol of KB Cells during Receptor–Mediated Endocytosis", *Cell 32:*607–617 (Feb., 1983).

Folk and Chung, "Transglutaminases", *Meth. Enzymol. 113:*358–375 (1985).

Fujiwara et al., "Novel Preparation Method of Immunogen for Hydrophobic Hapten, Enzyme Immunoassay for Daunomycin and Adriamycin", *J. Immunol. Meth. 45:*195–203 (1981).

Ginsberg et al., "Picornaviruses", in: *Microbiology*, 3rd Ed., Davis, B.D. et al. (eds.), New York: Harper & Row, pp. 1095–1117 (1980).

Goldstein and Brown, "Lipoprotein Receptors: Genetic Defense Against Atherosclerosis", *Clin. Res. 30:*417–426 (1982).

Goldstein et al., "Binding Site on Macrophages that Mediates Uptake and Degradation of Acetylated Low Density Lipoprotein, Producing Massive Cholesterol Deposition", *Proc. Natl. Acad. Sci. USA 76:*333–337 (Jan., 1979).

Goldstein et al., "What Should Be Called a Lectin?", *Nature 285:*66 (May 8, 1980).

Green et al., "Mutational Analysis of HIV–1 Tat Minimal Domain Peptides: Identification of Trans–Dominant Mutants that Suppress HIV–LTR–Driven Gene Expression", *Cell 58*:215–223 (Jul. 14, 1989).

Harris et al., "Gene Transfer to Primary Airway Epithelial Cells Employing Molecular Conjugate Vectors", *Clin. Res. Abst. 40*:317A (May, 1992).

Hearst and Thiry, "The Photoinactivation of an RNA Animal Virus, Vesicular Stomatitis Virus, with the Aid of Newly Synthesized Psoralen Derivates", *Nucl. Acids Res. 4*:1339–1347 (1977).

Heldin et al., "Interaction of a Platelet–Derived Growth Factor with its Fibroblast Receptor", *J. Biol. Chem. 257*:4216–4221 (Apr. 25, 1982).

Helenius et al., "Viruses as Tools in Drug Delivery", *Ann. N.Y. Acad. Sci. 507*:1–6 (1987).

Hirsch et al., "Integration of Foreign DNA Into Cells—by Conjugating Foreign DNA with Target Specific Antibody and Binding to Cells", *Derwent Abstract:*C89–1256505 (1989).

Hizuka et al., "Polypeptide Hormone Degradation and Receptor Regulation are Coupled to Ligand Internalization", *J. Biol. Chem. 256*:4591–4597 (May 10, 1981).

Holland, J., "Defective Viral Genomes", in: *Virology*, 2nd Ed., Fields, B.N. et al. (eds.), New York: Raven Press, Ltd., pp. 151–165 (1990).

Horvath and Weber, "Nonpermissivity of Human Peripheral Blood Lymphocytes to Adenovirus Type 2 Infection", *J. Virol. 62*:341–345 (Jan., 1988).

Hosang and Shooter, "The Internalization of Nerve Growth Factor by High–Affinity Receptors on Pheochromocytoma PC12 Cells", *EMBO J. 6*:1197–1202 (1987).

Huang, A., "The Role of Defective Interfering (DI) Particles in Viral Infection", in: *The Molecular Basis of Viral Replication*, Bercoff, R.P. (ed.), New York: Plenum Press, pp. 191–194 (1987).

Imamura et al., "Expression of Tumor Necrosis Factor Receptors on Human Monocytes and Internaliztion of Receptor Bound Ligand", *J. Immunol. 139*:2989–2992 (Nov. 1, 1987).

Iwanij, V., "The Use of Liver Transglutaminase for Protein labeling", *Eur. J. Biochem. 80*:359–368 (1977).

Jacobs et al., "Binding Sites of Attachment–Inhibiting Monoclonal Antibodies and Antibodies from Patients on Peptide Fragments of the *Mycoplasma pneumoniae* Adhesin", *Infection and Immunity 57*:685–688 (Mar., 1989).

Jung et al., "Biological Activity of the Antitumor Protein Neocarzinostatin Coupled to a Monoclonal Antibody by N–Succinimidyl 3–(2–pyridyldithio)–propionate", *Biochem. Biophys. Res. Comm. 101*:599–606 (Jul. 30, 1981).

Kaplan and Nielsen, "Analysis of Macrophage Surface Receptors", *J. Biol. Chem. 254*:7323–7328 (Aug. 10, 1979).

Kasid et al., "Human Gene Transfer: Characterization of Human Tumor–Infiltrating Lymphocytes as Vehicles for Retroviral–Mediated Gene Transfer in Man", *Proc. Natl. Acad. Sci. USA 87*:473–477 (Jan., 1990).

Keller et al., "Expression of a Foreign Gene in Myeloid and Lymphoid Cells Derived from Multipotent Haemotopoietic Precursors", *Nature 318*:149–154 (Nov. 14, 1985).

Klausner, R. et al., "Binding of Apotransferrin to K562 Cells: Explanation of the Transferrin Cycle", *Proc. Natl. Acad. Sci. USA 80*:2263–2266 (Apr., 1983).

Klausner, R. et al., "Receptor–Mediated Endocytosis of Transferrin in K562 Cells", *J. Biol. Chem. 258*:4715–4724 (Apr. 25, 1983).

Kuhn and Kraehenbuhl, "The Sacrificial Receptor–Translocation of Polymeric IgA Across Epithelia", *Trends Biochem. Sci. 7*:299–302 (Aug., 1982).

Kurachi and Davie, "Isolation and Characterization of a cDNA Coding for Human Factor IX", *Proc. Natl. Acad. Sci. USA 79*:6461–6464 (Nov. 1982).

Lapidot and Loyter, "Fusion–Mediated Microinjection of Liposome–Enclosed DNA into Cultured Cells with the Aid of Influenza Virus Glycoproteins", *Exp. Cell Res. 189*:241–246 (Aug., 1990).

Laver et al., "Purification and Properties of Chick Embryo Lethal Orphan Virus (an Avian Adenovirus):, *Virology 45*:598–614 (1971).

Lim and Chae, "A Simple Assay for DNA Transfection by Incubation of the Cells in Culture Dishes with Substrates for Beta–Galactosidase", *BioTechniques 7*:576–579 (1989).

Lori et al., "Non Retroviral Delivery of Protective Genes Against HIV–1", *Cold Spring Harbor Gene Therapy Conference* (Jul., 1992).

MacGregor and Caskey, "Construction of Plasmids that Express *E. coli* β–galactosidase in Mammalian Cells", *Nucl. Acids Res. 17*:2365 (1989).

Malim et al., "Functional Dissection of the HIV–1 Rev Trans–Activator—Derivation of a Trans–Dominant Repressor of Rev Function", *Cell 58*:205–214 (Jul. 14, 1989).

Marsh and Helenius, "Virus Entry into Animal Cells", *Adv. Virus Res. 36*:107–151 (1989).

Marshall, S., "Kinetics of Insulin Receptor Internaliztaion and Recycling in Adipocytes", *J. Biol. Chem. 260*:4136–4144 (Apr. 10, 1985).

McClure et al., "The pH Independence of Mammalian Retrovirus Infection", *J. Gen. Virol. 71*:767–773 (Apr., 1990).

McClure et al., "The pH Independence of Mammalian Retrovirus Infection", *J. Gen. Virol. 71*:767–773 (Apr., 1990).

Mellman and Plutner, "Internalization and Degradation of Macrophage Fc Receptors Bound to Polyvalent Immune Complexes", *J. Cell Biol. 98*:1170–1177 (Apr., 1994).

Mizel, S.I. et al., "The Interleukin 1 Receptor. Dynamics of Interleukin 1 Binding and Internalization in T Cells and Fibroblasts", *J. Immunol. 138*:2906–2912 (May 1, 1987).

Morin et al., "Recombinant Adenovirus Induces Antibody Response to Hepatitis B Virus Surface Antigen in Hamsters", *Proc. Natl. Acad. Sci. USA 84*:4626–4630 (Jul., 1987).

Orkin, S.H. and Mutulsky, A.G., "Report and Recommendations of the Panel to Assess the NIH Investment in Research on Gene Therapy," (Dec. 7, 1995).

Otero and Carrasco, "Proteins are Cointernalized with Virion Particles During Early Infection", *Virology 160*:75–80 (1987).

Parente et al., "Mechanism of Leakage of Phospholipid Vesicle Contents Induced by the Peptide GALA", *Biochem. 29*:8720–8728 (Sep., 1990).

Persson et al., "Virus Receptor Interaction in the Adenovirus System", *J. Virol. 46*:956–963 (Jun., 1983).

Piazza et al., "Attachment of Influenza A Virus to Ferret Tracheal Epithelium at Different Maturational Stages", *Am. J. Resp. Cell. Mol. Biol. 4*:82–87 (Jan., 1991).

Ponder et al., "Mouse Hepatocytes Migrate to Liver Parenchyma and Function Indefinitely after Intrasplenic Transplantation", *Proc. Natl. Acad. Sci. USA* 88:1217–1221 (Feb., 1991).

Posner et al., "Effect of Colchicine on the Uptake of Prolactin and Insulin into Golgi Fractions of Rat Liver", *J. Cell Biol.* 93:560–567 (Jun., 1982).

Precious and Russell, "Growth, Purification and Titration of Adenoviruses", in: *Virology,* Mahy, B.W.J. (ed.), Oxford: IRL Press, ppl 193–205 (1985).

Rafalski et al., "Phospholipid Interactions of Synthetic Peptides Representing the N–Terminus of HIV gp41", *Biochem.* 29:7917–7922 (Aug., 1990).

Reece et al., "Pathogenicity Studies with a Strain of Fowl Adenovirus Serotype 8 (VRI–33) in Chickens", *Austral. Vet. J.* 64:365–367 (Dec., 1987).

Riordan et al., "Identification of the Cystic Fibrosis Gene: Cloning and Characterization of Complementary DNA", *Science* 245:1066–1073 (Sep. 8, 1989).

Rosenberg et al., "Immunization of Cancer Patients Using Autologous Cancer Cells Modified by Insertion of the Gene for Interleukin–2", *Human Gene Therapy* 3:75–90 (Feb., 1992).

Rosenfeld et al., "Adenovirus–Mediated Transfer of the Normal Human Cystic Fibrosis Transmembrane Conductance Regulator (CFTR) cDNA to Freshly Isolated Normal and Cystic Fibrosis Respiratory Epithelium", *Clinical Res.* 40:317A (1992).

Sambrook, J., "Expression of Cloned Genes in Cultured Mammalian Cells", *J. Molec. Cloning,* 2nd Ed., 3:16.39–16.40 (1989).

Schalch et al., "Interaction of Insulin–Like Growth Factor I/Somatomedin–C with Cultured Rat Chondrocytes: Receptor Binding and Internalization", *Endocrinol.* 118:1590–1597 (1986).

Sennett and Rosenberg, "Transmembrane Transport of Cobalamin in Prokaryotic and Eukaryotic Cells", *Am. Rev. Biochmem.* 50:1053–1086 (1981).

Seth et al., "Evidence that the Penton Base of Adenovirus is Involved in Potentiation of Toxicity of Pseudomonas Exotoxin conjugated to Epidermal Growth Factor", *Mol. Cell. Biol.* 4:1528–1533 (Aug., 1984).

Severne et al., "Metal Binding 'Finger' Structures in the Glucocorticoid Receptor Defined by Site–Directed Mutagenesis", *EMBO J.* 7:2503–2508 (1988).

Shepard, V., "Intracellular Pathways and Mechanisms of Sorting in Receptor–Mediated Endocytosis", *Trends in Phys. Sci.* 10:458–462 (Nov., 1989).

Silver and Anderson, "Interaction of Human Adenovirus Serotype 2 with Human Lymphoid Cells", *Virology* 165:377–387 (1988).

Sly and Fischer, "The Phosphomannosyl Recognition System for Intracellular and Intercellular Transport of Lysosomal Enzymes", *J. Cell. Biochem.* 18:67–85 (1982).

Smith and Cantrell, "Interleukin 2 Regulates its Own Receptors", *Proc. Natl. Acad. Sci. USA* 82:864–868 (Feb., 1985).

Stahl et al., "Evidence for Receptor–Mediated Binding of Glycoproteins, Glycoconjugates, and Lysosomal Glycosidases by Alveolar Macrophages", *Proc. Natl. Acad. Sci. USA* 75:1399–1403 (Mar., 1978).

Strauss and Jaenisch, "Molecular Complementation of a Collagen Mutation in Mammalian Cells Using Yeast Artificial Chromosome", *EMBO J.* 11:417–422 (Feb., 1992).

Subbarao et al., "pH–Dependent Bilayer Destabilization by an Amphipathic Peptide", *Biochem.* 26:2964–2972 (1987).

Sullenger et al., "Overexpression of Tar Sequences Renders Cells Resistant to Human Immunodeficiency Virus Replication", *Cell* 63:601–608 (Nov. 2, 1990).

Svensson, U., "Role of Vesicles During Adenovirus 2 Internalization into HeLa Cells", *J. Virol.* 55:442–449 (Aug., 1985).

Takase et al., "Avian Adenovirus Isolated form Pigeons Affected with Inclusion Body Hepatitis", *Jpn. J. Vet. Sci.* 52:207–215 (Apr., 1990).

Trono et al., "HIV–1 Gag Mutants Can Dominantly Interfere with the Replication of the Wild–Type Virus", *Cell* 59:113–120 (Oct. 6, 1989).

Uchida et al., "Distribution of Neuraminidase in Arthrobacter and Its Purification by Affinity Chromatography", *J. Biochem.* 82:1425–1433 (1977).

Urakawa et al., "Synthesis of Immunogenic, but Non–Infectious, Poliovirus Particles in Insect Cells by a Baculovirus Expression Vector", *J. Gen. Virol.* 70:1453–1463 (1989).

Valerio et al., "Cloning of Human Adenosine Deaminase cDNA and Expression in Mouse Cells", *Gene* 31:147–153 (1984).

Wagner, E. et al., "Coupling of adenovirus to transferrin–polylysine/DNA complexes greatly enhances receptor–mediated gene delivery and expression of transfected genes," *Proc. Natl. Acad. Sci. USA* 89:6099–6103 (Jul., 1992).

Wagner et al., "DNA–Binding Transferrin Conjugates as Functional Gene–Delivery Agents: Synthesis by Linkage of Polylysine or Ethidium Homodimer to the Transferrin Carbohydrate Moiety", *Bioconjugate Chem.* 2:226–231 (Jun.–Aug., 1991).

Wagner et al., "Transferrin–Polycation–DNA Complexes: The Effect of Polycations on the Structure of the Complex and DNA Delivery to Cells", *Proc. Natl. Acad. Sci. USA* 88:4255–4259 (May, 1991).

Wagner et al., "Transferrin–Polycation Conjugates as Carriers for DNA Uptake into Cells", *Proc. Natl. Acad. Sci. USA* 87:3410–3414 (May, 1990).

Walker and Burgess, "Internalisation and Recycling of the Granulocyte–Macrophage Colony–Stimulating Factor (GM–CFS) Receptor on a Murine Myelomonocytic Leukemia", *J. Cell. Physiol.* 130:255–261 (1987).

Walker et al., "Long–Term Culture and Fine Specificity of Human Cytotoxic T–Lymphocyte Clones Reactive with Human Immunodeficiency Virus Type 1", *Proc. Natl. Acad. Sci. USA* 86:9514–9518 (Dec., 1989).

Wharton et al., "Membrane Fusion by Peptide Analogues of Influenza Virus Haemagglutinin", *J. Gen. Virol.* 69:1847–1857 (1988).

Wienhues et al., "A Novel Method for Transfection and Expression of Reconstituted DNA–Protein Complexes in Eukaryotic Cells", *DNA* 6:81–89 (1987).

Wilchek and Bayer, "The Avidin–Biotin Complex in Bioanalytical Applications", *Analyt. Biochem.* 171:1–32 (1988).

Willumsen et al., "Intracellular Cl– Activity and Cellular Cl– Pathways in Cultured Human Airway Epithelium", *Am. J. Physiol.* 256:C103–C1044 (1989).

Wood et al., "Expression of Active Human Factor VIII from Recombinant DNA Clones", *Nature* 312:330–337 (Nov. 22, 1984).

Wu and Wu, "Evidence for Targeted Gene Delivery to HepG2 Hepatoma Cells In Vitro", *Biochem.* 27:887–892 (1988).

Wu and Wu, "Receptor–Mediated Gene Delivery and Expression In Vivo", *J. Biol. Chem. 263:*14621–14624 (Oct. 15, 1988).

Wu and Wu, "Receptor–Mediated In Vitro Gene Transformation by a Soluble DNA Carrier System", *J. Biol. Chem. 262:*4429–4432 (Apr. 5, 1987).

Yankaskas et al., "E6 and E7 Genes of Human Papilloma Virus 18 (HPV 18) Transform Human Airway Epithelial Cells", in: *Genetics and Epithelial Cell Dysfunctions in Cystic Fibrosis,* Alan R. Liss, Inc., p. 139A (Apr., 1990).

Zamecnik et al., "Inhibition of Replication and Expression of Human T–Cell Lymphotropic Virus type III in cultured Cells by Exogenous Synthetic Oligonucleotides Complementary to Viral RNA", *Proc. Natl. Acad. Sci. USA 83:*4143–4146 (Jun., 1986).

Zatloukal et al., "Hepatocellular Cytokeratins as Substrates of Transglutaminases", *Lab. Investig. 61:*603–608 (1989).

Zatloukal et al., "Transferrinfection: Receptor–Mediated Gene Delivery In Vitro and In Vivo", *Cold Spring Harbor Gene Therapy Conference* (Jul., 1992).

Zenke et al., "Receptor–Mediated Endocytosis of Transferrin–Polycation Conjugates: An Efficient Way to Introduce DNA into Hematopoietic Cells", *Proc. Natl. Acad. Sci. USA 87:*3655–3659 (May, 1990).

Zhang and Nagaraja, "Differentiation of Avian Adenovirus Type–II Strains by Restriction Endonuclease Fingerprinting", *Am. J. Vet. Res. 50:*1466–1470 (Sep., 1989).

\* cited by examiner

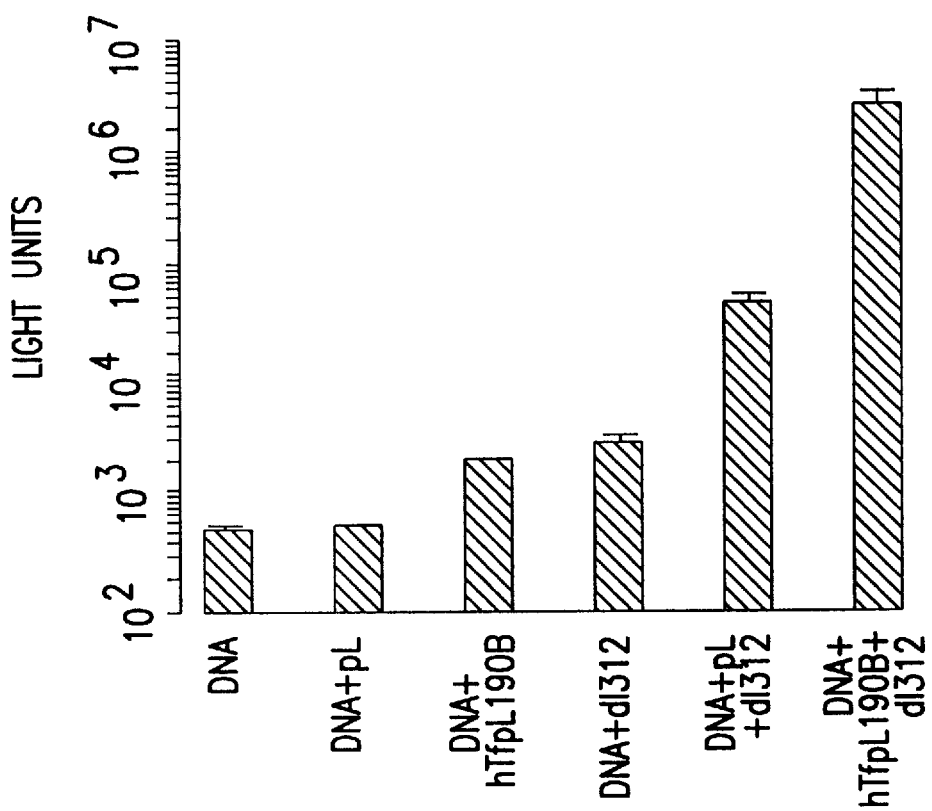

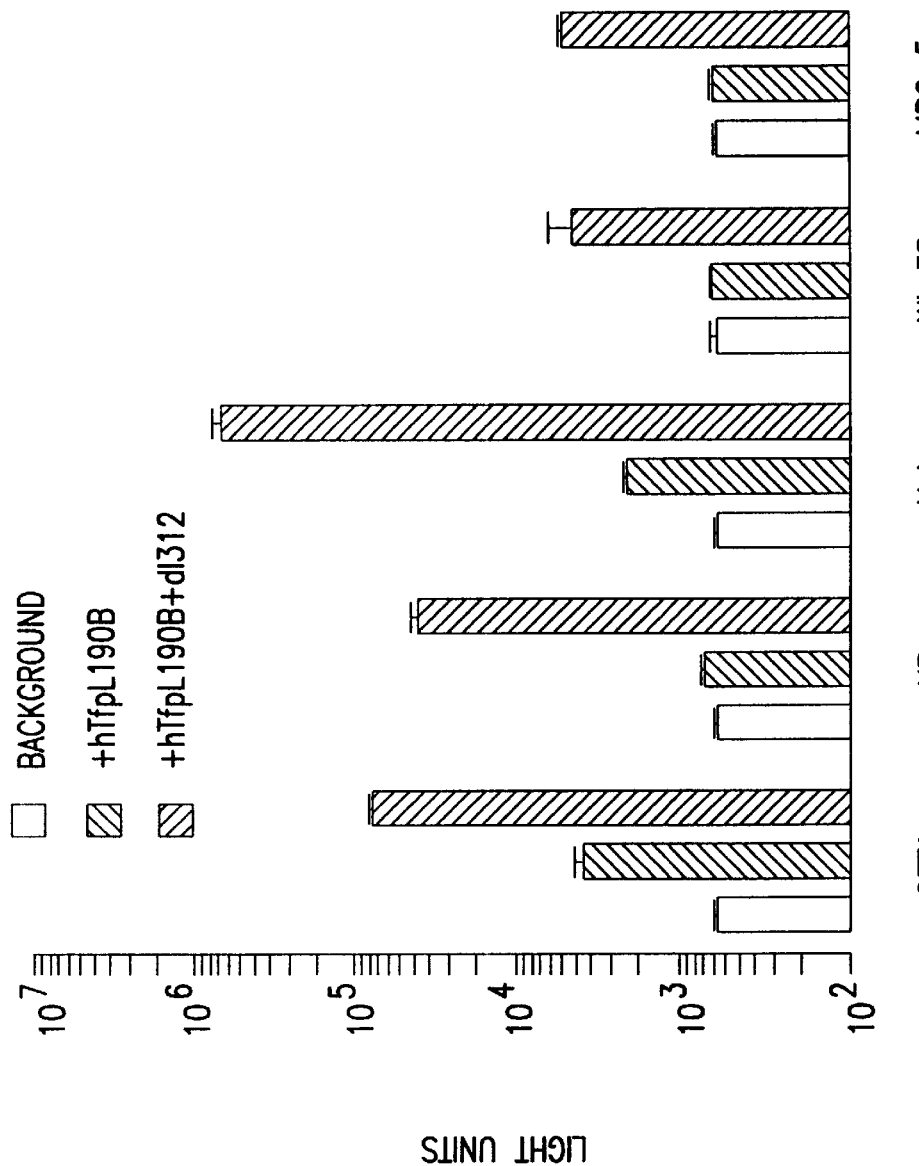

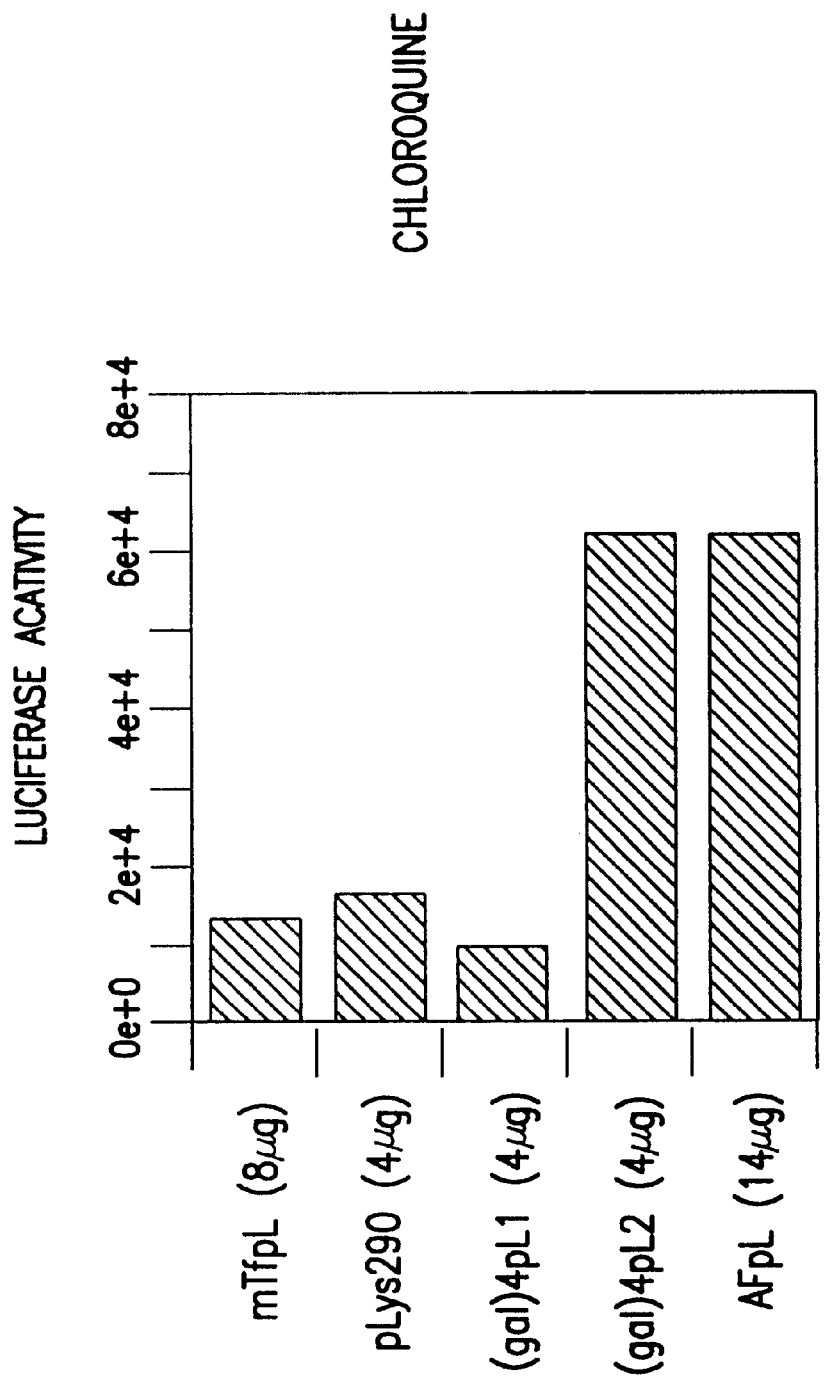

FIG.21A      FIG.21B
FIG.21C      FIG.21D
FIG.21E

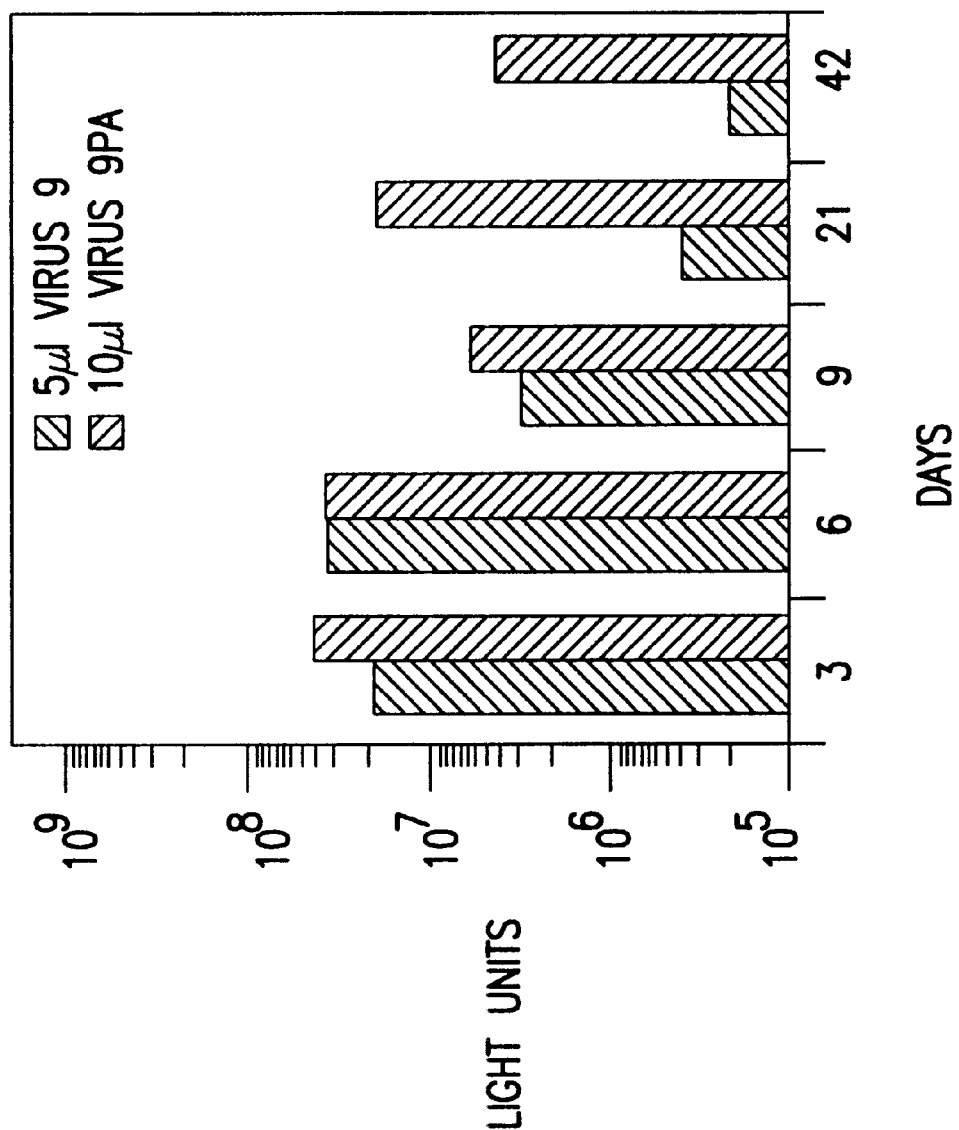

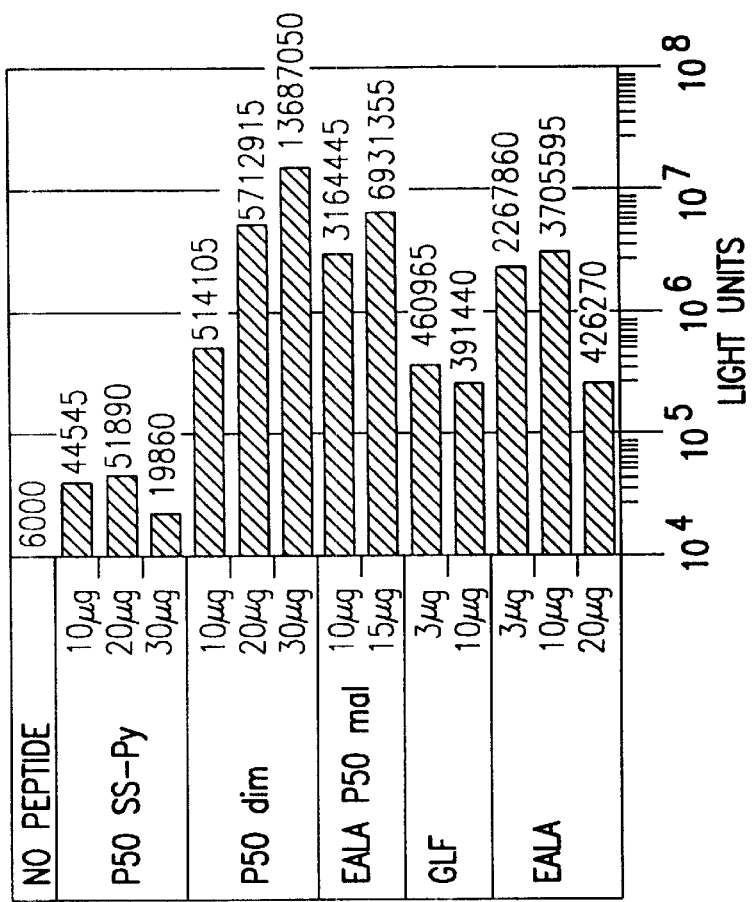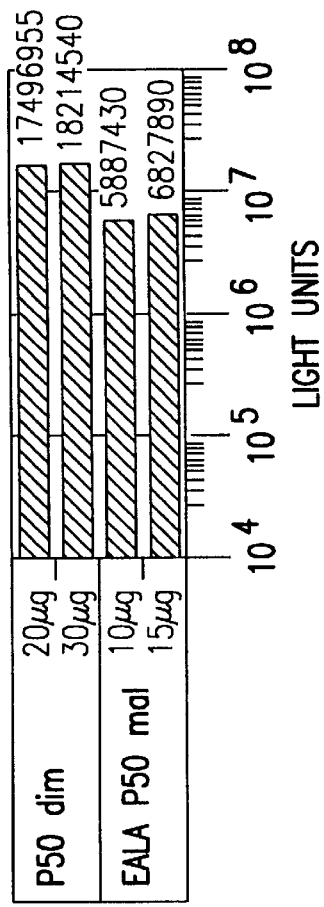
FIG.50A
FIG.50B

IMMUNOHISTOCHEMICAL STAINING RESULTS

| TISSUE | CONJUGATE | PRIMARY ANTIBODY | SECONDARY ANTIBODY | RESULTS |
|---|---|---|---|---|
| HUMAN TRACHEA | HBS | ANTI-TRANSFERRIN | ANTI-MOUSE | − |
| " | SNApL/hTfpL | " | " | + |
| " | " | PY203 | " | − |
| " | pL | ANTI-TRANSFERRIN | " | − |
| " | SNApL | " | " | − |
| " | hTfpL | " | " | + |

FIG. 55

COMPOSITION FOR INTRODUCING NUCLEIC ACID COMPLEXES INTO HIGHER EUCARYOTIC CELLS

CROSS REFERENCE TO RELATED APPLICATIONS

The present application is a divisional of U.S. application Ser. No. 08/449,754, filed May 25, 1995 now U.S. Pat. No. 6,077,663, which is a continuation-in-part of U.S. application Ser. No. 07/937,788, filed Sep. 2, 1992, now abandoned which is a continuation-in-part of U.S. application Ser. No. 07/864,759, filed Apr. 7, 1992, which is a continuation-in-part of U.S. application Ser. No. 07/827,102, filed Jan. 30, 1992, now abandoned which is a continuation-in-part of U.S. application Ser. No. 07/767,788, filed Sep. 30, 1991 now abandoned. The present application is also a continuation-in-part of U.S. application Ser. No. 07/827,103, filed Jan. 30, 1992, now abandoned and is a continuation-in-part of U.S. application Ser. No. 07/768,039, filed Sep. 30, 1991 now abandoned. The contents of each of these related applications is fully incorporated by reference herein.

FIELD OF THE INVENTION

The invention is in the field of DNA technology. In particular, the invention relates to new compositions which can be used for the introduction of nucleic acids into higher eucaryotic cells.

BACKGROUND OF THE INVENTION

There is a need for an efficient system for introducing nucleic acid into living cells particularly in gene therapy. Genes are transferred into cells in order to achieve in vivo synthesis of therapeutically effective genetic products, e.g. in order to replace the defective gene in the case of a genetic defect. "Conventional" gene therapy is based on the principle of achieving a lasting cure by a single treatment. However, there is also a need for methods of treatment in which the therapeutically effective DNA (or mRNA) is administered like a drug ("gene therapeutic agent") once or repeatedly as necessary. Examples of genetically caused diseases in which gene therapy represents a promising approach are hemophilia, beta-thalassaemia and "Severe Combined Immune Deficiency" (SCID), a syndrome caused by the genetically induced absence of the enzyme adenosine deaminase. Other possible applications are in immune regulation, in which humoral or intracellular immunity is achieved by the administration of functional nucleic acid which codes for a secreted protein antigen or for a non-secreted protein antigen, which may be regarded as a vaccination. Other examples of genetic defects in which a nucleic acid which codes for the defective gene can be administered, e.g. in a form individually tailored to the particular requirement, include muscular dystrophy (dystrophin gene), cystic fibrosis (cystic fibrosis transmembrane conductance regulator gene), hypercholesterolemia (LDL receptor gene). Gene therapy methods are also potentially of use when hormones, growth factors or proteins with a cytotoxic or immune-modulating activity are to be synthesized in the body.

Gene therapy also appears promising for the treatment of cancer by administering so-called "cancer vaccines". In order to increase the immunogenicity of tumor cells, they are altered to render them either more antigenic or to make them produce certain immune modulating substances, e.g. cytokines, in order to trigger an immune response. This is accomplished by transfecting the cells with DNA coding for a cytokine, e.g. IL-2, IL-4, IFN gamma, TNF alpha. To date, most gene transfer into autologous tumor cells has been accomplished via retroviral vectors.

The technologies which are hitherto most advanced for the administration of nucleic acids in gene therapy, make use of retroviral systems for transferring genes into the cells (Wilson et al., 1990, Kasid et al., 1990). However, the use of retroviruses is problematic because it brings, at least to a small degree, the danger of side effects such as infection with the virus (by recombination with endogenous viruses or contamination with helper viruses and possible subsequent mutation into the pathogenic form) or the formation of cancer. Moreover, the stable transformation of the somatic cells in the patient, as achieved with retroviruses, is not desirable in every case because it might make the treatment difficult to reverse, e.g. if side effects occur. Moreover, with this type of therapy, it is difficult to obtain a high enough titer to infect enough cells.

Nucleic acids as therapeutically effective substances are also used to inhibit specific cell functions, e.g. antisense RNAs and DNAs have proved effective in the selective inhibition of specific gene sequences. Their mode of activity enables them to be used as therapeutic agents for blocking the expression of certain genes (such as deregulated oncogenes or viral genes) in vivo. It has already been shown that short antisense oligonucleotides can be imported into cells and exert their inhibiting effect therein (Zamecnik et al., 1986), even if their intracellular concentration is low, caused, inter alia, by their restricted uptake by the cell membrane as a result of the strong negative charge of the nucleic acids. Another approach to the selective inhibition of genes is the use of ribozymes. Again there is the need to ensure the highest possible concentration of active ribozymes in the cell, transportation into the cell being one of the limiting factors.

Application of gene therapy for achieving intracellular immunity involves transduction of genes which protect against viruses, so-called "protective genes", e.g. transdominant mutants of genes coding for viral proteins, or DNA molecules coding for so-called RNA decoys.

There is consequently a need for methods of enabling the transfer and expression of DNA into the cell.

Various techniques are known for gene transformation of mammalian cells in vitro, but their use in vivo is limited (these include the introduction of DNA by means of liposomes, electroporation, microinjection, cell fusion, DEAE-dextran or the calcium phosphate precipitation method).

In recent times, recombinant viral vectors have been developed to bring about the transfer of genes by using the efficient entry mechanisms of their parent viruses, this strategy was used in the construction of recombinant retroviral and adenoviral vectors in order to achieve a highly efficient gene transfer in vitro and in vivo (Berkner, 1988). Despite their efficiency, these vectors are subject to restrictions in terms of the size and construction of the DNA which is transferred. Furthermore, these agents represent safety risks in view of the transfer of the viable viral gene elements of the original virus.

In order to circumvent these restrictions, alternative strategies for gene transfer have been developed, based on mechanisms which the cell uses for the transfer of macromolecules. One example of this is the transfer of genes into the cell via the extremely efficient route of receptor-mediated endocytosis (Wu and Wu, 1987, Wagner et al., 1990 and EP-A1 0388 758, the disclosure of which is hereby referred to). This approach uses bifunctional molecular conjugates which have a DNA binding domain and a domain with specificity for a cell surface receptor (Wu and Wu, 1987, Wagner et al., 1990). If the recognition domain is recognized by the cell surface receptor, the conjugate is internalized by the route of receptor-mediated endocytosis, in which the DNA bound to the conjugate is also transferred. Using this method, it was possible to achieve gene transfer rates at least as good as those achieved with the conventional methods (Zenke et al., 1990). Furthermore, it has been shown that the activity of a nucleic acid, e.g. the inhibitory effect of a ribozyme, is not impaired by the transport system.

The PCT application WO 91/17773 relates to a system for transporting nucleic acids with a specific activity for T-cells. This system makes use of cell surface proteins of the T-cell lineage, e.g. CD4, the receptor used by the HIV virus. The nucleic acid to be imported is complexed with a protein-polycation conjugate, the protein component of which, i.e. the recognition domain, is a protein capable of binding to the T-cell surface protein, e.g. CD4, and cells which express this surface protein are brought into contact with the resulting protein-polycation/nucleic acid complexes. It has been shown that DNA transported into the cell by means of this system is expressed in the cell.

One feature common to both inventions is that they use specific cell functions to enable or facilitate the transfer of nucleic acid into the cell. In both cases, the uptake mechanisms take place with the participation of recognition domains which are termed "internalizing factors" within the scope of the present invention. This term denotes ligands which, being cell-type-specific in the narrower or wider sense, bind to the cell surface and are internalized, possibly with the cooperation of other factors (e.g. cell surface proteins). (In the case of the two inventions mentioned above, the internalizing factor is transferrin or a protein which binds to a T-cell surface antigen, e.g. an anti-CD4 antibody). The internalizing factor is conjugated with a substance of a polycationic nature which, by virtue of its affinity with nucleic acids, forms a strong association between the internalizing factor and the nucleic acid. (Substances of this kind are hereinafter referred to as "substances with an affinity for nucleic acid" or with regard to DNA, "DNA binding domain". If a substance of this kind forms a bond between the nucleic acid and an internalizing factor it is hereinafter referred to as a "binding factor").

In the course of these two inventions the optimum uptake of nucleic acid into the cell was achieved when the ratio of conjugate to nucleic acid was such that the internalizing factor-polycation/nucleic acid complexes were approximately electroneutral. Starting from this observation, the methods which use internalizing factor-binding factor/nucleic acid complexes to introduce nucleic acids into higher eucaryotic cells was improved.

A method for improving the efficiency of systems in which the uptake of nucleic acids is carried out by means of internalizing factors, was described by Wagner et al., 1991a. In this method, the quantity of nucleic acid taken up into the cell is not reduced if part of the transferrin-polycation conjugate is replaced by non-covalently bound ("free") polycation; in certain cases, this may even increase the DNA uptake considerably. Investigations into the molecular state of transferrin-polycation-plasmid DNA complexes produced with optimum ratios of DNA/conjugate showed that the plasmid DNA in the presence of the conjugates is condensed into toroidal structures (resembling doughnuts) with a diameter of about 80 to 100 nm).

Experiments conducted with proteins binding to T-cells as internalizing factor produced similar results.

The addition of "free" substances with an affinity for nucleic acid also results in an increase in the efficiency of the introduction system even when other binding factors are used.

The complexes described by Wagner et al., 1991a, which are taken up into higher eucaryotic cells via endocytosis by means of internalizing factor, contain nucleic acid complexed with a conjugate of internalizing factor and binding factor. In addition, the complexes contain one or more substances with an affinity for nucleic acid which may possibly be identical to the binding factor, in a non-covalently bonded form, such that the internalization and/or expression of the nucleic acid achieved by means of the conjugate is increased, which would appear to be due primarily to a condensing effect but might possibly be due to other mechanisms.

Even if the rates of expression of the imported nucleic acid could be increased by this method, it is still subject to restrictions. The practicality of this system in a given context is not solely determined by the presence of the cell surface receptor relevant to the system; the limitations associated with the use of this system are presumably a result of the fact that the conjugate-DNA complexes internalized in endosomes enter the lysosomes, where they are enzymatically degraded. In order to increase the proportion of nucleic acid which reaches the cell nucleus and is expressed there, as intended, attempts were made, in experiments preceding this invention, to carry out the transfection of the cells in the presence of substances which inhibit the enzymatic activity in the lysosomes, so-called lysosomatropic substances. By using this strategy, augmented expression of transferred DNA was achieved; however, the reactions achieved were highly variable, depending on the substance used; selected lysosomatropic substances brought about an increase in gene transfer, whereas others actually inhibited it. Thus, for example, it was found that the effective transfer of DNA depends on the presence of the weak base chloroquine (Zenke et al., 1990, Cotten et al., 1990). This effect achieved by means of chloroquine may not, or not exclusively, be due to the fact that chloroquine increases the pH in the lysosomes; it was found, from a number of different experiments, that other substances which, like chloroquine, have the ability to modulate pH, such as monensin, ammonium chloride or methylamine, could not replace chloroquine and in some experiments some of these substances even showed an inhibiting effect. It was further found that various target cells show different responses to the same substance having a lysosomatropic activity.

Since gene transfer by the physiological route, as represented by receptor-mediated endocytosis using nucleic acid complexes, has major advantages (non-toxic mechanism of passage through the cell membrane; the possibility of administering biologically active nucleic acids, such as nucleic acids which specifically inhibit genes, or cellular functions, on a repeated or continuous basis; the possibility of cell-specific targeting; the possibility of producing the conjugates in large quantities), there is a need to make this system more efficient.

SUMMARY OF THE INVENTION

The present invention is directed to a composition for the transfection of higher eucaryotic cells with a complex of nucleic acid and a substance having affinity for nucleic acid, which substance is optionally coupled with an internalizing factor for the cells, characterized in that the composition contains an agent which has the ability of being internalized into the cells, either per se or as a component of the nucleic acid complex, and of releasing the contents of the endosome, in which the complex is located after entering the cell, into the cytoplasm.

The present invention also relates to a nucleic acid complex useful as constituent of the composition of the invention, wherein the complex comprises one or more nucleic acids to be expressed in the cell, an endosomolytic agent which originally has a nucleic acid binding domain or which is bound to a substance having affinity for nucleic acid, and wherein the complex optionally further comprises an internalizing factor which is bound to a substance having affinity for nucleic acid.

The invention also relates to an endosomolytic peptide useful as a constituent of the composition of the invention, characterized in that it has an endosomolytic domain and a nucleic acid binding domain.

The invention also relates to a process of preparing a conjugate of the invention which is useful for enhancing the uptake of nucleic acid into higher eucaryotic cells, characterized in that a virus or a (poly)peptidic endosomolytic agent and a polyamine are enzymatically coupled in the presence of a transglutaminase.

The invention also relates to a process of preparing a conjugate of the invention which is useful for enhancing the uptake of nucleic acid into higher eucaryotic cells, characterized in that a virus or a (poly)peptidic endosomolytic agent and a polyamine are chemically coupled.

The invention also relates to a process of preparing a conjugate of the invention which is useful for enhancing the uptake of nucleic acid into higher eucaryotic cells, comprising a) modifying a virus or a virus component with biotin, and
b) binding the modified virus or modified virus component obtained in step a) to a streptavidin-coupled polyamine.

The invention also relates to a process for introducing nucleic acid into higher eucaryotic cells, characterized in that the cells are contacted with a composition according to the invention.

The invention also relates to a process for introducing nucleic acid into liver cells in vivo, wherein the composition according to the invention is administered to the liver via the bile duct.

The invention also relates to a process for producing a protein of interest in a higher eucaryotic cell, characterized in that the cells are treated with a DNA complex of the invention, the nucleic acid comprising a DNA sequence encoding the desired protein, the cells are cultivated under conditions suitable for expression of the protein, and the protein is recovered.

The invention also relates to a pharmaceutical preparation comprising a DNA complex of the invention, wherein the nucleic acid is therapeutically active, and a pharmaceutically acceptable carrier.

The invention also relates to a transfection kit, comprising a carrier means having in close confinement therein two or more container means, wherein a first container means contains a substance having an affinity for nucleic acid, which substance is optionally coupled with an internalizing factor for a higher eucaryotic cell; and a second container means contains an agent which has the ability per se of being internalized into the cells and of releasing the contents of the endosome into the cytoplasm.

The invention also relates to a transfection kit, comprising a carrier means having in close confinement therein one or more container means, wherein a first container means contains a substance having an affinity for nucleic acid, which substance is optionally coupled with an internalizing factor for a higher eucaryotic cell, and wherein a second container means contains a substance having an affinity for a nucleic acid which is coupled to an agent which has the ability of being internalized into the cells as a component of a nucleic acid complex, and of releasing the contents of the endosome, in which the complex is located after entering the cell, into the cytoplasm.

The invention also relates to a transfection kit, comprising a carrier means having in close confinement therein one or more container means, wherein a first container means contains a biotin-modified endosomolytic agent and a second container means contains a streptavidin-modified substance having affinity for nucleic acid.

A) Effect on complexed DNA.
B) Effect on receptor-bound DNA.
C) Effect on gene transfer by means of transferrin-polylysine conjugates.

FIG. 4: Effect of adenovirus infection on gene transfer by means of transferrin-polylysine conjugates in selected cell lines.

FIG. 5: Investigation into whether the enhancement of gene expression is based on gene transfer or on transactivation.

A) Cell line K562.
B) Cell line K562 10/6 which constitutively expresses luciferase.

Figure 6:
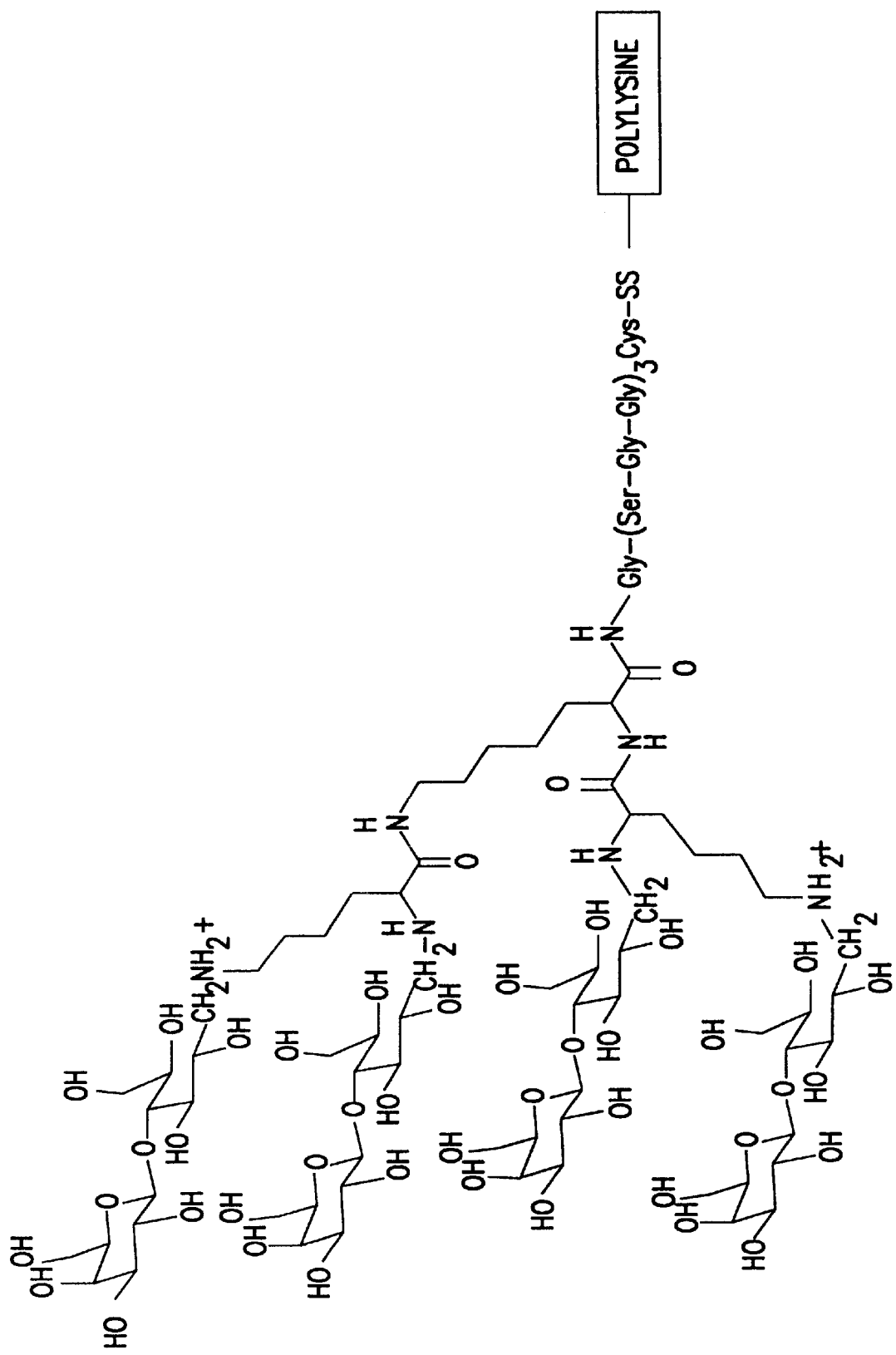

FIG. 6: Tetra-galactose peptide-polylysine conjugate.

Figure 7:
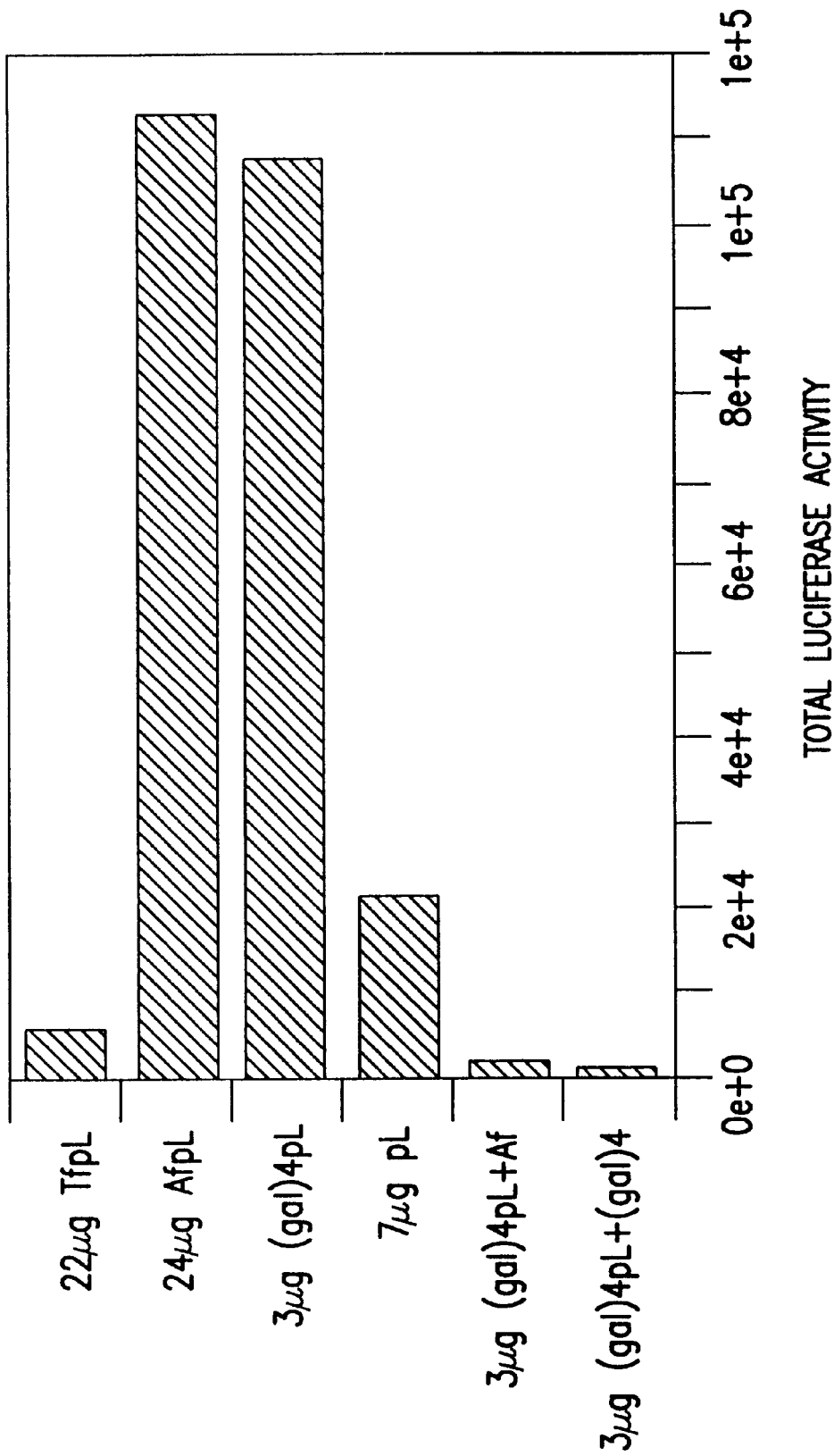

FIG. 7: Transfection of HepG2 cells in the presence of adenovirus.

Figure 8:
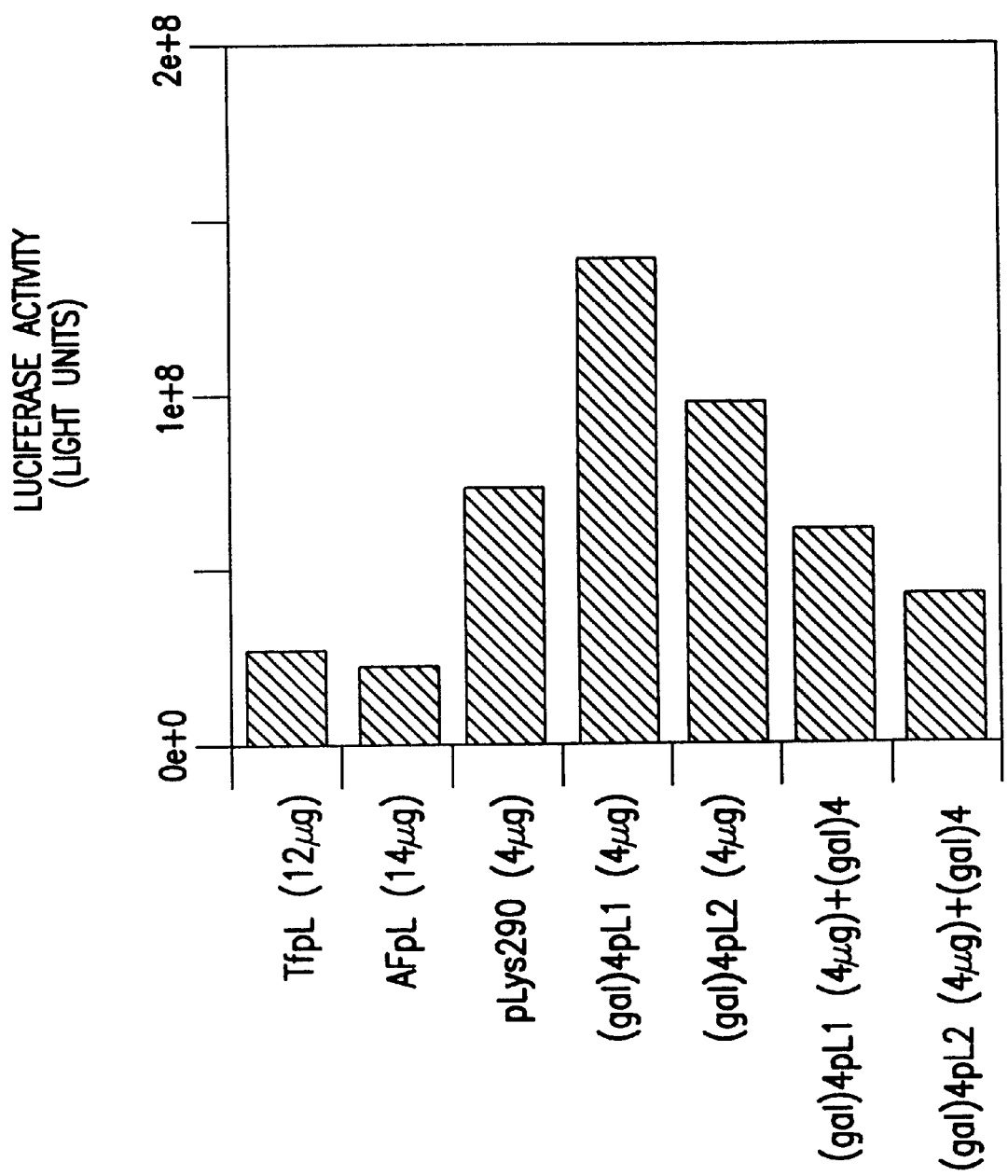

FIG. 8: Transfection of HepG2 cells in the presence of adenovirus.

FIG. 9: Transfection of TIB73 cells.

A) Comparison values with chloroquine.
B) In the presence of adenovirus.

Figure 10A:
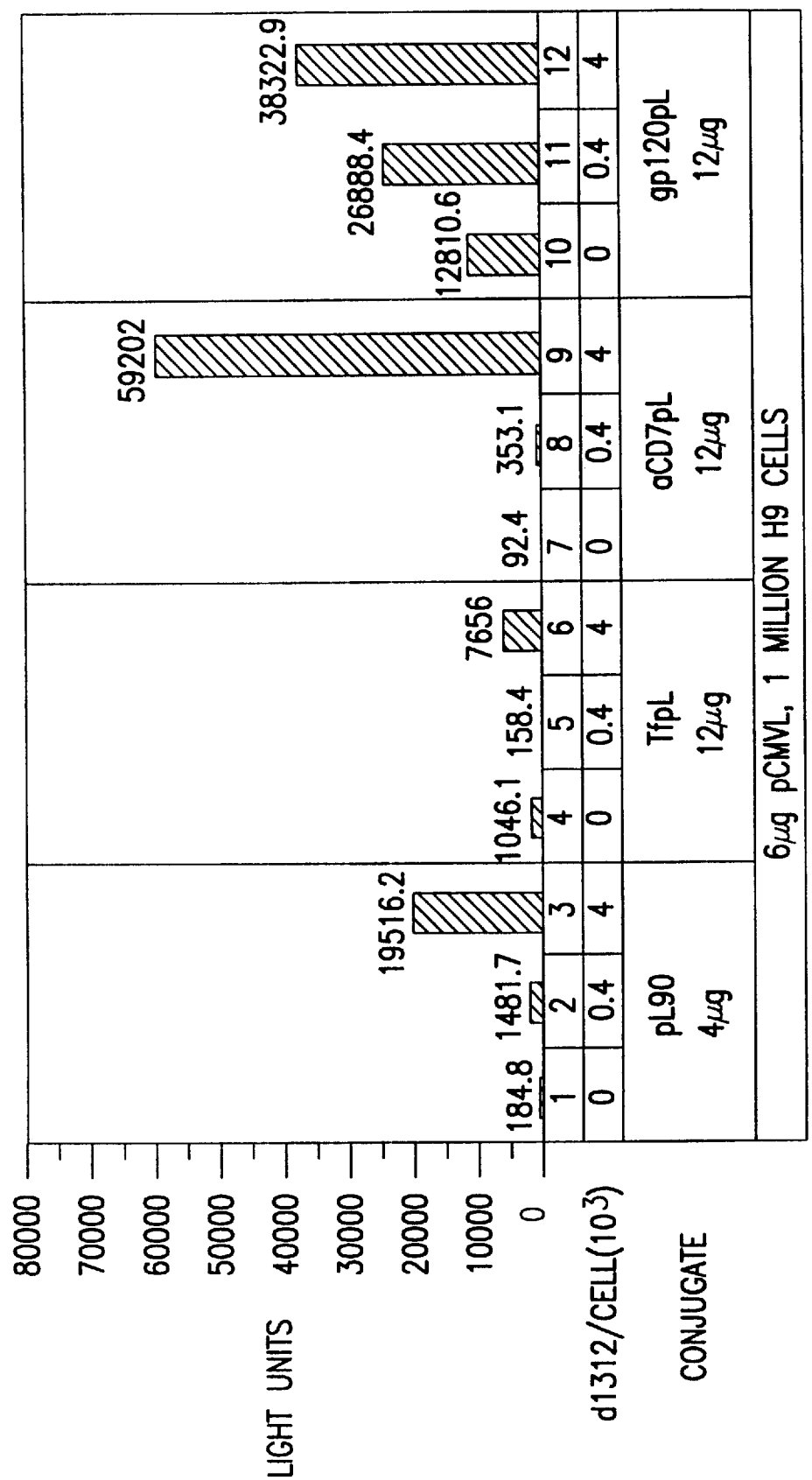

FIG. 10: Transfection of T cells in the presence of adenovirus:

A) H9 cells.
B) Primary lymphocytes.

FIG. 11: UV-inactivation of adenoviruses:

A) Enhancement of gene transfer effect in HeLa cells by UV-inactivated viruses.
B) Comparison of UV-inactivation with the gene transfer effect.

FIG. 12: Inactivation of adenoviruses by means of formaldehyde.

Figure 13:
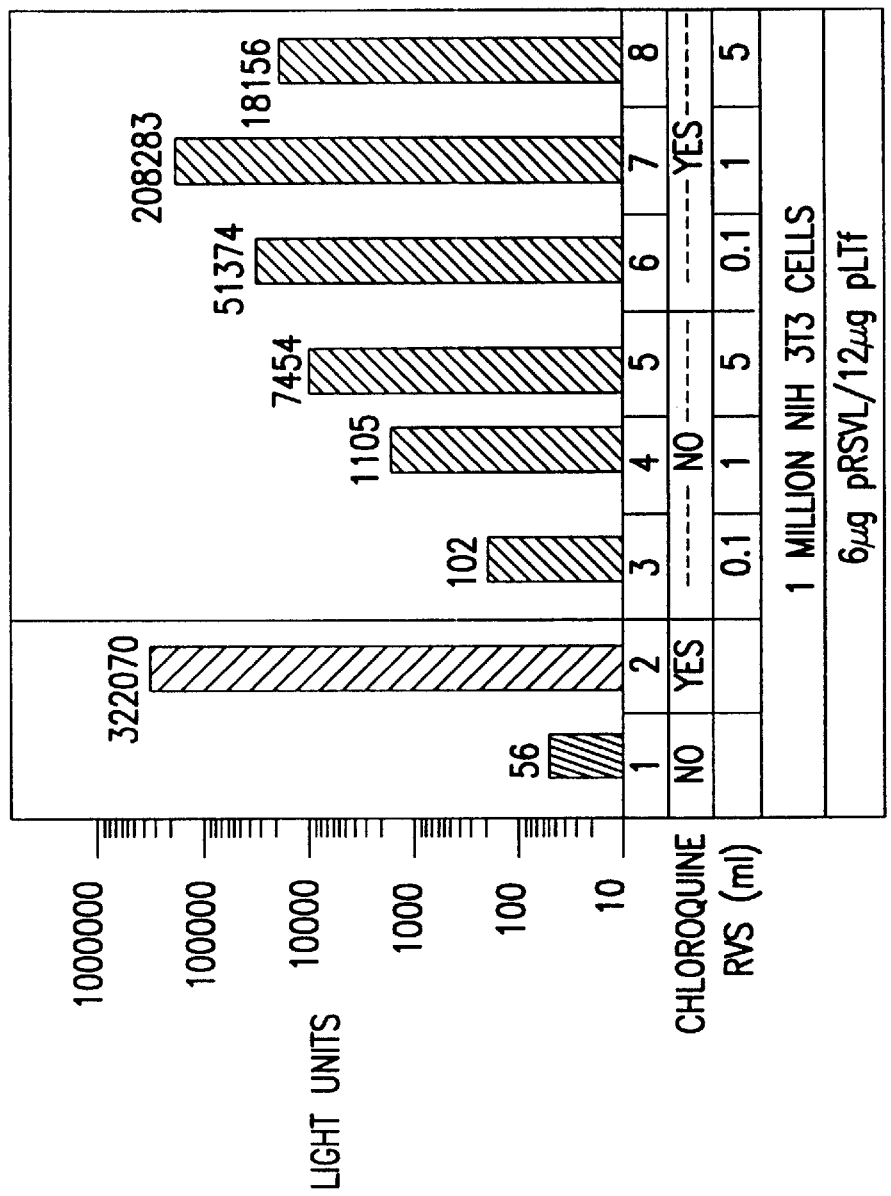

FIG. 13: Transfection of NIH3T3 cells in the presence of Moloney virus.

Figure 14:
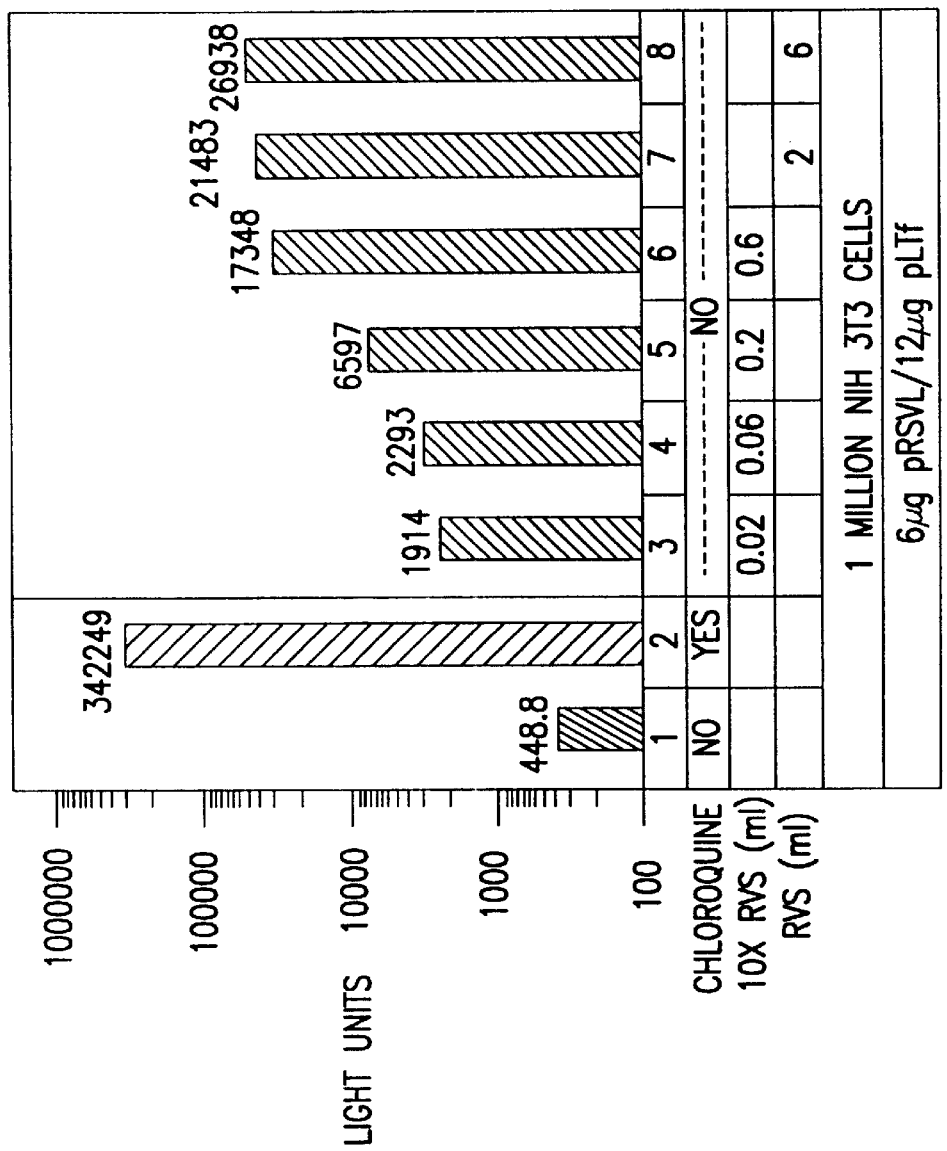

FIG. 14: Investigation into whether the gene transfer effect in the transfection of NIH3T3 cells with transferrin-polylysine DNA complexes can be attributed to Moloney virus.

Figure 15:
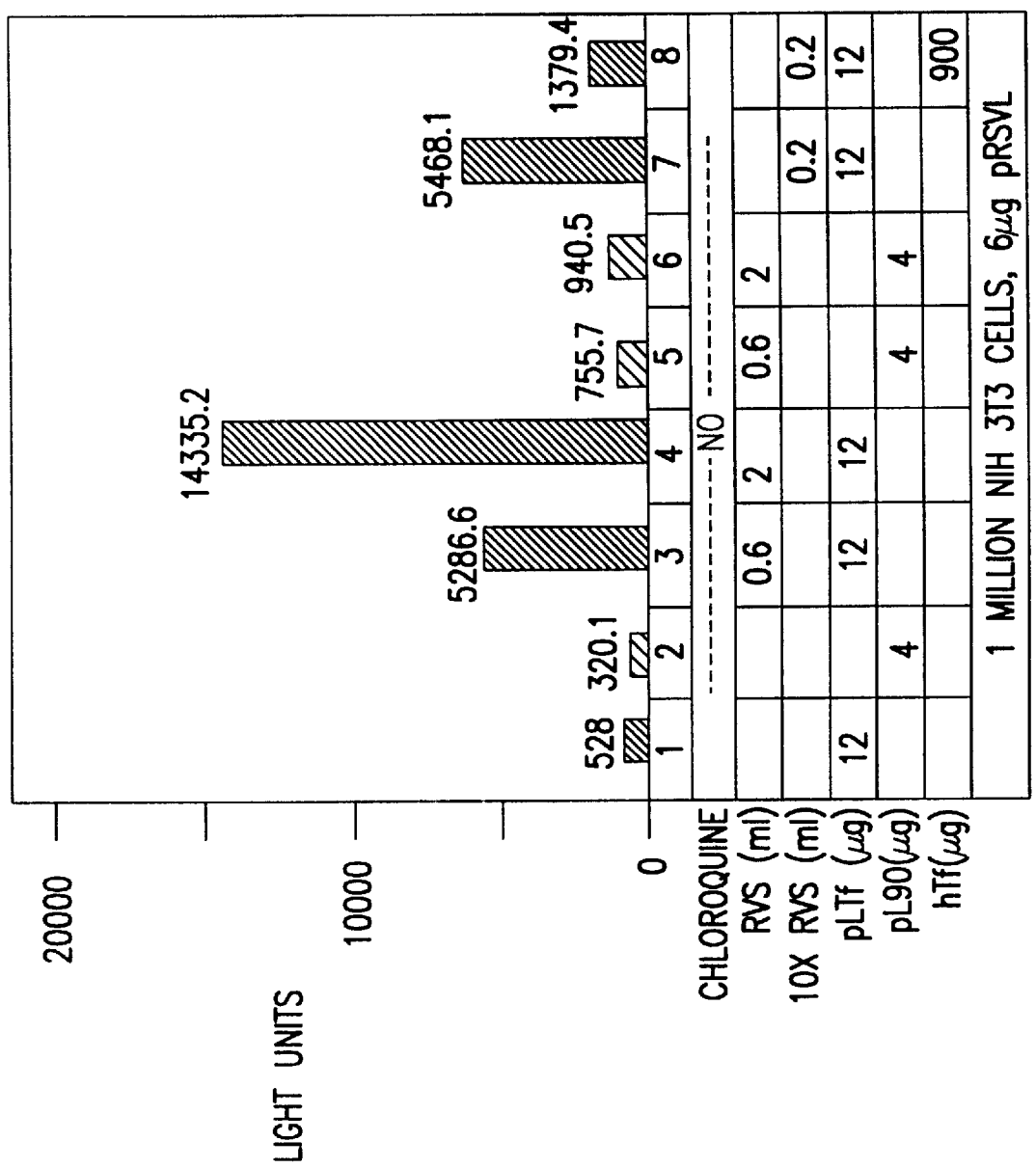

FIG. 15: Interactions between transferrin and its receptor play a part in the gene transfer effect of Moloney virus.

Figure 16:
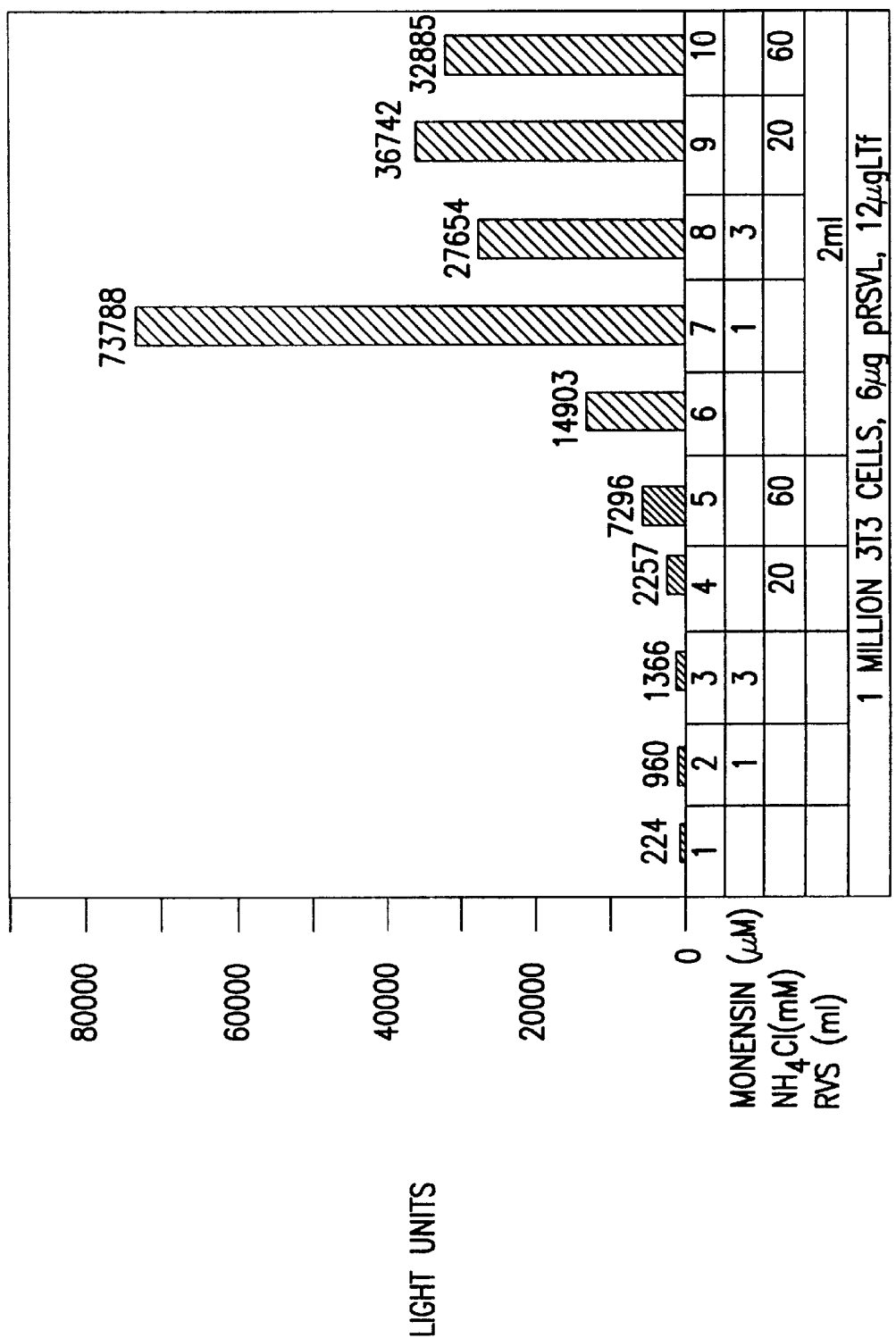

FIG. 16: Influence of pH on the gene transfer effect of retroviruses.

Figure 17:
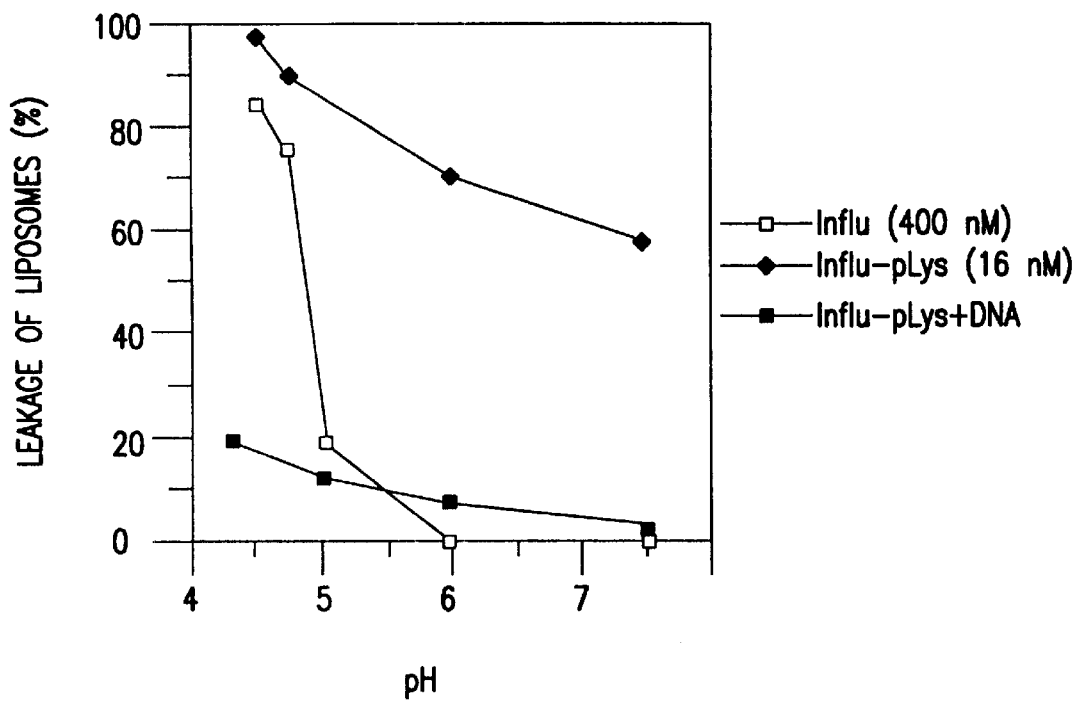

FIG. 17: Influenza-hemagglutinin peptide; liposome leakage assay.

Figure 18:
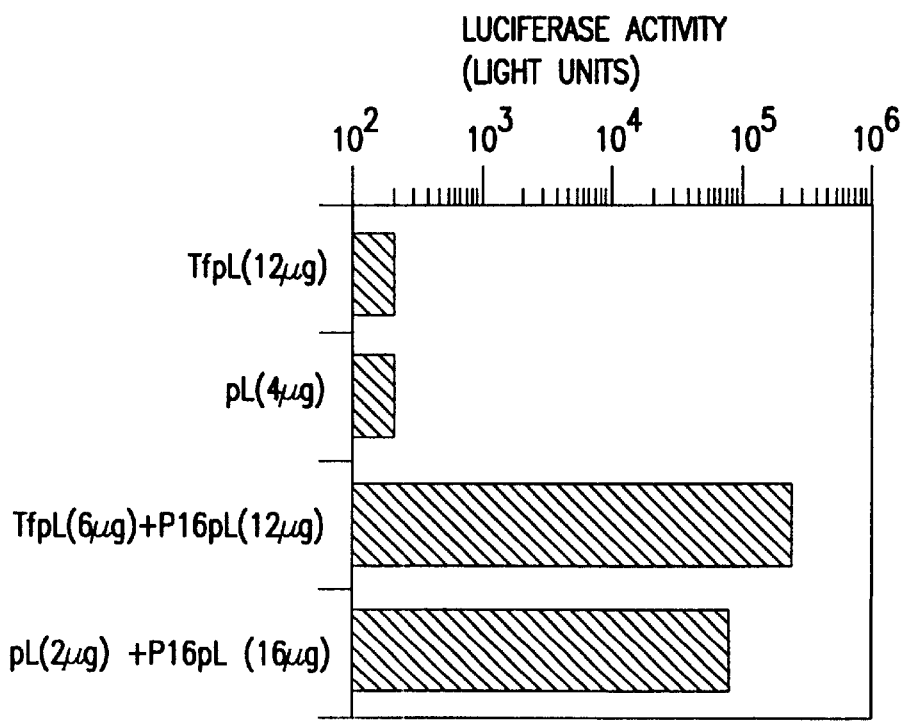

FIG. 18: Transfection of K562-cells in the presence of influenza peptide-polylysine conjugate p16pL.

Figure 19:
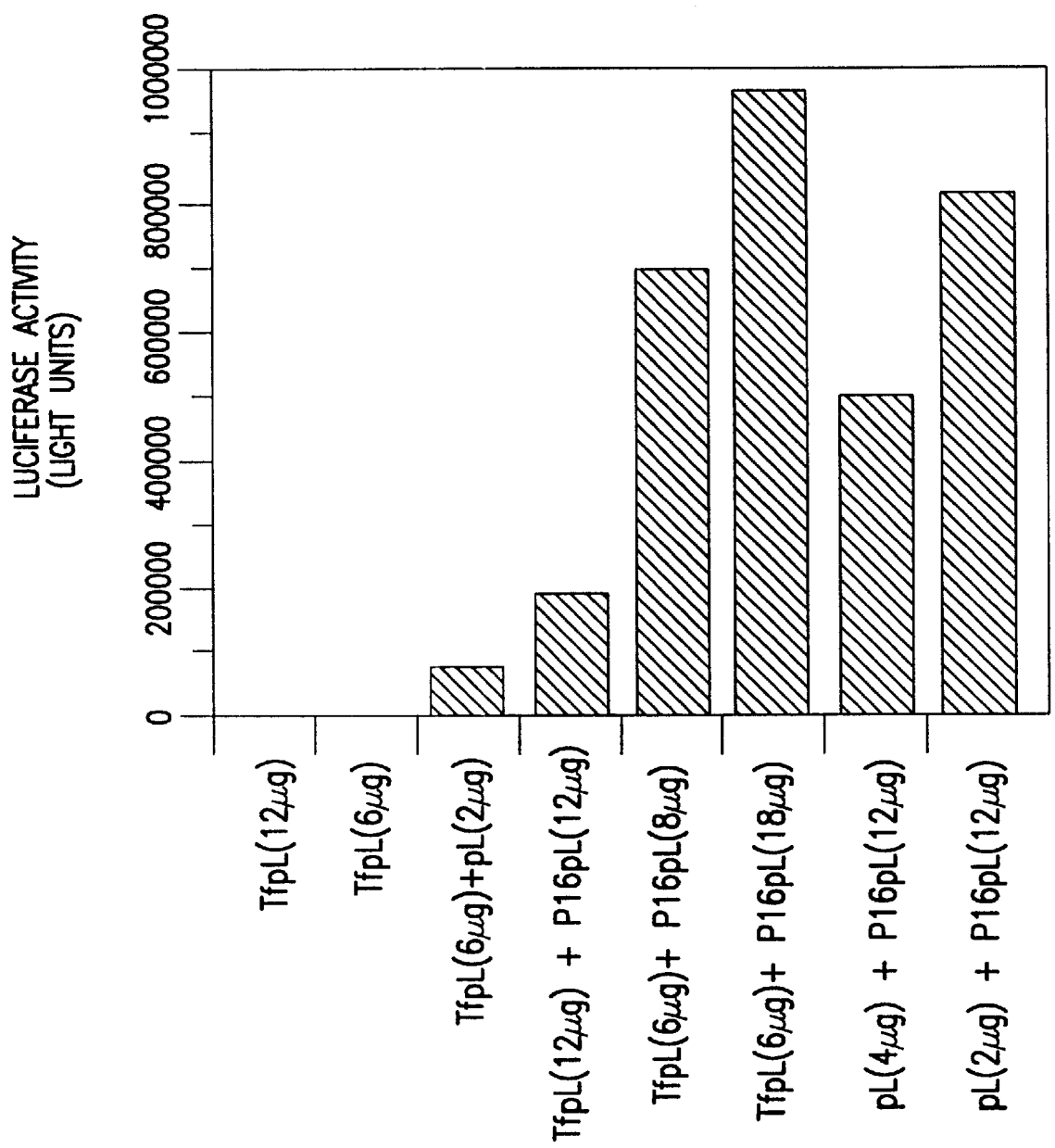

FIG. 19: Transfection of HeLa cells in the presence of influenza peptide-polylysine conjugate p16pL.

Figure 20B:
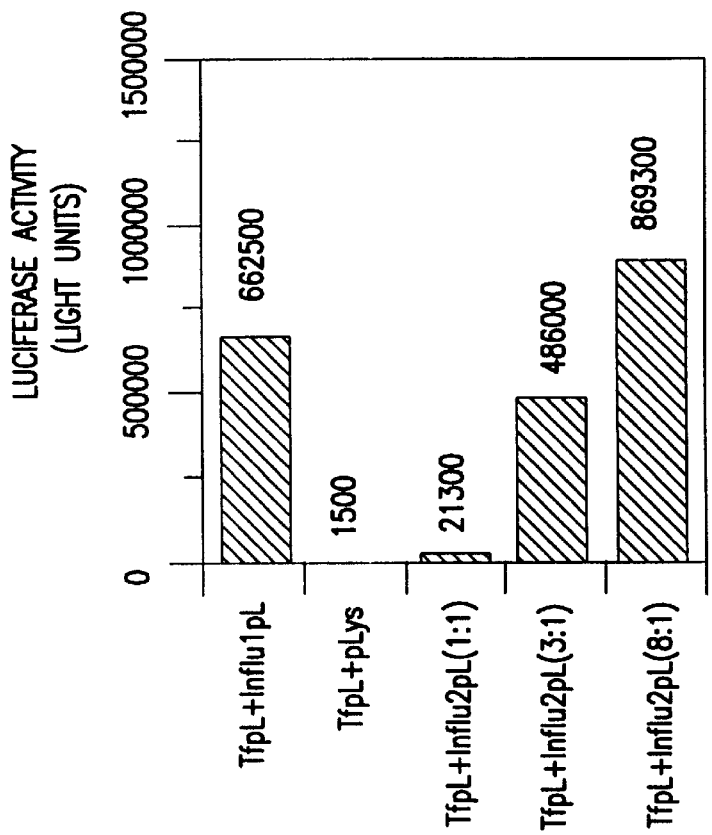
Figure 20A:
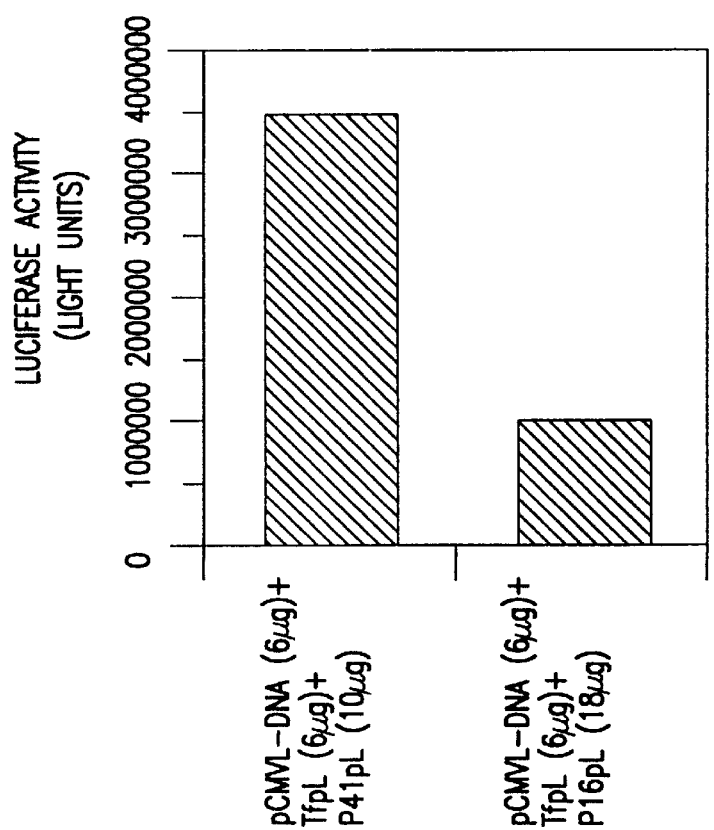
Figure 20C:
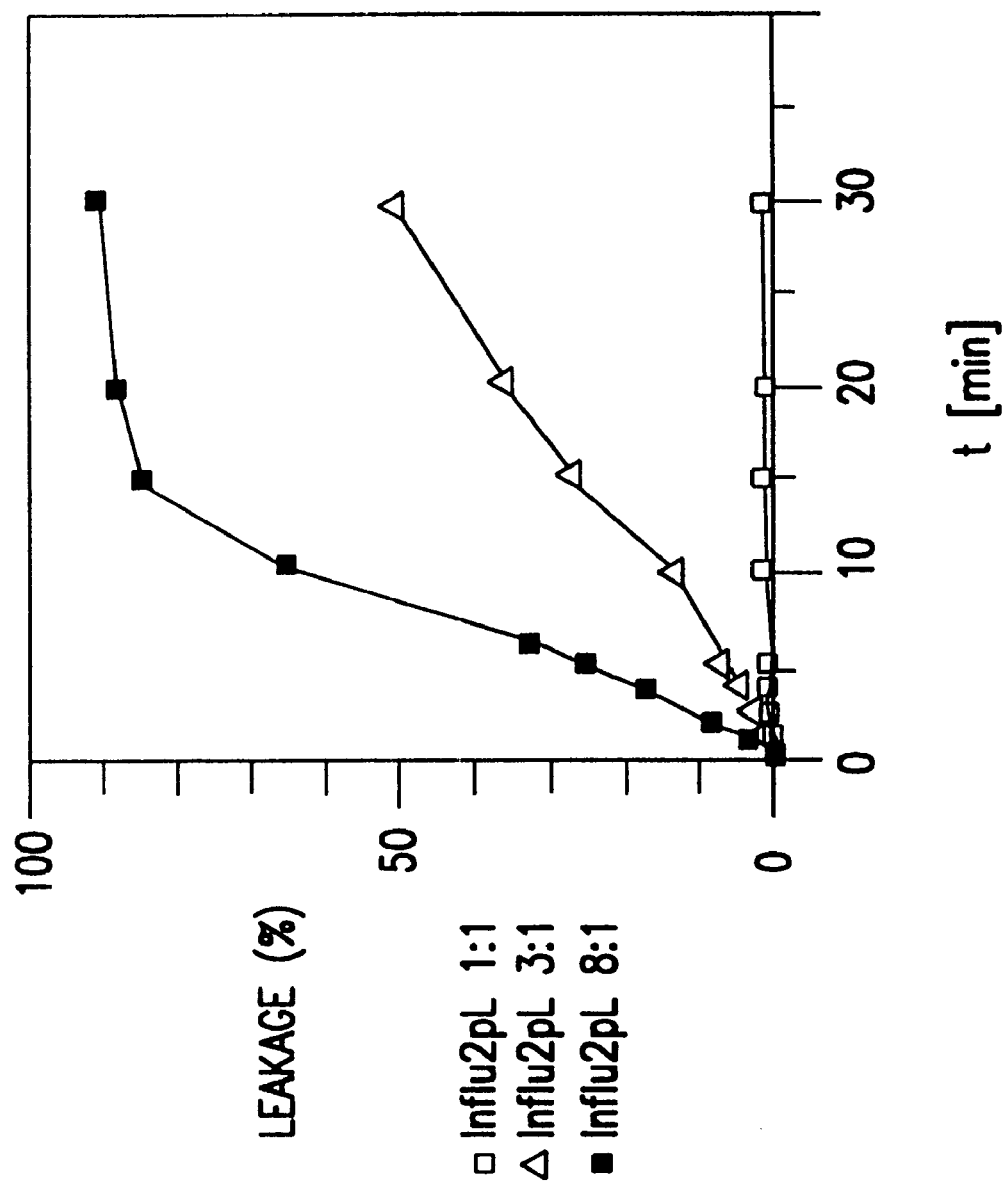

FIG. 20: Transfection of HeLa cells with transferrin-polylysine conjugates in the presence of influenza peptide-polylysine conjugate p41pL.

FIG. 21: In situ evidence of β-galactosidase expression after transfection of HeLa cells in the presence of adenovirus.

FIG. 22: Transfection of cells with a 48 kb cosmid in the presence of adenovirus.
A: HeLa cells.
B: Neuroblastoma cells.

Figure 23:
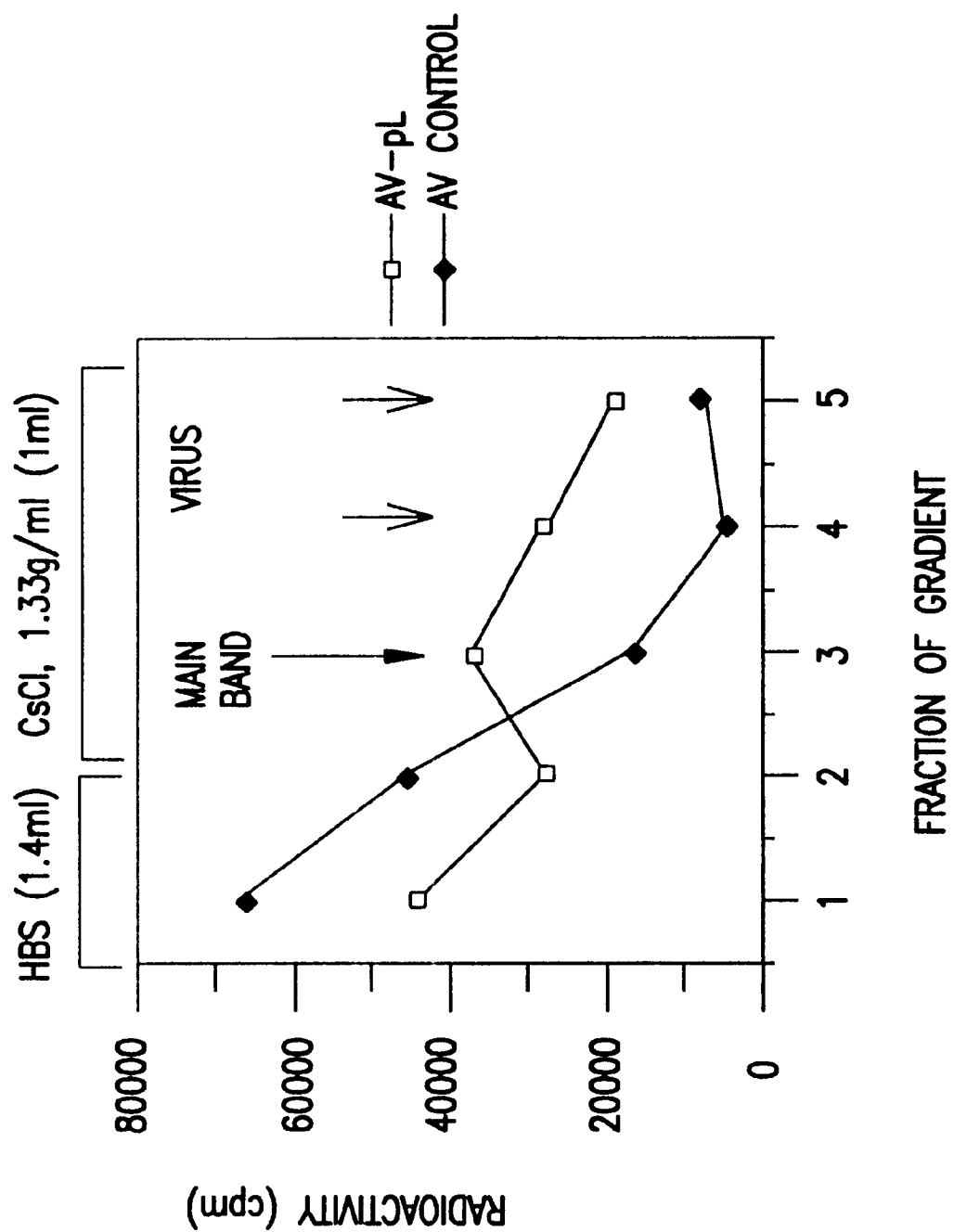

FIG. 23: Preparation of adenovirus-polylysine conjugates by chemical coupling.

Figure 24:
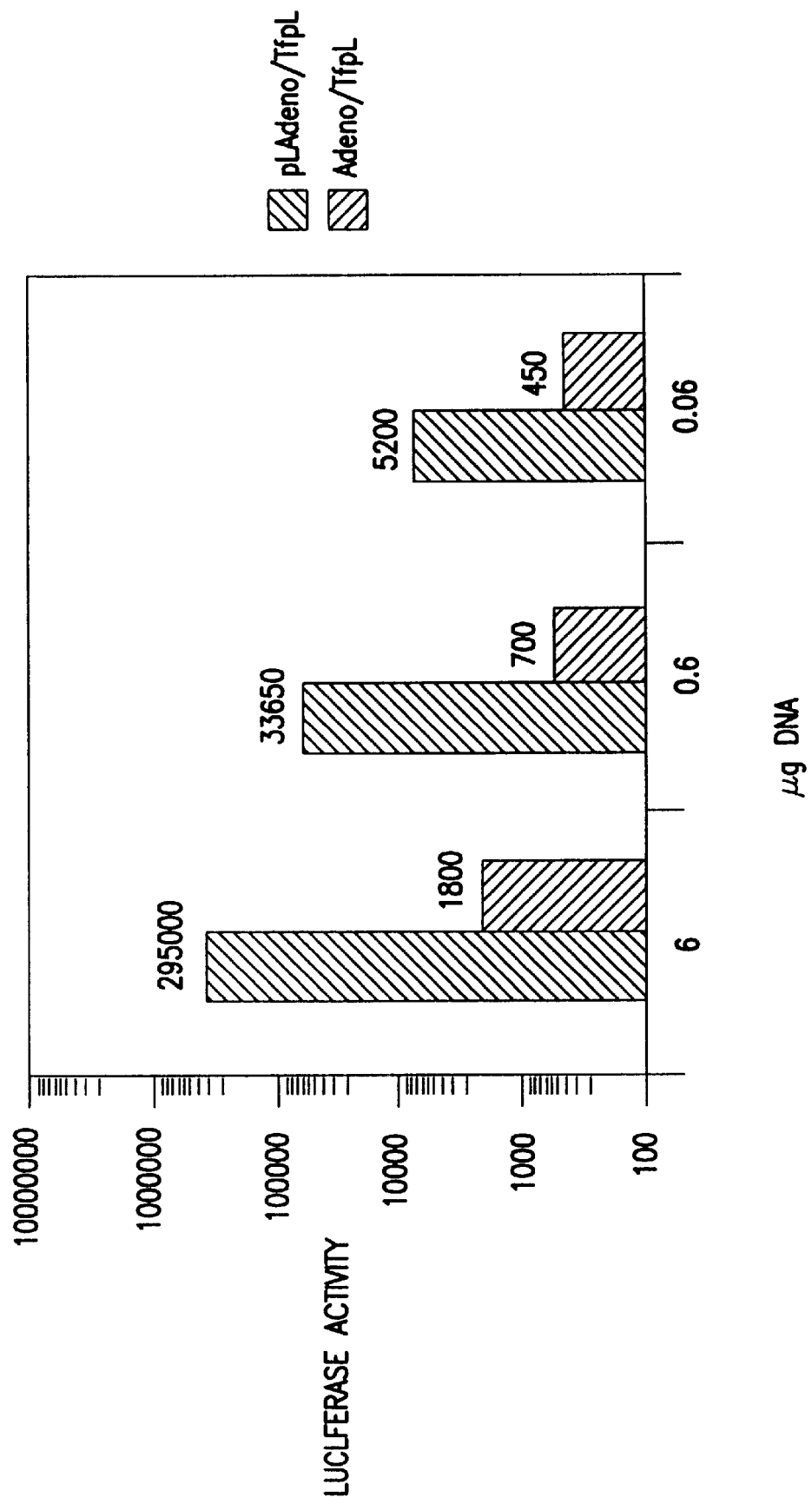

FIG. 24: Transfection of KS62 cells by means of chemically coupled adenovirus conjugates.

Figure 25:
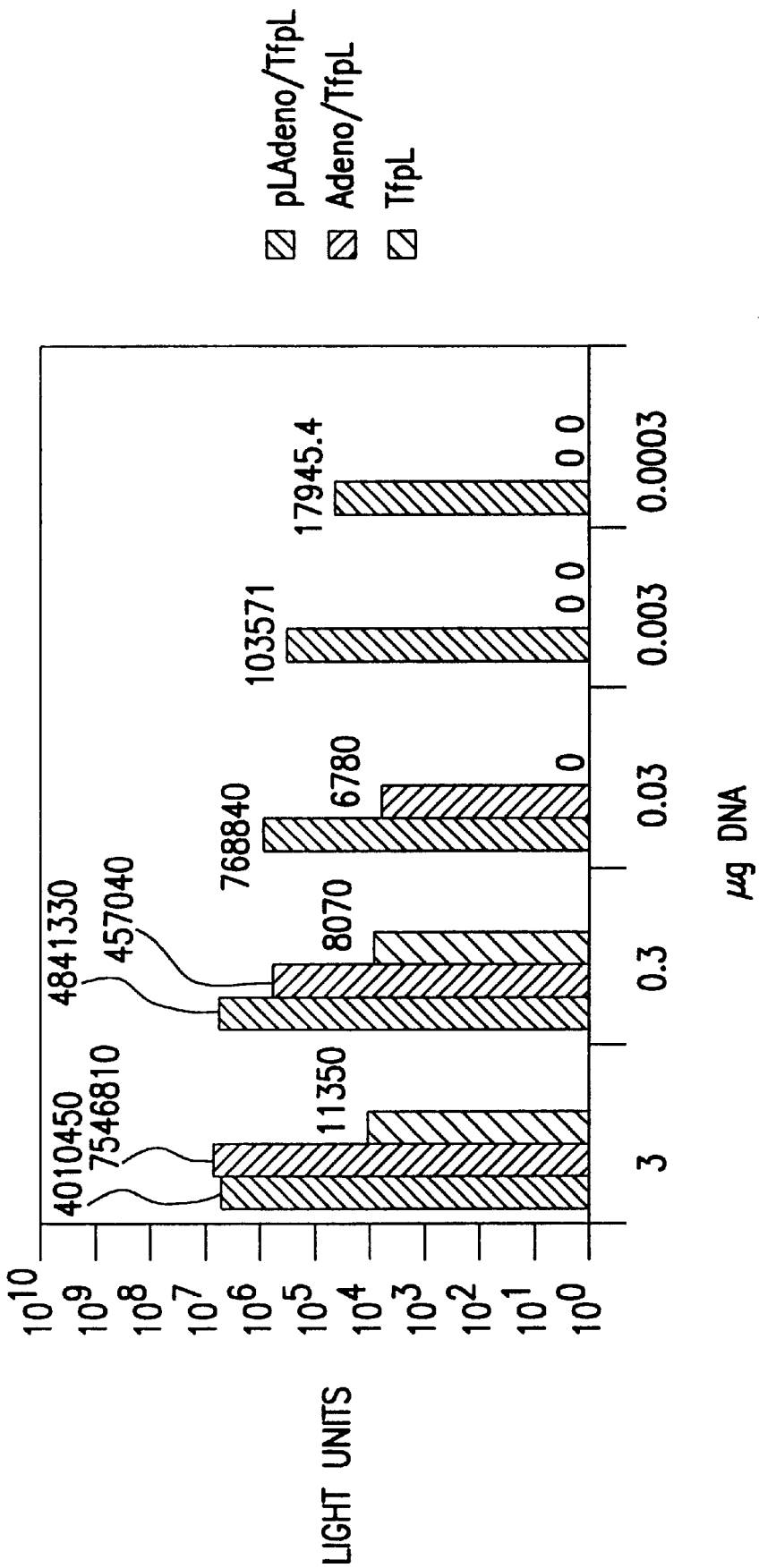

FIG. 25: Transfection of HeLa cells by means of chemically coupled adenovirus conjugates.

Figure 26:
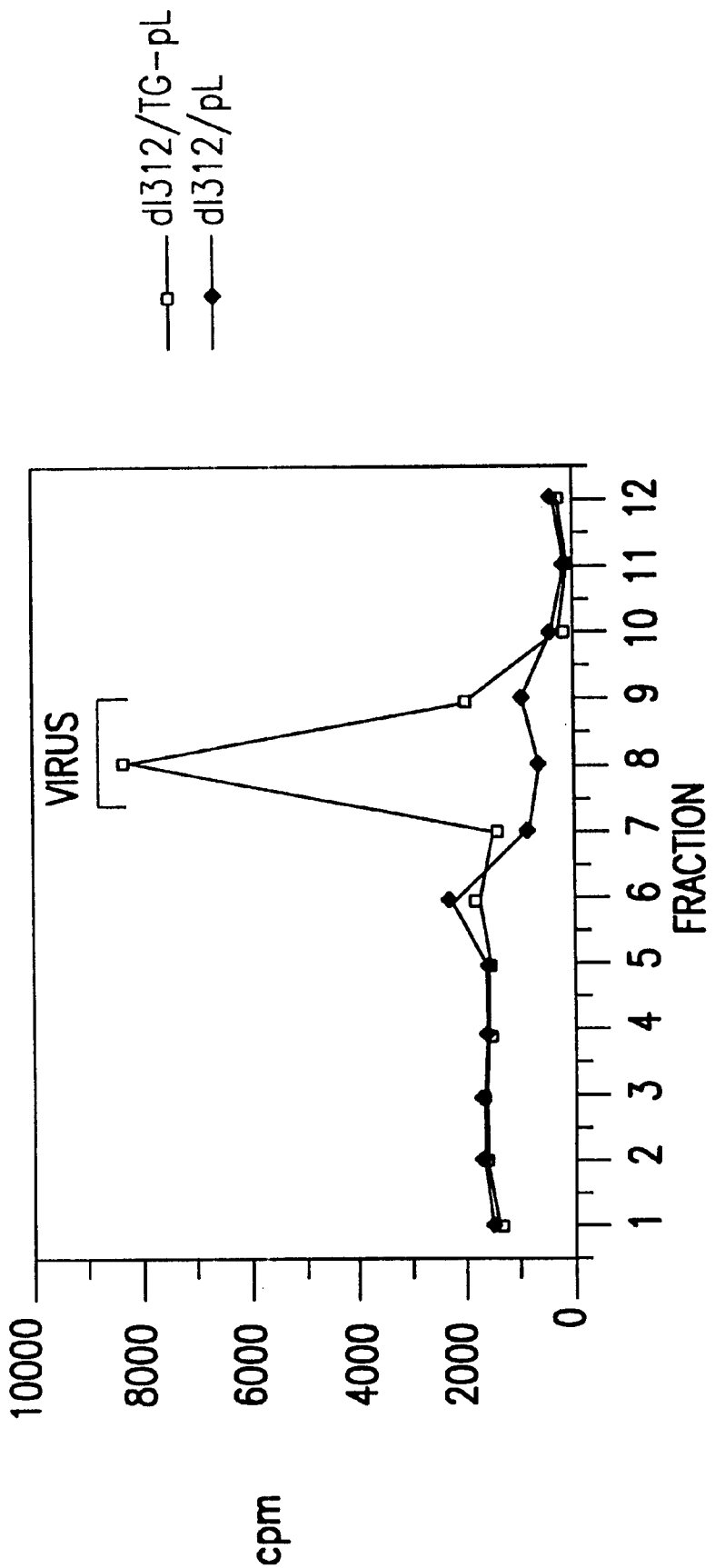

FIG. 26: Binding of polylysine to adenovirus by means of transglutaminase.

Figure 27:
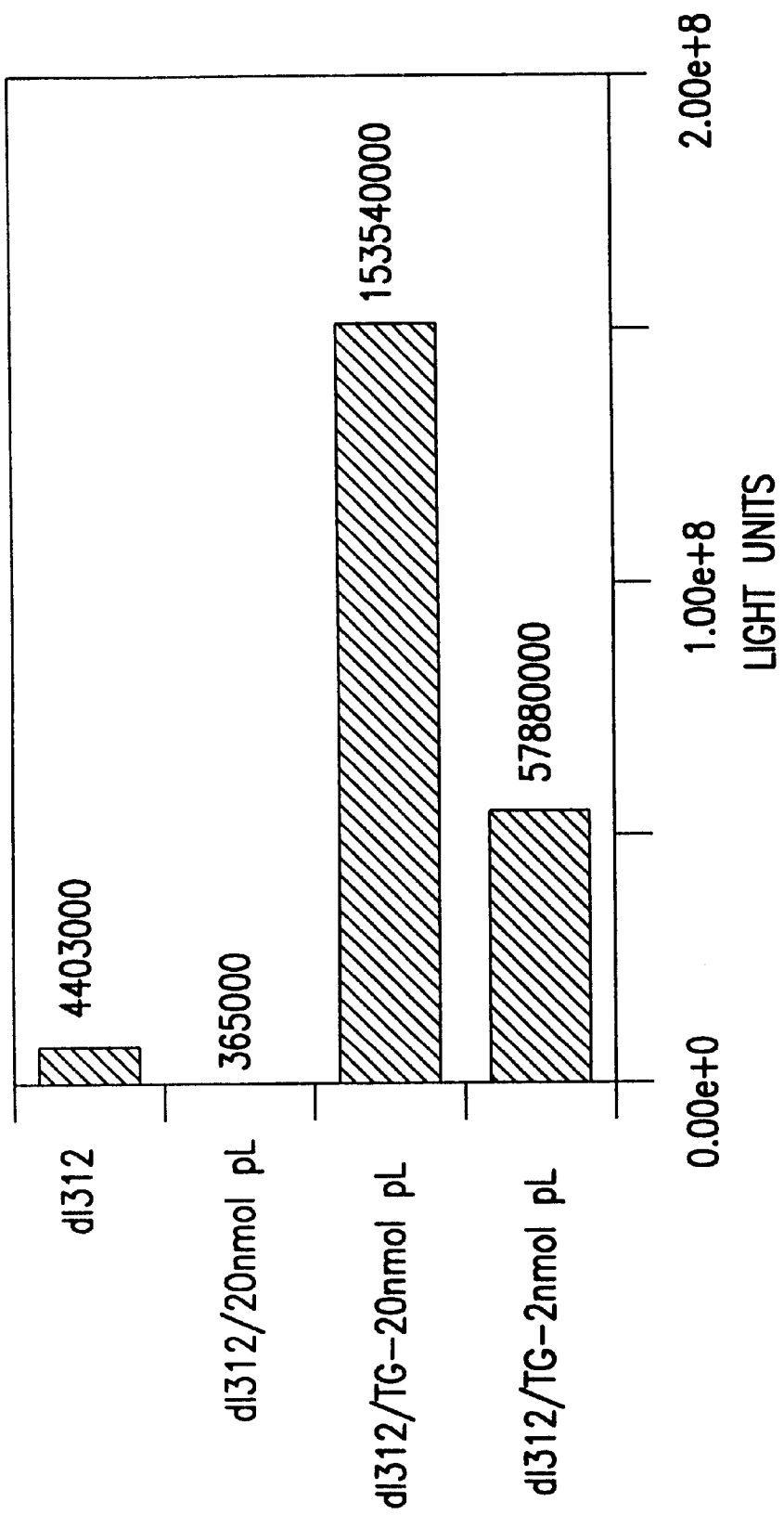

FIG. 27: Transfection of murine hepatocytes by means of transglutaminase-coupled adenovirus conjugates.

Figure 28:
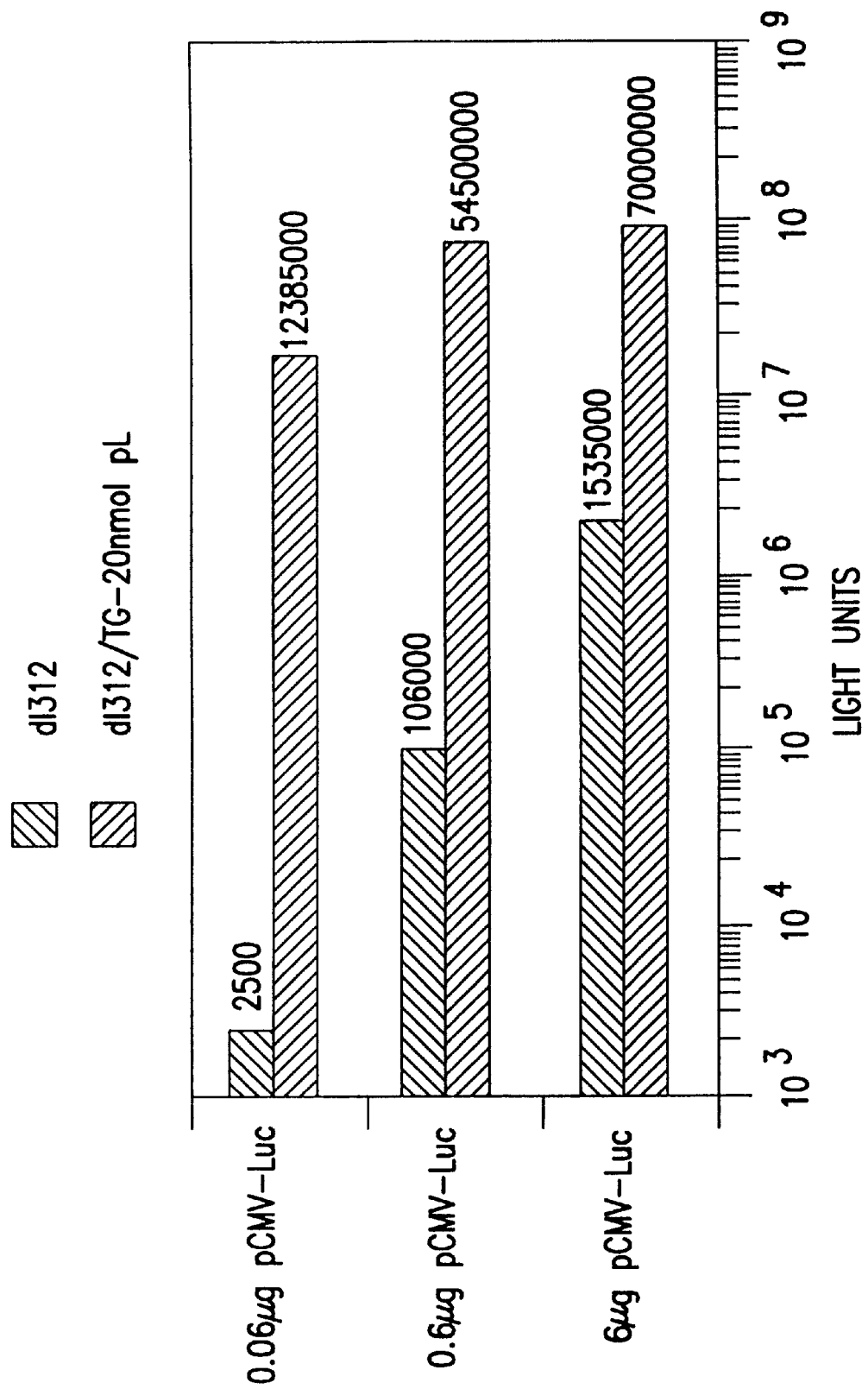

FIG. 28: Increasing the efficiency of transfection by transglutaminase-coupled adenovirus conjugates.

Figure 29:
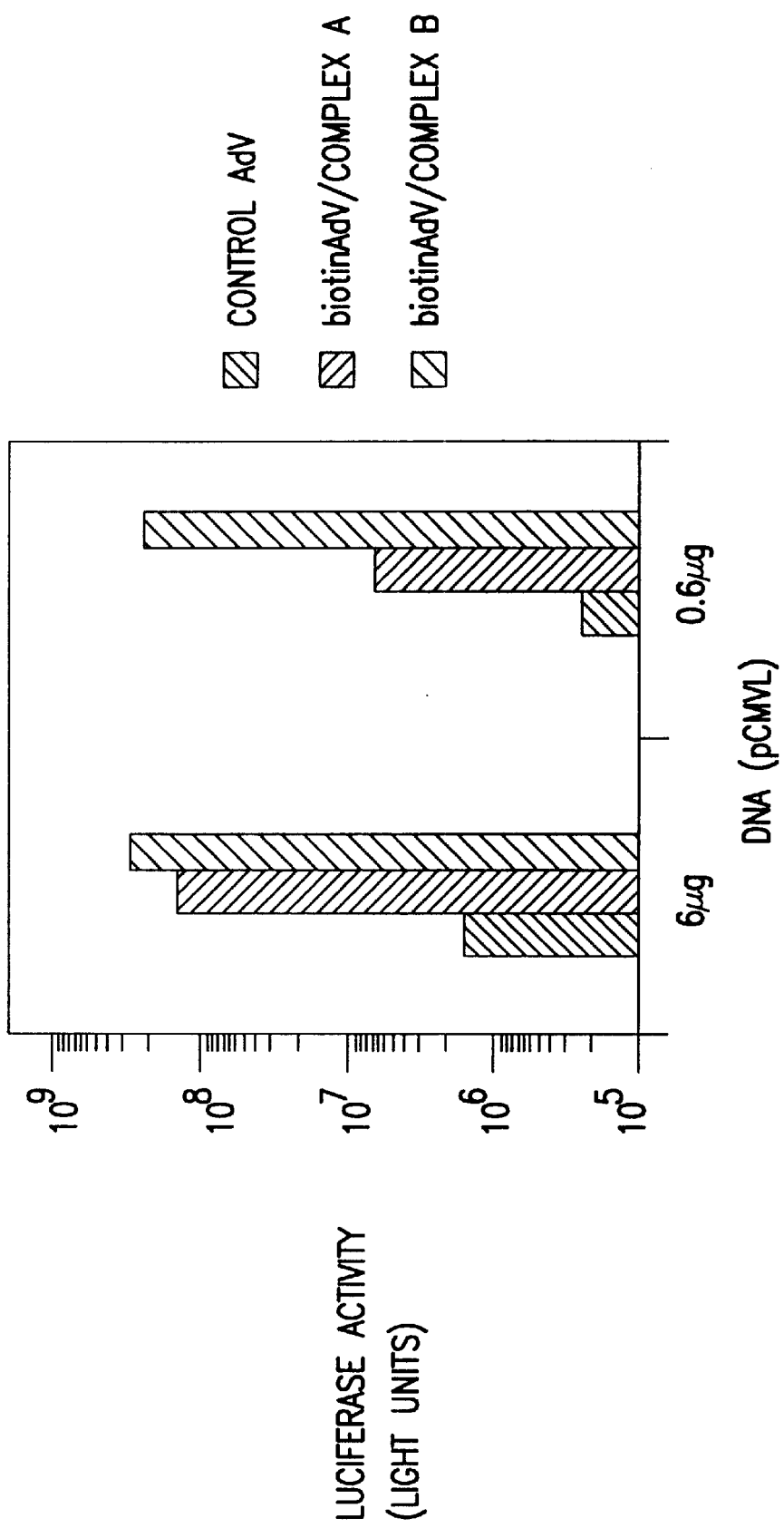

FIG. 29: Transfection of HeLa cells with biotin-streptavidin-coupled adenovirus conjugates.

Figure 30:
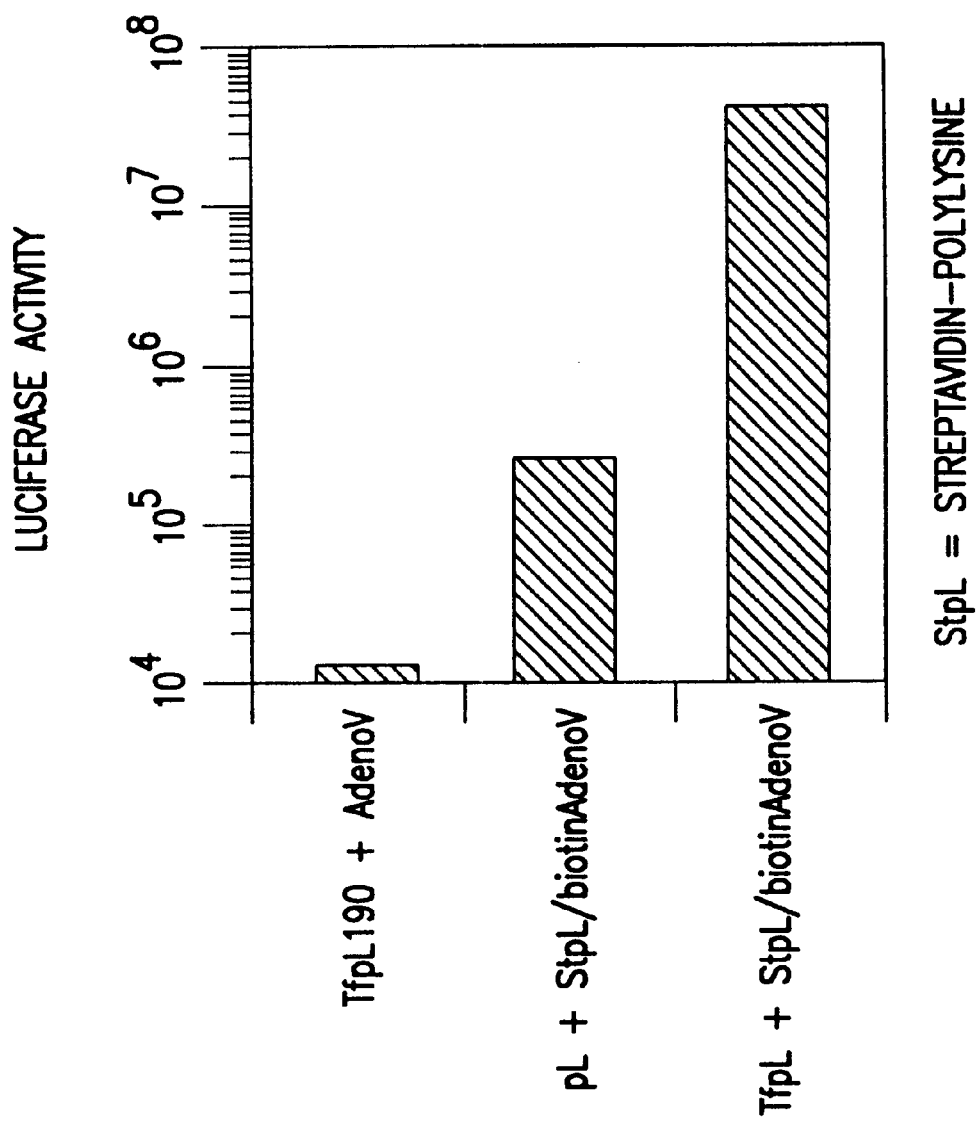

FIG. 30: Transfection of K562 cells with biotin-streptavidin coupled adenovirus conjugates.

Figure 31:
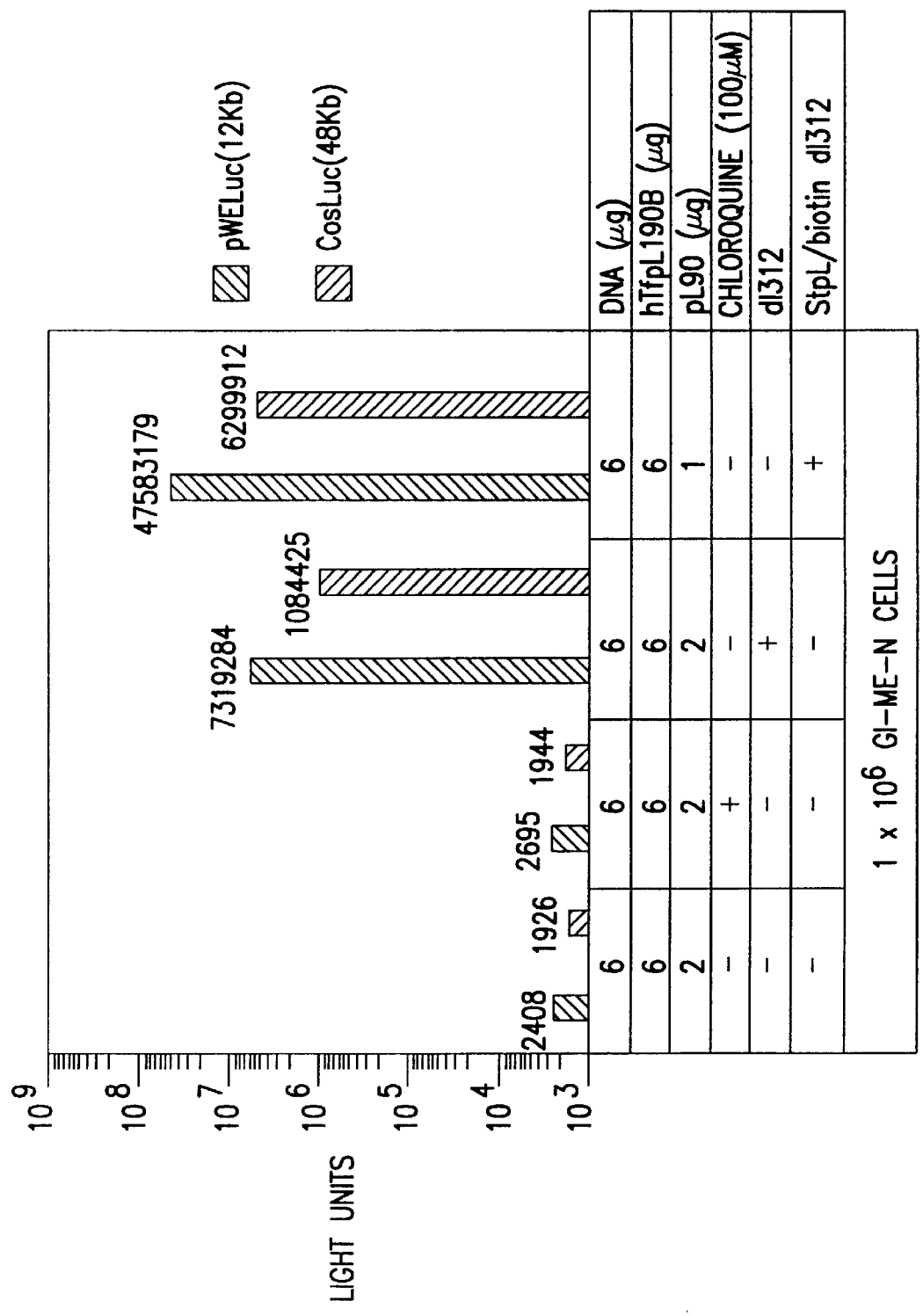

FIG. 31: Transfection of neuroblastoma cells with a 48 kb cosmid by means of biotin-streptavidin coupled adenovirus.

Figure 32A:
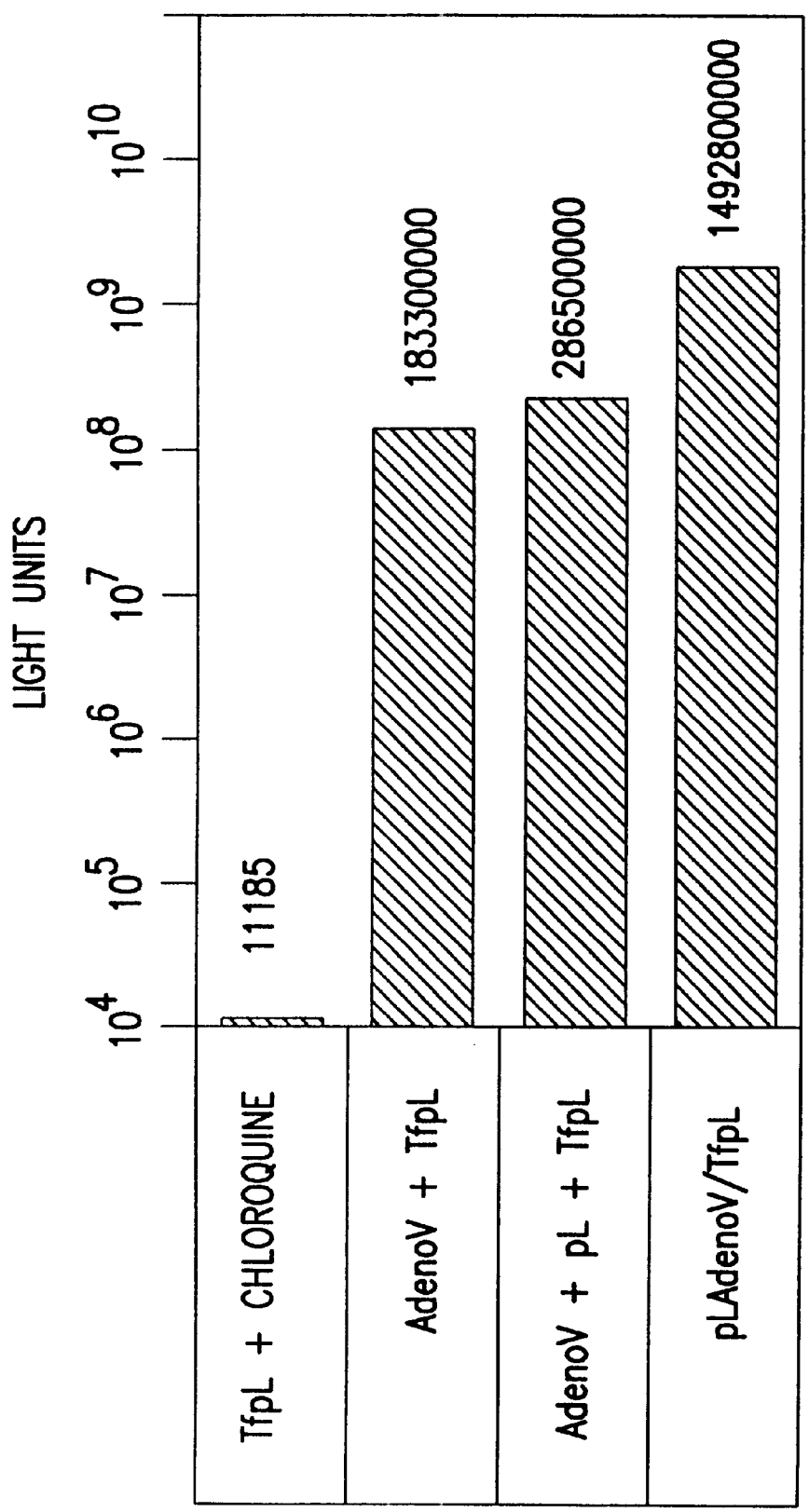
Figure 32B:
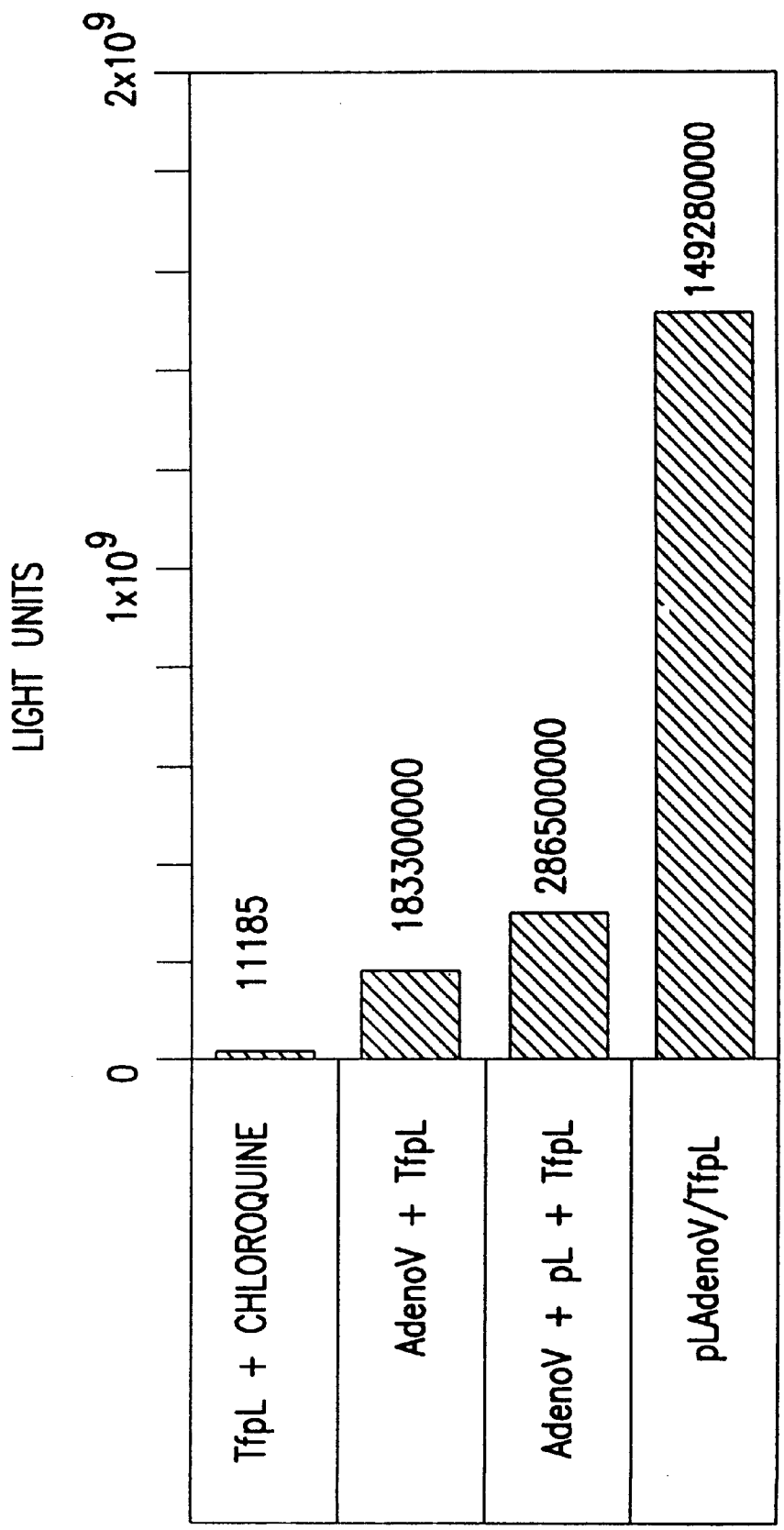

FIG. 32: Transfection of hepatocytes in the presence of chloroquine or in the presence of adenovirus.

Figure 33A:
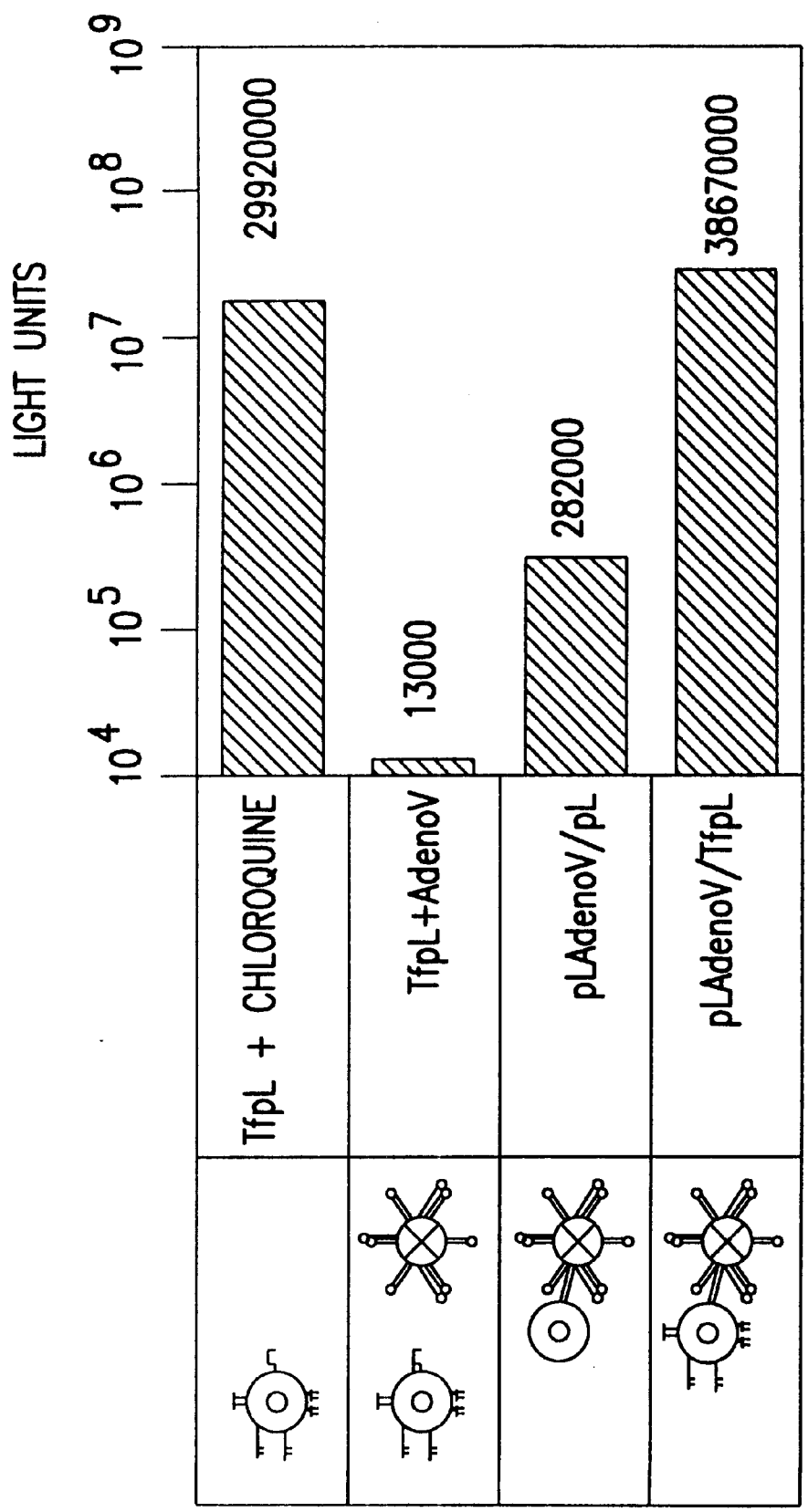
Figure 33B:
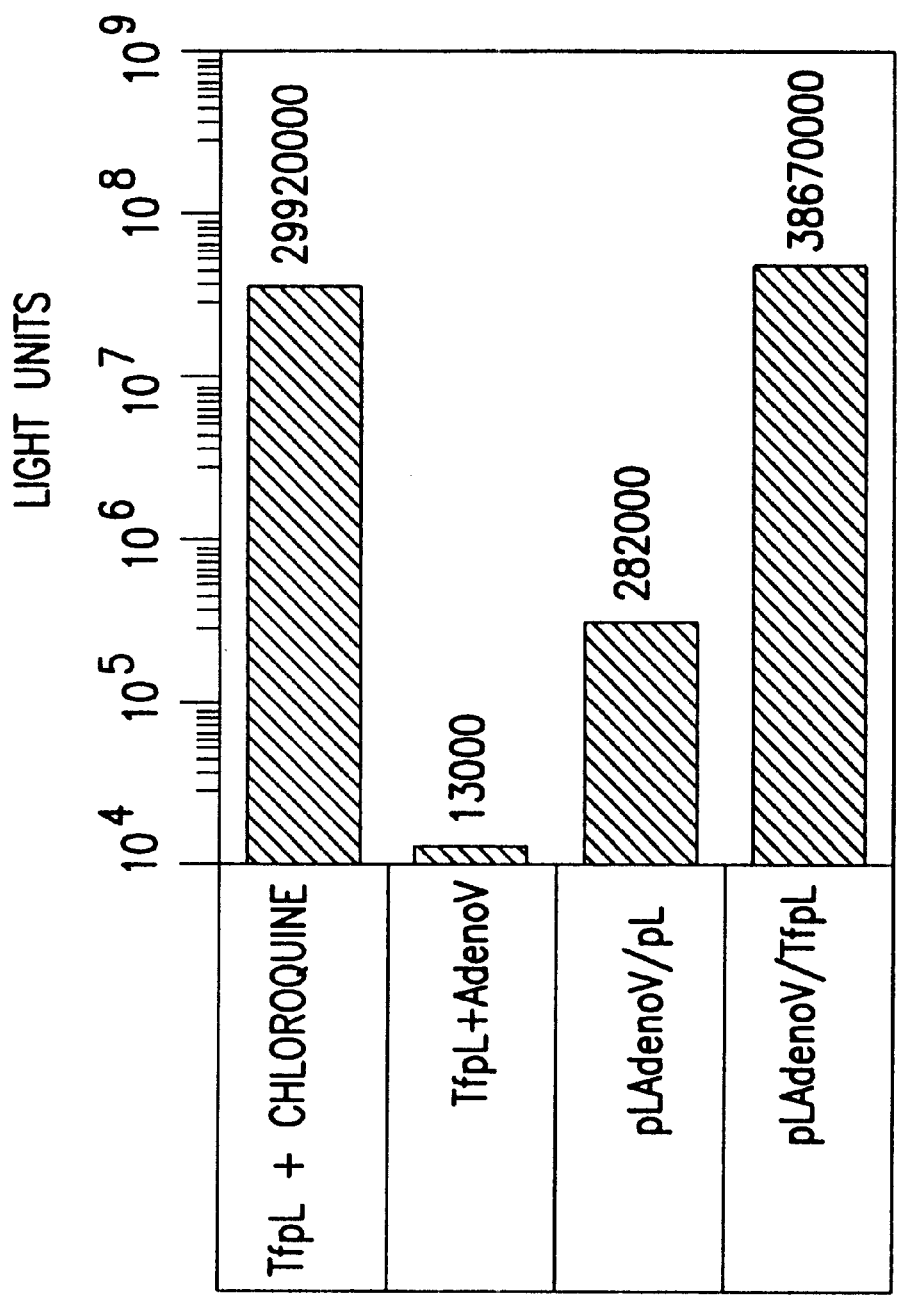

FIG. 33: Transfection of K562 cells in the presence of various endosomolytic agents.

FIG. 34: Comparison of transfection protocols at the cellular level with β-galactosidase as a reporter gene in the presence of various endosomolytic agents.

FIG. 35: Long term persistence of luciferase expression in confluent, non-dividing hepatocytes.

Figure 36:
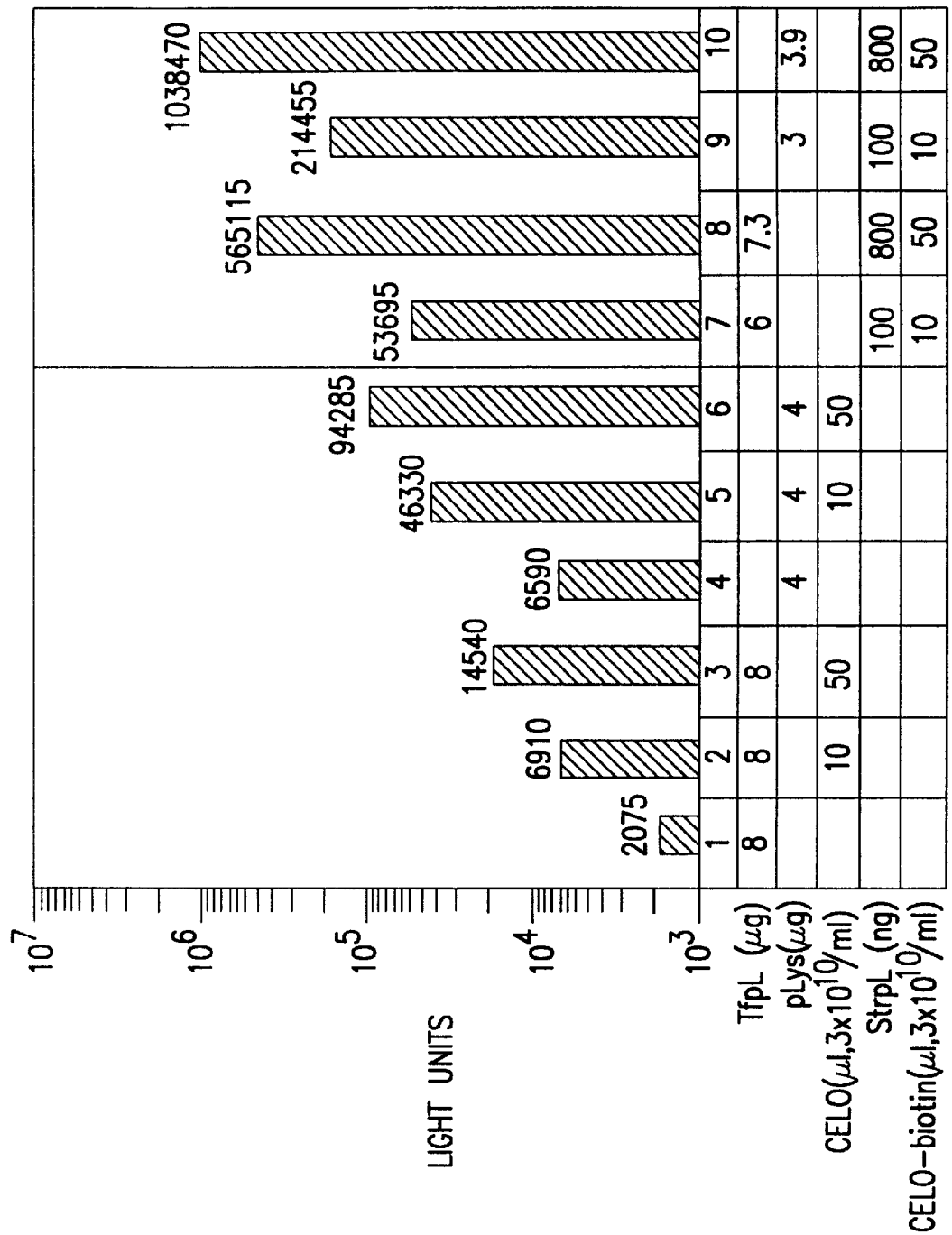

FIG. 36: Comparison of expression in HeLa cells transfected in the presence of the chick embryo lethal orphan virus (CELO) in the free form and with CELO virus linked to polylysine via biotin-streptavidin.

Figure 37:
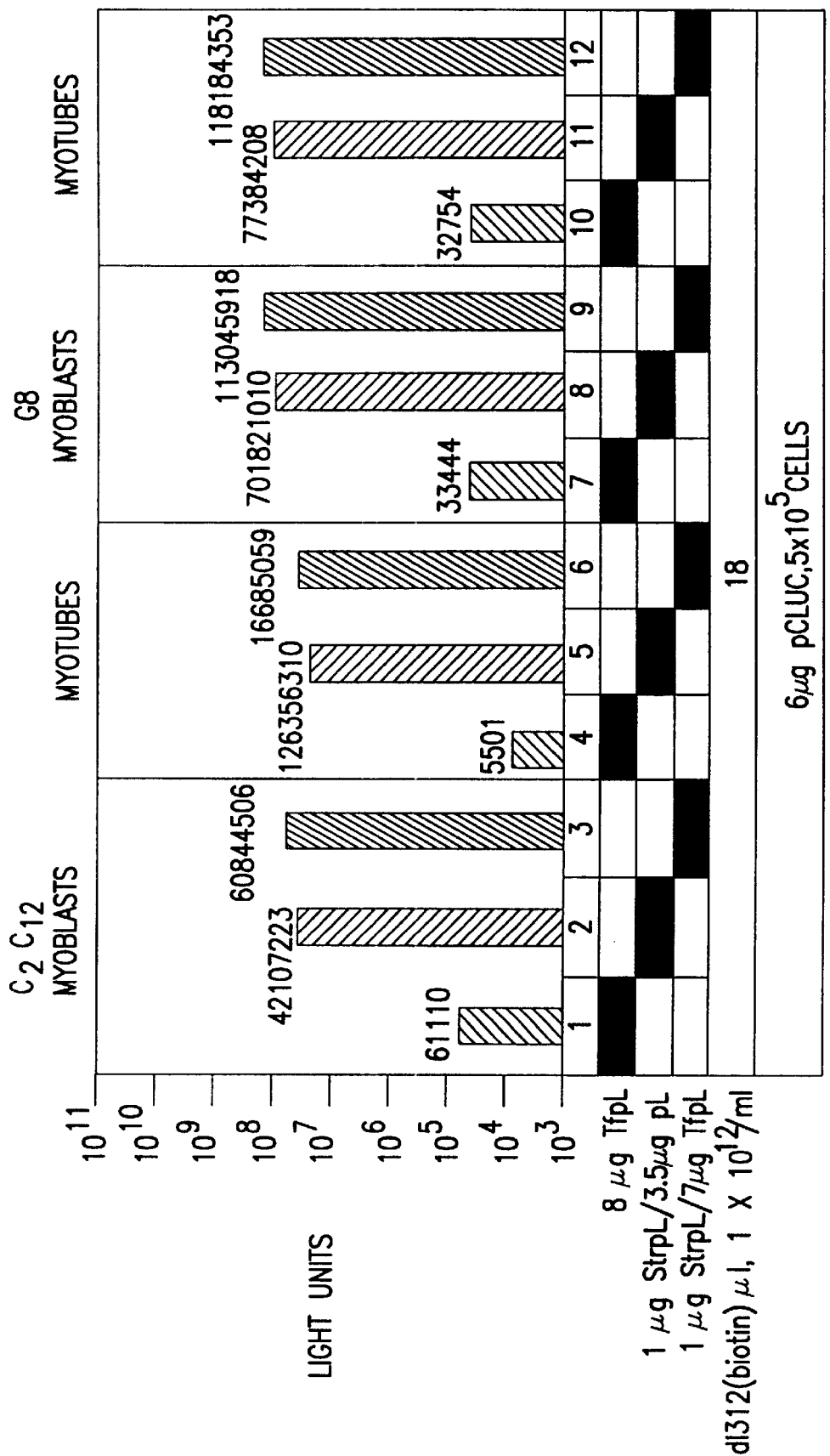

FIG. 37: Transfection of myoblasts and myotubes with DNA/transferrinpolylysine complexes in the presence of free adenovirus and in the presence of biotin/streptavidin-coupled adenovirus.

Figure 38:
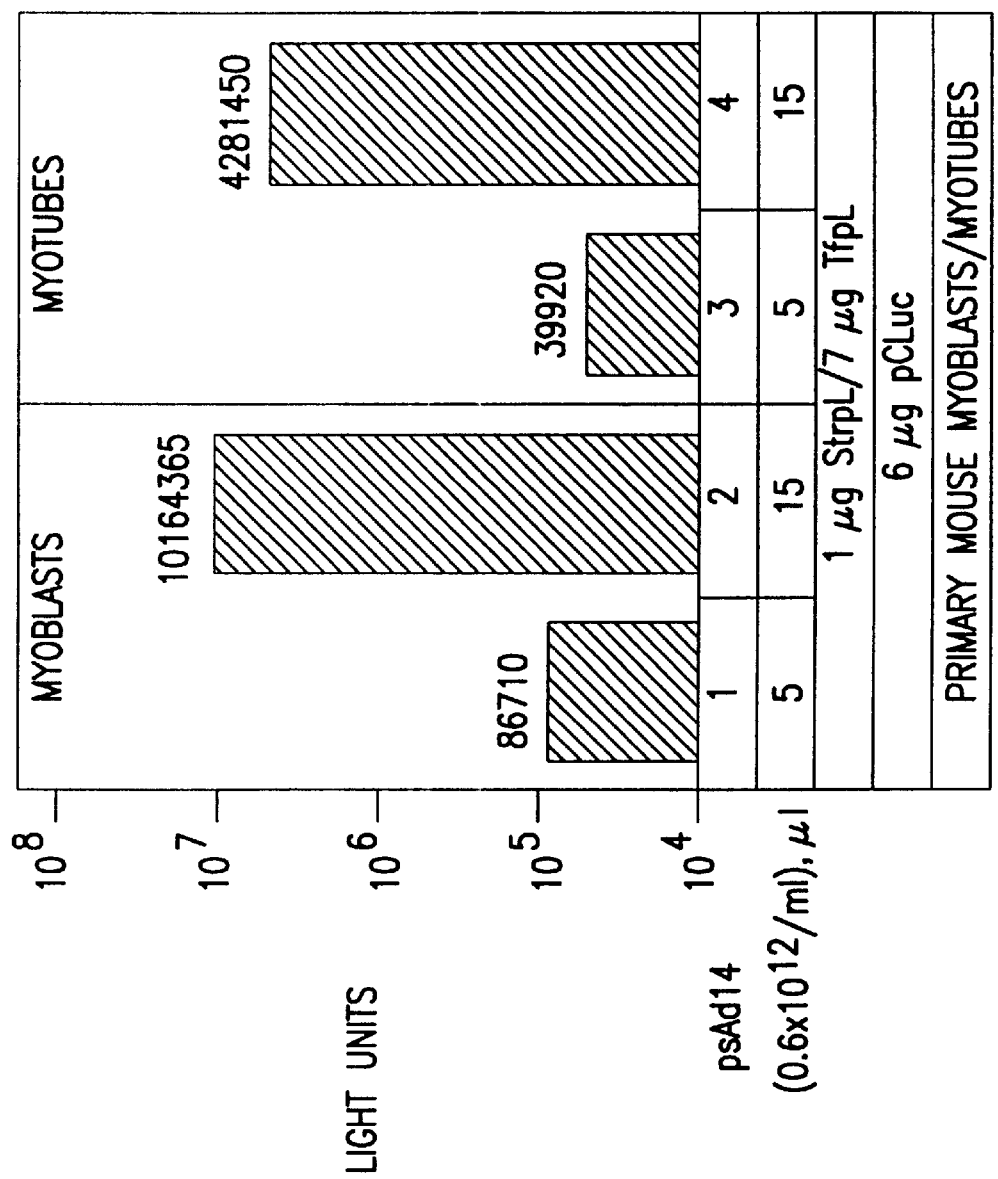

FIG. 38: Delivery of DNA to mouse primary myoblast and myotube cultures.

Figure 39:
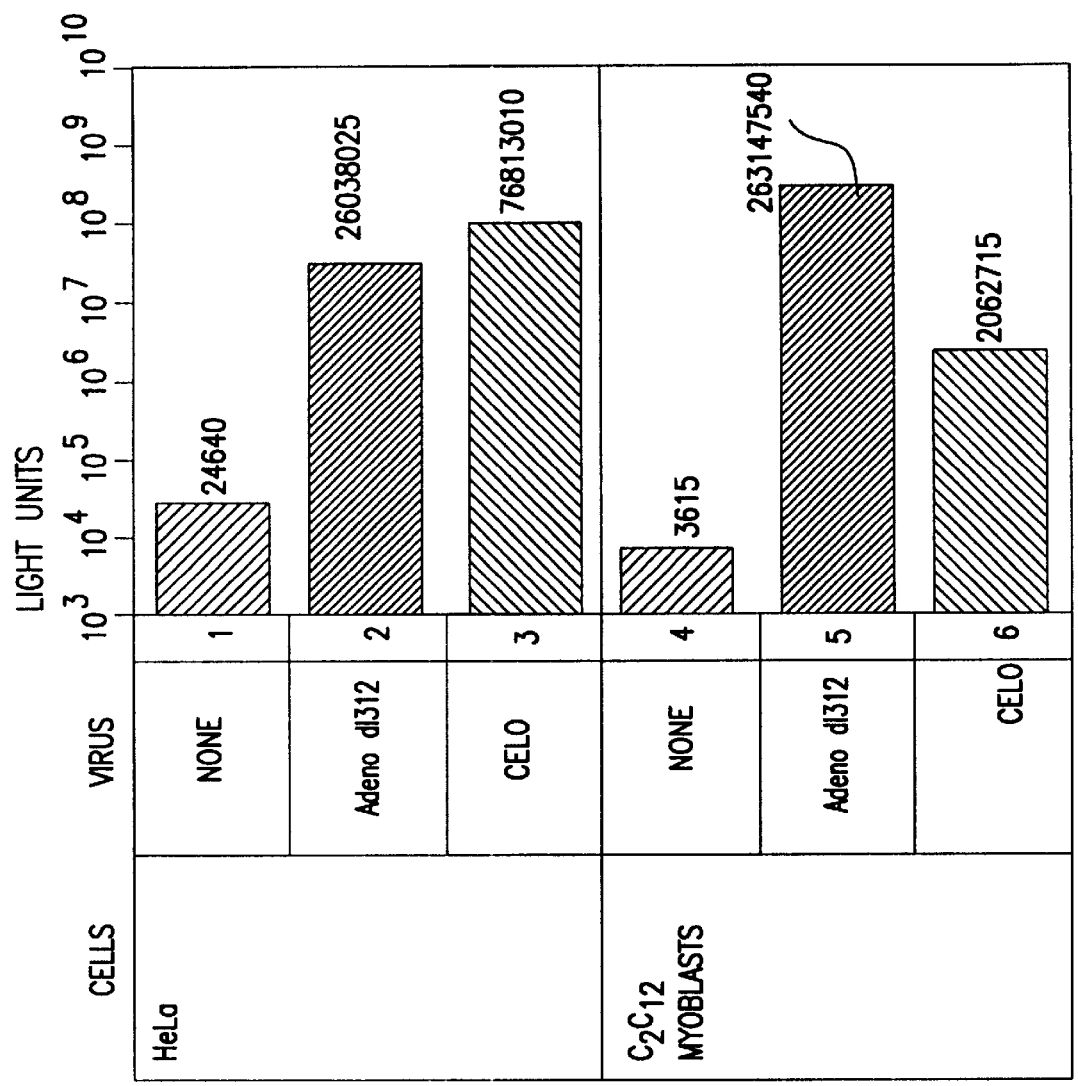

FIG. 39: Comparative analysis of adenovirus d1312 and CELO virus in the transfection of HeLa cells and C2C12 myoblasts.

Figure 40:
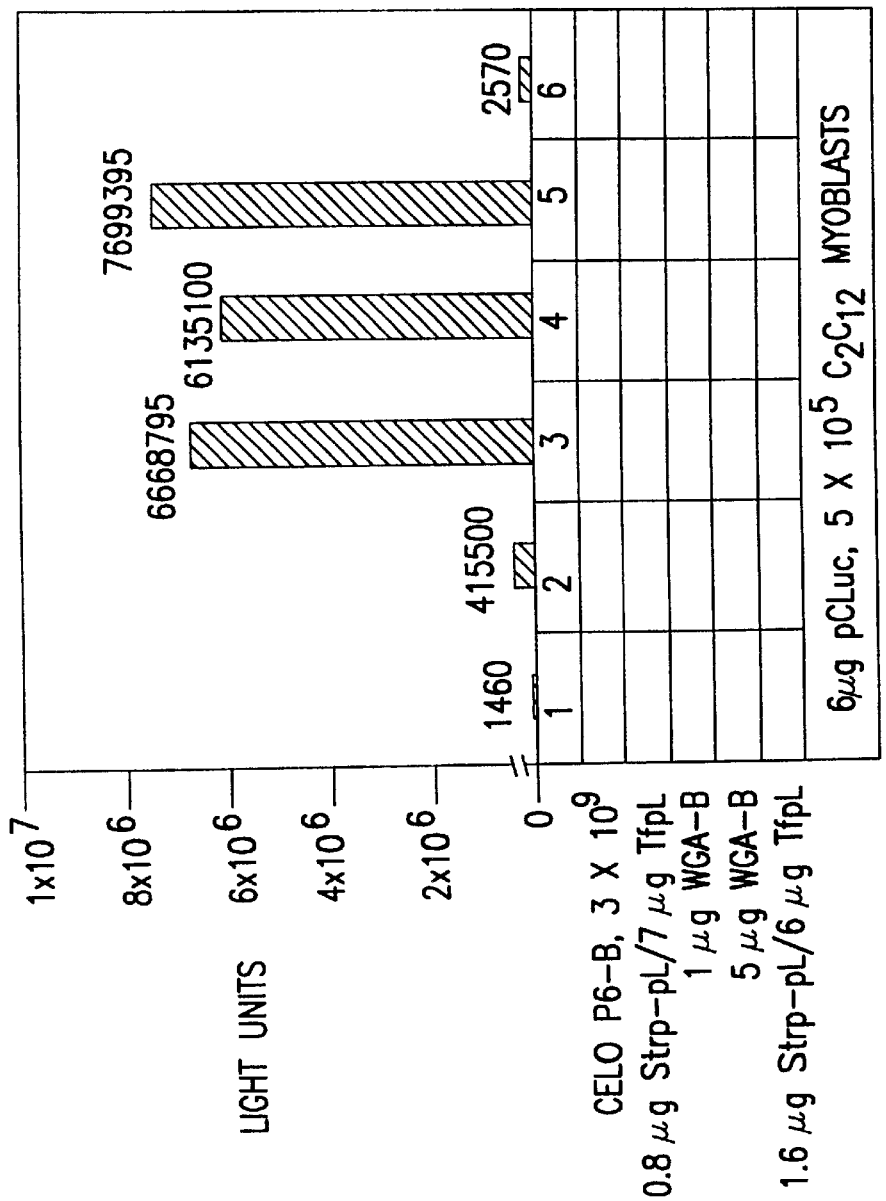

FIG. 40: Improvement of CELO virus delivery to myoblasts using a lectin ligand.

Figure 41:
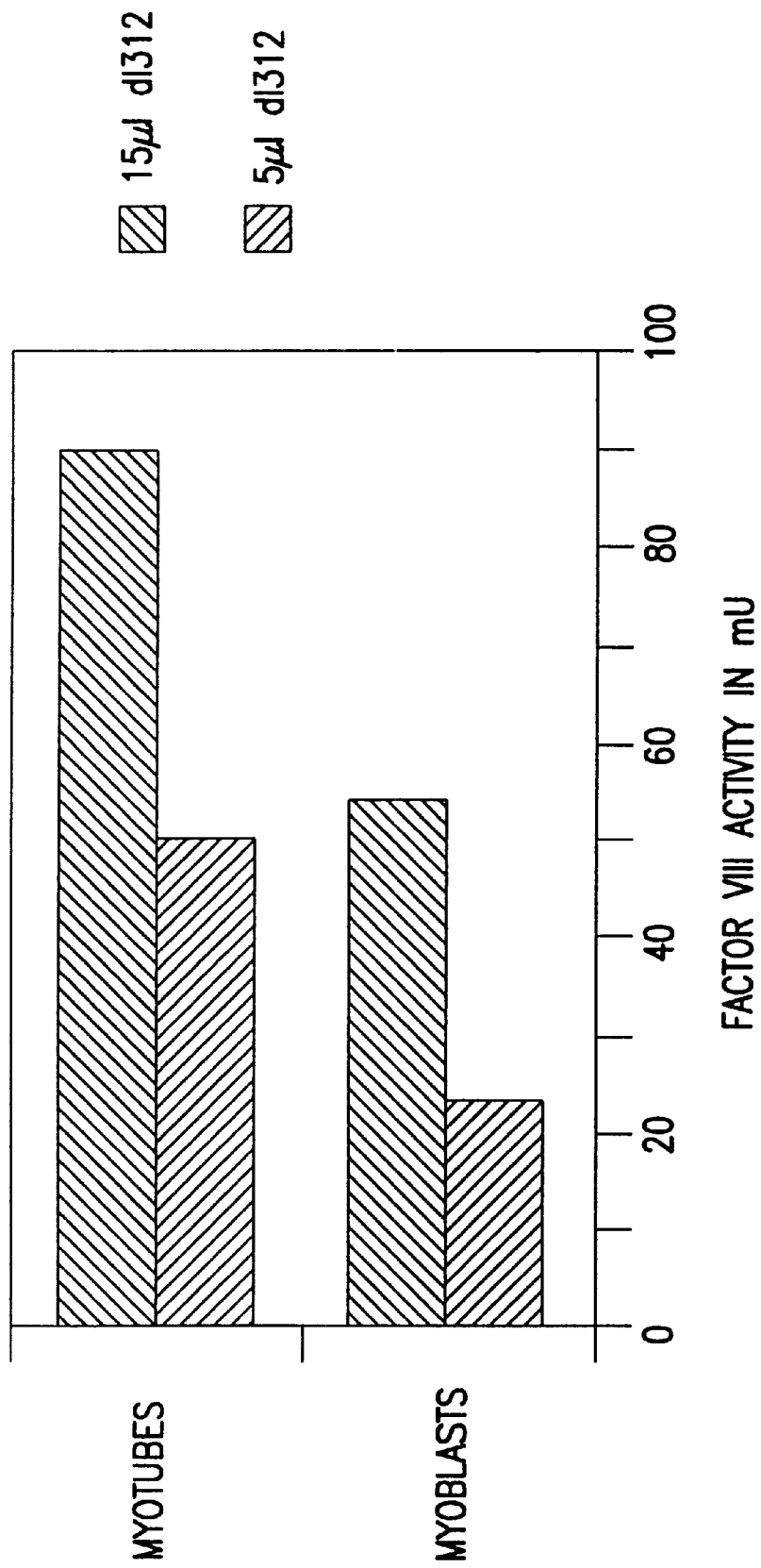

FIG. 41: Expression of a full length factor VIII cDNA in C2C12 myoblast and myotube cultures.

Figure 42A:
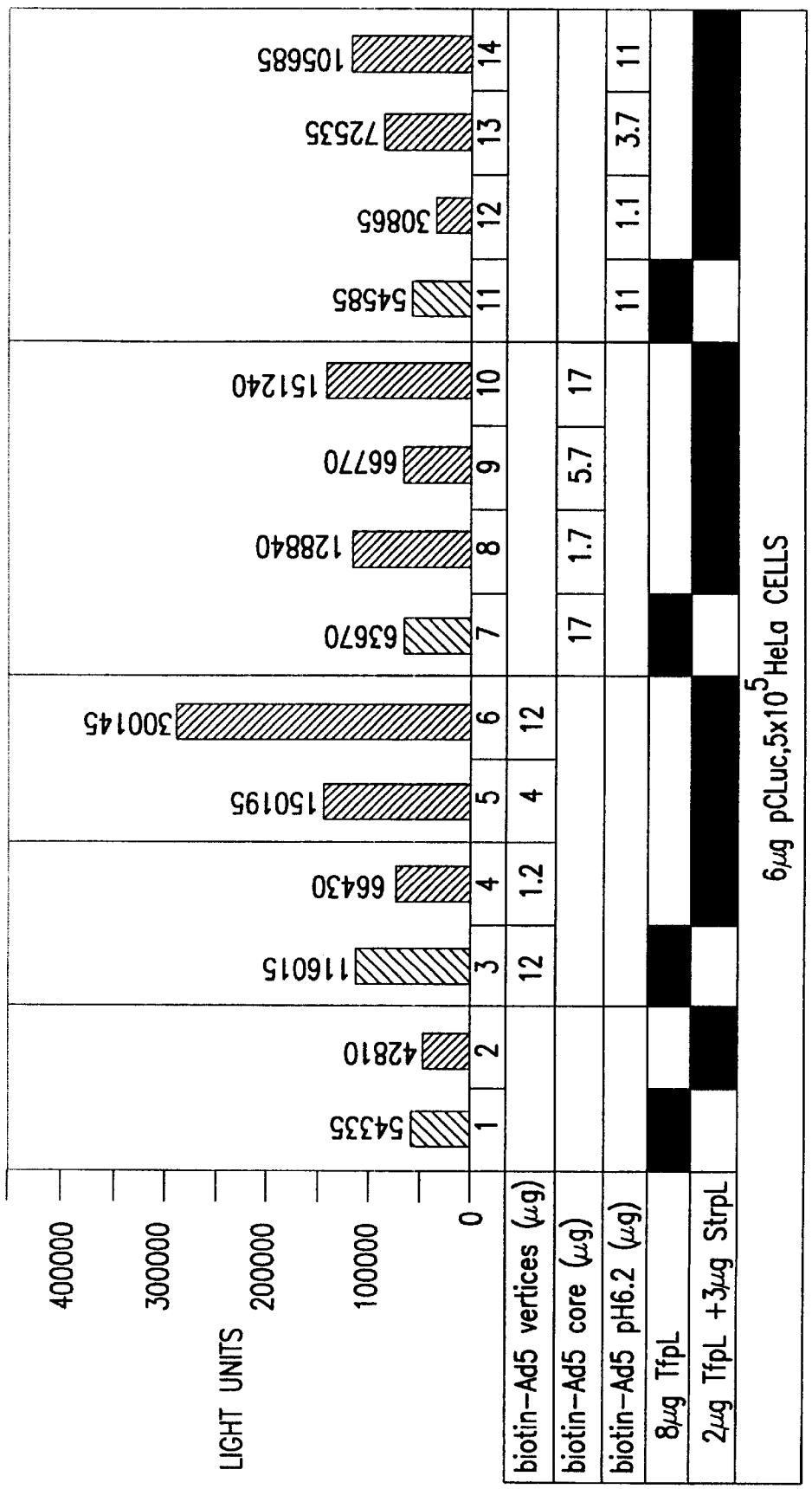
Figure 42B:
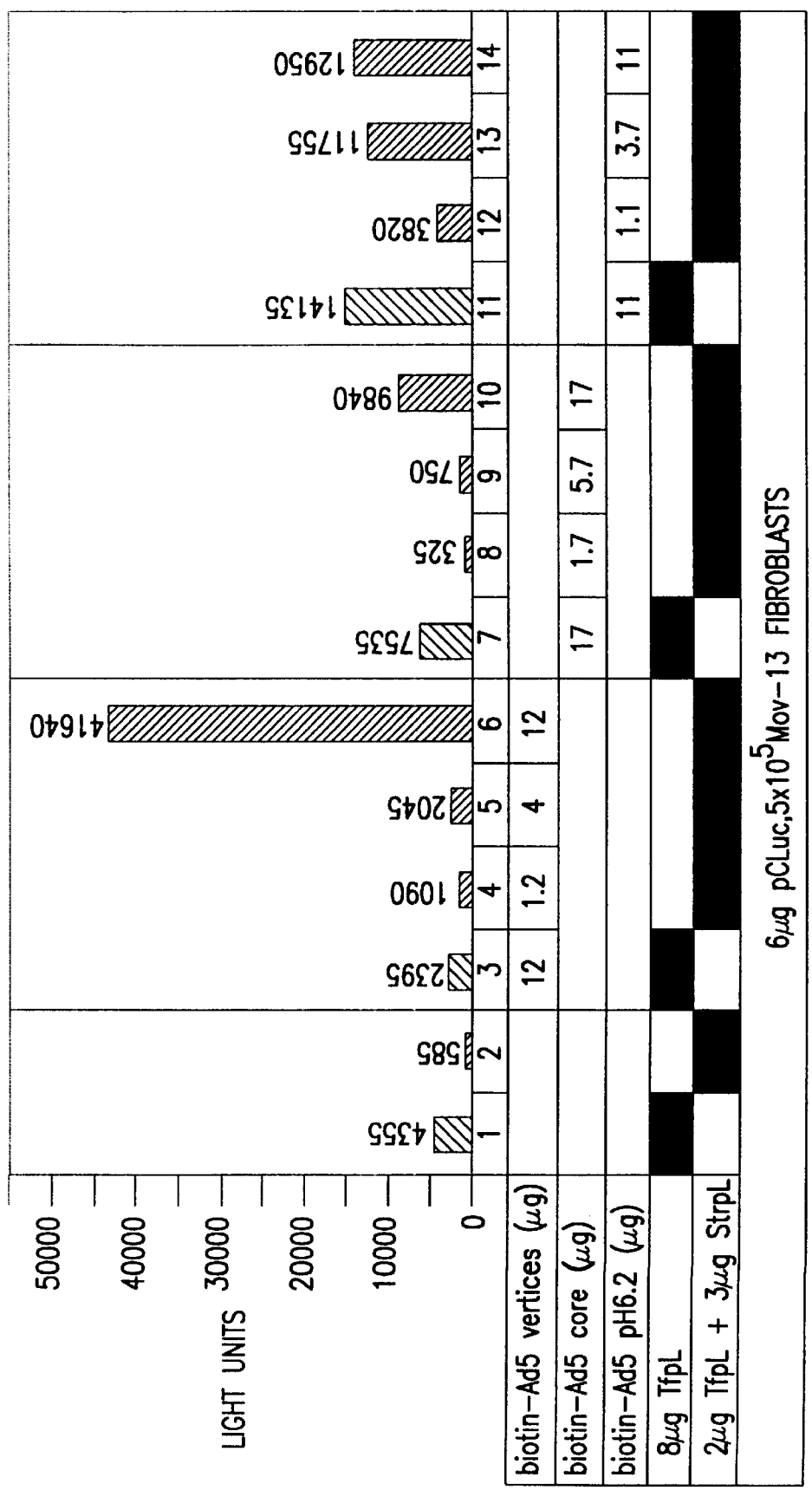

FIG. 42: Augmentation of DNA delivery by adenovirus proteins.
A) HeLa cells B) fibroblasts.

Figure 43:
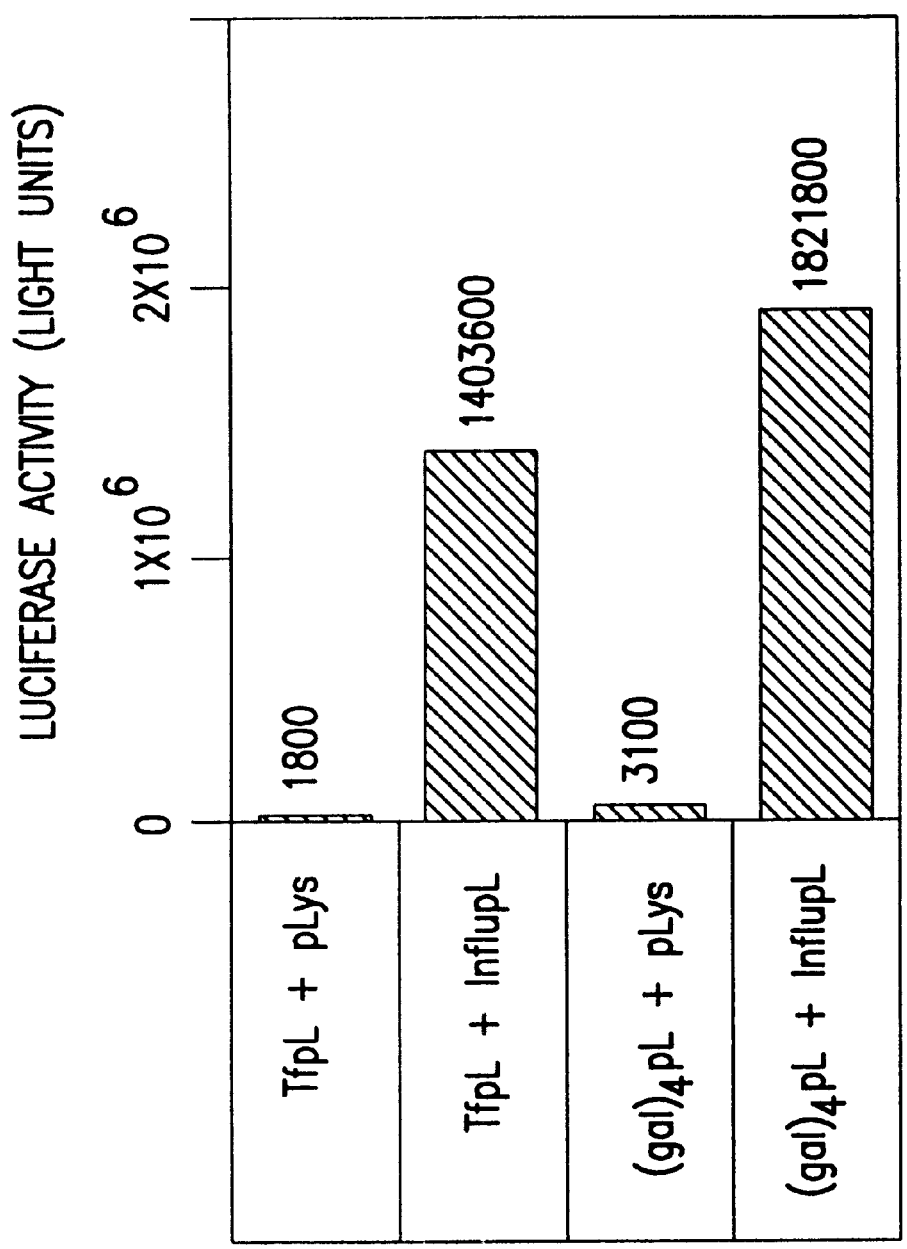

FIG. 43: Galactose-influenza peptide conjugates for DNA transfer into hepatocytes.

Figure 44:
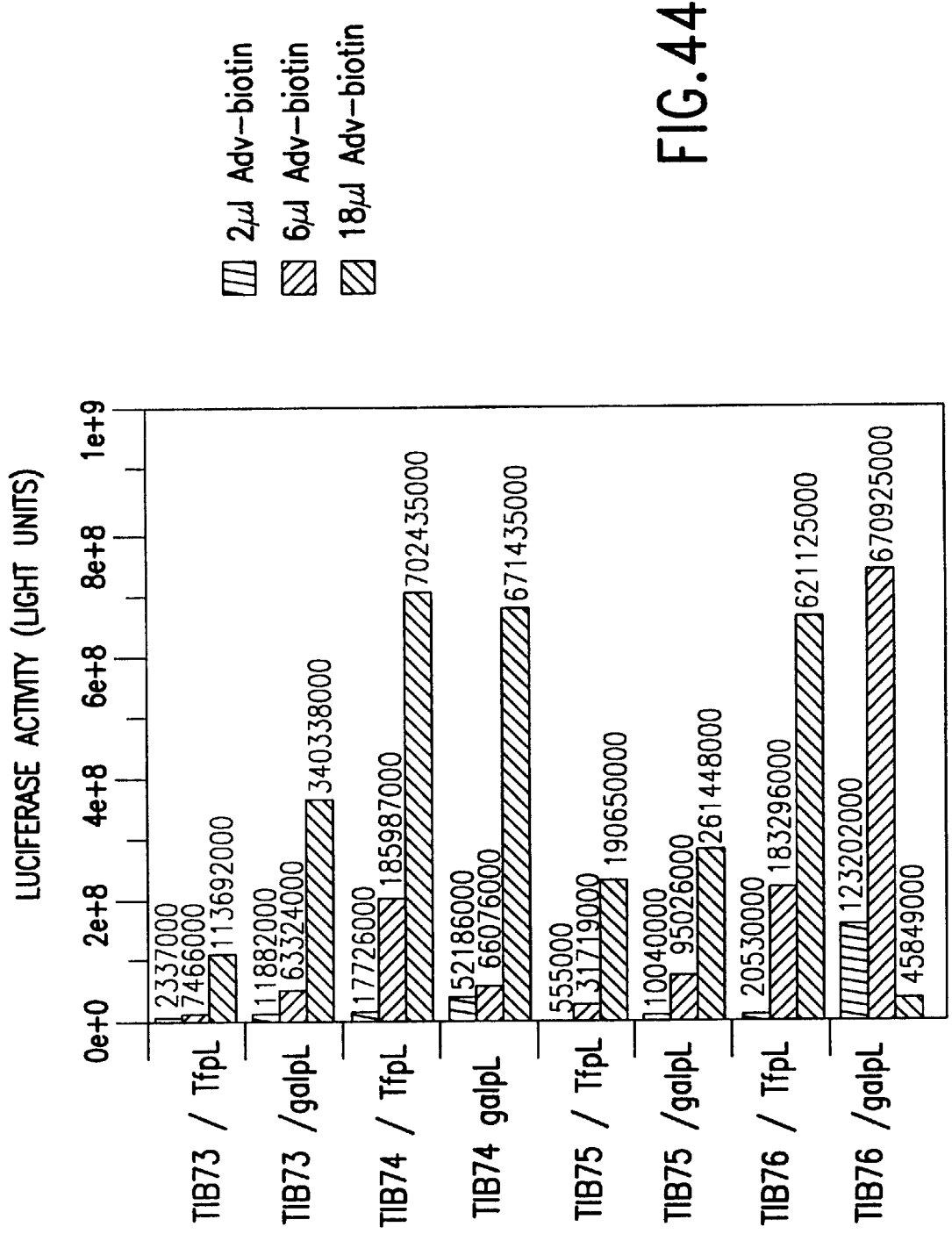

FIG. 44: Galactose-adenovirus conjugates for DNA transfer into hepatocytes.

FIG. 45: DNA transfer with transferrin-polylysine in the presence of rhinovirus. A) free rhinovirus B) conjugated rhinovirus.

Figure 46:
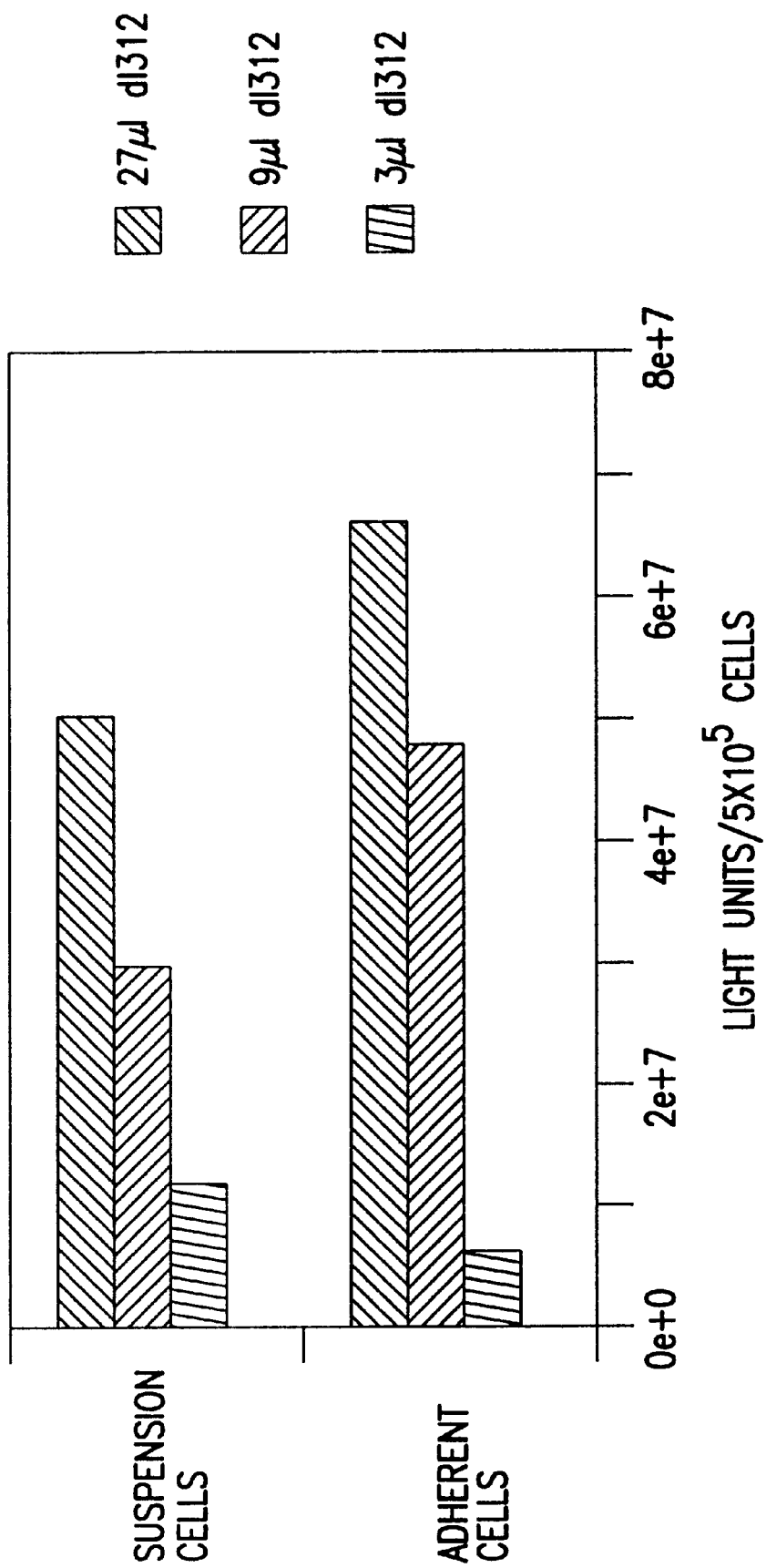

FIG. 46: Transfection of primary human melanoma cells with combination complexes containing adenovirus conjugates.

Figure 47A:
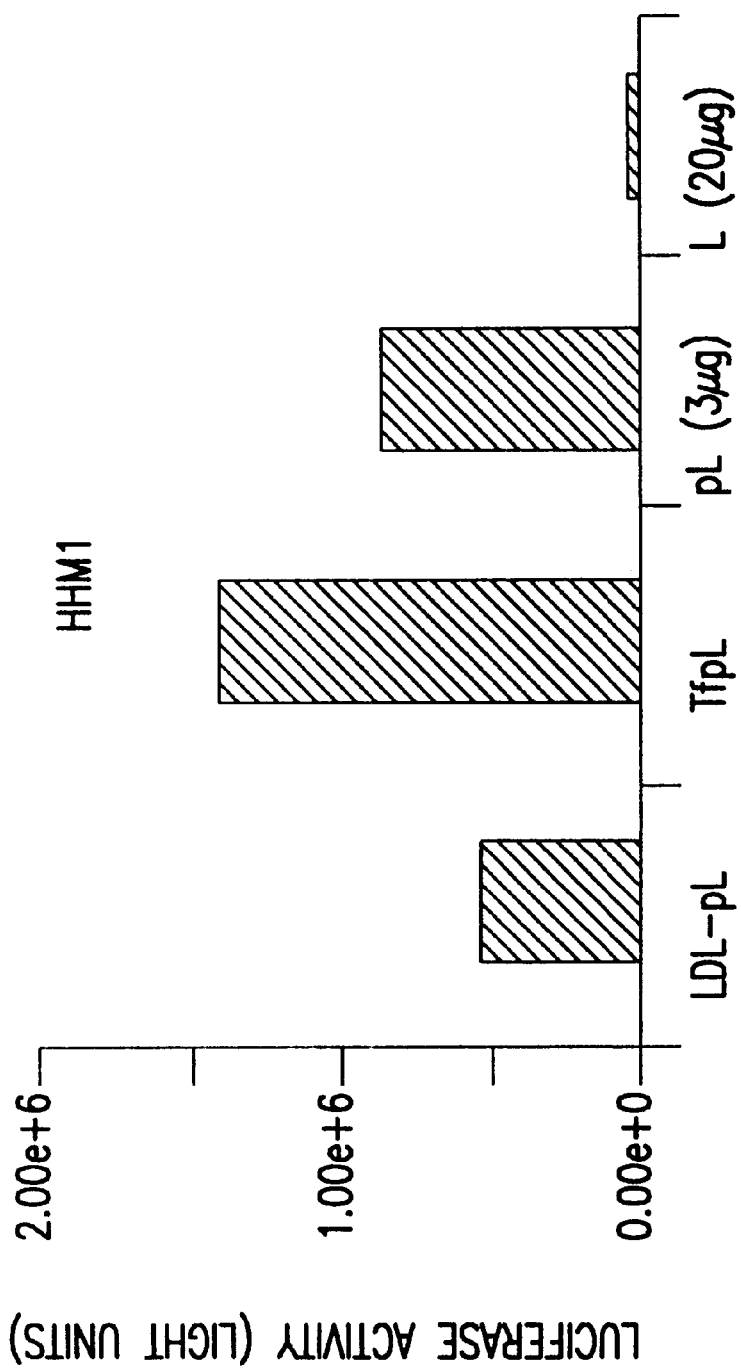
Figure 47B:
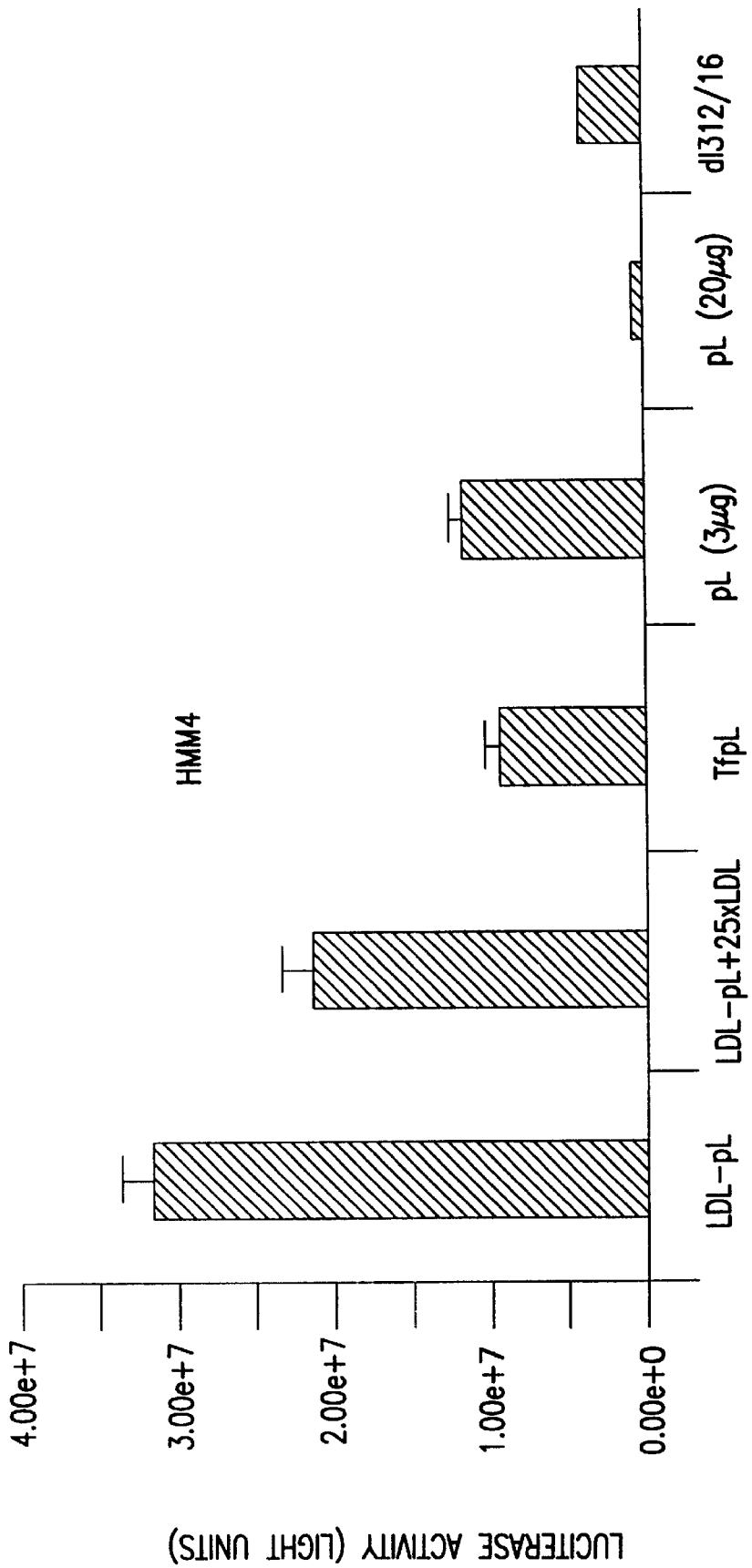

FIG. 47: Transfection of primary human melanoma cells with combination complexes comprising the low density lipoprotein.

Figure 48:
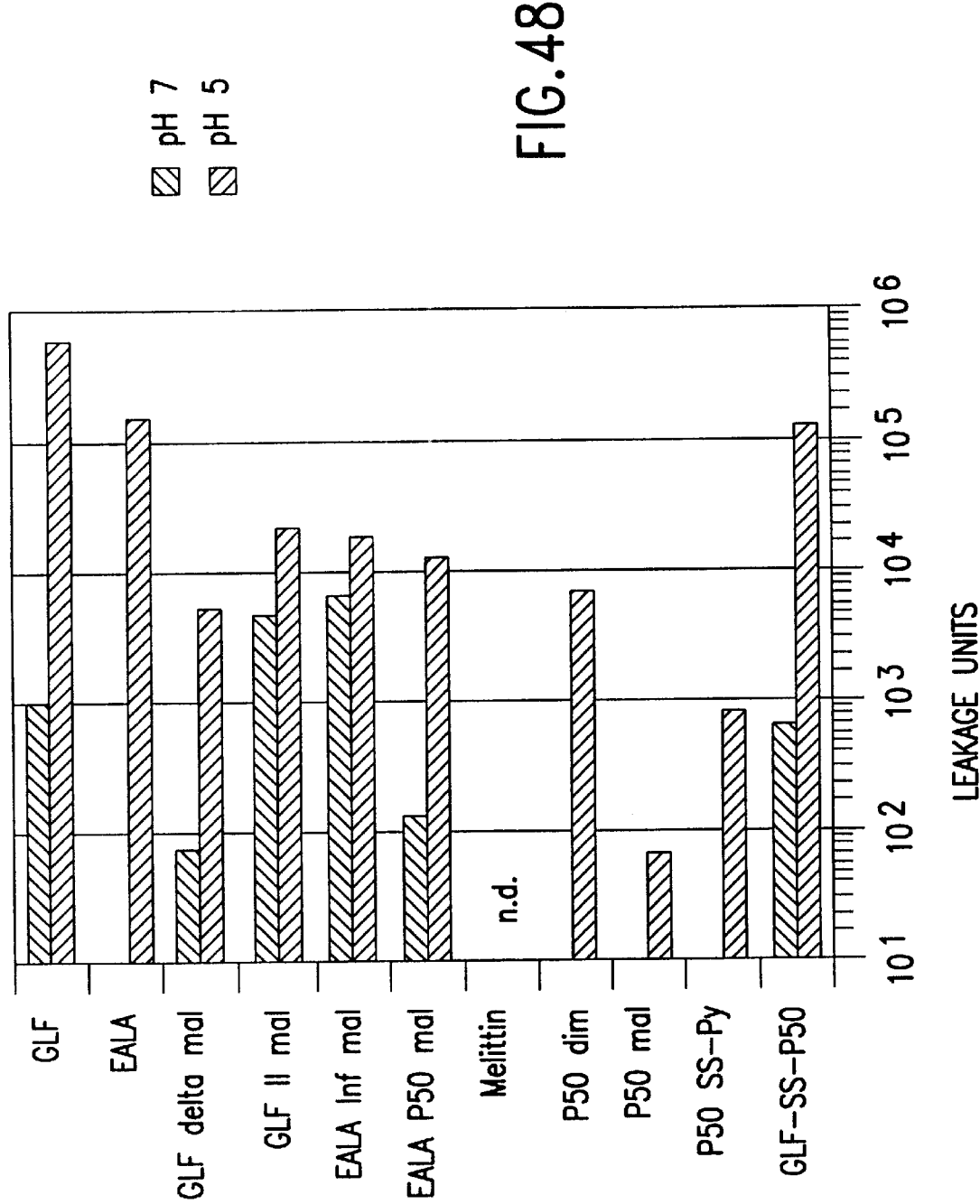

FIG. 48: Liposome leakage assay of amphipathic peptides.

Figure 49:
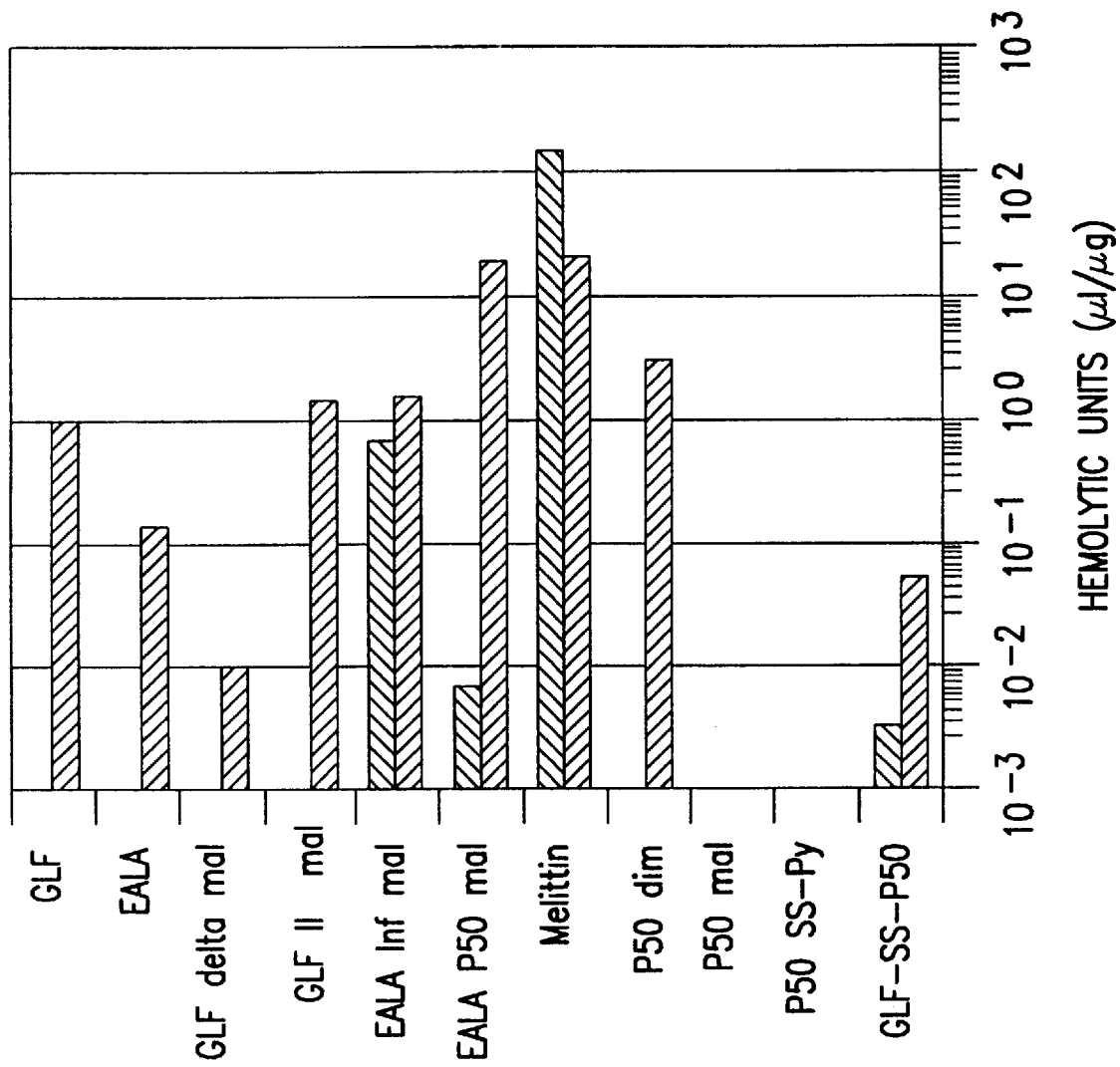

FIG. 49: Erythrocyte leakage assay of amphipathic peptides.

FIG. 50: Transfection of BNL CL.2 cells in the presence of amphipathic peptides.

Figure 51A:
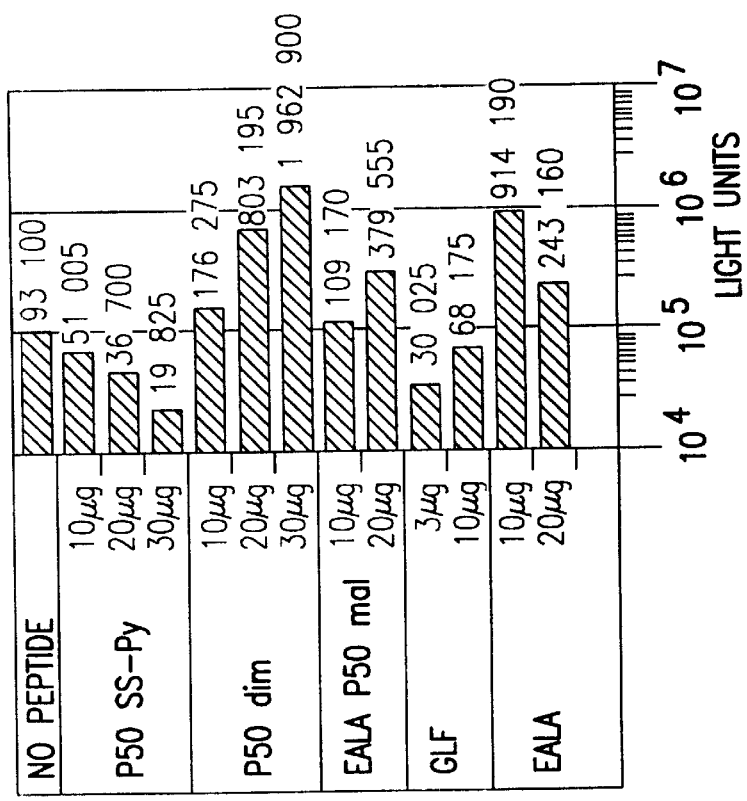
Figure 51B:
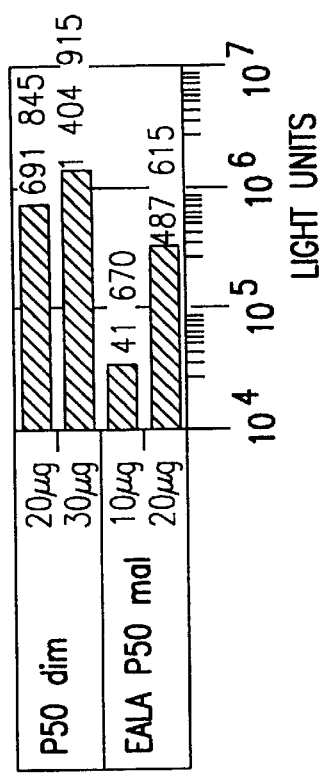

FIG. 51: Transfection of NIH3T3 cells in the presence of amphipathic peptides.

Figure 52:
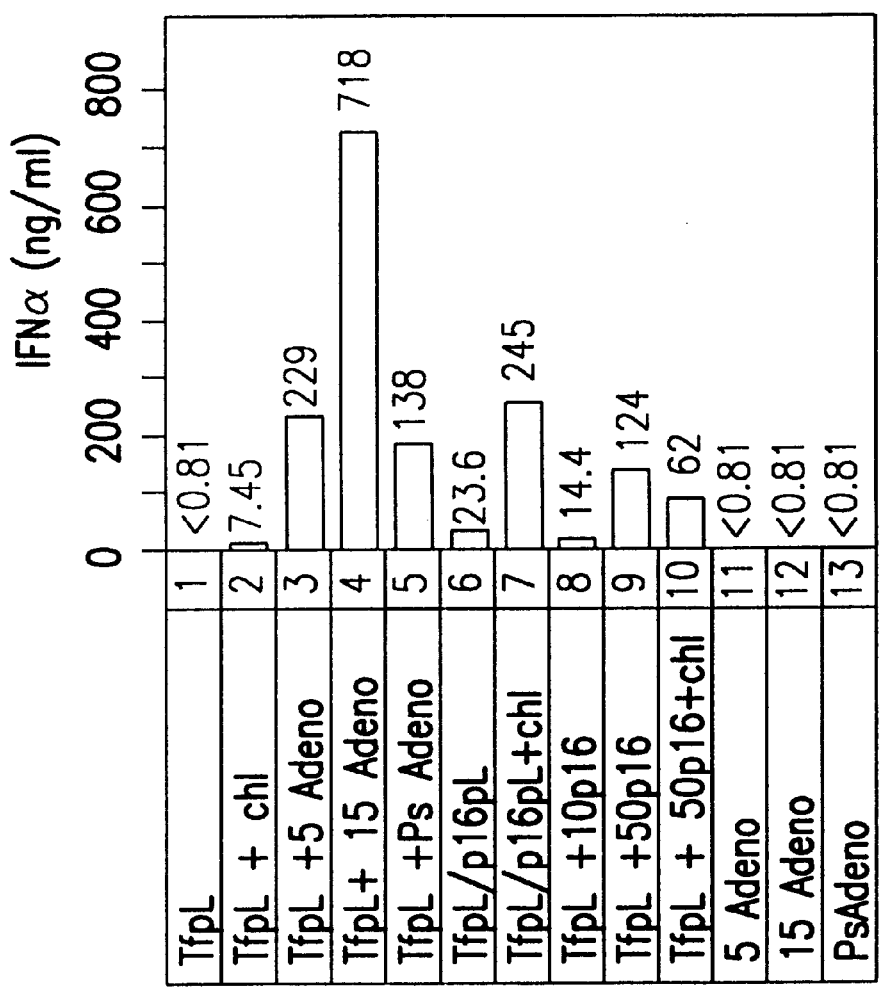

FIG. 52: Expression of interferon alpha in HeLa cells transfected in the presence of various endosomolytic agents.

Figure 53:
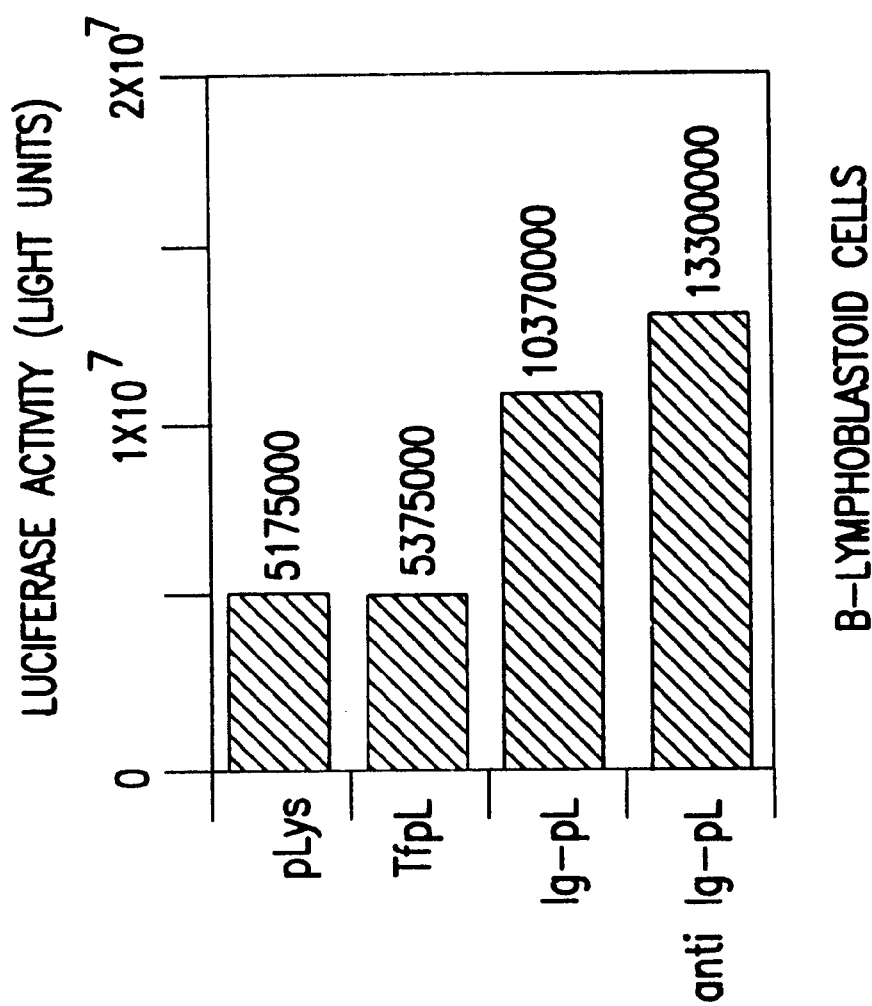

FIG. 53: Transfection of B-lymphoblastoid cells with human-Ig polylysine conjugates and anti-human-Ig polylysine conjugates.

Figure 54:
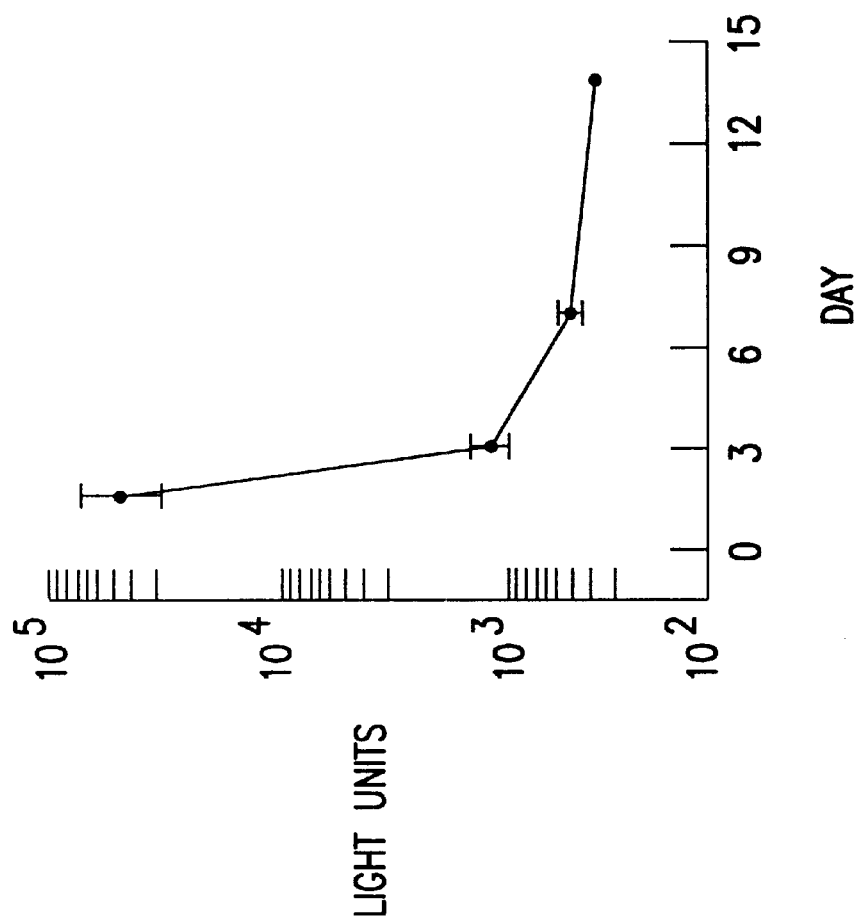

FIG. 54 The time course of heterologous gene expression in cotton rat airway epithelium transduced with human transferrin-adenovirus-polylysine-DNA complexes.

FIG. 55: The results of the immunohistochemical staining of conjugate-DNA complexes and parts thereof with human trachea.

DESCRIPTION OF THE PREFERRED EMBODIMENTS

The aim of the present invention was to improve the transfer of nucleic acid into higher eucaryotic cells. (The word "transfer" within the scope of this invention means, apart from the introduction of the nucleic acid complexes into the cell through the cell membrane, the transport of the complexes or the nucleic acid released therefrom within the cell until it reaches an appropriate site to be expressed). The higher eucaryotic cells are well known and do not include yeast. See *Molecular Biology of the Gene,* James D. Watson et al., the Benjamin/Cummings Publishing Company, Inc., pp. 676–677 (1987).

A plurality of viruses effect their entry into the eucaryotic host by means of mechanisms which correspond in principle to the mechanism of receptor-mediated endocytosis. Virus infection based on this mechanism generally begins with the binding of virus particles to receptors on the cell membrane. After this, the virus is internalized into the cell. This internalizing process follows a common route, corresponding to the entrance of physiological ligands or macromolecules into the cell: first of all, the receptors on the cell surface arrange themselves in groups, and the membrane is inverted inwardly and forms a vesicle surrounded by a clathrin coating. After this vesicle has rid itself of its clathrin coat, acidification takes place inside it by means of a proton pump located in the membrane. This triggers the release of the virus from the endosome. Depending on whether the virus has a lipid coat or not, two types of virus release from the endosome were taken into account: in the case of so-called "naked" viruses (e.g. adenovirus, poliovirus, rhinovirus) it was suggested that the low pH causes changes in configuration in virus proteins. This exposes hydrophobic domains which are not accessible at the physiological pH.

These domains thus acquire the ability to interact with the endosome membrane and thereby cause the release of the virus genome from the endosome into the cytoplasm. As for viruses with a lipid coat (e.g. vesicular stomatitis virus, Semliki Forest virus, influenza virus) it is presumed that the low pH modifies the structure or configuration of some virus proteins, thereby promoting the fusion of the virus membrane with the endosome membrane. Viruses which penetrate into the cell by means of this mechanism have certain molecular peculiarities which enable them to break up the endosome membrane in order to gain entry into the cytoplasm.

Other viruses, e.g. the coated viruses Sendai, HIV and some strains of Moloney leukaemia virus, or the uncoated viruses SV40 and polyoma, do not need a low pH for penetration into the cell; they can either bring about fusion with the membrane directly on the surface of the cell (Sendai virus, possibly HIV) or they are capable of triggering mechanisms for breaking up the cell membrane or passing through it. It is assumed that the viruses which are independent of pH are also capable of using the endocytosis route (McClure et al., 1990).

When solving the problem of the invention, the starting premise was to make use of the mechanism used by certain viruses to penetrate into eucaryotic cells, in order to improve the transfer of nucleic acid complexes into the cell and thereby increase expression.

Attempts have been made to internalize proteins together with viruses into the cell (Otero and Crasco, 1987). It was found that the permeability achieved in the cell by the virus is used to deliver macromolecules. The procedures taking place would appear to be fluid phase uptake mechanisms.

Using epidermal growth factor, EGF, conjugated to a toxin, it was found that this natural ligand, which is taken up into the cell by endocytosis after binding to its receptor, lands in the same endosome together with the adenovirus, which is also taken up into the cell by receptor-mediated endocytosis, and is released from this endosome, again together with the virus, into the cytosol (FitzGerald et al., 1983).

It was found with the present invention, surprisingly, that certain agents (e.g. viruses, virus components or other compounds), which exhibit the characteristics of certain viruses with regard to their mechanism to enter into eucaryotic cells, substantially increase the rate of expression of a nucleic acid imported into the cell as part of a complex. This finding was particularly surprising as the nucleic acid complexes taken up into the cell are very large.

The present invention thus relates to a composition for the transfection of higher eucaryotic cells with a complex of nucleic acid and a substance having an affinity for nucleic acid, which substance is optionally coupled with an internalizing factor, characterized in that it contains an agent which has the ability of being internalized into the cells which are being transfected, either per se or as a component of the nucleic acid complexes, and of releasing the contents of the endosomes, in which the complex is located after entering the cell, into the cytoplasm.

This agent is hereinafter referred to as "endosomolytic agent".

The ability of the endosomolytic agents to be taken up into the cells and to release the contents of the endosomes, in which they are located after entering the cell, into the cytoplasm, is hereinafter referred to as "uptake function". This uptake function comprises the ability to be internalized into the cell actively, via receptor-dependent endocytosis mechanisms, or passively, via the liquid phase or as a constituent of the nucleic acid complex, and the ability to break up endosomes, which is generally referred to as endosomolysis.

In one embodiment of the invention the endosomolytic agent is a virus. In another embodiment the endosomolytic agent is a virus component. The virus or virus component employed in these embodiments of the invention is hereinafter referred to as "free" virus (component).

Within the scope of the present invention, the activity of an increasing dose of free adenovirus on the gene transfer capacity of a constant quantity of transferrin-polylysine conjugate in HeLa cells was investigated, using the luciferase gene as reporter gene. The augmentation in gene transfer brought about by the addition of free adenovirus reached a peak at $1 \times 10^4$ virus particles per cell, a number which corresponds to the approximate number of adenovirus receptors per HeLa cell. The augmentation, up to 2000-fold, of luciferase expression compared with the expression achieved with the transferrin-polylysine conjugates alone, corresponded to the higher dose of virus. In another series of experiments, the capacity of limiting quantities of conjugate-DNA complexes was investigated in the presence of a constant dosage of free adenovirus. It was found that the uptake of adenoviruses into the cells augmented the gene transfer mediated by transferrin-polylysine over a wide range of DNA dosages. The maximum intensity of gene expression achieved by means of the conjugate-DNA complexes corresponded to the intensity achieved with 100 times less DNA when adenoviruses were used to increase the efficiency of transfection.

The effect of adenoviral infection on gene transfer was examined for both uncomplexed DNA and DNA that had been complexed with polylysine or transferrin-polylysine conjugates (FIG. 3A). By this analysis, adenoviral infection did not significantly augment transfer of naked, uncompleted DNA during transfection. In marked contrast, transfer of DNA complexed to polylysine or transferrin-polylysine conjugates was augmented by adenoviral infection. This effect was, however, much greater for the transferrin-polylysine conjugates. Since the polycation portion of the conjugate molecule not only serves to attach transferrin to DNA, but also effects significant structural changes in the DNA (Compacting into toroidal structures; Wagner et al., 1991a; the disclosure of which is fully incorporated by reference herein), these experiments could not initially differentiate whether the observed effect was on the basis of enhanced fluid-phase transport of the polycation-condensed DNA or virus-augmented delivery of receptor-bound conjugate-DNA complex. To distinguish between these possibilities, sequential binding experiments were performed (FIG. 3B). Binding of transferrin-polylysine-DNA or polylysine-DNA complexes at low temperature without internalization allowed removal of excess complex in the fluid phase prior to adenoviral infection (FitzGerald et at., 1983). When administered in this fashion, delivery of the receptor-bound transferrin-polylysine-DNA complexes was significantly augmented by the addition of adenoviral particles, whereas the polylysine-DNA complexes were not. Thus, it is the entry of DNA by the receptor-mediated endocytosis pathway which is specifically enhanced.

Figure 3C:
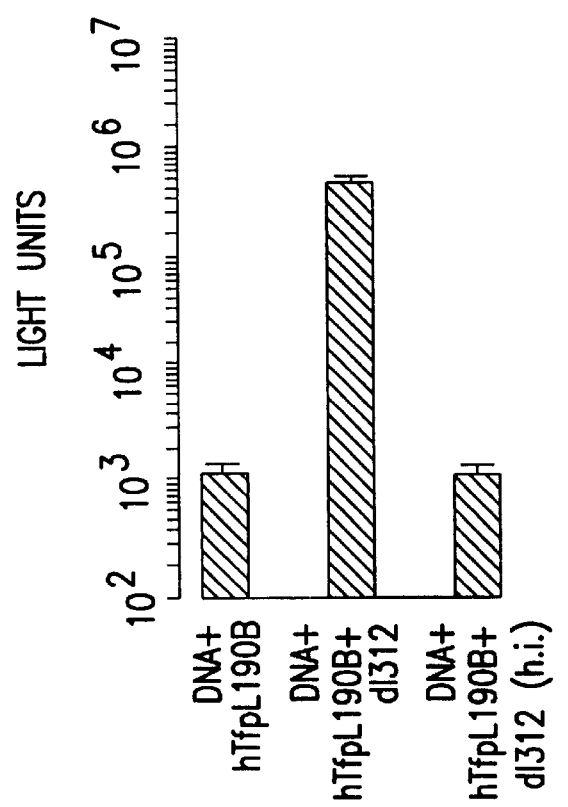
FIG. 3: Enhancement of transferrin-polylysine mediated gene transfer by adenoviruses occurs by means of receptor-mediated endocytosis.
Figure 3B:
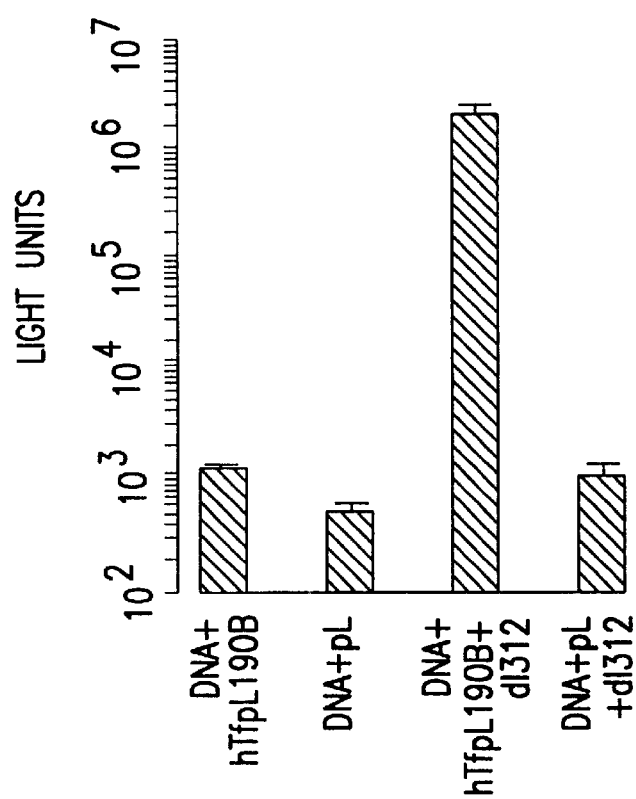

Next, analysis was made of the specific adenoviral function which brings about enhanced receptor-mediated gene transfer (FIG. 3C). Mild heat treatment of virions does not alter their ability to bind to target cell membranes but does affect their capacity to disrupt endosomes after internalization (Defer et al., 1990). Thus, the distinct effects of viral binding and viral entry could be separately evaluated. In this analysis, heat inactivation of the adenoviruses completely abolished their ability to enhance receptor-mediated gene transfer. This suggests that it is the capacity of the adenoviruses to disrupt endosomes as part of their entry mechanism which specifically effects enhancement of gene delivery by transferrin-polylysine conjugates. The fact that a replication-defective virus strain could result in an increase in gene expression confirms the assumption that this phenomenon is not due to the replication function but due to the uptake function of the virion.

To rule out the possibility that the increase in gene expression can be ascribed to possible transactivation of the imported gene by the virus, experiments were carried out with a cell line which constitutively expresses the RSV-LTR luciferase gene: adenoviruses show no effects in this cell line, whereas in the parental cell line into which the gene had been introduced by means of transferrin-polylysine conjugates, there was a significant increase in gene expression. This finding demonstrates that the adenovirus influences events which take place before transcription and that its enhancing effect on gene transfer thus acts at the gene transfer level and not at the gene expression level (FIG. 5).

Investigations were also carried out within the scope of the invention to find out what effect free adenovirus has on gene transfer by means of transferrin-polylysine conjugates in selected cell lines. It was found that the presence of transferrin receptors on target cells is necessary, but not sufficient in every case, to permit gene transfer by transferrin-polylysine conjugates. Cell-specific factors relating to the fate of endosome-internalized conjugate-DNA complexes appear to be an extremely important determining factor in the levels of gene transfer achievable by this route. In this regard, selected cell lines were examined for both gene transfer by transferrin-polylysine conjugates and augmentation of gene transfer by adenoviruses (FIG. 4). Cells of a cystic fibrosis cell line (CFT1) showed moderate levels of luciferase gene expression after treatment with transferrin-polylysine-DNA complexes. This level of expression was significantly augmented by treatment with the adenovirus d1312. In marked contrast, KB cells treated with the transferrin-polylysine-DNA complexes exhibited levels of luciferase gene expression barely above background levels, despite the presence of transferrin receptors. Treatment with adenovirus d1312, however, resulted in readily detectable luciferase activities in these cells. Treatment with adenoviruses on HeLa cells had a similar effect, although this effect was substantially stronger in these cells. Since HeLa cells and KB cells possess approximately the same number of receptors for the adenovirus, the difference in augmentation of the gene transfer may reflect the number of transferrin receptors characteristic of each cell type. However, in marked contrast to these results, the cell lines WI-38 and MRC-5, which are known to support adenoviral infection very poorly (Precious and Russell, 1985), showed very little augmentation with d1312 of the gene expression achieved by means of the conjugate-DNA complexes alone. Treatment with free virus, e.g. adenovirus, would therefore appear to augment gene transfer by means of conjugate-DNA complexes in those cases where the gene transfer is possible by receptor-mediated endocytosis, as in the case of CFT1 cells, and also in some instances where gene transfer by this route appears to be ineffective, as for HeLa and KB cells. The level of augmentation achieved varies significantly among different target cells, suggesting that this effect is a function of both the number of virus receptors, e.g. adenovirus receptors, of a certain cell type and also the number of transferrin receptors.

In case of the use of free virus, the substance having an affinity for nucleic acid, preferably an organic polycation, is preferably conjugated with an internalizing factor. It has, however, been found, according to the invention, that under certain circumstances DNA complexed only with a substance having an affinity for nucleic acid, i.e. without internalizing factor, can be introduced into the cell in the presence of free virus. It was also found that, in some cell lines, the complexes consisting of nucleic acid and a substance having an affinity for nucleic acid can be introduced through the fluid phase if the concentration of the complexes is high enough. The experiments carried out within the scope of the present invention and previous ones showed that an essential element for the uptake capacity of the nucleic acid complexes is their compactness, which can be ascribed to the condensing of the nucleic acid by the substance having an affinity for nucleic acid. If the substance having an affinity for nucleic acid has sufficient capacity for binding to the cell surface in order to enter into the cell together with the virus, as well as being able to render the complex substantially electroneutral and condense the nucleic acid into a compact structure, there may not be a need to increase the entry capacity by covalently binding an internalizing factor to the substance having an affinity for nucleic acid in order to transfer the complex into the cell by receptor-mediated endocytosis. Many cells have a relatively high affinity for certain substances having an affinity for nucleic acid, so that the conjugates of nucleic acid and binding factor are taken up into the cell without the need for an internalizing factor. This is true, for example, of hepatocytes, which have been found within the scope of the present invention to take up DNA-polylysine complexes.

In a preferred embodiment of the invention, the endosomolytic agent is a virus which is bound to a substance having an affinity for nucleic acid and which has the ability to enter the cell as part of a conjugate/nucleic acid complex and release the contents of the endosomes, in which the complex is located after entering the cell, into the cytoplasm.

In another preferred embodiment, the endosomolytic agent is a virus component which is bound to a substance having an affinity for nucleic acid and which has the ability to enter the cell as part of a conjugate/nucleic acid complex and release the contents of the endosomes, in which the complex is located after entering the cell, into the cytoplasm.

Viruses or virus components bound to the nucleic acid binding domain, irrespective of the type of binding, are hereinafter designated "viral conjugates".

The viral conjugates, which are also subject of the present invention, contain the virus or virus component as an integral part of their functional construct and combine the advantages of vector systems based on internalizing factor conjugates with the advantages which the viruses bring into these systems.

Furthermore, the viral conjugates according to these embodiments of the invention have the advantage that they circumvent the fundamental restriction inherent in the known molecular conjugate systems, in that, unlike the known conjugates employed for gene transfer by receptor-mediated endocytosis, they have a specific mechanism which enables them to be released from the cell vesicle system.

The vector system employing viral conjugates constitutes a fundamental conceptual departure from the recombinant viral vectors, in that the foreign DNA which is to be transported is carried on the outside of the virion. Consequently, the viral conjugates according to the preferred embodiments of the invention can transport very large gene constructs into the cell, with no restrictions as to the sequence.

The suitability of a virus, which is to be employed as free or bound virus or part of a virus as virus component within the scope of the present invention is defined by its uptake function as defined herein. Suitable viruses are, on the one hand, those which have the ability to enter into the cell by receptor-mediated endocytosis during transfection of the cells with the nucleic acid complex and bring about their release—and hence the release of the nucleic acid—from the endosome into the cytoplasm. Such viruses are those disclosed herein as well as other viruses capable of being taken up by a particular cell and causing the release of the endosome contents into the cytoplasm.

For examples of viruses and higher eucaryotic cells into which they are capable of penetrating, reference in made to Fields, B. N. and Knipe, D. M. (1990), the disclosure of which is fully incorporated by reference herein. The susceptibility of a given cell line to transformation by a virus as a facilitator of conjugate entry as "free virus" is dependent upon the presence and number of target cell surface receptors for the virus. With regard to the adenoviral cell surface receptor methods for determining its number on HeLa and KB cells are taught by Svensson, 1990, and Defer, 1990, the disclosures of which are fully incorporated by reference herein. It is thought that the receptor for the adenovirus is rather ubiquitously expressed.

Suitable viruses include, on the one hand, those which are able to penetrate into the cell by receptor-mediated endocytosis during the transfection of the cells with the nucleic acid complex and to bring about their release—and hence the release of the nucleic acid—from the endosome into the cytoplasm. Without wishing to be tied to this theory, this endosomolysis activity could, in the case of employing free virus, benefit the nucleic acid complexes transferred into the cell in so far as these complexes are conveyed together with the viruses from the endosomes into the cytoplasm, assuming that they arrive in the same endosomes as the viruses on being internalized. When the complexes contain the virus in bound form they benefit from the virus' endosomolytic activity and are conveyed from the endosomes into the cytoplasm. This avoids the fusion between endosomes and lysosomes and consequently the enzymatic degradation which normally takes place in these cell organelles.

In particular, viruses which are suitable for the composition according to the invention and whose uptake function, occurring at the start of infection, occurs by receptor-mediated endocytosis, include on the one hand viruses without a lipid coat such as adenovirus, poliovirus, rhinovirus, and on the other hand the enveloped viruses vesicular stomatitis virus, Semliki Forest virus, influenza virus; pH-dependent strains of Moloney virus are also suitable. Particularly preferred viruses which may be used in the practice of the invention include Adenovirus subgroup C, type 5, Semliki Forest Virus, Vesicular Stomatitis Virus, Poliovirus, Rhinoviruses and Moloney Leukemia Virus.

The use of RNA viruses which have no reverse transcriptase, in the present invention has the advantage that transfection in the presence of such a virus does not result in generation of viral DNA in the transfected cell. In the present invention, Rhinovirus HRV2, a representative of the Picornavirus group, was shown to increase expression of a reporter gene. The efficacy of the Rhinovirus was demonstrated both in free form and in the form of virus conjugates.

Within the scope of the present invention, the term viruses—provided that they are taken up into the cell and release the contents of the endosomes in which they arrive—includes in addition to the wild types, mutants which have lost certain functions of the wild type, other than their uptake function, especially their ability to replicate, as a result of one or more mutations.

Mutants are produced by conventional mutagenesis processes by mutations in virus-protein regions which are responsible for the replicative functions and which may be complemented by a packaging line. These include, e.g. in the case of adenovirus, ts-mutants (temperature sensitive mutants), E1A- and E1B-mutants, mutants which exhibit mutations in MLP-driven genes (Berkner, 1988; the disclosure of which is fully incorporated by reference herein) and mutants which exhibit mutations in the regions of certain capsid proteins. Virus strains which have corresponding natural mutations are also suitable. The ability of viruses to replicate can be investigated, for example, using plaque assays known from the literature, in which cell cultures are covered with suspensions of various virus concentrations and the number of lysed cells which is visible by means of plaques is recorded (Dulbecco, 1980; the disclosure of which is fully incorporated by reference herein).

Other viruses which may be suitable for use within the scope of the invention include so-called defective viruses, i.e. viruses which lack the function necessary for autonomous virus replication in one or more genes, for which they require helper viruses. Examples of this category are DI-particles (defective interfering particles) which are derived from the infectious standard virus, have the same structural proteins as the standard virus, have mutations and require the standard virus as a helper virus for replication (Huang, 1987; Holland, 1990; the disclosures of which are fully incorporated by reference herein). Examples of this group also include the satellite viruses (Holland, 1990). Another group is the class of parvoviruses called adeno-associated virus (Berns, K. I., 1990; the disclosure of which is fully incorporated by reference herein).

Since the entry cycles of many viruses are not completely characterized, it is likely that there will be other viruses that will exhibit the endosomolytic activity required for their suitability in the present invention.

Also suitable within the scope of this invention may be attenuated live vaccines (Ginsberg, 1980; the disclosure of which is fully incorporated by reference herein) or vaccination strains.

The term viruses within the scope of the present invention also includes inactivated viruses, e.g. viruses inactivated by chemical treatment such as treatment with formaldehyde, by UV-radiation, by chemical treatment combined with UV-radiation, e.g. psoralen/UV-radiation, by gamma-radiation or by neutron bombardment. Inactivated viruses, e.g. such as are also used for vaccines, may be prepared by standard methods known from the literature (Davis and Dulbecco, 1980, Hearst and Thiry, 1977; the disclosures of which are fully incorporated by reference herein) and tested for their suitability to increase the transfer of DNA complexes. In experiments carried out within the scope of the present invention, adenovirus preparations were inactivated using a conventional UV sterilization lamp or with formaldehyde. It was surprisingly found that the degree of inactivation of the viruses was substantially greater than the reduction in the gene transfer effect, which was achieved when adenovirus was added to the transfection medium. Experiments carried out by the inventors with preparations of psoralen(UV-inactivated biotinylated adenovirus, which was coupled with streptavidin-coupled polylysine, also showed that as a result of the inactivation the virus titer decreased considerably more sharply than the gene transfer capacity. This is a clear indication that mechanisms which are connected with the normal replication in the active virus can be destroyed without destroying the effect which is essential for gene transfer.

The term "virus components" denotes parts of viruses, e.g. the protein part freed from nucleic acid (the empty virus capsid, which may be produced by recombinant methods, e.g. Ansardi et al., 1991; Urakawa et al., 1989; the disclosures of which are fully incorporated by reference herein), proteins obtained by fractionation or peptides which have the endosomolytic functions of the intact virus. These virus components may be produced synthetically, depending on their size either by peptide synthesis or by recombinant methods. In the present invention adenovirus proteins conjugated via biotin/streptavidin to polylysine were demonstrated to enhance gene transfer. Examples of fragments or proteins from other than adenovirus, which are essential for internalization, include influenza virus hemagglutinin (HA). The N-terminal sequence of the influenza virus hemagglutinin HA2 subunit is responsible for releasing the virus from the endosome. It has been shown that peptides consisting of 20 amino acids of this sequence are capable of fusing lipid membranes and partly breaking them open or destroying them (Wharton et al., 1988). In the present invention, authentic and modified influenza peptides were successfully employed in various embodiments. Another example are coat proteins of retroviruses, e.g. HIV gp41 (Rafalski et al., 1990) or parts of these virus proteins.

The use of viruses which have the ability per se to enter cells and thus function as internalization factors, is but one aspect of the present invention.

Viruses or virus components which themselves do not bring the capacity to bind to the cell and enter into it, are preferably used as viral conjugates as defined above. Coupling to a DNA binding domain, e.g. a polycation, ensures that the virus (component) acquires a high affinity to DNA molecules and is thus complexed to it and transported into the cell as a component of the nucleic acid complex, which also contains a conjugate of internalizing factor and DNA binding domain. In addition to the transfer effect thus achieved, binding of the virus (component) to a nucleic acid binding domain may also result in an improvement of its endosomolytic properties.

By choosing other internalization factors described herein, practically any higher eucaryotic cell may be transfected with the compositions of the present invention.

One can determine with a simple screening assay whether a given virus (component) has an uptake function and can be employed in the practice of the invention. In this assay, e.g. for testing a virus for its applicability as free virus, the target cells are contacted with a DNA complex in the presence or absence of the virus. The amount of DNA complex released into the cytoplasm can then be easily determined by detection of a marker gene product, e.g. luciferase. If the presence of the virus causes the DNA complex to be taken up and released into the cytoplasm at a greater level than without the virus, this may be attributed to the uptake function of the virus. It is also possible to compare the level of DNA complex uptake with the test virus when compared to another virus known to have a suitable uptake function, e.g. adenovirus subgroup C, type 5. Tests of this kind may also be applied to viral conjugates, additional parameters such as various internalizing factor conjugates in varying amounts may be subject to such tests. Furthermore, a person skilled in the art can easily apply assays of this kind, optionally in combination with other tests, e.g. liposome leakage assays, for testing virus components or other agents with potential endosomolytic activity for their ability to enhance gene expression.

When intact viruses are used, tests are carried out, preferably parallel to the preliminary tests investigating the virus for its ability to augment gene transfer, to see whether the virus is capable of replicating. The investigation for ability to replicate is carried out by using plaque assays (see above) or CPE assays or determination of late gene expression in the case of cytopathic viruses or in the case of viruses which significantly impair the growth of the host cells. For other viruses, detection methods specific to the virus in question are used, e.g. the hemagglutination test or chemico-physical methods, e.g. using an electron microscope.

Within the scope of this invention, the preferred viruses, in particular those which are applied as free viruses, are those which can be produced in a high titer, which are stable, have low pathogenicity in their native state and in which a targeted elimination of the ability to replicate is possible, especially adenoviruses. If a specific cell population is to be transfected, viruses which specifically infect this cell population may be employed. If the transfection is intended to target different cell types, viruses which are infectious for a wide range of cell types may be used.

The requirements on the compositions of free virus essentially are that the virus preparation should be of the greatest possible purity and that a stabilizing buffer should be used which is matched to the particular virus.

In any case, for therapeutic use of the invention only those viruses or virus components may be used in which the safety risks are minimized as far as possible, particularly the risk of replication of the virus in the target cell and recombination of virus DNA with host DNA.

Advantageously, the entry mechanism of viruses which infect animals other than humans may be used to enhance the uptake and release of DNA into higher eucaryotic cells, especially of humans, so long as the virus exhibits endosome disruption activity in the higher eucaryotic cells. Members of the adenovirus family have been isolated from avian species, from amphibians and from a variety of other animals. See, for example, Laver, W. G. et al., 1971;, Bragg, R. R. et al., 1991; Akopian, T. A. et al., 1991; Takase, K. et al., 1990; Khang, C. and Nagaraji, K. V., 1989; and Reece, R. L. et al., 1987; the disclosures of which are fully incorporated by reference herein. Amphibian, avian, bovine, canine, murine, ovine, porcine, and simian adenoviruses, as well as human adenoviruses, are available from the American Type Culture Collection, Rockville, Md. (See the American Type Culture Collection Catalogue of Animal Viruses and Antisera, Chlamydae and Rickettsiae, Sixth Edition, 1990, C. Buck and G. Paulino eds., pp. 1–17).

One possible advantage of using a virus, e.g. an adenovirus, from a distant species might be a reduced toxicity in the target cells (e.g. the chicken or frog adenovirus would not be expected to replicate or initiate early gene expression in mammalian cells), a reduced hazard to the investigator preparing the distant adenovirus, compared to the human adenovirus, and reduced interference in the target organism from antibodies against human or murine adenovirus. The absence of interference by the human or murine antibodies is particularly important when the viruses are employed in gene therapy in humans and mice.

The chicken adenovirus CELO (chick embryo lethal orphan virus) shows no reactivity to antibodies that recognize the major group epitopes of the adenoviruses infecting mammalian cells. Moreover, CELO may be grown in embryonated eggs to give high levels of virus (0.5 mg/egg; Laver et al., 1971). As shown in the Examples, CELO)-polylysine conjugates augment DNA delivery to HeLa cells at levels comparable to the human adenovirus dl312. Thus, the use of CELO conjugates to augment DNA delivery holds great promise in human gene therapy experiments.

Viruses of distant species are preferably used as constituents of viral conjugates in combination complexes, as herein defined.

In conjugates of the invention which contain a virus, binding of the virus to the nucleic acid binding domain may be covalent or non-covalent, e.g. a biotin-streptavidin bridge or a ionic binding in case the virus has areas on its surface proteins which are acidic and therefore can bind to a polycation.

In experiments of the present invention, complexes were formed under conditions which allow ionic interaction between adenovirus and polylysine before complexing with DNA. Control experiments were conducted under conditions where polylysine is first neutralized with DNA and is therefore not free to bind the adenovirus. The complexes with ionically bound adenovirus were superior in these experiments.

Examples for virus components in the endosomolytic conjugates of the invention are the empty virus capsids or viral peptides. Binding of the virus component to the nucleic acid binding domain may be covalent, e.g. by chemically coupling the viral peptide with polylysine, or non-covalent, e.g. ionic in case the virus component has acid residues to bind to a polycation.

The ratio of virus or virus component to the substance having affinity to nucleic acid may be varied. In the case of influenza haemagglutinin peptide-polylysine conjugate it was found in the present invention that gene transfer can be augmented to a greater extent when the content of viral peptide in the conjugates is higher.

In another aspect the present invention relates to methods of preparing the viral conjugates according to the invention.

The conjugates of virus or virus component and substance having an affinity for nucleic acid may be prepared (like the internalizing factor-polycation conjugates) by binding the compounds or, if the virus component and the nucleic acid binding domain are polypeptides, by the recombinant method; with regard to methods of preparation reference is made to the disclosure of EP 388 758; the disclosure of which is fully incorporated by reference herein.

Binding of virus or viral proteins or peptides, respectively, with polyamine compounds by the chemical method can be effected in the manner which is already known for the coupling of peptides and if necessary the individual components may be provided with linker substances before the coupling reaction (this measure is necessary if there is no functional group available which is suitable for the coupling, e.g. a mercapto or alcohol group). The linker substances are bifunctional compounds which are reacted first with functional groups of the individual components, after which the modified individual components are coupled.

Coupling may be carried out by means of
a) Disulphide bridges, which can be cleaved again under reducing conditions (e.g. when using succinimidyl-pyridyldithiopropionate (Jung et al., 1981; the disclosure of which is fully incorporated by reference herein).
b) Compounds which are substantially stable under biological conditions (e.g. thioethers by reacting maleimido linkers with sulfhydryl groups of the linker bound to the second component).
c) Bridges which are unstable under biological conditions, e.g. ester bonds, or acetal or ketal bonds which are unstable under slightly acidic conditions.

In experiments carried out within the scope of the present invention, endosomolytic influenza-hemagglutinin HA2-peptides were coupled with polylysine by the chemical method using succinimidylpyridyldithio-propionate (SPDP). It was shown that the modification of the peptide with polylysine increases the endosomolytic activity. Transfection experiments showed that the efficiency of gene transfer mediated by transferrin-polylysine is substantially increased if the influenza peptide-polylysine conjugates are present together with transferrin-polylysine in the DNA complex.

Moreover, within the scope of the present invention, adenovirus was bound to polylysine by various different methods. One way of conjugating the virus with polylysine was effected in a similar manner to the production of transferrin-polylysine conjugates (Wagner et al., 1990; the disclosure of which is fully incorporated by reference herein) after modification of the defective adenovirus dl312 using a heterobifunctional reagent. Unbound polylysine was removed by centrifuging. The DNA binding capacity was demonstrated in a binding experiment using radioactively labelled DNA. (In K562 cells in the absence of chloroquine, substantially higher gene transfer was found with complexes consisting of DNA, adenovirus-polylysine and transferrin-polylysine, than with unmodified adenovirus which is not bound to the DNA. It was also found that significant gene expression occurred with only 0.0003 $\mu$g of DNA in $5 \times 10^5$ HeLa cells using polylysine-modified adenovirus.)

If the virus or virus component (or the additional internalizing factor, as e.g. in the case of transferrin) contains suitable carbohydrate chains, they may be linked to the substance having an affinity for nucleic acid via one or more carbohydrate chains of the glycoprotein.

Another preferred method of preparing the viral conjugates of the invention is by enzymatic coupling of the virus or virus component to a substance having an affinity for nucleic acid, more particularly a polyamine, by means of a transglutaminase.

The category of transglutaminases comprises a number of different enzymes which occur inter alia in the epidermis (epidermal transglutaminase), in the blood (Factor XIII) and in the cells of various tissues (tissue transglutaminase, e.g. liver transglutaminase) (Folk, 1985; the disclosure of which is fully incorporated by reference herein). Transglutaminases catalyze the formation of $\epsilon$-($\gamma$-glutamyl)lysine bonds in the presence of Ca++ and with cleaving of $NH_3$. The prerequisite for this is that corresponding glutamines and lysines should be present in proteins, capable of being reacted by the enzyme. Apart from the $\epsilon$-amino group of lysine, (poly)amines such as ethanolamine, putrescine, spermine or spermidine may also be used as substrate (Clarke et al., 1959). At present it is not yet clear what the critical factors are which determine whether a glutamine or lysine of a protein or a polyamine can be reacted by the enzyme. What is known is that polyamines can be bound by means of tansglutaminase to numerous cell proteins such as cytokeratins (Zatloukal et al., 1989), tubulin, cell membrane proteins and also surface proteins of influenza viruses (Iwanij, 1977).

Within the scope of the present invention it has been shown that polylysine can be coupled to adenoviruses by means of transglutaminase. It was found that coupling can be carried out in the presence of glycerol. This has the advantage that a virus preparation, e.g. an adenovirus preparation which contains glycerol as stabilizing agent in the buffer, can be used directly for coupling. Using adenovirus-polylysine conjugates which were complexed with plasmid-DNA together with transferrin-polylysine conjugates, it was possible to achieve many times greater gene expression than with transferrin-polylysine conjugates in the presence of non-polylysine-coupled adenovirus.

Another method of preparing the conjugates according to the invention which is preferred within the scope of the invention consists in coupling the virus or virus component to the polycation via a biotin-protein bridge, preferably a biotin-streptavidin bridge.

The known strong association of biotin with streptavidin or avidin (Wilchek et al., 1988) was used for coupling adenovirus to polylysine by modifying adenovirus with biotin and chemically conjugating streptavidin to polylysine in a similar manner to the product of transferrin-polylysine conjugates (Wagner et al., 1990). Complexes consisting of DNA and streptavidin-polylysine, to which the biotin-modified virus is bound, and optionally non-covalently bound polylysine, having a very high transfection efficiency, even at lower concentrations of DNA. Particularly efficient complexes are formed if the biotin-modified virus is first bound to streptavidin-polylysine and the binding to DNA only occurs in a second step.

If desired, the binding to biotin may also be effected by means of avidin.

It is also possible to establish the bond between the virus (component) and polylysine by biotinylating the virus, on the one hand, and conjugating an anti-biotin antibody with polylysine, on the other hand, and establishing the bond between the virus and the polylysine by means of the biotin/antibody bond, using standard commercially available polyclonal or monoclonal anti-biotin antibodies.

Binding between the virus and polylysine may also be achieved by coupling polylysine with a lectin which has an affinity for a virus surface glycoprotein, the bonding in such a conjugate being effected by means of the bond between the lectin and the glycoprotein. If the virus does not have any suitable carbohydrate side chains itself, it may be suitably modified.

A virus may also be bound to a substance having an affinity for nucleic acid by first being modified on the surface with an antigen alien to the virus (e.g. digoxigenin DIG, obtainable from Boehringer Mannheim; or with biotin) and establishing the connection between the modified virus and the substance having an affinity for nucleic acid via an antibody which binds to this antigen. The particular method which will be used to produce the conjugates according to the invention depends on various criteria. Thus, for example, coupling by means of biotin is the least specific and therefore most widely applicable method, while the biotin-mediated binding constitutes a very strong non-covalent bonding. The enzymatic reaction with transglutaminase has the advantage that it can also be carried out on a very small scale. Chemical coupling is generally used when larger quantities of conjugate are to be synthesized and this method is generally also the best when coupling virus proteins or peptides. If inactivated viruses are used, the inactivation is generally carried out before the coupling, provided that the coupling is not affected by the inactivation.

If a virus, e.g. adenovirus, or an endosomolytic component thereof, has binding domains accessible, e.g. acidic domains for binding to a polycation, binding of the virus (component) to the polycation may also be ionic. In this case, the positive charges of the polycation, which is optionally conjugated with an internalizing factor, are partially neutralized by the acidic domain of the virus (component), the remainder of the positive charges will be essentially neutralized by the nucleic acid.

If the substance having an affinity for nucleic acid is an intercalating substance, it is modified with a linker which is suitable for the particular coupling of virus (component), e.g. for coupling with transglutaminase it is modified with spermine or with a bifunctional group competent for chemical coupling, e.g. an active ester.

The ratio of virus (component)/nucleic acid binding substances may vary, it is usually established empirically, e.g. by conjugating a constant amount of virus (component) with different amounts of polylysine and selecting the optimal conjugate for the transfection.

In another embodiment of the invention, the virus component, e.g. an endosomolytic viral peptide, may be modified in order to bind direct to DNA. To this end the peptide itself may contain a DNA binding domain which is obtainable by producing the peptide by means of peptide synthesis and providing a stretch of positively charged amino acids, preferably by extending the peptide, most preferably at the C-terminus.

In another embodiment of the invention the endosomolytic agent is a non-viral, optionally synthetic peptide. A peptide of this type is preferably contained in the composition according to the invention in such a way that it is ionically bound to the substance with affinity to nucleic acid, e.g. to polylysine in case of DNA-internalizing factor-polylysine complexes. Thereby incorporation of the endosomolytic peptide into the nucleic acid complexes is accomplished by binding the peptide via its acidic amino acid residues to the positively charged nucleic acid binding domain, preferably polylysine.

Depending on the chemical structure of the peptide, in particular with regard to its end group, binding to polylysine may also be accomplished by the methods described herein for linking peptides to polylysine. To this end, if a naturally occurring peptide is employed, it may be modified with a suitable terminal amino acid as a handle for conjugation.

Another way of incorporating non-viral endosomolytic peptides into the nucleic acid complexes is to provide them with sequences which bind to DNA. The location of such a sequence has to be such that it does not interfere with the peptide's endosomolytic activity. Therefore, for example, peptides whose N-terminus is responsible for this activity, are extended by DNA binding sequences at the C-terminus. Extensions of this kind may be homologous or heterologous cationic oligopeptides, e.g. an oligo-lysine tail, or a natural DNA binding domain, e.g a peptide derived from a histone. Preferably these DNA binding sequences as integral part of the endosomolytic peptide comprise approximately 10 to 40 amino acids. This embodiment of the invention offers the possibility of a higher ratio of endosomolytic sequence to DNA binding sequence than in peptide conjugates which contain larger portions of polycations in order to achieve a higher efficiency of the complexes.

The non-viral endosomolytic peptides should fulfil the following requirements:

With regard to endosomolytic activity the leakage of lipid membranes achieved by the peptide should preferably be higher at low pH (5–6) than at pH 7. Furthermore, the disrupted areas of the membrane should be large enough to allow passage of large DNA complexes (small pores are not sufficient). In order to determine whether a peptide fulfills these requirements, in vitro tests can be carried out by applying the peptides in free or bound form and/or incorporated in a DNA complex. Such assays may comprise liposome leakage assays, erythrocyte leakage assays and cell culture experiments, in which augmentation of gene expression is determined. Tests of this type are described in the Examples. The optimal amount of peptide can be determined in preliminary titrations by assaying the resulting gene transfer efficiency. It has to be born in mind that efficiency of various peptides and optimal composition of complex may depend on cell type.

Membrane disruptive peptides in general contain amphipathic sequences, namely a hydrophobic face that may interact with the lipid membrane, a hydrophilic face that stabilizes the aqueous phase at the membrane disruption site.

There are several examples of membane-disruptive peptides in nature, usually small peptides or peptide domains of large polypeptides. Such peptides may be classified according to their function in the natural context, namely either in membrane disrupting peptides (e.g. peptides of naked viruses) and/or membrane fusing peptides (e.g. enveloped viruses). For the purpose of endosome disruption in the context of synthetic peptides both classes of peptide sequences may be useful. Most of the natural peptides are able to form amphipathic α-helices.

pH-specificity may be achieved by incorporation of acidic residues onto the hydrophilic face of a putative amphipathic α-helix in such a way that the helix can form only at acidic pH, but not at neutral pH where charge repulsion between the negatively charged acidic residues prevents helix formation. This property is also found with naturally occurring sequences (e.g. influenza HA-2 N-terminus).

A completely synthetic, rationally designed amphipathic peptide with pH-specific membrane-disruption properties has been described (Subbarao et al., 1987; Parente et al., 1990; the disclosures of which are fully incorporated by reference herein). This peptide (in free form) was shown to form only small pores in membranes, allowing only the release of small compounds (Parente et al., 1990).

According to the embodiment of the invention which makes use of non-viral, optionally synthetic peptides, usually the following steps are taken: a amphipathic peptide sequence is selected from the groups of naturally occurring or artificial peptides. Peptides of this kind are known in the art, a survey of examples is given in Table 2. If necessary, acidic residues (Glu, Asp) are introduced to make the peptide's membrane disrupting activity more pH-specific (e.g. the double acid mutant of the influenza hemaggludinin peptide according to Example 35, designated p50).

If necessary, acidic residues may also be introduced in order to facilitate binding of the peptide to polylysine. One way to provide for such a polycation binding domain may be to introduce C-terminal acidic extensions, e.g. an oligo-Glu-tail.

Endosomolytic peptides suitable for the present invention may also be obtained by fusing naturally occurring and artificial sequences. In the present invention experiments were conducted with various peptides which were derived from the synthetic peptide GALA described by Parente et al., 1990. Some of the derivatives employed in the experiments of the present invention were obtained by combining the peptide GALA or modifications thereof with sequences of the influenza peptide or modifications thereof, e.g. the peptides designated EALA-Inf and EALA-P50 according to Example 35.

The length of the peptide sequence may be critical with regard to the stability of the amphipathic helix; an increase of stability of short domains derived from natural proteins, which lack the stabilizing protein context, may be achieved by elongation of the helix.

In order to increase the endosomolytic activity of the peptides, homodimers, heterodimers or oligomers may be formed; it has been shown in the experiments of the present invention that a P50 dimer has a much higher activity than the monomer.

The present inventors have shown the effect of synthetic peptides on DNA uptake mediated by transferrin-polylysine conjugates. Various different peptides were synthesized, their liposome and erythrocyte leakage capacity assayed and their effect on luciferase expression in TIB 73 cells and in NIH3T3 cells tested.

In another embodiment of the invention, the endosomolytic agent may be a non-peptidic amphipathic substance. The requirements such a substance must fulfil to be suitable for the present invention are essentially the same as for the amphipathic peptides, namely ability to be incorporated into the nucleic acid complexes, pH specificity, etc.

In another aspect the invention relates to complexes which are taken up into higher eucaryotic cells, containing nucleic acid and a conjugate which has the ability to form a complex with nucleic acid, for introducing nucleic acid into higher eucaryotic cells. The complexes are characterized in that the conjugate consists of a substance having an affinity for nucleic acid and an endosomolytic agent which is bound to the substance having an affinity for nucleic acid and has the ability of being internalized into the cell as part of a conjugate/nucleic acid complex and of releasing the contents of the endosomes, in which the complex is located after entering the cell, into the cytoplasm.

The nucleic acid complexes used within the scope of the invention are preferably those wherein the nucleic acid is complexed with a substance having an affinity for nucleic acid in such a way that the complexes are substantially electroneutral.

In a preferred embodiment of the invention, the endosomolytic agent is a virus or a virus component covalently bound to a polycation.

Within the scope of the present invention, the endosomolytic conjugates also encompass—in addition to conjugates in which endosomolytic agents are ionically bound to a DNA binding domain—endosomolytic agents which bind to DNA direct, e.g. via their basic extension, although "conjugates" of this kind are strictly speaking not obtained by conjugation, i.e. by binding two compounds to each other. The function of endosomolytc agents of this type as compounds of the composition according to the invention is independent of whether they were synthesized by conjugation of an endosomolytic agent and a DNA binding domain or whether a DNA binding domain was originally present in the endosomolytic agent.

In another preferred embodiment of the invention the complexes contain, in addition to the endosomolytic conjugate, another conjugate in which a substance having an affinity for nucleic acid, in case of an endosomolytic polycation conjugate generally the same polycation as in the conjugate, is conjugated to an internalizing factor having an affinity for the target cell. This embodiment of the invention is used particularly when the target cell has no or few receptors for the virus employed as part of the endosomolytic conjugate. Another application of this embodiment of the invention is when a virus component, e.g. a naturally occurring, optionally modified peptide, a non-viral, optionally synthetic endosomolytic peptide or a virus from a distant species are employed, which do not have the ability to penetrate by themselves into the cells which are to be transfected. In the presence of an additional internalizing factor-binding factor conjugate, the endosomolytic conjugates profit from the internalizing ability of the second conjugate, by being complexed to the nucleic acid together with the second conjugate and being taken up into the cell as part of the resulting complex which in the following is referred to as "combination complex" or "ternary complex". Without being pinned down to this theory, the combination complexes are taken up by cells either by binding to the surface receptor which is specific to the additional internalizing factor or, e.g. in case a virus or virus component is used, by binding to the virus receptor or by binding to both receptors and internalized by receptor-mediated endocytosis. When the endosomolytic agents are released from the endosomes the DNA contained in the complexes is also released into the cytoplasm and thereby escapes the lysosomal degradation.

In the experiments of the present invention, nearly all HeLa cells could be transfected with free adenovirus. The efficacy for hepatocytes could be still further improved when using ternary DNA complexes in which the reporter DNA is complexed to polylysine-transferrin conjugates and linked to adenovirus. Here, co-localization of the endosomolytic virus and the ligand receptor complex in the endosome is guaranteed yielding transfection in virtually all cells for a variety of cells such as BNL.CL2 and HepG2 cells. In this instance, both viral and transferrin receptors on the cell surface can act to capture the ternary DNA complexes. However, one can envisage also that DNA ternary complexes can be internalized solely by the action of the cellular ligand/receptor association. Such a situation might be approximated in the experiments where ternary DNA complexes containing transferrin gained access to K562 cells in the main via the transferrin receptor rather than the adenovirus receptor.

Unexpectedly, ternary complexes transferred DNA even when presented for DNA transfer at very low levels. Thus at an input of 30 pg DNA/$3 \times 10^5$ cells, $1.8 \times 10^4$ light units (resulting from expression of a luciferase encoding plasmid) are obtained. At this input there are as little as 60 DNA molecules and 1 PFU of virus per cell. This has to be compared to the less efficient calcium precipitation protocol which uses $2 \times 10^5$ DNA molecules per cell (*Molecular Cloning*, Sambrook, J. et al. (Eds.), 2nd Edition, Vol. 3, pp. 16.39–16.40 (1989)). Thus, the present invention represents a significant advance in the art since it allows for the efficient transformation of higher eucaryotic cells with very small amounts of DNA.

The presence of viruses, virus components or non-viral endosomolytic agents in the DNA complexes as constituents of endosomolytic conjugates has the following advantages:
1) Broader applicability of the gene transfer technology with nucleic acid complexes, since the endosomolytic agent itself, in particular in case a virus (component) is employed, may constitute the internalizing factor or may also be complexed to the DNA together with another internalizing factor (e.g. transferrin or asialofetuin etc.). In this way it is possible to make use of the positive effect of the viruses even for cells which do not have any receptor for the virus in question.
2) Improvement in the efficiency of gene transfer, since the binding of the endosomolytic conjugates to the DNA ensures that they are jointly taken up into the cells. The coordinated uptake and release of viruses and DNA also gives rise to the possibility of a reduction in the quantity of DNA and viruses required for efficient gene transfer, which is of particular importance for use in vivo.

The term "internalizing factor" for the purposes of the present invention refers to ligands or fragments thereof which, after binding to the cell are internalized by endocytosis, preferably receptor-mediated endocytosis, or factors, the binding or internalizing of which is carried out by fusion with elements of the cell membrane.

Suitable internalizing factors include the ligands transferrin (Klausner, R. D. et al.,, 1983), conalbumin (Sennett, C. et al., 1981), asialoglycoproteins (such as asialotransferrin, asialorosomucoid or asialofetuin) (Ashwell, G. et al., 1982), lectins (Goldstein et al., 1980, Shardon, 1987) or substances which contain galactose and are internalized by the asialoglycoprotein receptor; mannosylated glycoproteins (Stahl, P. D. et al, 1987), lysosomal enzymes (Sly, W. et al., 1982), LDL (Goldstein, J. L. et al., 1982), modified LDL (Goldstein, J. L. et al., 1979), lipoproteins which are taken up into the cells via receptors (apo B100/LDL); viral proteins such as the HIV protein gp120; antibodies (Mellman, I. S. et al., 1984; Kuhn, L. C. et al., 1982, Abrahamson, D. R. et at., 1982), or fragments thereof against cell surface antigens, e.g. anti-CD4, anti-CD7; cytokines such as interleukin-1 (Mizel, S. B. et al., 1987), Interleukin 2 (Smith, K. A. et al., 1985), TNF (Imamure, K. et al., 1987), interferon (Anderson, P. et al., 1982), colony-stimulating factor (Walker, F. et al., 1987); factors and growth factors such as insulin (Marshall, S., 1985), EGF (Carpenter, G., 1984), platelet-derived growth factor (Heldin, C. -H. et al., 1982), transforming growth factor β (Massague, J. et al., 1986), nerve growth factor (Hosang, M. et al., 1987), insulin-like growth factor I (Schalch, D. S. et al., 1986), LH, FSH, (Ascoli, M. et al., 1978), growth hormone (Hizuka, N. et al., 1981), prolactin (Posner, B. I. et al., 1982), glucagon (Asada-Kubota, M. et al., 1983), thyroid hormones (Cheng, S. -Y. et al., 1980); -2-macroglobulin protease (Kaplan, J. et al., 1979); and "disarmed" toxins. Further examples are immunoglobulins or fragments thereof as ligands for the Fc receptor or anti-immunoglobulin antibodies, which bind to SIgs (surface immunoglobulins). The ligands may be of natural or synthetic origin. See, *Trends Phamacol. Sci.* 10:458–462 (1989); the disclosure of which is fully incorporated by reference herein, and the references cited therein.

The following are essential requirements for the suitability of such factors according to the present invention,
a) that they can be internalized by the specific cell type into which the nucleic acid is to be introduced and their ability to be internalized is not affected or only slightly affected if they are conjugated with the binding factor, and
b) that, within the scope of this property, they are capable of carrying nucleic acid "piggyback" into the cell by the route they use.

In the experiments carried out according to the invention, the wide range of uses of the invention regarding the internalizing factor, or additional internalizing factor in the combination complexes, respectively, is demonstrated by means of human and mouse transferrin-polylysine (pL) conjugates, asialofetuin-pL conjugates, galactose-pL conjugates, wheat germ agglutinin conjugates, the T-cell-specific gp120pL and antiCD7-pL conjugates and by means of DNA polylysine complexes which do not contain any internalizing factor. Moreover, the performance of the virus conjugates according to the invention was demonstrated by means of complexes of DNA and polylysine-conjugated virus (or virus component) which contained no additional internalizing factor-binding factor conjugate.

Specifically preliminary tests can be carried out to determine whether, in case the endosomolytic agent is a free virus, the use of an internalizing factor, or in case the endosomolytic agent is a virus or a virus compound or a non-viral peptide which is part of an endosomolytic conjugate, an "additional" internalizing factor permits or improves the uptake of nucleic acid complexes. These tests comprise parallel transfections with nucleic acid complexes, firstly without (additional) internalizing factor, e.g. in case of virus conjugates with complexes consisting of nucleic acid and virus conjugate, and secondly with complexes in which the nucleic acid is complexed with another conjugate consisting of an additional internalizing factor for which the target cells have a receptor, and a substance having an affinity for nucleic acid.

If an internalizing factor is used, or if an additional internalizing factor is used, i.e. a combination complex is applied, it is defined particularly by the target cells, e.g. by specific surface antigens or receptors specific to a cell type which thus permit the targeted transfer of nucleic acid into this cell type.

Substances with an affinity for nucleic acid which may be used according to the invention include, for example, homologous organic polycations such as polylysine, polyarginine, polyornithine or heterologous polycations having two or more different positively charged amino acids, these polycations possibly having different chain lengths, and also non-peptidic synthetic polycations such as polyethyleneimine. Other substances with an affinity for nucleic acid which are suitable are natural DNA-binding proteins of a polycationic nature such as histones or protamines or analogues or fragments thereof, as well as spermine or spermidines.

The length of the polycation is not critical, as long as the complexes are substantially electroneutral. The preferred range of polylysine chain lengths is from about 20 to about 1000 lysine monomers. However, for a given length of DNA, there is no critical length of the polycation. Where the DNA consists of 6,000 bp and 12,000 negative charges, the amount of polycation per mole DNA may be, e.g.:

60 moles of polylysine 200

30 moles of polylysine 400; or 120 moles of polylysine 100, etc.

One of ordinary skill in the art can select other combinations of polycation length and molar amount with no more than routine experimentation.

Other suitable substances with an affinity for nucleic acid as part of the conjugates are intercalating substances such as ethidium dimers, acridine or intercalating peptides, containing tryptophan and/or tyrosine and/or phenylalanine.

As for the qualitative composition of the nucleic acid complexes, generally the nucleic acid to be transferred into the cell is determined first. The nucleic acid is defined primarily by the biological effect which is to be achieved in the cell and, in the case of use for gene therapy, by the gene or gene section which is to be expressed, e.g. for the purpose of replacing a defective gene, or by the target sequence of a gene which is to be inhibited. The nucleic acids to be transported into the cell may be DNAs or RNAs, while there are no restrictions imposed on the nucleotide sequence.

If the invention is applied on tumor cells in order to use them as a cancer vaccine, the DNA to be introduced into the cell preferably codes for an immune modulating substance, e.g. a cytokine like IL-2, IL-4, IFN gamma, TNF alpha. Combinations of cytokine encoding DNAs may be particularly useful, e.g. IL-2 and IFN gamma. Another useful gene to be introduced into tumor cells may be the multi drug resistance gene (mdr). In the present invention, transferrin-polylysine conjugates and low density lipoprotein-polylysine conjugates were successfully employed together with the adenoviral conjugates to transfect tumor cells (melanoma cells). Depending on the individual application, preliminary experiments may be carried out with no more than routine experimentation in order to determine which ligand is best for a given tumor cell type.

It is also possible to introduce two or more different nucleic acid sequences into the cell, e.g. a plasmid containing cDNAs coding for two different proteins under the control of suitable regulatory sequences or two different plasmid constructs containing different cDNAs.

Therapeutically effective inhibiting nucleic acids for transfer into the cells in order to inhibit specific gene sequences include gene constructs from which antisense-RNA or ribozymes are transcribed. Furthermore, it is also possible to introduce oligonucleotides, e.g. antisense oligonucleotides, into the cell. Antisense oligonucleotides comprise preferably 15 nucleotides or more. Optionally, the oligonucleotides may be multimerized. When ribozymes are to be introduced into the cell, they are preferably introduced as part of a gene construct which comprises stabilizing gene elements, e.g. tRNA gene elements. Gene constructs of this type are disclosed in EP A 0 387 775; the disclosure of which is fully incorporated by reference herein.

Apart from nucleic acid molecules which inhibit genes, e.g. viral genes, due to their complementarity, genes with a different mode of inhibitory action may be employed. Examples are genes coding for viral proteins which have so-called trans-dominant mutations (Herskowitz, 1987). Expression of the genes in the cell yields proteins which dominate the corresponding wildtype protein and thus protect the cells, which acquires "cellular immunity" by inhibiting viral replication.

Suitable are trans-dominant mutations of viral proteins which are required for replication and expression, e.g. Gag-, Tat and Rev mutants which were shown to inhibit HIV replication (Trono et al., 1989; Green et al., 1989; Malim et al., 1989; the disclosure of which is fully incorporated by reference herein).

Another mechanism of achieving intracellular immunity involves expression of RNA molecules containing the binding site for an essential viral protein, e.g. so-called TAR decoys (Sullenger et al., 1990; the disclosure of which is fully incorporated by reference herein).

Examples of genes which can be used in somatic gene therapy and which can be transferred into cells as components of gene constructs by means of the present invention include factor VIII (hemophilia A) (see, e.g. Wood et al., 1984), factor IX (hemophilia B) (see, e.g. Kurachi, K. et al., 1982), adenosine deaminase (SCID) (see, e.g. Valerio, D. et al., 1984), -1 antitrypsin (emphysema of the lungs) (see, e.g. Ciliberto, G. et al., 1985) or the cystic fibrosis transmembrane conductance regulator gene (see, e.g. Riordan, J. R. et al., 1989; the disclosure of which is fully incorporated by reference herein). These examples do not constitute a restriction of any kind.

As for the size of the nucleic acids, a wide range is possible; gene constructs of about 0.15 kb (in case of a tRNA gene containing a ribozyme) to about 50 kb or more may be transferred into the cells by means of the present invention; smaller nucleic acid molecules may be applied as oligonucleotides.

It is clear that the widest possible applications are made possible precisely by the fact that the present invention is not subject to any limitations on the gene sequence and the fact that very large gene constructs may also be transferred by means of the invention.

Starting from the nucleic acid, the substance having an affinity for nucleic acid, preferably an organic polycationic substance, is determined, to ensure complexing of the nucleic acid, the obtained complexes preferably being substantially electroneutral. If the complexes contain a conjugate of additional internalizing factor and substance having an affinity for nucleic acid, the polycation component of both conjugates is taken into consideration with respect to the electroneutrality aspect.

In the course of earlier inventions it had been found that the optimum transfer of nucleic acid into the cell can be achieved if the ratio of conjugate to nucleic acid is selected so that the internalizing factor-polycation/nucleic acid complexes are substantially electroneutral. It was found that the quantity of nucleic acid taken up into the cell is not reduced if some of the transferrin-polycation conjugate is replaced by non-covalently bound polycation; in certain cases there may even be a substantial increase in DNA uptake (Wagner et al., 1991a). It had been observed that the DNA of the complexes is present in a form compressed into toroidal structures with a diameter of 80 to 100 nm. The quantity of polycation is thus selected, with respect to the two parameters of electroneutrality and the achievement of a compact structure, while the quantity of polycation which results from the charging of the nucleic acid, with respect to achieving electoneutrality, generally also guarantees compacting of the DNA.

Thus, in a further embodiment of the invention, the complexes also contain nucleic acid-binding substances in a non-covalently bound form, which may be identical to or different from the binding factor. In case the endosomolytic agent is free virus, the complexes comprise nucleic acid and internalizing factor conjugate. In case an endosomolytic, e.g. a viral conjugate is employed, the nucleic acid is complexed with this conjugate, optionally in concert with a conjugate of an additional internalizing factor. The choice of non-covalently bound "free" substances having an affinity for nucleic acid, in their nature and quantity, is also determined by the conjugate(s), particularly taking account of the binding factor contained in the conjugate: if, for example, the binding factor is a substance which has no or limited capacity for DNA condensation, it is generally advisable, with a view to achieving efficient internalization of the complexes, to use substances having an affinity for DNA which possess this property in a high degree. If the binding factor itself is a nucleic acid condensing substance and if it has already brought about compacting of the nucleic acid sufficient for effective internalization, it is advisable to use a substance having an affinity for nucleic acid which brings about an increase in expression by virtue of other mechanisms.

The suitable "free" substances having an affinity for nucleic acid according to the invention include compounds capable of condensing nucleic acid and/or of protecting them from undesirable degradation in the cells, particularly the substances of a polycationic nature mentioned hereinbefore. Another group of suitable substances comprises those which, by binding to the nucleic acid, bring about an improvement in the transcription/expression thereof, by improving the accessibility of the nucleic acid for the expression machinery of the cell. An example of a substance of this kind is chromosomal non-histone protein HMG1, which has been found to possess the capacity to compact DNA and promotes expression in the cell.

With regard to the complexes, when determining the molar ratios of endosomolytic agent and/or internalizing factor/substance having an affinity for nucleic acid/nucleic acid(s), care should be taken that complexing of the nucleic acid(s) takes place, that the complex formed can be bound to the cell and internalized, and that, either by itself or with the aid of the endosomolytic agent is released from the endosomes.

The internalizing factor/binding factor/nucleic acid ratio depends particularly on the size of the polycation molecules and the number and distribution of the positively charged groups, criteria which are matched to the size and structure of the nucleic acid(s) to be transported. Preferably, the molar ratio of internalizing factor/substance having an affinity for a nucleic acid will range from about 10/1 to about 1/10.

After the construction and synthesis of the conjugates and determination of the optimum ratio of conjugate:DNA for effective transfection, the quantity of the conjugate proportion which can be replaced, if desired, by free substance having an affinity for nucleic acid can be determined by titration. If polycations are used both as the binding factor and also as a free substance having an affinity for nucleic acid, the polycations may be identical or different.

For the embodiment of the invention which employs viral conjugates a method suitable for determining the ratio of the components contained in the complexes may consist in first defining the gene construct which is to be introduced into the cells and, as described above, finding a virus or virus component which is suitable for the particular transfection. Then the virus or virus component is bound to a polycation and complexed with the gene construct. Starting from a defined quantity of viral conjugate, titrations may be carried out by treating the target cells with this (constant) quantity of conjugate and decreasing concentrations of DNA, or vice versa. In this way the optimum ratio of DNA:virus conjugate is determined. If an additional internalizing factor is used the procedure may be, for example, to determine the optimum ratio of virus conjugate to internalizing factor conjugate starting from a constant quantity of DNA by titration.

The complexes may be prepared by mixing together the components i) nucleic acid, ii) viral conjugate optionally iii) internalizing factor/binding factor conjugate, and optionally iv) non-covalently bound substance having an affinity to nucleic acid, all of which may be present in the form of dilute solutions. If polycations are used as a binding factor and at the same time as "free" polycations, it is generally advisable first of all to prepare a mixture of conjugates with "free" polycations and then combine this mixture with DNA. The optimum ratio of DNA to the conjugate(s) and polycations is determined by titration experiments, i.e. in a series of transfection experiments using a constant amount of DNA and increasing amounts of conjugate(s)/polycation mixture. The optimum ratio of conjugate(s): polycations in the mixture is obtained by routine experimentation or by comparing the optimum proportions of the mixtures used in the titration experiments.

The DNA complexes may be prepared at physiological salt concentrations. Another possibility is to use high salt concentrations (about 2 M NaCl) and subsequent adjustment to physiological conditions by slow dilution or dialysis.

The most suitable sequence for mixing the components nucleic acid, conjugate(s), possibly non-covalently bound substance with an affinity to nucleic acid is determined by prior experimentation. In some cases, it may prove advisable first to complex the nucleic acid with the conjugate(s) and then to add the "free" substance with an affinity for nucleic acid, e.g. the polycation, e.g. in the case of conjugates of transferrin-ethidium dimer and polylysine.

In a preferred embodiment of the invention, the internalizing factor or the additional internalizing factor, respectively, is transferrin and the binding factor is a polycation. The term "transferrin" denotes both the natural transferrins and also those transferrin modifications which are bound by the receptor and transported into the cell.

The nucleic acid is taken up in the form of complexes in which internalizing factor-polycation conjugates are complexed with nucleic acid. When there is a content of a non-covalently bound substance with an affinity for nucleic acid, this is preferably a polycation. This second polycation is identical to or different from the polycation contained in the conjugate or in both conjugates.

In case of "combination complexes" the nucleic acid is internalized in the form of complexes in which internalization factor conjugates on the one hand and endosomolytic conjugates on the other hand are complexed with nucleic acid.

The conjugates of internalizing factor and polycation, which are used together with free virus or together with the viral conjugates in the combination complexes, may be prepared by a chemical method or, if the polycation is a polypeptide, by a recombinant method; for methods of preparation, reference is made to the disclosure of EP 388 758; the disclosure of which is fully incorporated by reference herein.

Preferably, within the scope of the present invention, conjugates are used in which the glycoprotein, e.g. transferrin, and the binding factor are connected to each other via one or more carbohydrate chains of the glycoprotein.

Unlike the conjugates prepared by conventional coupling methods, conjugates of this kind are free from modifications originating from the linker substances used. In the case of glycoproteins which have only one or a few carbohydrate groups suitable for coupling, e.g. transferrin, these conjugates also have the advantage that they are precisely defined in terms of their binding site for glycoproteins/binding factor.

A suitable method of preparing glycoprotein-polycation conjugates is disclosed in German Patent application P 41 15 038.4; it was described recently by Wagner et al., 1991b; the disclosure of which is fully incorporated by reference herein.

The quantity of endosomolytic agent used and the concentration thereof depend on the particular transfection being undertaken. It is desirable to use the minimum quantity of virus or virus conjugate which is necessary to ensure the internalization of the virus (conjugate) and the nucleic acid complex and release from the endosomes. The quantity of virus (conjugate) is matched to the particular cell type and the infectivity of the virus for this type of cell must be taken into consideration above all. Another criterion is the particular conjugate of internalizing factor and binding factor, particularly with regard to the internalizing factor, for which the target cell has a specific number of receptors. Moreover, the quantity of virus (conjugate) will depend on the amount of DNA to be imported. Generally, a small amount of virus is sufficient for a stable transfection which requires only a small amount of DNA, whereas a transient transfection, which requires larger amounts of DNA, requires a larger quantity of virus. For a particular application, preliminary tests are carried out with the target cells intended for transfection, possibly with a mixed cell population, and the vector system envisaged for the transfection, in order to determine the optimum virus concentration by titration, while the DNA used is conveniently a gene construct which largely coincides with the one intended for concrete use, in terms of its size, and contains a reporter gene for easier measurement of efficiency of gene transfer. Within the scope of the present invention, the luciferase and β-galactosidase genes have been shown to be suitable reporter genes for such tests.

Another aspect of the invention relates to a process for introducing complexes of nucleic acid, a nucleic acid binding substance and optionally an internalizing factor, into higher eucaryotic cells. The method is characterized in that the cells are brought into contact with an agent which has the ability of being internalized into the cells either per se or as a component of the nucleic acid complexes and of releasing the contents of the endosomes, in which the nucleic acid complexes are located after entering the cell, into the cytoplasm.

In general, it is preferred to apply nucleic acid complex and endosomolytic agent simultaneously, but they may also be applied one after the other. In case of separate applications, the sequence of application is not critical as long as the steps are carried out shortly after each other in order to guarantee that the components are in effective simultaneous contact.

In case of using free virus in a separate preparation, simultaneous administration of the preparation of free virus with the complexes may be guaranteed by having the virus preparation as part of the transfection medium which contains the nucleic acid complex.

In the case of simultaneous administration of free virus, the nucleic acid complexes and virus preparation are mixed together before being administered.

In a preferred embodiment, the endosomolytic agent is a component of a combination complex.

In order to increase gene expression, the compositions according to the invention may also be administered repeatedly.

In a preferred embodiment, the cells are primary tumor cells. In a particularly preferred embodiment the nucleic acid is a DNA which contains one or more sequences coding for an immune modulating substance, preferably a cytokine.

In another embodiment the cells are myoblasts, preferably primary myoblasts.

In another embodiment the cells are fibroblasts, preferably primary fibroblasts.

In another embodiment the cells are hepatocytes, preferably primary hepatocytes.

In another embodiment the cells are primary endothelial cells.

In another embodiment the cells are primary airway epithelial cells.

Table 1 shows the transfection success of the present invention exemplified with various different cell types.

The composition of the invention was also investigated for transfection of canine hemophilia B fibroblasts. Luciferase and β-galactosidase could be successfully expressed in these cells. Furthermore, the system was used to deliver the 1.4 kb canine factor IX cDNA into fibroblasts from a hemophilic canine. In a sandwich ELISA, canine factor IX could be detected 24 hours after transfection.

In certain cases, it is advisable to use a lysosomatropic substance in addition to the endosomolytic agent, e.g. if the agent is a endosomolytic peptide conjugate or a retrovirus, the endosomolytic activities of which are not strictly dependent on an acidic pH.

It is known that lysosomatropic substances inhibit the activity of proteases and nucleases and may therefore inhibit the degradation of nucleic acids (Luthmann and Mangusson, 1983; the disclosure of which is fully incorporated by reference herein). These substances include chloroquine, monensin, nigericin and methylamine. It has been shown that monensin brings about an increase in the expression of reporter gene when a Moloney retrovirus is used.

The presence of chloroquine could be demonstrated to lead to expression of a reporter gene, imported by transferrin-mediated DNA transfer in virtually 100% of K562 cells. BNL.CL2 or HepG2 hepatocytes did not respond as well to chloroquine as did K562 cells but they could be transfected to a level of 5 –10% when exploiting the endosomolytic properties of added replication defective or chemically inactivated free adenovirus.

With the aid of the present invention, the advantages of the biological vectors are increased. As a result of the distribution of the receptors there is a tropism both for internalizing factor and for the virus. By matching these two components to the particular cell population, it is possible to achieve a greater selectivity which is of particular importance in the therapeutic application of this invention.

In another aspect the present invention relates to pharmaceutical compositions containing as active ingredient a complex of therapeutically active nucleic acid, preferably as part of a gene construct, endosomolytic agent (optionally conjugated) and optionally an internalizing factor conjugate, for administration to an animal, e.g. a human. Any inert pharmaceutically acceptable carrier may be used, such as saline, or phosphate-buffered saline, or any such carrier in which the DNA complexes have suitable solubility properties for use in the method of the present invention. Reference is made to Remington's Pharmaceutical Sciences, Mack Publishing Co., Easton, Pa., Osol (ed.) (1980) for methods of formulating pharmaceutical compositions.

The present invention offers the advantage of greatest possible flexibility for application, inter alia as pharmaceutical composition. The composition of the invention may occur as a lyophilisate or in a suitable buffer in deep-frozen state. It may also be provided as ready-to-use reagent in solution, preferably shipped cooled. Optionally, the components necessary for transfection, i.e. DNA, endosomolytic agent, optionally conjugated or ready for conjugation with a separate conjugation partner, DNA binding substance, optionally conjugated with an internalizing factor, optionally free polycation, may be present in a suitable buffer separate or partially separate as constituents of a transfection kit, which is also subject of the present invention. The transfection kit of the present invention comprises a carrier means having in close confinement therein one or more container means such as tubes, vials and the like, each of which contain the materials necessary to carry out the transfection of a higher eucaryotic cell in accordance with the present invention. In such a transfection kit, a first container means may contain one or more different DNAs, e.g. coding for different antigens. A second container means may contain one or more different internalizing factor conjugates that enable the use of the transfection kit as a modular system. Whether the constituents are supplied as a ready-to-use preparation or separately to be mixed immediately before use, depends, apart from the specific application, on the stability of the complexes, which can be determined routinely in stability tests. In a preferred embodiment, a transglutaminase coupled adenovirus-polylysine conjugate, which has proven to be stable at storage, is provided in one of the container means of a kit. In another preferred embodiment, biotinylated adenovirus and streptavidin-polylysine are provided in separate container means and are mixed before application. One of ordinary skill in the art can design numerous different transfection kits to take advantage of the flexibility of the invention.

For therapeutic use, the composition may be administered systemically, preferably by intravenous route, as part of a pharmaceutical composition. The target organs for this application may be, for example, the liver, spleen, lungs, bone marrow and tumors.

One example for local application is the lung tissue (use of the composition according to the invention as part of a pharmaceutical composition in fluid form for instillation or as an aerosol for inhalation). In addition, the pharmaceutical compositions of the invention may be administered by direct injection into the liver, the muscle tissue, into a tumor or by local administration in the gastro-intestinal tract. Another method of administration of the pharmaceutical composition is the application via the bile draining system. This method of application allows direct access to hepatocyte membranes at the bile canaliculi, avoiding interaction of the composition with blood constituents.

Recently, the feasibility of using myoblasts (immature muscle cells) to carry genes into the muscle fibres of mice was shown. Since the myoblasts were shown to secrete the gene product into the blood, this method may have a much wider application than treatment of genetic defects of muscle cells like the defect involved in muscular dystrophy. Thus, engineered myoblasts may be used to deliver gene products which either act in the blood or are transported by the blood. The experiments in the present invention have shown that both myoblast and myotube cultures, even primary ones, can be transfected with high efficiency. The most successful transfection media contained combination complexes of biotinylated adenovirus, transferrin-polylysine and streptavidin-polylysine. Besides the reporter genes luciferase and β-galactosidase, factor VIII was expressed in the muscle cells. Furthermore, the chicken adenovirus CELO was employed in combination complexes containing wheat germ agglutinin as an additional internalizing factor.

Therapeutic application may also be ex vivo, in which the treated cells, e.g. bone marrow cells, hepatocytes or myoblasts, are returned to the body (e.g., Ponder et at., 1991, Dhawan et al., 1991; the disclosures of which are fully incorporated by reference herein). Another ex vivo application of the present invention concerns so-called "cancer vaccines". The principle of this therapeutic approach is to isolate tumor cells from a patient, transfect the cells with a cytokine-encoding DNA. The next step may involve inactivation of the cells, e.g. by irradiation, in such a way that they no longer replicate but still express the cytokine. Then the genetically modified cells are applied to the patient from which they have been isolated, as a vaccine. In the environment of the vaccination site, the secreted cytokines activate the immune system, inter alia by activating cytotoxic T cells. These activated cells are able to exert their effect in other parts of the body and attack also non-treated tumor cells. Thus, the risk of tumor recurrency and of developing metastasis are reduced. A protocol suitable for the application of cancer vaccines for gene therapy was described by Rosenberg et al., 1992; the disclosure of which is fully incorporated by reference herein. Instead of retroviral vectors suggested by Rosenberg, the gene transfer system of the present invention may be used. In the experiments of the present invention primary melanoma cells were successfully transfected with a reporter gene contained in combination complexes of polylysine-coupled adenovirus and transferrin-polylysine.

The DNA complexes of the invention may be tested for in vivo efficacy in the treatment of cystic fibrosis. The CF "knock-out" mouse model demonstrates prominent GI disease with relative sparing of the lung (Clarke et al., 1992).

The DNA complexes of the present invention may be tested to treat the pulmonary disease in this mouse model and to correct the disease in the lower GI tract. Thus, in vivo gene transfer to GI epithelium in situ may be employed to achieve phenotypic correction experiments in the lower GI tract.

The present invention can also be used in assays for determining the host immune response to a given antigen. Such assays are based on gene transfer to antigen-expressing cells.

Antigen-specific cytotoxic T lymphocytes (CTL) that kill infected cells play an important role in the host defence against viral infections or tumors. The interaction between T-cell and antigen-presenting cell (APC) is HLA (human lymphocytic antigens=MHC, major histocompatibility molecules)-restricted; to study CTL killing of cells expressing antigen in an in vitro CTL killing assay, one must present the antigen to the CTL in the correct HLA context, which usually means on an autologous target cell.

A CTL-killing assay may be performed as follows: APCs are transfected with an DNA construct containing an antigen encoding sequence. Antigen epitopes will be bound to MHC class I molecules and presented at the cell surface as a target for a specific CTL response. Thus, upon incubation with a sample of patient's serum, depending on the presence of specific CTLs, the APCs will be lysed. Lysis is measured by monitoring the release of e.g. radioactive chromium that was incorporated into the APCs prior to the addition of the serum. Established protocols (Walker et al., 1989) use B-LCLs (B-lymphoblastoid cell lines) induced to express antigen genes by transfection with recombinant vaccinia viruses. However, cells expressing antigen efficiently for about one day, die due to the lytic effect of vaccinia.

These difficulties can be overcome by CTL killing assays employing the gene transfer system of the invention for introducing antigen encoding DNA constructs, e.g. constructs encoding HIV or tumor antigens into fibroblasts to render them antigen expressing.

Primary fibroblasts are easy to obtain from biopsies, easy to grow, and have been demonstrated to be transfectable with a particularly high efficiency (about 50 to about 70%) by means of the present invention.

Such assays are useful for identifying epitopes recognized by killer cells in view of the design of vaccines. Furthermore, they can be advantageously used in order to determine an individual's HLA restricted immune response against a given antigen.

Because a high level of expression of the transferred genes can be obtained in virtually all cells, the invention can be used to produce recombinant proteins. Here, there are no or few limitations as to the sequence and molecular weight of the transferred DNA, respectively. There is also a wide spectrum of cell types which are transfectable with the DNA constructs of the present invention. Thus, nearly any cell type can be used for the production of recombinant proteins which ensures that the recombinant protein is produced in a faithful and fully modified post-translationally processed form guaranteeing high biological activity of the product.

Gene transfer into cells may be accomplished as shown for luciferase and for interferon alpha, practically any gene construct that gives rise to a desired protein product can be delivered. The desired protein product can be recovered from the transfected cell culture (either the cell supernatant or an appropriate cell homogenate, according to the protocol for the particular protein product), 24 hours to one week or more after the transfection.

The application of the gene transfer system according to the present invention for the production of recombinant proteins has the following advantages:

1) Due to the high transfection efficiency (more than 90% of the transfected cells can express the delivered gene at high levels), no preselection of positively transfected cells is required and there is no need for establishing stable cell lines. Small scale cell culture can be sufficient to produce useful quantities of protein.

2) Large gene constructs may be delivered. Up to 48 kb have been successfully delivered thus far.

3) The gene expression can be performed in cells that guarantee the appropriate post-translational processing and modification (e.g. vitamin K-dependent carboxylation of clotting factors, see Armentano, et at., 1990, or cell type specific glycosylation).

4) A broader selection of target cell types is made available for gene expression using this method.

Having now generally described the invention, the same will be more readily understood through reference to the following examples which are provided by way of illustration, and are not intended to be limiting in any way. All patents and publications cited herein are incorporated by reference herein in their entirety.

EXAMPLES

In the Examples which follow, illustrating the present invention, the following materials and methods were used unless otherwise specified:

Preparation of transferrin-polylysine/DNA complexes a) Human transferrin-polylysine conjugates The method described by Wagner et al., 1991b, was used, in which polylysine is coupled to the carbohydrate side chains of transferrin.

A solution of 280 mg (3.5 $\mu$mol) of human transferrin (iron-free, Sigma) in 6 ml of 30 mM sodium acetate buffer, pH 5, was cooled to 0° C. and 750 $\mu$l of 30 mM sodium acetate buffer pH 5 containing 11 mg (51 $\mu$mol) of sodium periodate were added. The mixture was left to stand in the dark in an ice bath for 90 minutes.

In order to remove the low molecular products, gel filtration was carried out, (Sephadex G-25, Pharmacia), yielding a solution which contained about 250 mg of oxidized transferrin (measured by ninhydrin assay). (In order to reveal the oxidized form which contains aldehydes and gives a color reaction when stained with anisaldehyde, the samples were added dropwise to a thin layer plate of silica gel and dried and the plates were dipped into p-anisaldehyde/sulfuric acid/ethanol (1/1/18), dried and heated.) The modified transferrin solution was added quickly (within 10 to 15 minutes) to a solution containing 1.5 $\mu$mol of fluorescein-labelled poly(L)lysine with an average chain length of 190 lysine monomers in 4.5 ml of 100 mM sodium acetate, pH 5. The pH of the solution was adjusted to pH 7.5 by the addition of 1 M sodium bicarbonate buffer. At intervals of 1 hour, 4 batches of 28.5 mg (450 $\mu$mol) of sodium cyanoborohydride were added to the mixture. After 17 hours, 2 ml of 5 M sodium chloride were added to adjust the solution to a total concentration of 0.75 M. The reaction mixture was loaded on a cation exchange column (Pharmacia Mono S HR 10/10) and eluted with a salt gradient of 0.75 M to 2.5 M sodium chloride with a constant content of 25 mM HEPES, pH 7.3. The high salt concentration when loading the column and at the beginning of the gradient was essential for obtaining the polycation conjugates. Some transferrin (about 30%) together with a weak fluorescence activity was eluted in the flow through; the majority of fluorescence-labelled conjugate was eluted at a salt concentration of between 1.35 M and 1.9 M and was pooled in 3 fractions. These fractions (in the sequence in which they were eluted) yielded, after two lots of dialysis against 2 1 25 mM HEPES pH 7.3, a fraction A (TfpL190A) containing 45 mg (0.56 µmol) of transferrin, modified with 366 nmol of polylysine, a fraction B (TfpL190B) containing 72 mg (0.90 µmol) transferrin, modified with 557 nmol polylysine and a fraction C(TfpL190C), containing 7 mg (85 nmol) transferrin, modified with 225 nmol polylysine. If they were not used immediately, the transferrin conjugates were flash-frozen in liquid nitrogen and stored at −20° C. in iron-free form. Before the incorporation of iron, samples (0.5 to 1 mg) were adjusted to a physiological salt concentration (150 mM) with sodium chloride. The iron was incorporated by adding 4 µl of 10 mM iron (111) citrate buffer (containing 200 mM citrate, adjusted to a pH of 7.8 by the addition of sodium bicarbonate) per mg of transferrin content. The conjugates containing iron were divided up into small aliquots before being used for DNA complexing, then flash frozen in liquid nitrogen or dry ice/ethanol and stored at −200° C. (this procedure proved advisable once it was found that repeated thawing and freezing causes the conjugates to lose activity.)

b) Murine transferrin polylysine conjugates

A similar method was used as for human transferrin, in that coupling was effected by means of the carbohydrate side chains. Conjugates of 15.5 nmol murine transferrin and 13 nmol pL290 were obtained from 4.1 mg (51 nmol) of murine transferrin and 2.1 mg (34 nmol) of pL 290.

Plasmid-DNA a) pRSVL-DNA

The DNA plasmid pRSVL (containing the *Pholinus pyralis* luciferase gene under the control of the Rous Sarcoma Virus LTR Enhancer/Promoter (Uchida et al., 1977, De Wet et al., 1987; the disclosures of which are fully incorporated by reference herein), was prepared using the Triton-x Lysis standard method (Maniatis), followed by CsCl/EtBr equilibrium density gradient centrifugation, decolorizing with butanol-1 and dialysis against 10 mM Tris/HCl pH 7.5, 1 mM EDTA). For complex formation, in general, 6 µg of the DNA plasmid material in 350 µl HBS (150 mM NaCl, 20 mM HEPES, pH 7.3) were mixed with 12 µg of transferrin-polylysine conjugate in 150 µl HBS, 30 minutes before adding to the cells.

b) pCMVL-DNA

The plasmid pCMVL (reporter gene construct containing the *Photinus pyralis* luciferase gene under the control of the cytomegalovirus promoter) was prepared by removing the BamHI-Insert of the plasmid pSTCX556 (Severne et al., 1988; the disclosure of which is fully incorporated by reference herein), the plasmid was treated with Klenow fragment and the HindIII/Ssp1 and Klenow-treated fragment from the plasmid pRSVL which contains the sequence coding for luciferase was inserted. pCMVβ gal was described by Macgregor and Caskey (1989); the disclosure of which is fully incorporated by reference herein. DNA preparation was carried out analogously to pRSVL.

Production of Virus Preparations a) Adenovirus preparations

The adenovirus strain d1312 described by Jones and Shenk, 1979, having a deletion in the Ela region was used. Replication of the virus was carried out in the Ela-trans-complementing cell line 293, and the purification was carried out on a large scale as described by Davidson and Hassell, 1987; the disclosure of which is fully incorporated by reference herein. The purified virus was taken up in storage buffer (100 mM Tris, pH 8.0, 100 mM NaCl, 0.1% BSA, 50% glycerol) or in HBS/40% glycerol and aliquots were stored at −70° C. The virion concentration was determined by UV-spectrophotometric analysis of the extracted genomic viral DNA (Formula: one optical density unit (OD, $A_{260}$) corresponds to $10^{12}$ viral particles/ml; (Chardonnet and Dales, 1970)).

b) Retrovirus-Preparation

The Moloney murine leukaemia retrovirus N2 was packaged in an ecotropic packaging line (Keller et al., 1985, Armentano et al., 1987; the disclosures of which are fully incorporated by reference herein). Supernatants from virus expressing cells were collected, flash frozen in liquid nitrogen and stored at −20° C. The supernatants used in the Examples had a titer of approximately $10^6$ cfu/ml, as measured by neomycin-resistance colony formation with NIH3T3 cells. For the virus concentration experiments, the supernatants were passed through a 300 kD exclusion membrane (FILTRON) in an AMICON stirred cell concentrator under nitrogen pressure. Normally, 10 to 30 ml of supernatant were concentrated tenfold by this method.

Cells and Media

HeLa cells were cultivated in DMEM-Medium, supplemented with 5% heat-inactivated fetal calf serum (FCS), penicillin in amounts of 100 I.U./ml, streptomycin (100 µg/ml) and 2 mM glutamine. WI-38, MRC-5, and KB cells were cultivated in EMEM-medium (Eagle's modified essential medium), supplemented with 10% heat inactivated FCS, antibiotics such as DMEM medium, 10 mM non essential amino acids and 2 mM glutamine. CFT1, a respiratory cystic fibrosis epithelial cell line (prepared by the method described by Yankaskas et al., 1991; the disclosure of which is fully incorporated by reference herein; the CFT1 cell line is characterized in that it is homozygous for the δF508 deletion CF-mutation) was cultivated in F12-7X-medium (Willumsen et al., 1989). For the gene transfer experiments the cells were cultivated in 6 cm cell culture plates until they were about 50% confluent ($5 \times 10^5$ cells). The medium was removed and 1 ml of DMEM or EMEM/2% FCS medium was added. Then the conjugate-DNA complexes were added, followed immediately by the adenovirus d1312 ($0.05$–$3.2 \times 10^4$ particles per cell) or a comparable volume of virus storage buffer (1–80 µl). The plates were returned to the incubator for one hour (5% $CO_2$, 37° C.), then 3 ml of complete medium were added. After a further 24 hours' incubation the cells were harvested in order to measure the luciferase gene expression. In the case of the CFT1, the cells were cultivated for 4 hours in F12-7X medium without human transferrin before the gene transfer experiments.

The following cell lines were obtained from ATCC, obtainable under the Catalogue Numbers given; HeLa cells: CCL 2, K562 cells: CCL 243, HepG2 cells: HB 8065, TIB-73-cells: TIB 73 (BNL CL.2), NIH3T3 cells: CRL 1658, 293 cells: CRL 1573, KB cells: CCL 17, WI-38 cells: CCL 75, MRC 5 cells: CCL 171. H9 cells were obtained from the AIDS Research and Reference Reagent Program, U.S. Department of Health and Human Services, Catalogue Number 87.

Primary lymphocytes were obtained by taking up a 25 ml sample of umbilical cord blood in test tubes containing EDTA. Aliquots were underlayed with 4.5 ml of Ficoll-hypaque (Pharmacia) and centrifuged for 15 minutes at 2,500 rpm. The brownish layer between the upper plasma layer and the clear Ficoll layer was removed (about 10 ml). 40 ml of IMDM plus 10% FCS was added, the sample was centrifuged at 1200 rpm for 15 minutes and the cell pellet was suspended in 50 ml of fresh IMDM plus 10% FCS (the cell density was about $2 \times 10^6$ cells/ml). A 250 µl aliquot of phytohaemagglutinin PHA P, DIFCO) was added, the culture was incubated for 48 hours at 37° C. and 5% $CO_2$, the recombinant IL-2 (BMB) was added (concentration: 20 units per ml). The cells were then split 1:3 with IMDM/20% FCS, 2 units/ml IL2. Aliquots of the cells were deep frozen in liquid nitrogen in FCS plus 5% DMSO. Before use, the cells were grown in IMDM plus 20% FCS plus 2 units ml/IL-2.

For the sequential binding investigations HeLa cells were equilibrated at 4° C. in 1 ml DMEM, supplemented with 2% FCS. The conjugate-DNA complexes were added as in the other tests and the plates were incubated for 2 hours at 4° C. Then the plates were exhaustively washed with ice cold DMEM/2% FCS, then 2 ml of this medium were added. Adenovirus d1312 or virus buffer was then added, the cells were left to warn up slowly, before being placed in the incubator for a further 24 hours. After this incubation, the cells were harvested and investigated for luciferase gene expression.

Luciferase Assay

The preparation of cell extracts, standardization of the protein content and determination of the luciferase activity were carried out as described by Zenke et al., 1990, Cotten et al., 1990, and in EP 388 758; the disclosures of which are fully incorporated by reference herein.

Example 1

Figure 1:
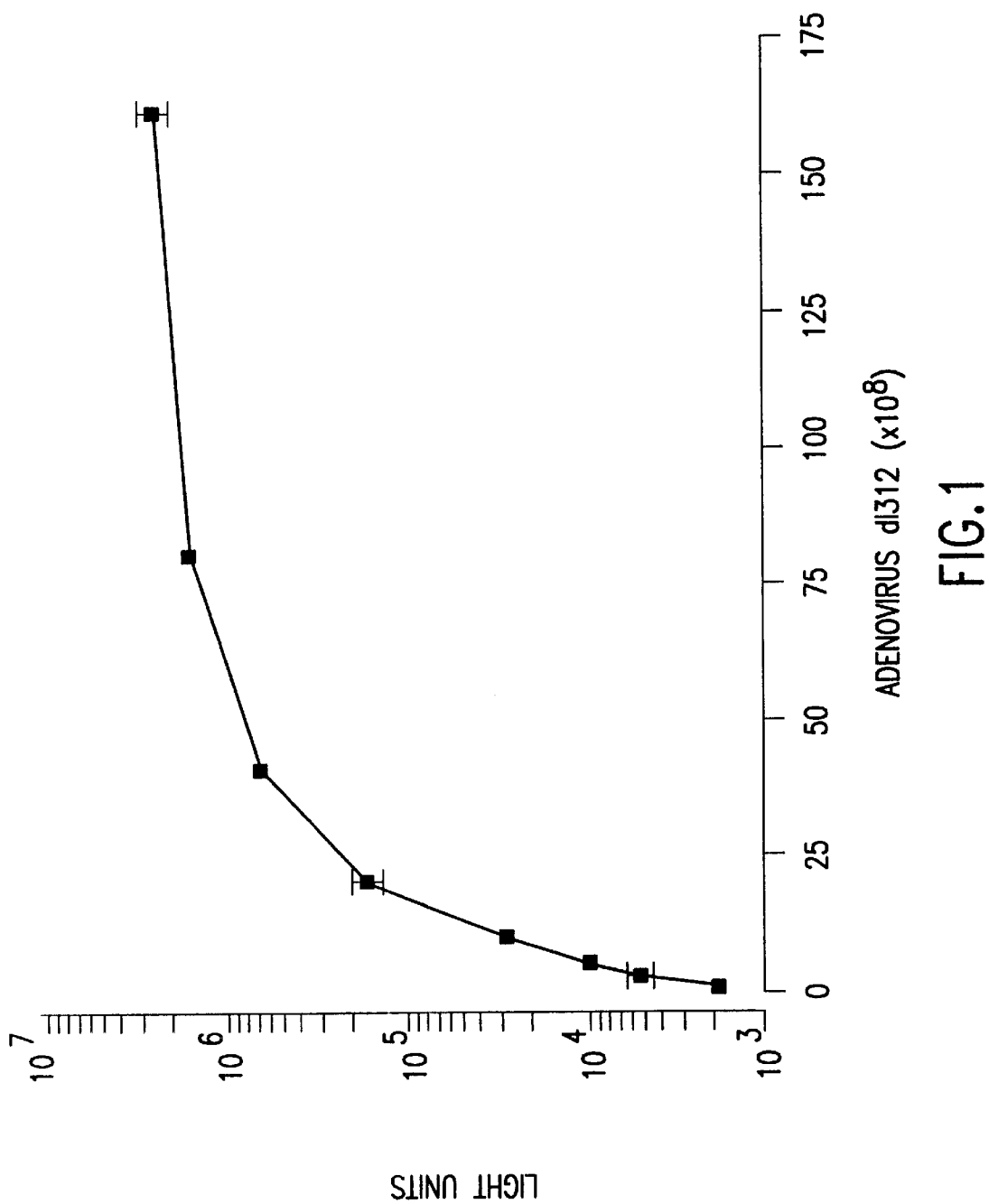
FIG. 1: Effect of adenovirus infection on gene transfer by means of transferrin-polylysine conjugates.

Determination of the Effect of the Adenovirus Treatment on Gene Transfer by Transferrin-Polylysine Conjugates First of all, the effect of an increase in dosage of virus on the ability of a defined amount of conjugate-DNA complex to achieve gene transfer was investigated. For the complex formation, 6 µg of the plasmid pRSVL were mixed with 12 µg of human transferrin-polylysine conjugate (hTfpL190B). The conjugate-DNA complex plus various amounts of the adenovirus d1312 ($0.05-3.2 \times 10^4$ virus particles per cell) were added to the HeLa cells. The results of this analysis are shown in FIG. 1. The luciferase activity is expressed in light units of 50 µg of total cell protein. According to this analysis, increasing amounts of added adenovirus resulted in corresponding increases in gene transfer. The figure shows the averages from 2 to 4 separate experiments; the bars indicate standard deviation.

Example 2

Conjugate-DNA Complex Dosage Effect

Figure 2:
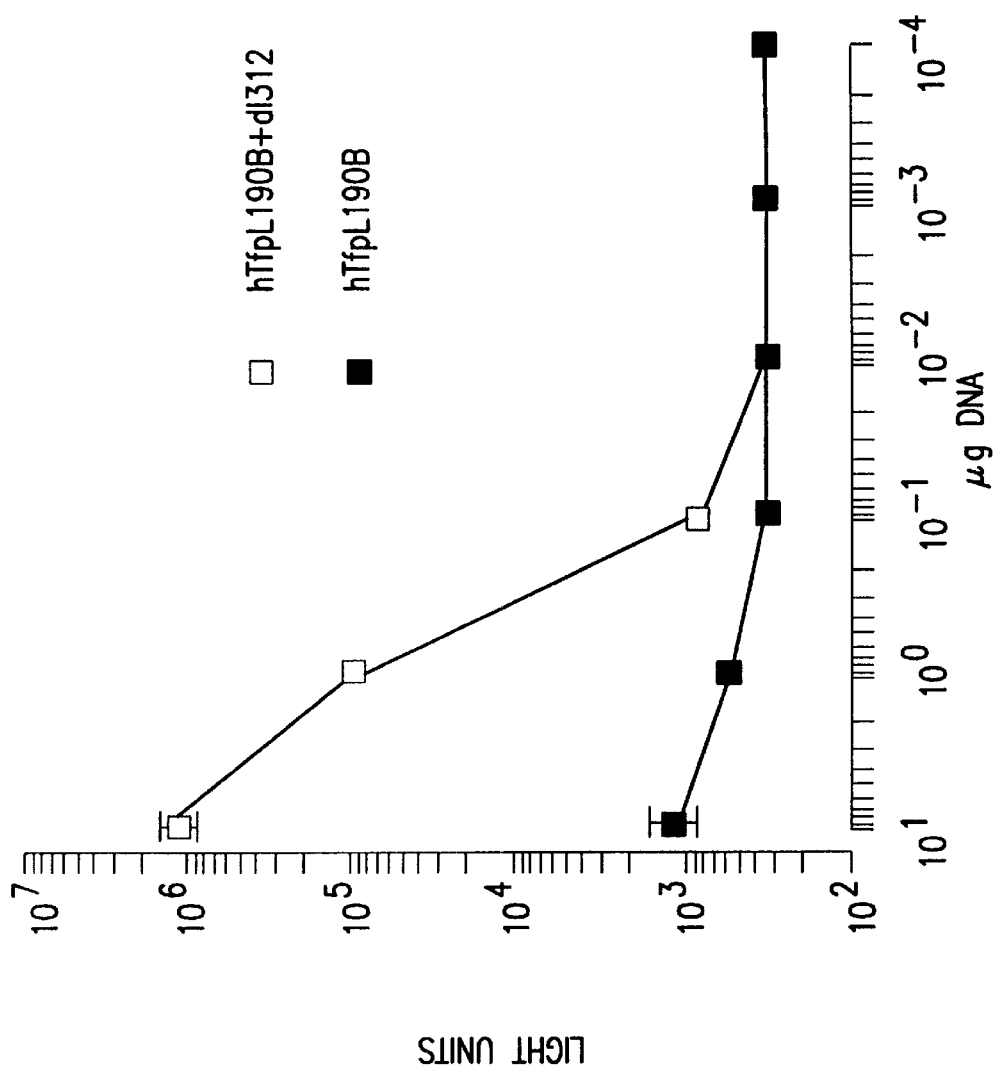
FIG. 2: Conjugate-DNA-complex dosage effect.

Logarithmic dilutions of conjugate-DNA complexes prepared as in Example 1, were added to HeLa cells either with or without the addition of a constant dosage of adenovirus d1312 ($1 \times 10^4$ viral particles per cell). The luciferase activity was determined as in Example 1. The results are shown in FIG. 2.

Example 3

Enhancement of the Gene Transfer Effected by Transferrin Polylysine by Means of Adenovirus Occurs through Receptor-mediated Endocytosis a) Effect of adenovirus treatment on the transfer of the complexed DNA The following components were used for transfection: 6 µg pRSVL-DNA without transferrin-polylysine conjugate (DNA); 6 µg pRSVL-DNA plus 6 µg of non-conjugated polylysine 270 (DNA+pL); 6 µg of pRSVL-DNA plus 12 µg of transferrin-polylysine conjugates used in previous examples (DNA+hTfpL190B). These transfection materials were added to the HeLa cells with or without adenovirus d1312 (dl1312) ($1 \times 10^4$ viral particles per cell). The preparation of the cell extracts, standardization for total protein and determination of the luciferase activity were carried out as in the previous examples. The results of the tests are shown in FIG. 3A.

b) Effect of adenovirus treatment on the transfer of receptor-bound DNA

Conjugate-DNA complexes (DNA+hTfpL190B) or polylysine-DNA complexes (DNA+pL) were bound to HeLa without being internalized, by incubating at 4° C. Non-bound complex was removed before the addition of adenovirus d1312 (dl1312) ($1 \times 10^4$ viral particles per cell) or a comparable buffer volume. Subsequent incubation was carried out at 37° C. in order to permit internalization of the bound DNA complexes and adenoviruses. The luciferase activity was determined as described (FIG. 3B).

c) Effect of adenovirus treatment of gene transfer by transferrin-polylysine conjugates Conjugate-DNA complexes containing 6 µg pRSVL-DNA plus 12 µg transferrin-polylysine (DNA+hTfpL190B) were added to the HeLa cells with $\times 10^4$ adenovirus particles (d1312) per cell or a comparable quantity of heat-inactivated adenovirus d1312 (d1312 h.i.). Heat inactivation was carried out by incubating for 30 minutes at 45° C. (Defer et al., 1990). FIG. 3C shows the luciferase activity.

Example 4

Effect of Adenovirus Treatment on Gene Transfer by Transferrin-polylysine Conjugates in Selected Cell Lines Conjugate-DNA complexes (6 µg pRSVL+12 µg hTfpL190B) were added to cells of the cell lines CFT1, KB, HeLa, W138 and MRC5 with or without adenovirus d1312 ($1 \times 10^4$ virus particles per cell). The efficiency of gene transfer for the various cell lines was determined as in the previous examples by luciferase assay (FIG. 4).

Example 5

Enhancement of Luciferase Gene Expression Functions at the Level of Gene Transfer, Not at the Level of Transactivation A cell line designated K562 10/6 constitutively expressing luciferase was prepared by transfecting cells with a plasmid which contained an RSV-luciferase gene fragment (an Apa1/Pvu1 fragment of pRSVL (De Wet et al., 1987); the disclosure of which is fully incorporated by reference herein), cloned into the Cla1 site of the pUCµ Locus (Collis et al., 1990; the disclosure of which is fully incorporated by reference herein). This plasmid was complexed with a transferrin-polylysine conjugate and K562 cells were transfected with these complexes, using the method described by Cotten et al., 1990; the disclosure of which is fully incorporated by reference herein. Since the pUCµ Locus plasmid contains a neomycin resistance gene it was possible to select for luciferase-expressing clones on the basis of neomycin resistance. For the further experiments, clone K562 10/6 was selected.

Figure 5A:
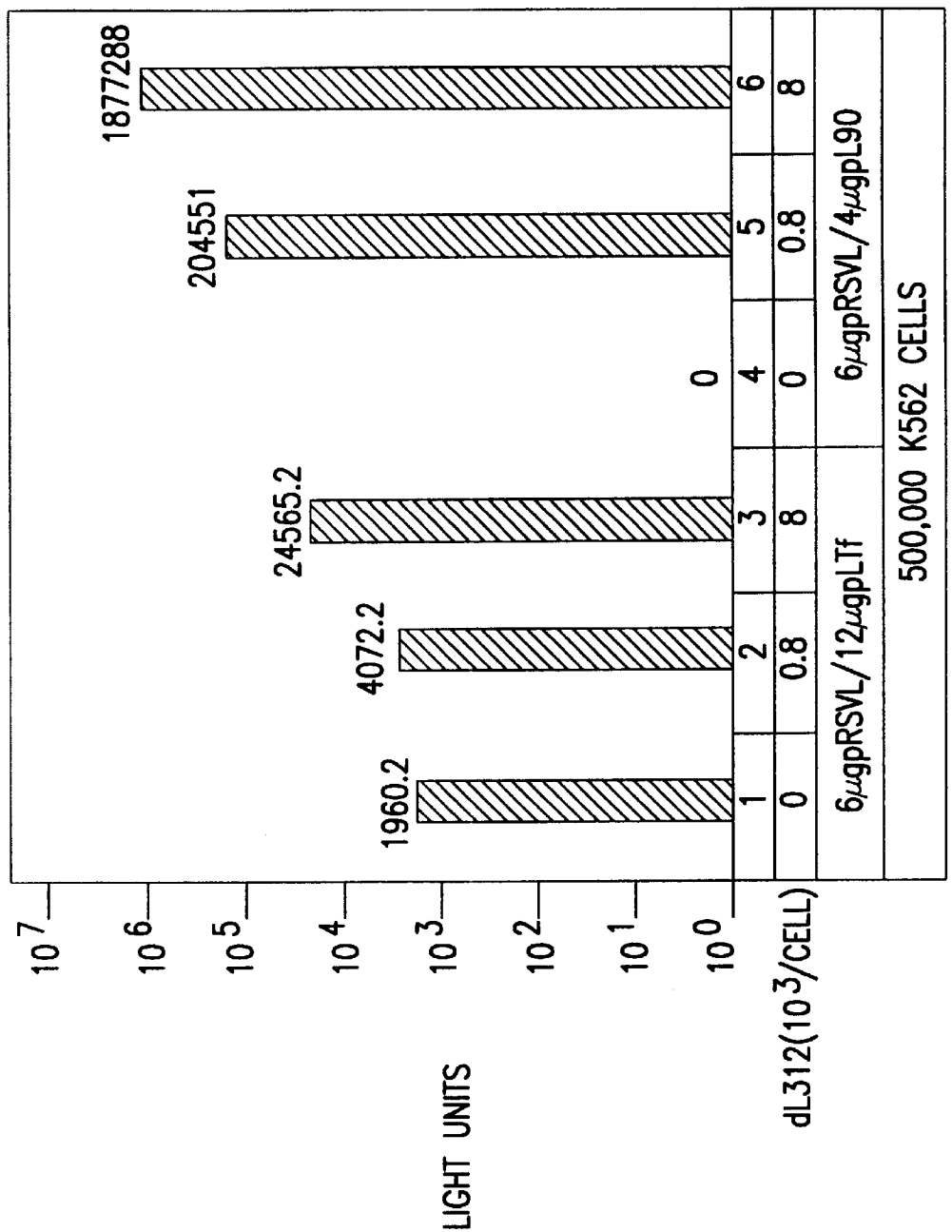

Aliquots of the parental cell line K562 (in 200 µl RPMI 1640 plus 2% FCS; 500,000 cells per sample) were treated either with 12 µg TfpL plus 6 µg pRSVL or with 4 µg pL 90 plus 6 μg pRSVL, in 500 μl HBS in either case. The quantities of adenovirus d1312 specified (FIG. 5) were allowed to act on the cells for 1.5 hours at 37° C., after which 2 ml of RPMI and 10% FCS were added. Then incubation was continued at 37° C. for a further 24 hours and the cells were then prepared for measurement for the luciferase activity. It was found that incubation with adenovirus results in a significant increase in the luciferase activity (FIG. 5A). This applies both to the TfpL complexes (2000 light units as against 25,000 light units) and also to the pL 90 complexes (0 as against $1.9 \times 10^6$ light units). This shows that the K562 cell line has the capacity to internalize pRSVL polylysine complexes and that this internalization, measured by luciferase expression, is significantly increased by the presence of adenovirus.

Figure 5B:
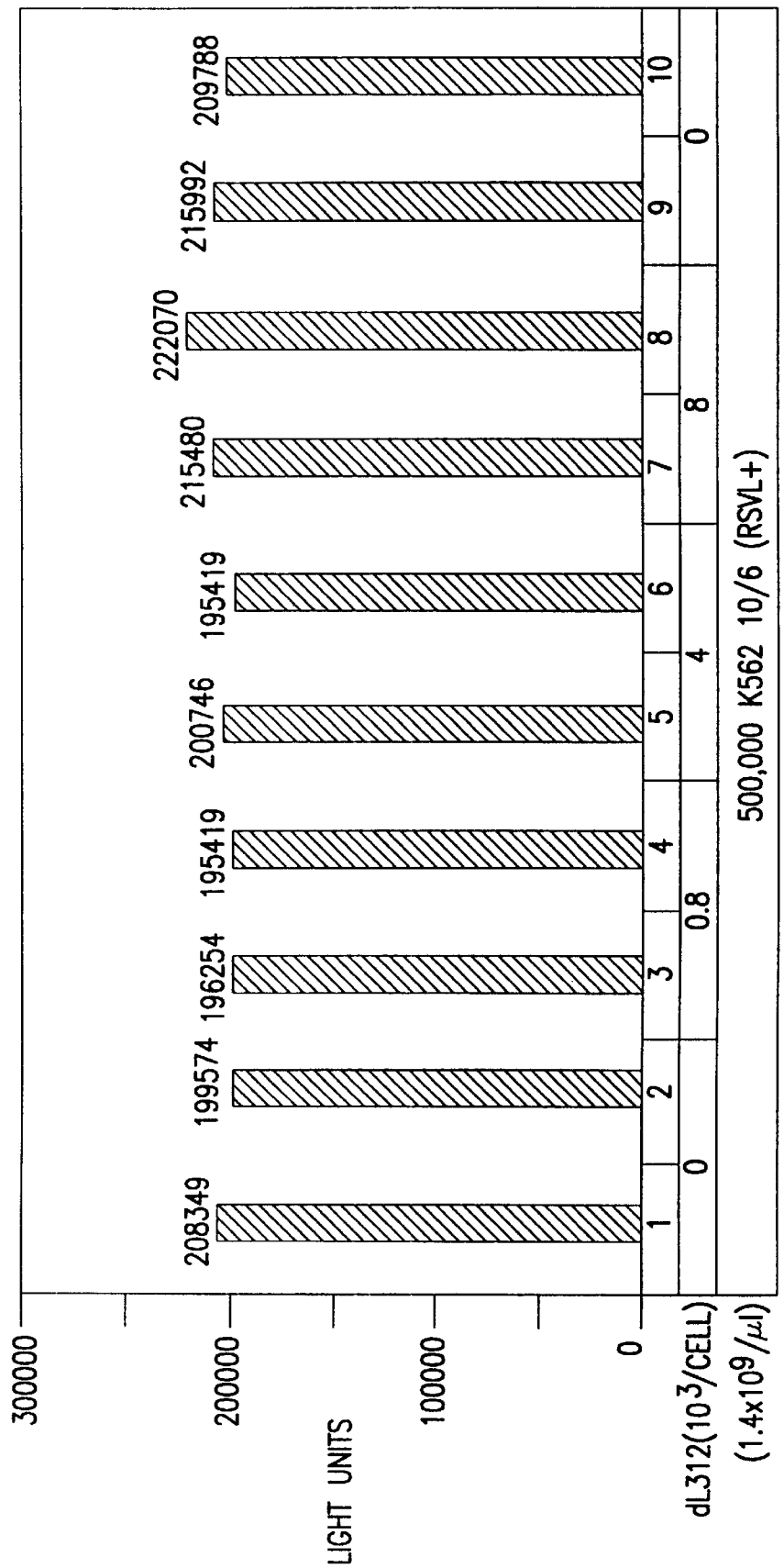

Analogous tests were carried out with the K561 10/6 cells which constitutively express the RSVL luciferase gene, and similar amounts of adenovirus d1312 were used. Aliquots of 500,000 cells (in 200 μl RPMI plus 2% FCS) were incubated at 37° C. for 1.5 hours with the quantities of adenovirus d1312 specified in FIG. 5B. Then, as in the parental cell line RPMI plus 10% FCS was added, incubation was continued for a further 24 hours and the luciferase activity was determined. As shown in FIG. 5B, the treatment of these cells with the adenovirus does not have a detectable effect on the luciferase activity; the control values are in the same range as the values for the virus treated samples.

Example 6

Transfection of Liver Cells with Asialofetuin-polylysine Conjugates (AFpL) or with Tetra-galactose Peptide-pL Conjugates (gal 4pL) in the Presence of Adenovirus a) Preparation of the lactosylated peptide 3.5 mg (1.92 μmol) of the branched peptide Lys-($N_\epsilon$-Lys) Lys-Gly-Ser-Gly-Gly-Ser-Gly-Gly-Ser-Gly-Gly-Cys, prepared by the Fmoc method using an Applied Biosystems 431A Peptide Synthesizer, containing a dithiopyridine group for Cys, were treated with a solution of 7.85 mg of lactose in 40 μl of 10 mM aqueous sodium acetate pH 5 at 37° C. To the solution were added four aliquots of 0.6 mg (10 μmol) of sodium cyanoborohydride at intervals of about 10 hours. After a total of 64 hours at 37° C. 0.5 ml of HEPES pH 7.3 and 15 mg of dithiothreitol (DTT) were added. Fractionation by gel filtration (Sephadex G-10, 12×130 mm Eluent: 20 mM NaCl) under argon yielded 3.6 ml of solution of lactosylated peptide in the free mercapto form (1.74 μmol corresponding to the Ellmann test; 84% yield). The samples of modified peptide showed a color reaction with anisaldehyde but no color reaction with nihydrin; this accords with the assumption that all 4 N-terminal amino groups are lactosylated. The tetra-galactose peptide-polylysine conjugate is shown in FIG. 6.

b) Preparation of 3-dithiopyridinepropionate-modified polylysine

400 μl of a 15 mM ethanol solution of SPDP (6.0 μmol) were added, with intensive mixing, to a gel-filtered solution of 0.60 μmol poly-L-lysine with an average chain length of 290 lysine monomers (pL290, hydrobromide, Sigma) in 1.2 ml of 100 mM HEPES pH 7.9. 1 hour later, 500 μl of 1 M sodium acetate pH 5 were added after gel filtration (Sephadex G-25) with 100 mM sodium acetate, the solution contained 0.56 μmol pL290 with 5.77 μmol of dithiopyridine linker.

c) Conjugation of the Peptide with Polylysine

Conjugates were prepared by mixing 1.5 μmol of the lactosylated peptide prepared in a) in 3 ml of 20 mM NaCl with 0.146 μl of the modified pL290 obtained from b) in 620 μl of 100 mM sodium acetate buffer under an argon atmosphere. After the addition of 100 μl of 2 M HEPES pH 7.9, the reaction mixture was left to stand for 18 hours at ambient temperature. By the addition of NaCl, the salt concentration was adjusted to 0.66 M and the conjugates were isolated by cation exchange chromatography (Pharmacia Mono S column HR 5/5; gradient elution, Buffer A: 50 mM HEPES pH 7.3; Buffer B: Buffer A plus 3 M NaCl). The product fractions eluted at salt concentrations of about 1.2 M–1.8 M and were pooled in two conjugate fractions: the conjugate fractions were named gal4pL1 and gal4pL2. Dialysis against 25 mM HEPES pH 7.3 resulted in the conjugate fractions gal4pL1, containing 24 nmol of modified pL290 and gal4pL2, containing 24.5 nmol of modified pL290.

d) Preparation of asialofetuin conjugates

The conjugates were prepared on the same principle as the transferrin conjugates; a similar method of preparing asialoorosomucoid-polylysine conjugates was described by Wu and Wu in 1988; the disclosure of which is fully incorporated by reference herein.

The coupling of asialofetuin to polylysine was carried out by bonding via disulfide bridges after modification with the bifunctional reagent SPDP (Pharmacia). A solution of 100 mg (2.2 μmol) of asialofetuin (Sigma) in 2 ml of 100 mM HEPES pH 7.9 was subjected to gel filtration on a Sephadex G-25 column. 330 μl of a 15 mM ethanolic solution of SPDP (5.0 μmol) were added to the resulting 4 ml solution with vigorous stirring. After 1 hour at ambient temperature, purification was carried out by another gel filtration (Sephadex G-25); this resulted in 5 ml of a solution of 1.4 μmol asialofetuin, modified with 2.5 μmol of dithiopyridine linker.

Conjugates were prepared by mixing 1.4 μmol of asialofetuin in 5 ml of 100 mM HEPES pH 7.9 with 0.33 μmol of modified pL190 (containing 1.07 μmol of mercaptopropionate groups; the same process was used as for the preparation of the transferrin conjugates) in 6.5 ml of 200 mM HEPES pH 7.6, under an Argon atmosphere. The reaction mixture was left to stand for 24 hours at ambient temperature. The conjugates were isolated from the reaction mixture by cation exchange chromatography (Pharmacia Mono S-column HR 10/10; gradient elution, Buffer A: 50 mM HEPES pH 7.9; Buffer B: Buffer A plus 3 M sodium chloride) and sodium chloride was added until a final concentration of 0.6 M was achieved before loading the column. The product fraction eluted at a salt concentration of about 1.5 M. Dialysis with HBS yielded conjugates containing 0.52 μmol of asialofetuin, modified with 0.24 μmol of pL190.

e) Transfection of HepG2 cells with pRSVL-DNA complexes

HepG2 cells were grown in DMEM medium plus 10% FCS 100 I.U./ml penicillin, 100 μg/ml streptomycin and 2 mM glutamine in T25 flasks. Transfections were carried out at a density of 400,000 cells per flask. Before the transfection, the cells were washed with 4 ml of fresh medium containing 10% FCS. Immediately before the transfection, chloroquine (Sigma) was added so that the final concentration in the cell suspension (plus DNA solution) was 100 μM.

10 μg pRSVL-DNA in 330 μl HBS were, mixed with the quantities of TfpL190B conjugate (TfpL), asialofetuin pL90 conjugate (AFpL), polylysine 290 (pL) or Tetra-galactosepeptide polylysine conjugate gal4pL specified in FIG. 7 in 170 μl of HBS. In the competition experiments, 240 μg of asialofetuin ((gal)4pL+Af) or 30 μg lactosylated peptide ((gal)4pL+(gal)4) were added after 30 minutes. The mixture was added to the cells; the cells were incubated at 37° C. for 4 hours, then the transfection medium was replaced by 4 ml of fresh DMEM medium plus 10% FCS. After 24 hours the cells were harvested for the luciferase assay. The values given in FIG. 7, represent the total luciferase activity of the transfected cells as shown in the figure, pL and TfpL show slight luciferase activities; (gal) 4pL shows values as high as AfpL; (gal)4 or Af compete for the asialoglycoprotein receptor and, as expected, lower the values.

f) Transfection of HepG2 cells with pCMVL-DNA complexes

HepG2 cells were grown in 6 cm plates to a cell density of 300,000 cells per plate, as described in e). Before transfection, the cells were washed with 1 ml of fresh medium containing 2% of FCS.

6 μg of pCMVL-DNA in HBS were mixed with the quantities of TfpL10B conjugate (TfpL), asialofetuin-pL conjugate (AFpL), polylysine290 (pLys290), (gal)4pL1 or (gal)4pl2 specified in FIG. 8, in 170 μl HBS. After 30 minutes, 1 ml of DMEM, containing 2% FCS and 50 μl adenovirus stock solution d1312C, were added to each DNA-conjugate complex. In the competition experiments, 30 μg of lactosylated peptide (gal)4pL ((gal)4pL1+(gal)4 or (gal)4pL2+(gal)4) were added, as specified. The mixture was added to the cells; the cells were incubated for 2 hours at 37° C., then 1.5 ml of medium, containing 10% FCS were added. Two hours later, the transfection medium was replaced by 4 ml of fresh DMEM medium plus 10% FCS. After 24 hours the cells were harvested for the luciferase assay; the values in FIG. 8, represent the total luciferase activity of the transfected cells. pLys290 exhibits an effect, gal)4pL exhibits a stronger effect; an addition of (gal)4, which competes for the asialoglycoprotein receptor, reduces the values to the value obtained for polylysine.

g) Transfection of TIBB73 cells with pCMVL-DNA complexes

Cells of the embryonic murine liver cell line ATCC TIB73 (BNL CL.2; Patek et al., 1978; the disclosure of which is fully incorporated by reference herein) were grown at 37° C. in a 5% $CO_2$ atmosphere in "high glucose" DMEM (0.4% glucose), supplemented with 10% heat-inactivated FCS containing 100 I.U./ml penicillin, 100 μg/ml streptomycin and 2 mM glutamine in 6 cm plates.

The transfections were carried out at a cell density of 300,000 cells per plate. Before the transfection, the cells were washed with 1 ml of fresh medium plus 2% of FCS.

Figure 9B:
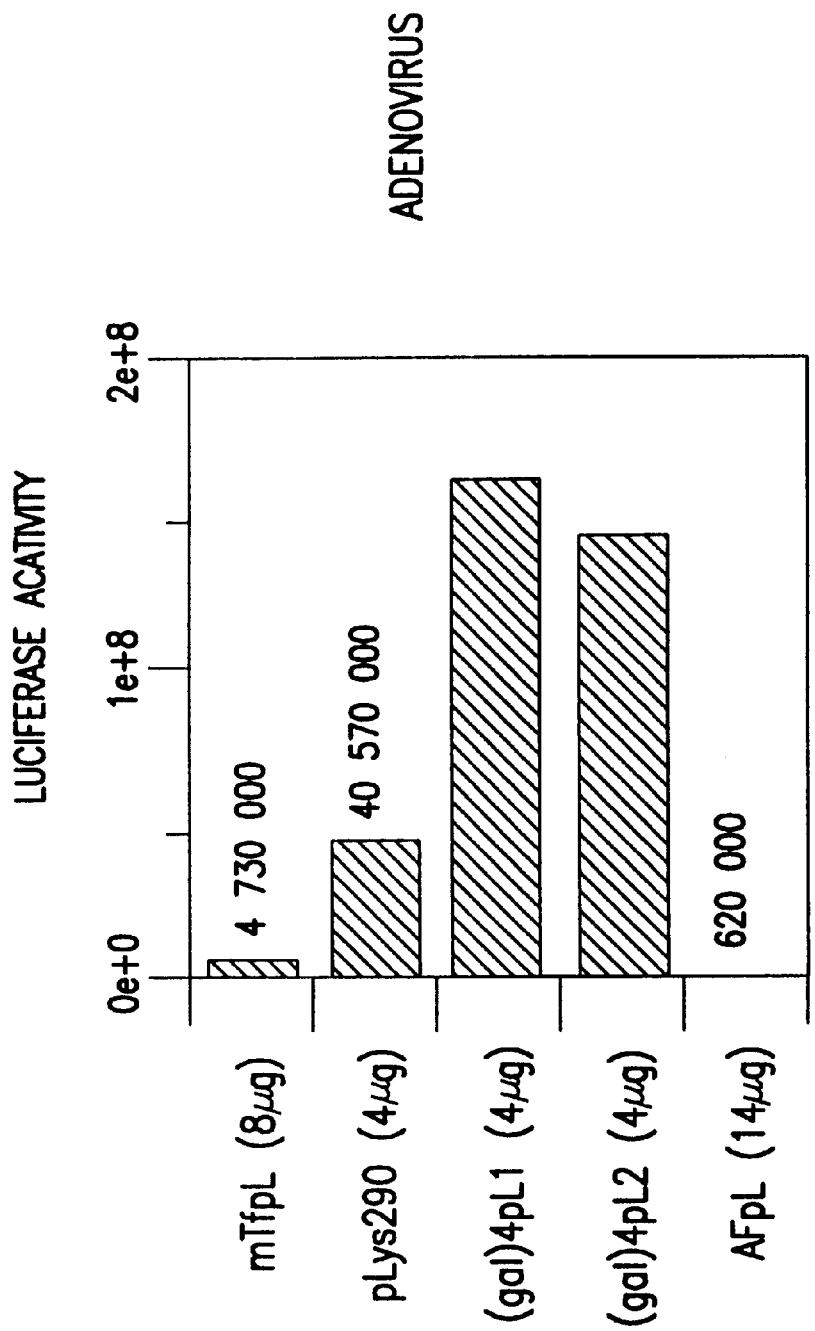

6 μg pCMVL-DNA in 300 μl HBS were mixed with the specified amounts of murine transferrin-polylysine290 conjugate (mTfpL), asialofetuin-pL conjugates (AFpL), polylysine290 (pLys290), (gal)4pL1 or (gal)4pL2 in 170 μl HBS. After 30 minutes, 1 ml of DMEM, containing 2% FCS and 50 μl of adenovirus stock solution d1312 were added to each DNA conjugate complex. The mixture was added to the cells, the cells were incubated for 2 hours at 37° C., then 1.5 ml of medium containing 10% FCS. Two hours later, the transfection medium was replaced by 4 ml of fresh medium. After 24 hours the cells were harvested for the luciferase assay; the values shown in FIG. 9B represent the total luciferase activity of the transfected cells.

As a comparison, transfection was carried out without adenovirus in the presence of chloroquine: the transfection was performed at a cell density of 300,000 cells per plate. Before the transfection, the cells were washed with 1 ml of fresh medium containing 2% FCS. Immediately before transfection, chloroquine (Sigma) was added so that the final concentration in the cell suspension (plus DNA-solution) was 100 μM. 6 μg of pCMVL-DNA in 330 μl HBS were mixed with the specified amounts of mTfpL, AFpL, pLys290, (gal)4pL1 or (gal)4pL2 in 170 μl of HBS. After 30 minutes the DNA complexes were added to the cells. The cells were incubated for 2 hours at 37° C., then 1.5 ml of medium containing 10% of FCS and 100 μM chloroquine were added. Two hours later the transfection medium was replaced by 4 ml of fresh medium. After 24 hours the cells were harvested for the measurement of luciferase. The values obtained for the luciferase activity are shown in FIG. 9A.

Example 7

Introduction of DNA in T Cells a) Preparation of antiCD7 Polylysine190 conjugates A solution of 1.3 mg of antiCD7 of antibody (Immunotech) in 50 mM HEPES pH 7.9 was mixed with 49 μl 1 mM ethanolic solution of SPDP (Pharmacia). After 1 hour at ambient temperature the mixture was filtered over a Sephadex G-25 gel column (eluent 50 mM HEPES Buffer pH 7.9), thereby obtaining 1.19 mg (7.5 nmol) of antiCD7, modified with 33 nmol pyridyldithiopropionate groups. Poly (L)lysine190, fluorescent labelled using FITC, was modified analogously with SPDP and brought into the form modified with free mercapto groups by treating it with dithiothreitol and subsequent gel filtration. A solution of 11 nmol of polylysine190, modified with 35 nmol mercapto groups, in 0.2 ml of 30 mM sodium acetate buffer was mixed with modified antiCD7 (in 0.5 ml 300 mM HEPES pH 7.9) with the exclusion of oxygen, and left to stand overnight at ambient temperature. The reaction mixture was adjusted to a content of about 0.6 M by the addition of 5 M NaCl. Isolation of the conjugates was carried out by ion exchange chromatography (Mono S, Pharmacia, 50 mM HEPES pH 7.3, salt gradient 0.6 M to 3 M NaCl); after dialysis against 10 mM HEPES pH 7.3, corresponding conjugates were obtained consisting of 0.51 mg (3.2 nmol) of antiCD7-antibody, modified with 6.2 nmol polylysine190.

b) Preparation of gp120-Polylysine 190 conjugates

Coupling was carried out by methods known from the literature by thioether-linking after modification with N-hydroxysuccinimide ester of 6-maleimidocaproic acid (EMCS, Sigma) (Fujiwara et al., 1981; the disclosure of which is fully incorporated by reference herein).

Figure 10B:
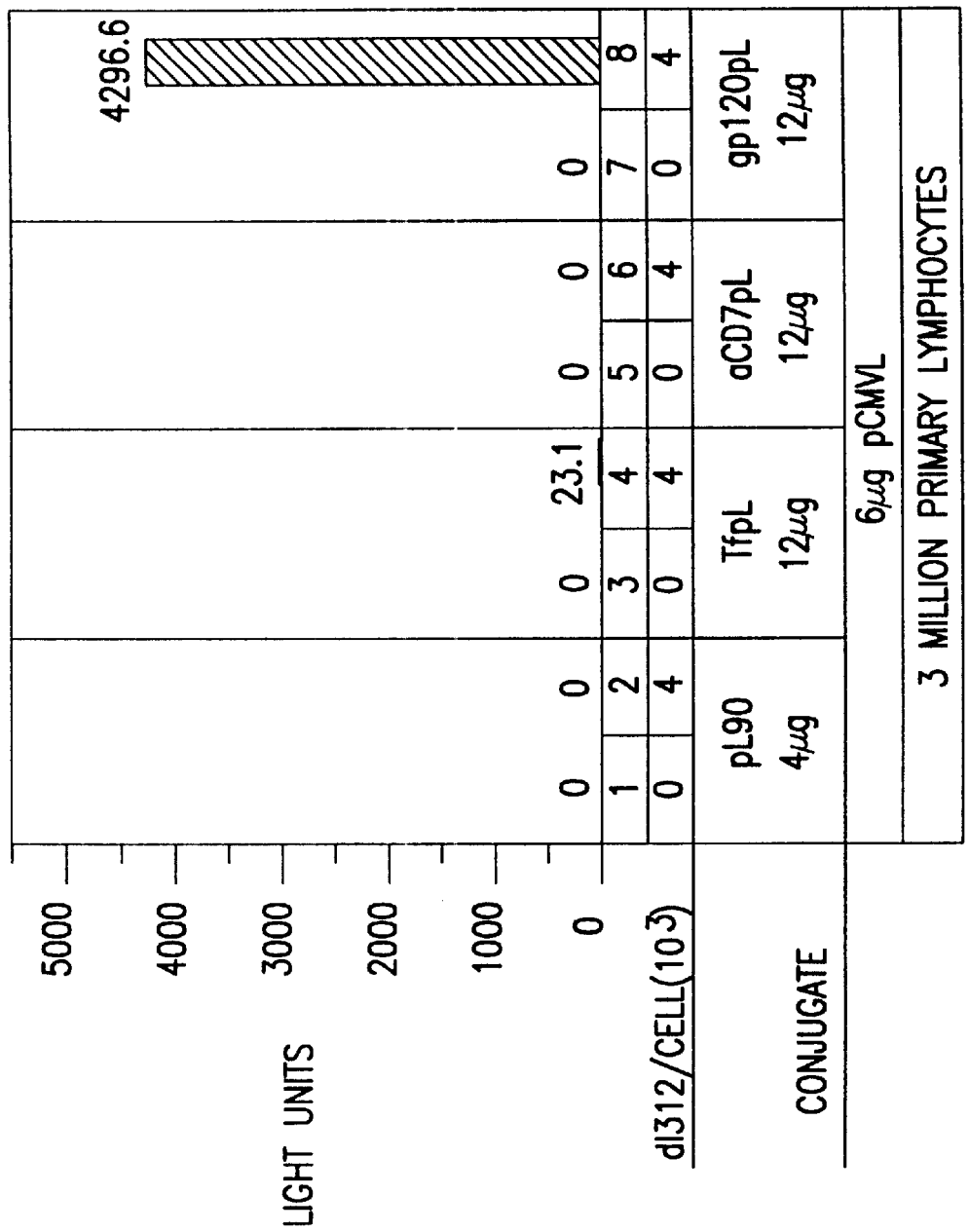

Thioether-linked gp120-Polylysine 190-conjugates:

A solution of 2 mg of recombinant gp120 in 0.45 ml of 100 mM HEPES pH 7.9 was mixed with 17 μl of a 10 mM solution of EMCS in dimethylformamide. After 1 hour at ambient temperature, filtration was carried out over a Sephadex G-25 gel column (eluent 100 mM HEPES-Buffer 7.9). The product solution (1.2 ml) was immediately reacted, with the exclusion of oxygen, with a solution of 9.3 nmol Polylysine 190, fluorescence-labelled and modified with 30 nmol mercapto groups (in 90 μl 30 mM sodium acetate pH 5.0), and left to stand overnight at ambient temperature. The reaction mixture was adjusted to a content of about 0.6 M by the addition of 5 M NaCl . The conjugates were isolated by ion exchange chromatography (Mono S, Pharmacia 50mM HEPES pH 7.3, salt gradient 0.6 M to 3 M NaCl); after fractionation and dialysis against 25 mM HEPES pH 7.3, 3 conjugate fractions A, B and C were obtained, consisting of 0.40 mg of rgp120 modified with 1.9 nmol polylysine 190 (in the case of Fraction A), or 0.25 mg rgp120 modified with 2.5 nmol polylysine 190 (Fraction B), or 0.1 mg rgp120 modified with 1.6 nmol of polylysine 190 (Fraction C).

pCMVL-DNA (6 $\mu$g/sample) were complexed with the specified amounts of polylysine90 or the specified polylysine conjugates in 500 $\mu$l HBS. In the meantime, aliquots of H9 cells ($10^6$ cells in 5 ml of RPMI with 2% FCS) or primary human lymphocytes ($3 \times 10^6$ cells in Iscove's modified Dulbecco's medium (IMDM) plus 2% FCS) were prepared. The polylysine-DNA complexes were added to each cell sample. 5 minutes later, the specified amount of adenovirus dl312 was added. The cells were then incubated for 1.5 hours at 37° C., then 15 ml of RPMI (in the case of H9 cells) or IMDM (in the case of the primary lymphocytes) plus 20% FCS were added to each sample. The cells were incubated for 24 hours at 37° C., harvested and treated as in the other examples, to determine the luciferase activity. The results of the tests carried out are given in FIG. 10A (H9 cells) and FIG. 10B (primary lymphocytes): in H9 cells, the antiCD7 conjugate (FIG. 10A, lanes 7 to 9) and the gp120 conjugate (lanes 10 to 12) showed the best results in terms of the gene transfer achieved with adenovirus, while the gp120 conjugate achieved a clear expression of the luciferase gene even in the absence of adenovirus. It is worth noting that, in the tests carried out, only the gp120 conjugate had the ability to introduce DNA into primary lymphocytes, and then only in the presence of defective adenovirus (FIG. 10B, lanes 7 and 8).

Example 8

Inactivation of Adenoviruses a) UV Inactivation

An adenovirus dl312 preparation, prepared and stored as described in the introduction to the Examples, was placed in 2 cm diameter wells of a cell culture plate (300 $\mu$l per well) on ice at an 8 cm spacing from 2 UV lamps (Philips TUV15 (G15 T8) lamps). The virus was exposed to the UV radiation for the times specified in FIG. 11A and aliquots of each preparation were investigated for their virus titer and to determine whether and to what extent they were capable of augmenting gene transfer with polylysine-transferrin conjugates into HeLa cells.

Figure 11A:
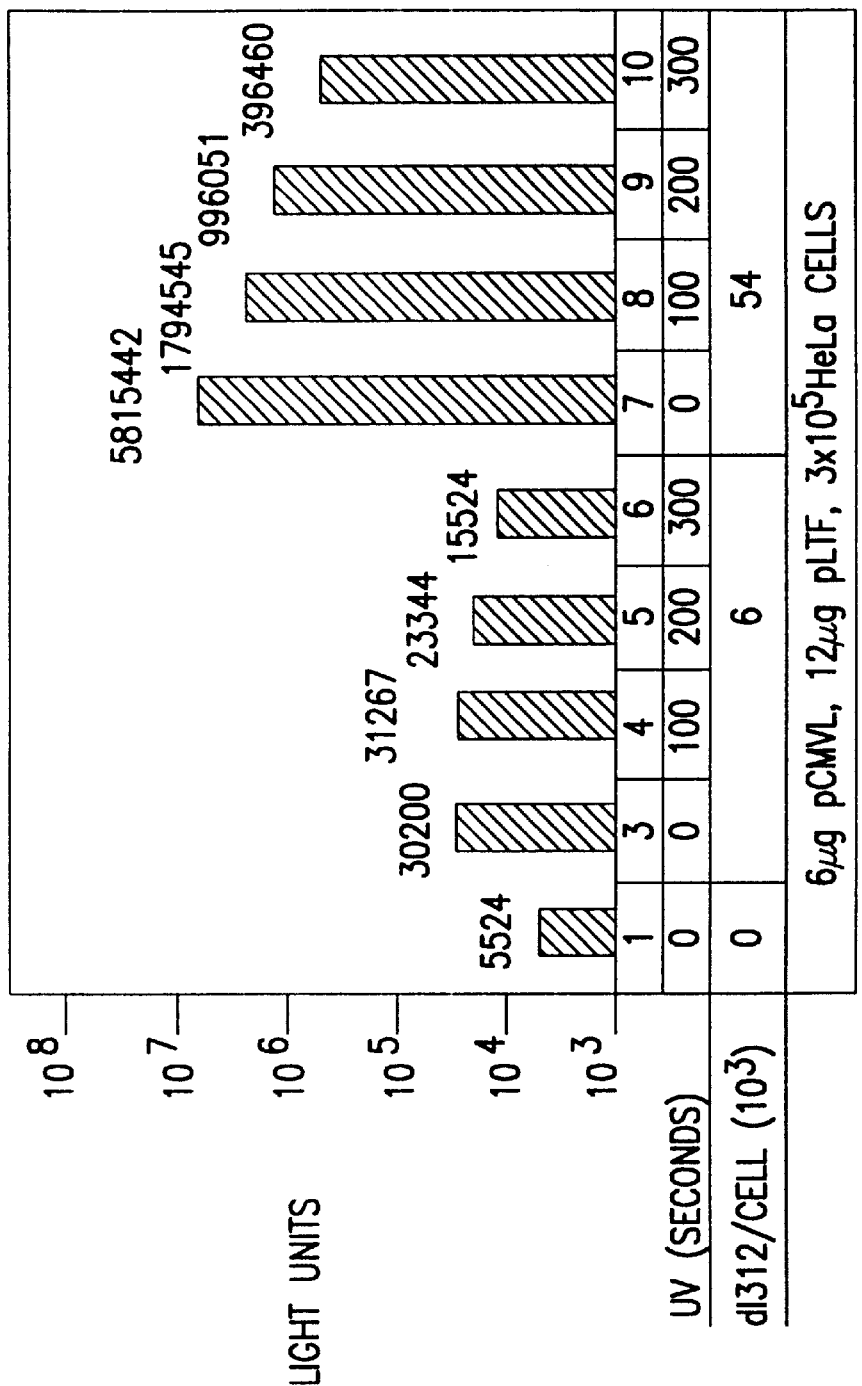
Figure 11B:
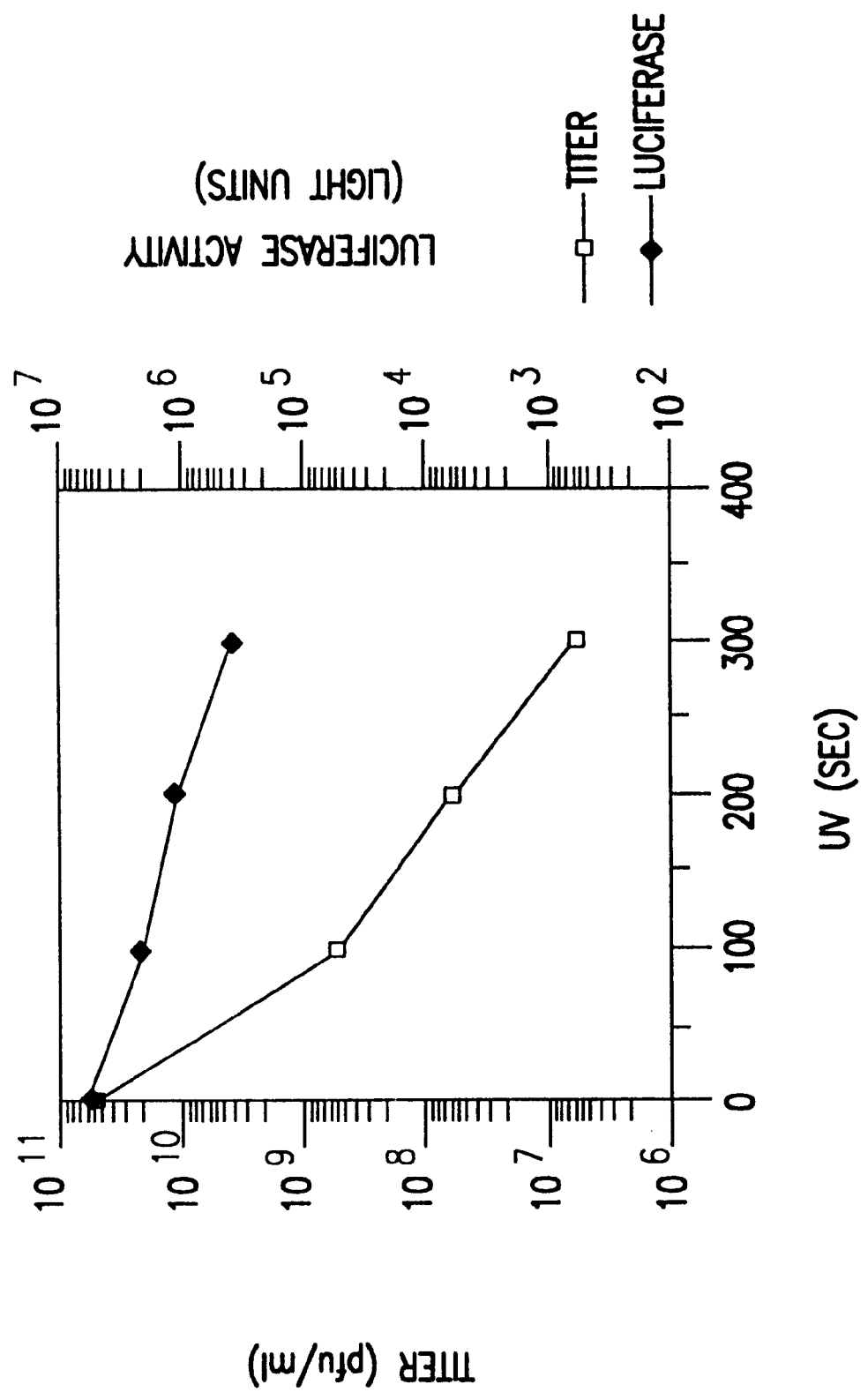

The cultivation of the cells and the transfection were carried out essentially as described above under "cells and media"; the components used for transfection are shown in FIG. 11A. The complexes of pCMVL-DNA and 12 $\mu$g TfpL were prepared in 500 $\mu$l HBS and added to $3 \times 10^5$ HeLa cells (in 1 ml DMEM plus 2% FCS). About 5 minutes later, 54 $\mu$l of each virus preparation was added to each culture and the culture was incubated at 37° C. for one and a half to two hours. Then a 5 ml aliquot of DMEM plus 10% FCS was added to each culture, incubation was continued at 37° C. for 24 hours and the cultures were harvested and investigated for luciferase activity. The quantity of 54 $\mu$l of non-irradiated virus is not in the saturation range, i.e. the test is sensitive to a quantity of virus at least 3 times greater. The results obtained for the luciferase expression are shown in FIG. 11B (shaded rectangles). The virus titer of each preparation was determined using the E1a complementing cell line 293. Serial dilutions of the non-irradiated and irradiated virus samples were prepared in DMEM plus 2% FCS. Parallel to this, samples of $5 \times 10^4$ 293 cells were prepared (in a 2 cm well) in 200 $\mu$l DMEM plus 2% FCS. A 5$\mu$l aliquot of each dilution was placed in each well. In order to allow the virus to bind to the cells, incubation was carried out at 37° C. for one and a half hours, then 2 ml of DMEM plus 10% FCS were placed in each well. 48 Hours later, the cultures were examined in order to determine the cytopathic effect. The virus dilution above which less than 50% of the cells in the culture show a significant cytopathic effect after 48 hours indicates the relative amount of infectious virus in each virus preparation. The results obtained are shown in FIG. 11B (open rectangles). The results of the tests carried out in this Example, show the decrease of 4 logs in the virus titer resulting from UV radiation is associated with only a twentyfold reduction in the luciferase gene transfer. This demonstrates that mechanisms which are crucial to the infectivity of the virus can be destroyed without affecting the ability of the virus to augment gene transfer.

It was observed that at low doses of the virus, the increase in gene transfer caused by the virus fell slightly (FIG. 11A, lanes 3 to 6) and that this effect was more significant at the high doses (lanes 7 to 10).

b) Inactivation of Adenoviruses with Formaldehyde 2 ml of adenovirus preparation were passed over a 10 ml G25 column (Pharmacia Sephadex G 25, PD10), pre-equilibrated with 150 mM NaCl, 25 mM HEPES pH 7.9, 10% glycerol, and taken up in a volume of 2.5 ml. Aliquots of the gel-filtered virus preparation were incubated without (0), with 0.01%, 0.1% or 1% formaldehyde for 20 hours over ice. Then Tris pH 7.4 was added to give a concentration of 100 mM, then the samples were dialyzed first for 2 hours against 1 liter of 150 mM NaCl, 50 mM Tris pH 7.4 and 50% glycerol and then overnight against $2 \times 1$ liter 150 mM NaCl, 20 mM HEPES pH 7.9 and 50% glycerol.

Aliquots of the virus were then examined for their titer on 293 cells (CPE endpoint assay or plaque assay, Precious and Russel, 1985). Then the effect of the formaldehyde-treated viruses on gene transfer into HeLa cells (300,000) was determined as in the previous examples by measuring the luciferase activity. 90 $\mu$l of the virus preparation, resulted in a DNA transfer corresponding to more than $10^8$ light units. Treatment of the virus with 0.01 % or with 0.1% formaldehyde resulted in a slight reduction in gene transfer activity (approximately tenfold reduction at 0.1%). Although the treatment with 1% formaldehyde causes a striking loss of gene transfer activity, 90 $\mu$l of the virus was still able to produce a gene expression corresponding to $10^4$ light units.

Figure 12A:
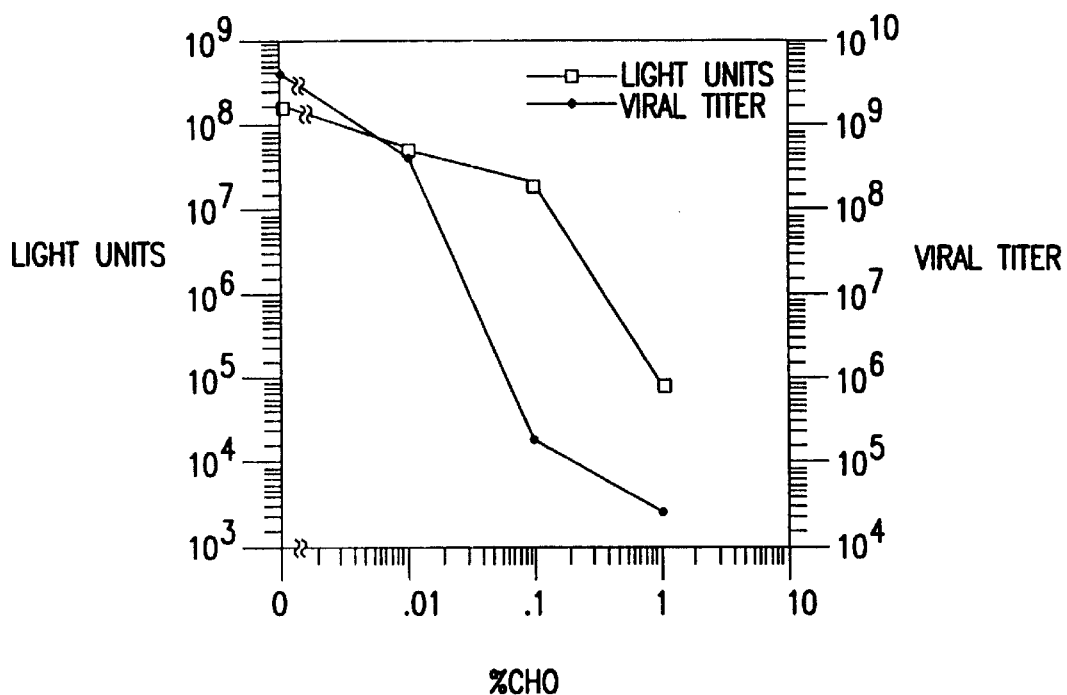

In the treatment with 0.1% formaldehyde, a reduction in the virus titer to $10^5$ PFU (plaque forming units) was coupled with a decrease in the luciferase activity of only 10%. The results of the test are shown in FIG. 12A.

c) Inactivation of Adenoviruses with long-wave UV+8-methoxy psoralen treatment

Aliquots of purified virus were adjusted to 0.33 $\mu$g/$\mu$l 8-methoxy psoralen (stock concentration 33 $\mu$g/$\mu$l 8-methoxy psoralen dissolved in DMSO) and exposed to a 365 nm UV light source (UVP model TL-33), on ice, at a distance of 4 cm from the lamp filter. Exposure to the UV light was for 15–30 minutes, as indicated in the figure legends. The virus samples were then passed over a Sephadex G-25 column (Pharmacia, PD-10) equilibrated with HBS+40% glycerol and stored at −70° C.

Figure 12B:
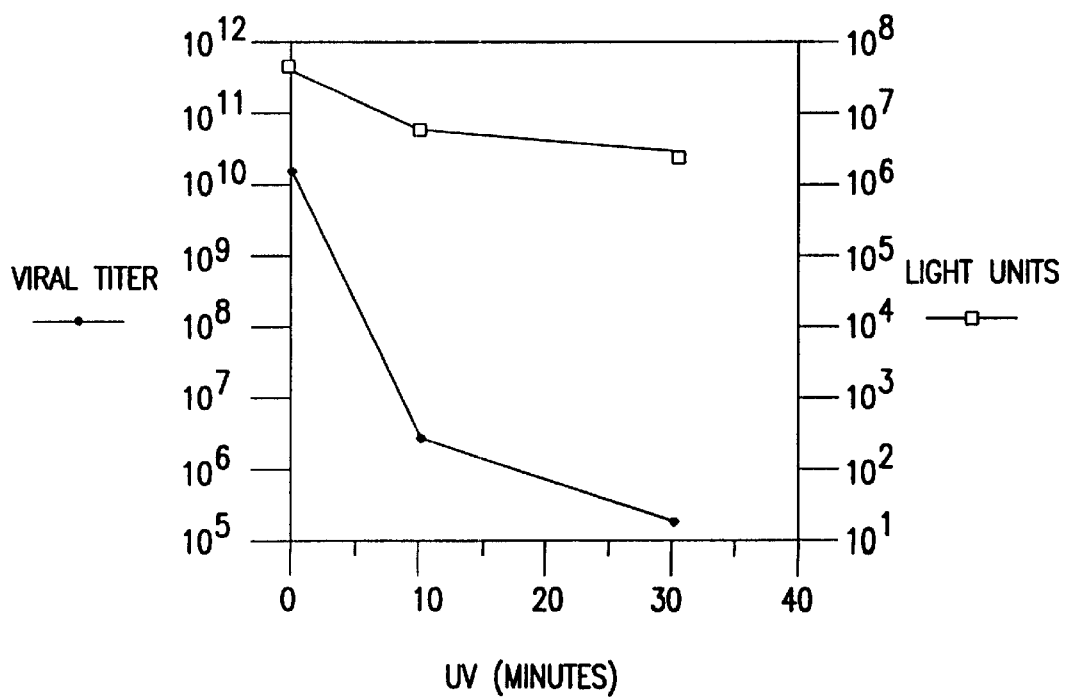

Viral preparations were tested for either their activity in augmenting pCMVL/hTfpL conjugate delivery into HeLa cells (as evidenced by the resulting light units of luciferase activity, right-hand axes FIG. 12B) or for the ability to replicate in 293 cells (viral titer, left-hand axes FIG. 12B).

In the Examples which follow, illustrating the increase in the internalization of transferrin-polylysine-DNA complexes by means of retroviruses, the following materials and methods were used:

Transferrin-polylysine190 conjugates and conjugate-DNA complexes were prepared analogously to the preceding Examples.

NIH3T3 cells were grown in DMEM medium with the addition of 10% FCS, 100 I.U./ml penicillin, 100 μg/ml streptomycin and 2 mM glutamine. For the transfections, 5 to $7 \times 10^5$ cells per T25 were plated out 18 to 24 hours before transfection. Immediately before transfection, the cells were placed in fresh medium and the various components used for transfection were added in the following order: Chloroquine (100 μM, where stated), polylysine-transferrin-DNA complex and retrovirus preparation. The cells were then incubated for 4 hours at 37° C., and the medium was changed and the cells were harvested 24 hours later. Extracts were prepared using three freeze/thaw cycles; aliquots of the extract, standardized for of protein content, were examined for luciferase activity as stated in the preceding Examples.

Example 9

Transfection of NIH3T3 Cells with Moloney Virus

Under the conditions specified, transfections of $10^6$ NIH3T3 cells were carried out with TfpL-DNA complexes in the presence of 100 μM chloroquine or without chloroquine as shown in FIG. 13. It was found that without chloroquine the values for the luciferase activity reached only a background level (lane 1), whereas in the presence of chloroquine a high expression of the pRSVL reporter gene was measured (lane 2). Increasing amounts of the Moloney leukaemia virus (designated RVS in the Figure), which were added to the cells at the same time as the DNA complexes, were able to increase the luciferase gene expression still further.

Example 10

Investigation into Whether the Gene Transfer Effect in the Transfection of NIH3T3 Cells with Transferrin-polylysine DNA Complexes Can be Attributed to Moloney Virus The virus preparation used in Example 9 was a crude, unfractionated supernatant of retrovirus expressing cells. In order to obtain evidence that the increase in the DNA transfer achieved with this virus preparation could actually be ascribed to the virus, the supernatant was subjected to the dialysis/concentration purification described above, the retrovirus supernatant (shown as RVS in the drawing) being concentrated by a factor 10. If the retrovirus is responsible for the increase, the activity retained by the membrane, apart from any inactivation of the extremely unstable retrovirus during the concentration step, should be approximately 10 times that of the original supernatant. As in the previous Example, $10^6$ NIH3T3 cells were transfected under the conditions given in FIG. 14. FIG. 14 shows that the gene transfer increasing effect is present in the membrane retentate (20 to 600 μl were used, lanes 3 to 6). It was also found that 200 and 600 μl of the ten fold concentrated preparation are about half as active as 2 or 6 ml of the original, unconcentrated retrovirus preparation (lanes 7 and 8). Parallel tests were carried out with human K562 cells having no receptor for the ecotropic murine retrovirus. As expected, there was no increase in gene expression.

Example 11

Interactions between Transferrin and its Receptor Play a Role in the Gene Transfer Effect of Moloney Virus In order to rule out the possibility that the transfer of TfpL/pRSVL complexes into the cells can be ascribed to non-specific binding of polylysine to the retrovirus, and in order to clarify the entry mechanism further, the retrovirus was examined for its ability to transport plasmid DNA, complexed only with polylysine, into the cell. The quantity of polylysine used corresponds to the optimum amount determined earlier which brings about total condensation of the plasmid DNA and is similar to the quantity of the polylysine used with the polylysine-transferrin conjugate (Wagner et al., 1991a; the disclosure of which is fully incorporated by reference herein). The tests, the results of which are shown in FIG. 15, demonstrated that the reporter gene, in the absence of chloroquine, is not expressed either in the form of TfpL-RSVL complexes or in the form of pL-pRSVL complexes (lanes 1 and 2). In the presence of the retrovirus, on the other hand, the reporter DNA applied as a TfpL complex was expressed, but not in the form of pL-DNA complex (see lanes 3 and 4 together with lanes 5 and 6). Moreover, the tests carried out showed that the presence of excess free transferrin resulted in the reduction in the DNA transfer facilitated by the retrovirus (lanes 7 and 8). These results support the proposition that interactions between transferrin and its receptor play an essential part in augmenting the DNA uptake effected by the retrovirus.

Example 12

Influence on pH on the Gene Transfer Effect of Retroviruses

The experiments carried out in this Example were performed in order to examine the influence of the pH on the ability of retroviruses to augment gene transfer. The transfection experiments were carried out as in the preceding Examples. The two well-characterized inhibitors of endosome pH reduction, monensin and ammonium chloride, were used. The experimental results are shown in FIG. 16. The effect of the two substances on TfpL-DNA transfer was investigated and it was found that neither of the two substances can functionally replace chloroquine. However, a slight increase in the luciferase gene expression was found at higher ammonium chloride concentrations (lanes 1 to 5). The retrovirus alone shows the slight augmentation in DNA transfer as observed in the previous Examples (lane 6). A sharp increase was observed when the retrovirus was used in the presence of 1 μM monensin (lane 7). A less powerful effect was observed at a higher monensin concentration (lane 8) and in the presence of ammonium chloride (lanes 9 and 10).

Example 13

Augmentation of the Gene Transfer Achieved by Transferrin Conjugates by Means of the N-terminal Endosomolytic Peptide of Influenza Hemagglutinin HA2 a) Synthesis of the peptide

The peptide of the sequence (SEQ ID NO:1) of the Gly-Leu-Phe-Glu-Ala-Ile-Ala-Gly-Phe-Ile-Glu-Asn-Gly-Trp-Glu-Gly-Met-Ile-Asp-Gly-Gly-Gly-Cys was synthesized using the Fmoc (fluorenylmethoxycarbonyl) method (Atherton et al., 1979), using an Applied Biosystems 431A peptide synthesizer. The side chain protecting groups were t-butyl for Cys, Glu and Asp and trityl for Asn. After the coupling reaction, a ninhydrin test was carried out which showed a coupling level of >98% for each step. Beginning with amino acid 19, double couplings were carried out. The N-terminal Fmoc group was removed from part of the peptide resin with 20% piperidine in NMP (N-methylpyrrolidine). Then the Fmoc-protected and unprotected fractions were washed with DCM (dichloromethane) and dried under high vacuum. The yields were 294 mg Fmoc-free peptide resin and 367 mg of Fmoc-protected peptide resin. 111 mg of the Fmoc-free peptide resin was subjected to trifluoroacetic acid cleaving for one and half hours using a mixture of 10 ml TFA, 0.75 g of phenol, 300 $\mu$l of EDT (ethanedithiol), 250 $\mu$l of Et-S-Me (ethylmethylsulfide) and 500 $\mu$l of water. The peptide was filtered from the resin through a sintered glass filter. The resin was washed with DCM and added to the filtrate. The filtrate was concentrated down to about 2 ml and then added dropwise with stirring to 40 ml of ether. The peptide deposit was removed by centrifuging and the ether supernatant was discarded. The precipitate was washed three times with 40 ml of ether and dried in a high vacuum. The 58 mg of crude product obtained were dissolved in 3.5 ml of 20 mM $NH_4HCO_3$, containing 300 $\mu$l of 25% $NH_3$/1. The solution was gel-filtered using the same buffer on a pre-packaged Sephadex G-25 column (Pharmacia PD-10). All the material was placed on a Mono Q column (Pharmacia 100×14 mm) gradient: 0–10 min 100% A, 10–100 min 0–100% B. A: 20 mM $NH_4HCO_3$+300 $\mu$l $NH_3$/1. B: A+3 M NaCl. Measured at 280 nm, Trp-fluorescence detection at 354 nm. Flow rate 1 ml/min. The product is eluted with 1 M NaCl. The main fraction of the Mono Q column, was further purified by reverse phase HPLC using a BIORAD-Hi-Pore RP 304 column (250×10 mm) (gradient 50 to 100% Buffer B in 12.5 min, 12.5 to 25 min 100% B. A: 20 mM $NH_4HCO_3$+300 $\mu$l $NH_3$/1, B: A in 98% methanol. Flow rate: 3 ml/min. Measured at 237 nm). The product is eluted at 100% B. The product fractions were evaporated down in a Speedvac, re-dissolved in buffer A and finally lyophilized. The yield was 8.4 mg of the HPLC-purified product in the cysteine-protected form. This peptide was designated P16. In order to obtain P16 in the free mercapto form, the t-butyl-protected substance was treated for 30 minutes at ambient temperature with thioanisol/edmanedithiol/trifluoraceticacid/trifluoro-methanesulfonic acid (2/1/40/3; trifluoromethanesulfonic acid was added in the proporation specified after the other components). The peptide was isolated by ether precipitation and subsequent gel filtration (Sephadex G-25) using the above mentioned buffer A under an argon atmosphere.

b) Coupling of the influenza peptide to polylysine b1) Direct binding via SPDP (Succinimidylpyridyl-dithiopropionate)

19.8 mg of polylysine 300 hydrobromide (Sigma) were gel-filtered on a Sephadex G-25 column (Pharmacia PD-10) in sodium acetate pH 5 in order to eliminate the low molecular fractions. On the basis of the ninhydrin test, the pL concentration after gel filtration was 3.16 mg/ml. The pH of the solution was adjusted to 7–8 using 1 M NaOH. 0.64 $\mu$mol of SPDP (Pharmacia: 40 mM solution in absolute EtOH) were added to 2.5 ml of the pL solution (7.9 mg pL=0.13 $\mu$mol). This corresponds to a molar ratio of SPDP:pL of 5:1. The mixture was left to react overnight and gel-filtered in 20 mM $NH_4HCO_3$ pH 8.2 on a G25 column. After reduction of 1 aliquot of the filtrate with DTT (dithiothreitol) the measurement of thiopyridone showed that the reaction was complete. 0.3 $\mu$mol of pL PDP-modified (based on $\mu$mol of PDP) in 2.2 ml were left to react with 0.35 $\mu$mol of peptide in the thiol form. A white precipitate which appeared when the peptide and pL were mixed was dissolved by adjusting the solution to 2 M guanidinium hydrochloride, the reaction taking place overnight. Photometric measurement of thiopyridone in the reaction mixture again confirmed that the reaction was complete. The mixture was then dialyzed twice against 2 liters of 20 mM HEPES/0.5 M guanidinium hydrochloride. The resulting solution was added to a Mono S column (0.7×6 cm, Pharmacia) (gradient: 0 to 20 min 100% A, 20–140 min 0–100% B. A: 20 mN HEPES pH 7.3/0.5 M guanidinium hydrochloride, B: 20 mM HEPES pH 7.3/3 M guanidinium hydrochloride, 0.3 ml/min. Detection at 280 nm and fluorescence detection at 354 nm, excitation at 280 nm). The product fraction which was eluted with 1.5 M guanidinium hydrochloride was dialyzed against 2 liters of HBS. Subsequent determination of the pL concentration by the ninhydrin test showed a concentration of about 1.14 mg/ml. The quantity of peptide in the solution of the conjugate was calculated from its absorption at 280 nm; this gave a molar ratio of peptide:pL of 4:1.

b2) Binding via a polyethyleneglycol linker 14.6 mg of pL 300 hydrobromide (Sigma) were gel filtered as described in b1). According to the ninhydrin test, the pL concentration after gel filtration was 4.93 mg/ml. The pH of the solution was adjusted to 7–8 with 1 M NaOH. 4.33 $\mu$mol PDP (Pharmacia; 30 mM solution in absolute EtOH) were added to 2.7 ml of pL solution (13.3 mg pL=0.22 $\mu$mol). This corresponds to a molar ratio of PDP:pL of 20:1. After one and a half hours the reaction mixture was gel filtered on a Sephadex G-25 column in 0.1 M sodium acetate 3 M guanidinium hydrochloride. After reduction of 1 aliquot of the filtrate with DTT, thiopyridone was determined, indicating that the product fraction contained 3.62 $\mu$mol of PDP. The PDP-modified pL was reduced by adding 79 mg of DTT to the solution. After 2 hours reduction the solution was again filtered on G-25 under the conditions specified. The thiol measurement using the Ellman test showed a thiol concentration of 3.15 $\mu$mol in 2.224 ml.

17.6 mg=5 $\mu$mol POE (Polyoxyethylene-bis(6-aminohexyl), Sigma) were dissolved in 500 $\mu$l of 20 mM $NaHCO_3$/3 M guanidinium hydrochloride, pH 7–8, and reacted with 13.8 mg of EMCS ($\epsilon$-maleimidocaproic acid-N-hydroxysuccinimide ester) (Sigma) (=44.7 $\mu$mol), dissolved in 300 $\mu$l DMF (dimethylformamide). After 30 minutes, the solution was gel filtered on G-25 (20 mM $NaHCO_3$/3 M guanidinium hydrochloride). Photometric measurement of the maleimido group at 300 nm showed a concentration of 6.36 $\mu$mol of reacted EMCS in 2 ml of solution.

1.39 $\mu$mol of the peptide in thiol form in (2.5 ml of 20 mM $NaHCO_3$/3 M guanidinium hydrochloride) were added dropwise to 1.05 ml of this solution (corresponding to 3.34 $\mu$mol EMCS) while the mixture was intensively mixed with a vortex in an argon current. After 15 minutes no more free thiol groups could be detected by the Ellman test.

The solution of the reduced mercapto-modified pL was adjusted to a pH of 7–8 by the addition of 1 M NaOH. 1.37 ml of this solution were added to the above reaction mixture while intensive mixing was carried out by means of a Vortex. This gave a molar ratio of peptide-SH:POE-EMCS:pL-SH of 1:2.4:1.4 (based on EMCS and SH). After 2.5 hours reaction, no more free thiol groups could be detected by the Ellman test. The material was dialyzed overnight against 2 liters of 20 mM HEPES pH 7.3/0.6 M NaCl and then added to a Mono S column (gradient 0 to 20 min 22% A, 20–150 min 22–100% B. A: 20 mM HEPES pH 7.3, B: A+3 M NaCl. Flow rate 0.3 ml/min. UV-measurement was carried out at 280 nm and fluorescence measurement at 354 nm). The product which was eluted with 1.5 to 1.6 M NaCl was dialyzed against 2 liters of HBS. The measurement of the pL concentration using the ninhydrin test and photometric determination of the peptide concentration at 280 nm yielded a calculated pL ratio of 12:1 at a pL concentration of 0.49 mg/ml in a total volume of 4.5 ml.

c) Liposome preparation

Using the REV method (reverse phase evaporation) liposomes were prepared (Szoka and Papahadjopoulos, 1978; Straubinger and Papahadjopoulos 1983; the disclosures of which are fully incorporated by reference herein): aqueous phase 10 mM HEPES pH 7.3; 100 mM calcein; 150 mM NaCl; organic phase: a solution of 300 μmol L- -lecithin (from egg yolk, chiefly palmitoyloleoylphosphatidylcholine; Avanti Polar Lipids) in 260 μl of chloroform was evaporated down using a rotary evaporator. The material was then dried in a high vacuum and then dissolved again in 3 ml of diethylether. 1 ml of the aqueous phase was thoroughly washed with the ether phase using a vortex and treated with ultrasound for 5 minutes at 0° C. in a sonicator (bath type). After 30 minutes on ice, the material was treated with ultrasound for a further 10 minutes. The resulting stable emulsion was slowly evaporated down in a rotary evaporator. After the diethylether had been eliminated at 100 mbar, 0.75 ml of the aqueous phase were added. Residual traces of diethylether were eliminated by further evaporation at 50 mbar for 30 minutes. The resulting preparation (1.7 ml) was centrifuged at 500 rpm. 1.0 ml thereof was extruded through a nucleopore polycarbonate membrane (0.1 μm), giving a final volume of 0.7 ml liposome solution. The liposomes were separated from the non-incorporated material by gel filtration (Sephadex G-50 medium, Pharmacia; 23 ml gel volume, 10 mM HEPES pH 7.3/150 mM NaCl). 6 fractions of 500 μl were collected. Lipid phosphorus was determined using the method of Bartlett, 1959, at 2 mM.

d) Liposome Leakage Assay

The release of the liposome content (leakage) was measured by means of the emergence of the enclosed calcein and the resulting dilution which stops the quenching of fluorescence (Bondeson et al., 1984). The calcein fluorescence was measured with a Kontron SMF 25 spectralfluorometer (excitation at 490 nm, emission at 515 nm). For this purpose, 100 μl aliquots of the above liposome solution were diluted 100 times with 0.1 M sodium acetate/50 mM NaCl or 10 mM HEPES/150 mM NaCl buffer with the corresponding pH (4.3, 4.5, 5.0, 6.0, 7.3) in order to obtain a value of 1 ml. To these solutions were added 2.5 μl of the peptide (t-butyl-protected form; 1 μg/μl of solution in HBS) in cuvettes, while mixing with a gentle stream of argon (final concentration 400 nM peptide). The calcein fluorescence was measured at different times after the addition of the peptide. The values for 100% leakage were determined by the addition of 2 μl Triton X-100 (Fluka).

The same procedure was used to measure the calcein fluorescence after the addition of peptide-pL conjugates to the liposome solution. 2.5 μg of the conjugate (1 μg/μl concentration based on the quantity of pL alone) were added to 1 ml of liposome solution (final concentration 20 nM modified peptide). Similarly, 2.5 μg of peptide-polylysine conjugate were subjected to the leakage assay after incubation with 5 μg DNA (15 minutes).

It was found that the peptide only causes the release of the liposome content in the acidic range (FIG. 17). The peptide conjugate was active at a substantially lower pH, while even at a neutral pH a strong activity was found which was further increased as the pH was lowered. Complexing of the conjugate with DNA eliminated the activity at a neutral pH, whereas at an acidic pH there was a significant activity.

e) Transfection of K562-cells

K562-cells were grown in suspension in RPMI 1640 medium (Gibco BRL plus 2 g sodium bicarbonate/l) plus 10% FCS, 100 I.U. per ml penicillin, 100 μg/ml streptomycin and 2 mM glutamine up to a density of 500,000 cells/ml. 12 to 20 hours before transfection the cells were placed in fresh medium containing 50 μM desferrioxamine (this measure was taken to increase the number of transferrin receptors). On the day of transfection, the cells were collected, suspended in fresh medium containing 10% FCS plus 50 μM desferrioxamine (250,000 cells per ml) and 2 ml portions were placed in a dish with 24 wells.

6 μg of pCMVL-DNA in 160 μl HBS were mixed with the quantities of TfpL conjugate specified in FIG. 18 or with pL300 in 160 μl HBS, then after 15 minutes the specified amounts of influenza peptide-pL-conjugate (P16pL) were added and after a further 15 minutes the mixture was added to the K562 cells. The cells were incubated for 24 hours at 37° C. and then harvested for the luciferase assay. The luciferase activity was determined as specified in the previous Examples. The values given in FIG. 18 represent the total luciferase activity of the transfected cells.

f) Transfection of HeLa cells

HeLa cells are cultivated in 6 cm culture dishes as described under "Cells and Media". The transfections were carried out at a density of 300,000 cells per plate. Before transfection, the cells were incubated with 1 ml of fresh medium containing 2% FCS. 6 μg of pCMVL-DNA in 160 μl HBS were mixed with the quantities of TfpL conjugate specified in FIG. 19 or with pL300 or a mixture of both in 160 μl HBS. After 15 minutes, the specified amounts of influenza peptide-pL-conjugates (P16pL) were added and after a further 15 minutes the mixture was added to the cells. The cells were incubated for 2 hours at 37° C., then 2.5 ml of fresh medium were added with an additional 10% FCS. The cells were incubated for 24 hours at 37° C. and then harvested for the luciferase assay. The luciferase activity was determined as described in the preceding Examples. The values given in the figure represent the total luciferase activity of the transfected cells.

Example 14

Augmentation of the Gene Transfer Achieved by Transferrin Conjugates by Means of a Second N-terminal Endosomolytic Peptide of Influenza Hemagglutinin HA2 a) Synthesis of influenza peptide-polylysine conjugate

The peptide of the sequence (SEQ ID NO:2) Gly-Leu-Phe-Gly-Ala-Ile-Ala-Gly-Phe-Ile-Glu-Asn-Gly-Trp-Glu-Gly-Met-Ile-Asp-Gly-Gly-Gly-Cys (designated P41) was synthesized in the same way as the peptide described in Example 13, a). The coupling of the influenza peptide to polylysine (pL300) was performed as in Example 13, b1) by binding via SPDP. Thereby conjugates (P41pL) with a molar ratio of peptide:pL of 4:1 were obtained.

b) Transfection of HeLa cells

HeLa cells were grown in DMEM medium plus 5% FCS, 100 units/ml penicillin, 100 μg/ml streptomycin and 2 mM glutamine in 6 cm plates. Transfections were performed at a density of 300,000 cells per plate. Before the transfection, cells are incubated with 1.5 ml of fresh medium containing 2% FCS.

6 μg pCMVL-DNA in 160 μl HBS (150 mM NaCl, 20 mM HEPES 7.3) were mixed with 6 μg of TfpL190B conjugate in 160 μl HBS, after 15 min 10 μg influenza peptide-pL-conjugate P41pL or, for comparison, 18 μg of influenza peptide-pL-conjugate P16pL (see Example 13) were added (FIG. 20); the specified amounts of the two peptide conjugates had been tested to be optimal amounts for the augmentation of the gene transfer. After further 15 min the mixture was added to the cells. The cells were incubated at 37° C. for 4 hours, then 2 ml of medium containing 18% FCS were added. After 24 hours the cells were harvested for the luciferase assay. Values as shown in FIG. 20 represent the total luciferase activity of the transfected cells.

The comparison of the experiments with the two peptide conjugates shows a more than 3.5 fold higher augmentation of the gene transfer obtained with the second peptide conjugate P41pL.

c) Transfection of BNL CL.2 cells with influenza peptide polylysine conjugates

BNL CL.2 cells were grown as described in Example 6. Influenza peptide P41 was conjugated with polylysine 300 at a molar ratio of peptide to polylysine of 1:1, 3:1 and 8:1. Complexes of 6 μg pCMVL-DNA and 20 μg of the conjugates were added to the cells. For comparison, 20 μg of pL$_{300}$ or 20 μg of P16 polylysine conjugate, prepared as described in Example 13, were used. The cells were incubated at 37° C. for 4 h, then 2 ml of medium containing 18% FCS was added. After 24 h, the cells were harvested for the luciferase assay, the results of which are shown in FIG. 20B. The content of peptide in the conjugates correlated with the augmentation of gene expression. In the liposome leakage assay (FIG. 20C), which was performed as described in Example 13, the activity of the conjugates (at pH 5, equivalents to 2.5 μg polylysine) increased with their content of peptide. (In the figure, P41 is designated "influ2")

Example 15

Transfection of HeLa Cells With a β-galactosidase Reporter Gene Construct and In Situ Demonstration of β-galactosidase Expression a) Culturing and transfection of cells For the transfection, HeLa cells were grown in DMEM medium containing 5% FCS, penicillin, streptomycin and glutamine, as described in the previous Examples, in 3 cm culture dishes on cover slips (3×10$^4$ cells per dish).

For the transfection, 6 μg of the β-galactosidase reporter gene construct (pCMV-β-gal) in 160 μl of HBS were complexed with 12 μg of TfpL190B in 160 μl of HBS and incubated for 30 minutes at ambient temperature.

In another experiment, 6 μg of pCMV-β-gal in 160 μl of HBS were incubated with 6 μg of TfpL190B in 80 μl of HBS for 15 minutes at ambient temperature. Then 12 μg of the influenza peptide conjugate (P16pL) prepared in Example 13 in 80 μl of HBS were added and the mixture was incubated for a further 15 minutes. These DNA-polycation complexes were then mixed with 1 ml of DMEM plus 2% FCS, antibiotics and glutamine, as described above. In order to demonstrate the effect of chloroquine and adenovirus on the success of the transfection, in additional experiments chloroquine was also added to the medium containing the DNA polycation complexes, in a final concentration of 100 μM or 50 μl of the adenovirus strain solution dl312.

For the transfections, the original culture medium was removed from the cells and 1 ml of medium containing the DNA complexes with or without chloroquine or virus was added. After an incubation period of 2 hours at 37° C., 1 ml of DMEM containing 10% FCS, antibiotics and glutamine was added to the cells and incubation was continued for a further 2 hours. Then all the medium was removed and the cells were cultivated in 3 ml of fresh DMEM plus 10% FCS, antibiotics and glutamine.

b) β-galactosidase assay 48 hours after transfection, the medium was removed, the cells were washed once with phosphate-buffered saline solution (PBS) and fixed with 0.5% glutardialdehyde in PBS for 5 minutes at ambient temperature. Then the fixative was discharged and the cells were washed once with PBS. Then incubation was carried out with the staining solution (10 mM phosphate buffer pH 7.0, 150 mM NaCl, 1 mM MgCl$_2$, 3.3 mM K$_4$Fe(CN)$_6$3H$_2$O, 3.3 mM K$_3$Fe(CN)$_6$ and 0.2% 5-bromo4-chloro-3-indolyl-β-galactopyranoside) at 37° C. for 20 minutes to 3 hours (Lim and Chae, 1989). Then the cover slips were rinsed in PBS, water and 96% ethanol, dried and mounted in Mowiol on slides. A Zeiss Axiophot Microscope was used for analysis.

FIG. 21 shows images of the microscopic magnifications (112 times). A: HeLa cells transfected with 6 μg pCMV-β-gal, complexed with 12 μg TfpL190B. The staining reaction for β-galactosidase was carried out for 3 hours. The Figure shows that very few cells (55 cells; a group of stained cells is indicated by an arrow) express the β-galactosidase gene. B: HeLa cells transfected with 6 μg pCMV-β-gal, complexed with 6 μg TfpL190B and 12 μg P16pL. Staining reaction: 3 hours. Few cells (250 cells) express the β-galactosidase gene. However, die reaction of the cells is stronger than in A. C: HeLa cells transfected with 6 μg pCMV-β-gal, complexed with 6 μg TfpL190B and 12 μg P16pL in the presence of 100 μM of chloroquine. Staining reaction: 3 hours. Numerous groups of cells show a strongly positive reaction (more than 1,000 cells). D: HeLa cells transfected with 6 μg pCMV-β-gal, complexed with 12 μg TfpL190B in the presence of adenovirus dl312. Staining 20 reaction 20 min. Nearly all the cells (more than 90%) show a positive reaction. E: Non-transfected HeLa cells (control for the specificity of the β-galactosidase reaction). Staining reaction: 3 hours.

Example 16

Transfection of HeLa Cells With a 48 kb Cosmid in the Presence of Adenovirus a) Preparation of a cosmid containing the luciferase coding sequence A 3.0 kb SalI fragment, containing a single P. pyralis luciferase coding sequence under control of the RSV promoter, was isolated from the plasmid p220RSVLucα and ligated into the unique SalI site of the cosmid clone C1-7aA1 to form concatamers. (C1-7aA1 comprises a 37 kb human genomic DNA Sau3A fragment (partial digest), encoding no apparent genes, cloned into the BamHI site of the cosmid vector pWE15 (Stratagene)). The ligation reaction product was then packaged in vitro and an aliquot of the resulting phage particles infected into E. coli NM544 and plated onto LB amp plates. The recombinants were screened by colony hybridization, using the 3.0 kb SalI fragment ($^{32}$P labelled by random priming) as a hybridization probe, and a number of positives analyzed by restriction mapping. A cosmid construct (CosLuc) containing a single copy of the SalI insert was grown and purified on a CsCl gradient (total size=48 kb).

A small control cosmid pWELuc (12 kb) was prepared by digesting CosLuc with NotI, religating, transforming bacteria and isolating a clone containing the appropriate plasmid. This resulted in a 12 kb DNA molecule lacking the human DNA insert and part of the polylinker of CosLuc. The plasmid pSPNeoLuc (8 kb) is the plasmid described in Example 5 which contains an RSV-luciferase gene fragment (an Apa1/Pvu1 fragment of pRSVL, cloned into the Cla1 site of the pUCµ Locus).

b) Delivery of the cosmid into HeLa cells

Figure 22A:
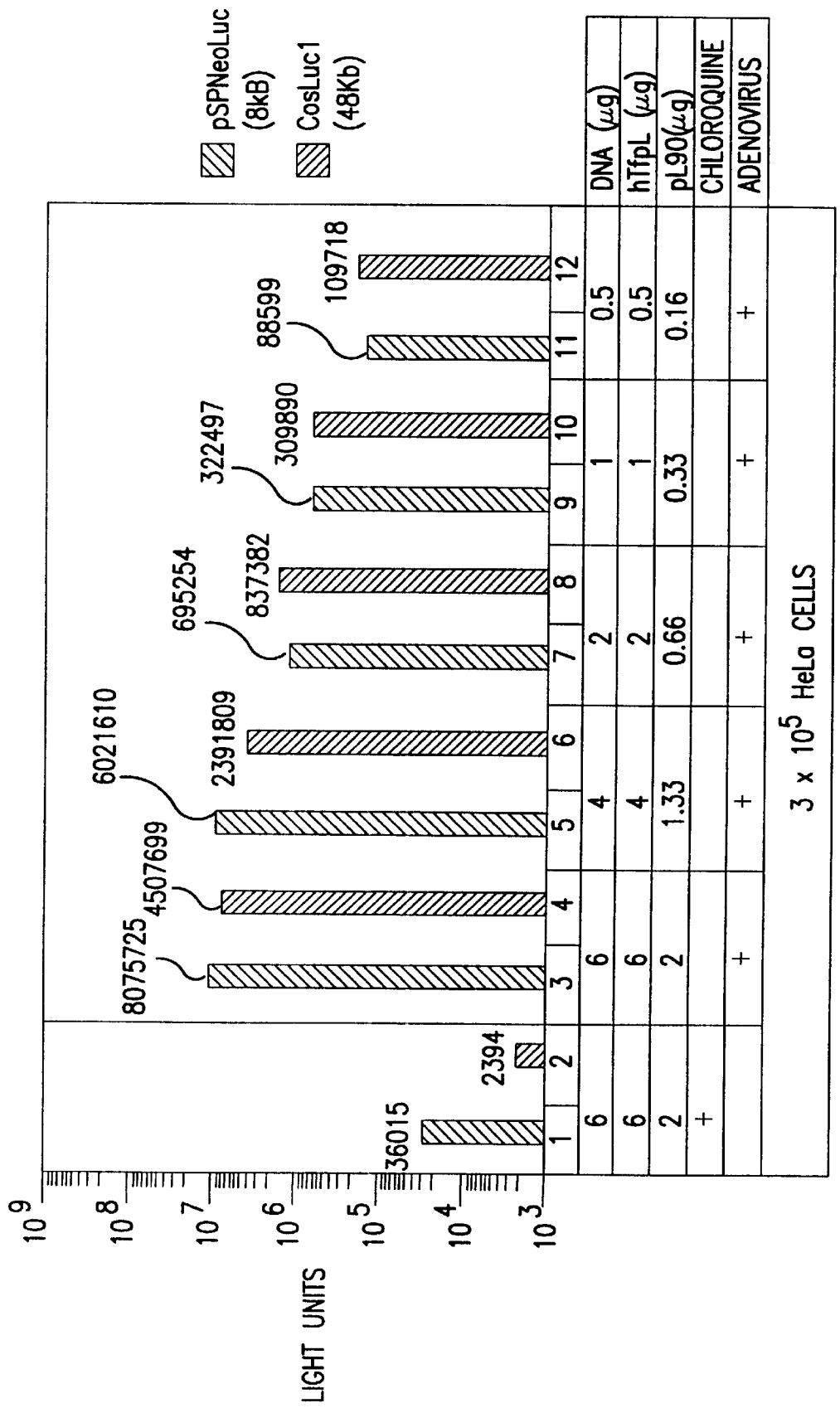

HeLa cells ($3 \times 10^4$ cells per 6 cm dish) covered with 1 ml DMEM+2% FCS were incubated with TfpL/DNA complexes prepared as described in the Materials and Methods section, containing the indicated quantities of hTfpL, free pL and DNA. Cell incubation mixtures included, in addition, either 100 µM chloroquine (lanes 1 and 2) or 10 µl adenovirus dl312 containing $5 \times 10^{11}$ particles per ml, (lanes 3–12). After a 2 hour incubation at 37° C., 4 ml of DMEM+10% FCS was added to each dish; 24 hours later, cells were harvested and luciferase activity was measured. Results are shown in FIG. 22A.

c) Delivery of the cosmid into Neuroblastoma cells

Figure 22B:
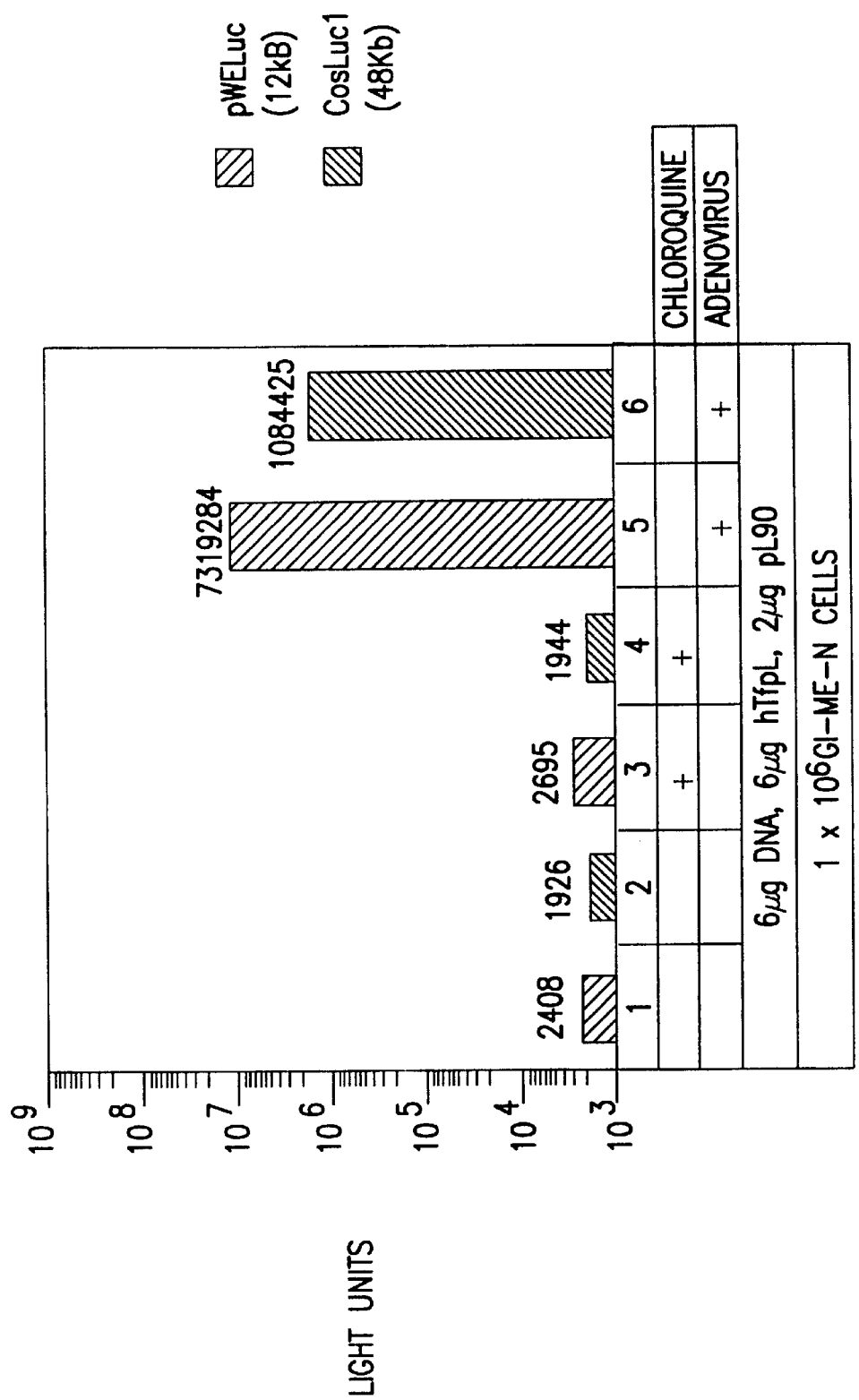

Cells of a neuroblastoma cell line designated GI-ME-N (Donti et al., 1988) ($1 \times 10^6$ cells per 6 cm dish) covered with 1 ml DMEM+2% FCS were incubated with TfpL-DNA complexes prepared as described in the Materials and Methods section, containing the indicated quantities of hTfpL, free pL and DNA. Cell incubation mixtures included, in addition, either 100 µM chloroquine (lanes 3 and 4) or 10 µl adenovirus dl312 containing $5 \times 10^{11}$ particles per ml, (lanes 5 and 6). After a 2 hour incubation at 37° C., 4 ml of DMEM+10% FCS was added to each dish; 24 hours later, cells were harvested and luciferase activity was measured. Results are shown in FIG. 22B.

Example 17

Gene Transfer by Means of Chemically Coupled Adenovirus-polylysine Conjugates a) Preparation of adenovirus-polylysine conjugates by chemical coupling 2.35 ml of a gel filtered (Sephadex G-25 PD10, Pharmacia) solution of adenovirus dl312 (approx. $10^{11}$ particles) in 150 mM NaCl/25 mM HEPES, pH 7.9/10% glycerol was mixed with 10 µl (10 nmol) of a 1 mM solution of SPDP (Pharmacia). After 3.5 hours at ambient temperature the modified virus was separated from the excess reagent by gel filtration (as above). The solution (2.5 ml) was purged with argon and allowed to react, under the exclusion of oxygen, under argon, with 42 µl of a solution of FITC-labelled polylysine (1 nmol), modified with 2.3 nmol of mercaptopropionate groups (prepared as described in EP 388 758). After 18 hours at ambient temperature half the solution was transferred into a centrifuge test-tube, carefully covered with 1 ml of a cesium chloride solution (density 1.33 g/ml) and centrifuged at ambient temperature for 2 hours at 35000 rpm (SW60 rotor). The virus band was collected as 200 µl cesium chloride fraction and diluted to 1 ml with HBS/50% glycerol. A DNA binding assay was carried out with 300 µl of the modified virus: the virus solution was diluted with 1 ml HBS and mixed with 100 µl of solution of a $^{35}$S-labelled DNA (15 ng pRSVL, prepared by Nick translation). As a control, the experiment was carried out in parallel with the same amount of unmodified virus dl312. After 30 minutes the samples were transferred into centrifuge tubes, carefully covered with 1 ml of a cesium chloride solution (density 1.33 g/ml) and centrifuged for 2 hours at 35000 rpm (SW60 rotor) at ambient temperature. The gradient was divided into 5 fractions; fraction 1, 1 ml; fraction 2, 0.6 ml, fractions 3–5, 200 µl each. The radioactivity of 200 µl portions of the fractions was measured and is shown in FIG. 23. The fractions which contain virus (3–5), especially fraction 3, show a significantly higher radioactivity than the control. This can be attributed to specific association of the polylysine-modified adenovirus with the labelled DNA, the presence of cesium chloride possibly causing partial dissociation of the complexes.

b) Transfection of K562 cells

K562-cells (ATCC CCL 243) were grown in suspension in RPMI 1640 medium (Gibco BRL, plus 2 g sodium bicarbonate/l 10% FCS, 100 units per ml penicillin, 100 µl/µl streptomycin and 2 mM glutamine) up to a density of 500,000 cells/ml. 12 to 20 hours before transfection the cells were placed in fresh medium containing 50 µM desferrioxamine (this measure was taken to increase the number of transferrin receptors). On the day of transfection, the cells were collected, suspended in fresh medium containing 10% FCS plus 50 µM desferrioxamine (250,000 cells per ml) and 2 ml portions were placed in a dish with 24 wells.

The specified amounts of pCMVL-DNA (6, 0.6, 0.06 µg) in 100 µl of HBS were mixed with 50 µl of polylysine adenovirus (pLadeno) or corresponding amounts (35 µl) of control adenovirus dl312. After 20 minutes, corresponding amounts (12, 1.2, 0.12 µg) of TfpL190B conjugate in 150 µl of HBS were added. After a further 20 minutes the mixture was added to the K562 cells. The cells were incubated for 24 hours at 37° C. and then harvested for the luciferase assay. The luciferase activity was determined as in the preceding Examples. The values given in FIG. 24 represent the total luciferase activity of the transfected cells.

c) Transfection of HeLa cells

One method of testing the activity of a polylysine-virus conjugate is by checking the conjugate for its ability to transport very small amounts of DNA (less than 0.1 µg). An increased DNA transfer capacity was expected when the adenovirus is directly bound to the polylysine-condensed DNA, as the internalizing factors (transferrin and adenovirus (protein)) are directly associated with the DNA which is to be transported. To test this assumption, a constant quantity of the polylysine-adenovirus conjugate (2.5 µl, about $5 \times 10^7$ virus particles) was completed with different amounts (3 µg to 0.0003 µg) of reporter plasmid in 475 µl of HBS. After 15 minutes incubation at ambient temperature a quantity of transferrin-polylysine corresponding to the mass of DNA was added to each sample (this quantity of TfpL was selected because it guarantees total packaging (electroneutrality) of 50% of the plasmid DNA and at the same time ensures binding space for the virus-polylysine conjugate. After the addition of TfpL the mixtures were incubated for 15 minutes, then each mixture was placed in a 6 cm culture dish containing 300,000 HeLa cells in 1 ml of DMEM/2% FCS. Then the cells were incubated for 1.5 hours at 37° C., then 4 ml of DMEM/10% FCS were added. In parallel, equivalent quantities of DNA were completed with a two-fold mass excess of TfpL (the quantity for total DNA condensation) and used for the gene transfer into HeLa cells (once on its own and once in the presence of 25 µl of the non-polylysine-coupled adenovirus dl312 preparation). After 24 hours the cells were harvested, extracts were prepared and aliquots were examined for luciferase activity. The results of these tests are shown in FIG. 25: in the absence of adenovirus, no luciferase activity can be detected in a quantity of DNA less than 0.3 µg. Both polylysine coupled and non-coupled adenovirus functioned well with large quantities of DNA (3 µg and 0.3 µg). However, with the non-coupled adenovirus there was an approximately 100 fold fall in activity at 0.03 µg and negligible activity below this amount of DNA. By contrast the polylysine-coupled virus retains its gene transfer capacity both at 0.003 and at 0.0003 µg of DNA. This quantity of DNA corresponds to about 150 DNA molecules per cell and about 1 virus particle per cell.

Example 18

Gene Transfer by Means of Adenoviruses Enzymatically Coupled to Polylysine a) Enzyme reaction 2 ml of the adenovirus preparation (stain d1312; $5 \times 10^{10}$ PFU/ml) were applied to a Sephadex G-25 gel filtration column (Pharmacia) equilibrated with 25 ml of reaction buffer (0.1 M Tris-HCl; pH 8.0, 2 mM DTT, 30% glycerol). Elution was carried out with 3.5 ml of reaction buffer. The reaction mixture for enzymatic coupling consists of 1150 µl of the virus elution fraction, 0.5 nmol guinea-pig liver transglutaminase (TG) (Sigma), 2 nmol or 20 nmol of Polylysine290, 10 mM $CaCl_2$ and reaction buffer in a final volume of 1500 µl. The reaction was carried out at 37° C. for 1 hour and then stopped by the addition of 30 µl of 0.5 M EDTA. In order to monitor the specificity of the coupling, reaction mixtures were also prepared without transglutaminase. Non-incorporated polylysine was separated from the viruses by centrifuging in a CsCl-gradient (density 1.33 g/ml; 170,000x g, 2 hours). The fraction containing the viruses was collected, mixed with an equal volume of glycerol, frozen in liquid nitrogen and stored at −70° C.

b) Demonstrating the binding of polylysine to adenoviruses

The reaction was carried out as described above with polylysine which had been labelled with $^{125}I$ with Bolton-Hunter reagent (Amersham). After the CsCl-gradient centrifugation the virus fraction was drawn off and separated by means of another CsCl gradient. The gradient was then fractionated and the radioactivity in every fraction was determined using a scintillation counter. As shown in FIG. 26, it became apparent that in the reaction mixture with TG (d1312/TG-pL), radioactive polylysine had accumulated in the virus fraction (virus). In the control mixture without TG (d1312/pL) there was no accumulation of radioactive polylysine in the virus fraction.

c) Testing the polylysine-modified adenovirus fractions for their effect on the efficiency of transfection i) Cells and media For the transfection, $5 \times 10^5$ cells (murine hepatocytes; ATCC No.: TIB 73) in DMEM with 10% heat-inactivated fetal calf serum (FCS), 2 mM glutamine, 100 I.U./ml penicillin and 100 µg/ml of streptomycin were seeded in 6 cm culture dishes.

ii) Formation of the virus-DNA-transferrin complexes

50 µl of the polylysine-modified virus fraction were mixed with 6 µg of the DNA plasmid pCMVL in 10 µl HBS and incubated for 20 minutes at ambient temperature. Then 8 µg of murine transferrin-polylysine290B (mTfpL) were added to the mixture and incubation was continued for a further 20 minutes.

iii) Transfection of the murine hepatocytes

The virus-DNA-transferrin complexes were mixed with 1.5 ml of medium (DMEM with 2% FCS, 2 mM glutamine and antibiotics) and added to the cells, after removal of the old medium. After 2 hours incubation at 37° C., 2 ml of DMEM with 10% FCS, glutamine and antibiotics were added to the cells. After a further 2 hours cultivation the entire medium was removed and 4 ml of fresh DMEM with 10% FCS, glutamine and antibiotics were added to the cells.

iv) Determining the luciferase expression 24 hours after transfection the cells were harvested and the luciferase assay was carried out as described above. As can be seen from FIG. 27, the virus preparation in which the adenoviruses had been treated with TG and 20 nmol of polylysine (d1312/TG-20 nmol pL) showed the strongest expression (153540000 light units). The virus preparation with TG and 2 nmol of polylysine (d1312/TG-2 nmol pL) was somewhat less active (57880000 light units). The control fraction in which the adenoviruses were treated with 20 nmol of polylysine but with no TG was less effective by a factor of 500 approximately. As a comparison, further complexes were used for transfection with the initial preparation of adenoviruses treated neither with TG nor with polylysine (d1312). This preparation yielded 4403000 light units.

(d) Increasing the transfection efficiency by polylysine-modified adenoviruses compared with unmodified adenoviruses, particularly with small amounts of DNA Transfection was carried out as described in Example c), using 50 µl of the adenovirus fraction d1312/TG-20 nmol pL and 6 µg pCMV-Luc/8 µg mTfpL, 0.6 µg pCMVL(=pCMV-Luc)/0.8 µg mTfpL or 0.06 µg pCMV-Luc/0.08 µg mTfpL for complexing. As a comparison, transfections were also carried out with 6 µg, 0.6 µg, 0.06 µg pCMV-Luc/mTfpL complexes and unmodified adenoviruses (d1312). It was found that the complexes with polylysine-modified adenoviruses yielded high expression levels even with small amounts of DNA, whereas expression was sharply reduced with unmodified adenoviruses (FIG. 28).

Example 19

Gene Transfer With Conjugates in Which the Binding Between the Adenovirus and Polylysine is Obtained by Means of a Biotin-streptavidin Bridge a) Biotinylation of adenovirus d1312

2.4 ml of a gel filtered (Sephadex G-25 PD10, Pharmacia) solution of adenovirus d1312 (about $10^{11}$ particles) in 150 mM NaCl/5 mM HEPES, pH 7.9/10% glycerol, was mixed with 10 µl (10 nmol) of a 1 mM solution of NHS-LC biotin (Pierce 21335). After 3 hours at ambient temperature the biotin-modified virus was separated from the excess reagent by gel filtration (as above). The solution was adjusted to a glycerol concentration of 40% by adding glycerol (total volume 3.2 ml) and stored at −25° C. The biotinylation of the virus was demonstrated by qualitative detection after dropwise addition of various dilutions onto cellulose nitrate membrane: after drying at 80° C. for 2 hours in a vacuum dryer, blocking with BSA, incubating with streptavidin-conjugated alkaline phosphatase (BRL), washing and incubating for 1 hour with the developing solution NBT/X-phosphate(nitroblue-tetrazolium salt/5-bromo-4chloro-3-indolylphosphate, toluidine salt; Boehringer Mannheim) a positive color reaction was found.

b) Preparation of streptavidin-polylysine conjugates

The coupling of streptavidin to polylysine was effected using the method described by Wagner et al., 1990, and in EP-A1 388 758. 79 nmol (4.7 mg) of streptavidin in 1 ml of 200 mM HEPES pH 7.9 and 300 mM NaCl were treated with a 15 mM ethanolic solution of SPDP (236 nmol). After 1.5 hours at ambient temperature the modified protein was gel filtered over a Sephadex G-25 column, thereby obtaining 75 nmol of streptavidin, modified with 196 nmol of dithiopyridine linker. The modified protein was reacted under an argon atmosphere with 3-mercaptopropionate-modified polylysine (75 nmol, average chain length 290 lysine monomers, modified with 190 nmol mercaptopropionate linker) in 2.6 ml of 100 mM HEPES pH 7.9, 150 mM NaCl. Conjugates were isolated by cation exchange chromatography on a Mono S HR5 column (Pharmacia). (Gradient: 20–100% buffer B. Buffer A: 50 mM HEPES pH 7.9; buffer B: buffer A plus 3 M sodium chloride). The product faction eluted at a salt concentration of between 1.2 M and 1.7 M. Dialysis against HBS (20 mM HEPES pH 7.3, 150 mM NaCl) resulted in a conjugate consisting of 45 nmol of streptavidin and 53 nmol of polylysine.

c) Transfection of HeLa cells

HeLa cells were grown in 6 cm culture dishes as described in Example 13. The transfections were carried out at a density of 300,000 cells per plate. Before the transfection the cells were incubated with 1 ml of fresh medium containing 2% FCS.

6 μg of pCMVL-DNA in 100 μl HBS were mixed with 0.8 μg of streptavidin-polylysine in 170 μl of HBS. After 20 minutes, 3 μg of polylysine pL300 in 170 μl of HBS were added. After another 20 minutes, 65 μl of biotinylated adenovirus or, as the control, corresponding amounts of adenovirus d1312 (30 μl, starting virus for modification), were added. The complex mixtures, ("biotinAdV/complex A" or "control AdV" see FIG. 29) were left to stand for a further 20 minutes.

Alternative complexing was carried out by mixing 65 μl of biotinylated adenovirus first with 0.8 μg of streptavidin-polylysine in 50 μl HBS then adding 6 μg of pCMVL-DNA in 170 μl of HBS after 20 minutes, and a further 20 minutes later adding 3 μg of polylysine pL300 in 200 μl HBS. (Complex mixture "biotinAdV/complex B").

0.6 μg of pCMVL-DNA in 67 μl HBS were mixed with 0.3 μg of streptavidin-polylysine in 33 μl of HBS. After 20 minutes, 65 μl of biotinylated adenovirus or, as the control, corresponding quantities of adenovirus d1312 (30 μl, starting virus for modification) were added. The complex mixtures ("biotinAdV/complex A" or "control AdV", see FIG. 29) were left to stand for a further 20 minutes and then diluted to 500 μl with HBS. Alternative complexing was carried out by mixing 65 μl of biotinylated adenovirus first with 0.3 μg of streptavidin-polylysine in 50 μl of HBS and after 20 minutes adding 0.6 μg of pCMVL-DNA in 50 μl HBS. The complex mixture ("biotinAdV/complex B") was left to stand for a further 20 minutes and then diluted with HBS to 500 μl.

The mixtures were added to the cells, the cells were incubated for 2 hours at 37° C., then 2.5 ml of fresh medium containing 10% added FCS were added. The cells were incubated for 24 hours at 37° C. and then harvested for the luciferase assay. The luciferase activity was determined as described in the preceding Examples. The values given in FIG. 29 represent the total luciferase activity of the transfected cells.

In parallel, transfections of HeLa cells were carried out using as the virus component of the conjugate a biotinylated virus which had been inactivated by psoralen/UV-treatment Inactivation was carried out as follows: 200 μl batches of biotinylated virus preparation were placed in two wells of a 1.6 cm tissue culture plate. 2 μl (33 mg/ml) of 8-methoxypsoralen (in DMSO) were added to each sample, the dish was placed on ice and irradiated for 10 minutes with a UV lamp (365 nm; UVP TL-33 lamp) with the sample being 4 cm from the filter. After the irradiation the two samples were combined and gel filtered (G50, Nick column, Pharmacia), the column having previously been equilibrated with 40% glycerol in HBS. Aliquots of 75 μl were complexed with 0.8 μg of streptavidin-polylysine and used for the transfection of HeLa cells as described above.

By cytopathic end point assay it was established that the virus titer was reduced by a factor of more than $10^4$ by the inactivation, whereas the transfer capacity was reduced by less than 50% at high concentrations and by a factor of 5 at low concentrations.

d) Transfection of K562 cells

K562 cells were grown in suspension in RPMI 1640 medium (Gibco BRL, plus 2 g sodium bicarbonate per 1 liter) plus 10% FCS, 100 units/ml penicillin, 100 μg/ml streptomycin and 2 mM glutamine reaching a density of 500,000 cells/ml. At 16 hours before transfection, the cells were placed in fresh medium containing 50 μM desferrioxamine (Sigma). The morning of the transfection, the cells were collected, resuspended in fresh medium containing 10% fetal calf serum (plus 50 μM desferrioxamine) at 250,000 cells per ml, and placed in a 24-well dish, 2 ml per well.

Three different types of DNA complexes were prepared: a) A solution of 6 μg pCMVL-DNA in 160 μl HBS (150 mM NaCl, 20 mM HEPES 7.3) was mixed with 12 μg of TfpL190B conjugate in 160 μl HBS, after 30 min 20 μl of adenovirus d1312 was added and the mixture was added to K562 cells. b) A solution of 800 ng streptavidin-polylysine in 160 μl HBS was mixed with 20 μl of biotinylated adenovirus, prepared as described in a), after 30 min a solution of 6 μg pCMVL-DNA in 160 μl HBS was added, and after further 30 min the solution was mixed with 10 μg TfpL190B conjugate in 160 μl HBS. After 30 min the mixture was added to the cells. c) The DNA complexes were prepared analogously to b) with the difference that instead of TfpL190B conjugate a solution of 3.5 μg poly(L)lysine p(Lys)290 was added.

The cells were incubated at 37° C. for 24 hours and then harvested for the luciferase assay. Values as shown in FIG. 30 represent the total luciferase activity of the transfected cells.

Example 20

Gene Transfer Into Primary Bone Marrow Cells a) Isolation of Primary Bone Marrow Cells Primary bone marrow cells were harvested from mice by flushing culture medium (IMDM containing 10% FCS, $5\times10^{-5}$ M β-mercaptoethanol, 1% IL-3 conditioned medium and antibiotics) with an injection needle (0.4 mm or 0.5 mm in diameter) attached to a 1 ml syringe through the isolated femura and tibiae. The cells were then washed once in culture medium by centrifugation at 100 xg for 8 min. Thereafter the cells were resuspended at a concentration of $10^7$ cells/ml and seeded into T25 culture flasks. After 4 h the non-attached cells were transferred into a new T25 culture flask and cultured overnight in the presence of 50 μM desferrioxamine.

b) Formation of adenovirus-DNA-transferrin complexes

For formation of adenovirus-DNA-transferrin complexes 50 μl of biotinylated adenovirus were incubated with 400 ng of streptavidin-modified polylysine in 20 μl HBS for 20 min. Then 20 μl of HBS containing 6 μg pCMVL were added.

After an incubation period for 20 min 7 μg of mouse transferrin-polylysine conjugate (mTfpL) in 160 μl HBS were added and the whole mixture was incubated for further 20 min.

c) Transfection

For transfection the bone marrow cells were recovered from the culture medium of the T25 flask by centrifugation at 100 xg for 8 min. The cell pellet was resuspended in 3 ml of culture medium containing 2% FCS and 250 μl of the adenovirus-DNA-transferrin complexes, and cultured in a new T25 flask for 3 h at 37° C. Then 3 ml and after a period of 2 h further 6 ml of culture medium containing 10% FCS were added.

d) Determination of luciferase expression

The bone marrow cells were harvested 48 h after transfection and analyzed for expression of luciferase as described above. The transfection led to an expression of luciferase activity corresponding to $310 \times 10^3$ light units/100 μg total cell protein.

Example 21

Transfection of Neuroblastoma Cells With a 48 kb Cosmid in Presence of Adenovirus a) Preparation of a cosmid containing the luciferase coding sequence A 3.0 kb Sal I fragment, containing a single P. pyralis luciferase coding sequence under the control of the RSV promoter (De Wet et al., 1987; the disclosure of which is fully incorporated by reference herein), was ligated in to the unique Sal I site of the cosmid clone C1-7aA1 to form concatamers. (C1-7aA1 comprises a 37 kb human genomic DNA Sau 3A fragment (partial digest), encoding no apparent genes, cloned into the Bam HI site of the cosmid vector pWE15 Stratagene)). The ligation reaction product was then packaged in vitro and an aliquot of the resulting phage particles infected into E. coli NM544 and plated on to LB amp plates. The recombinants were screened by colony hybridization, using the 3.0 kb Sal I fragment ($^{32}$P labelled by random priming) as a hybridization probe, and a number of positives analyzed by restriction mapping. A cosmid construct (CosLuc) containing a single copy of the Sal I insert was grown and purified on a CsCl gradient (total size=48 kb).

A small control cosmid pWELuc (12 kb) was prepared by digesting CosLuc with Not I, religating, transforming bacteria and isolating a clone containing the appropriate plasmid. This resulted in a 12 kb DNA molecule lacking the human DNA insert and part of the polylinker of CosLuc.

b) Delivery of the cosmid into Neuroblastoma cells

Cells of a Neuroblastoma cell line designated GI-ME-N (Donti et al., 1988) ($1 \times 10^6$ cells per 6 cm dish) covered with 1 ml DMEM+2% FCS were incubated with TfpL/DNA complexes prepared as described in materials and methods section, containing the indicated quantities of hTfpL, free pL and DNA. As indicated, cell incubation mixtures included, in addition, either 100 μM chloroquine Canes 3 and 4) or 10 μl adenovirus d1312 containing $5 \times 10^{11}$ particles per ml, (lanes 5 and 6). The last two samples (indicated as StpL/Biotin) contained 15 μl biotinylated adenovirus d1312 ($1 \times 10^{11}$ particles) incubated with streptavidin-polylysine (0.8 μg prepared as in Example 19) for 30 minutes in 150 μl HBS. 6 μg DNA in 150 μl HBS was then added to the sample for 30 minutes, room temperature, followed by 150 μl HBS containing 6 μg hTfpL+1 μg free pL. After a further 30 minutes room temperature incubation the mixture was added to the cells. After a 2 hour incubation at 37° C., 4 ml of DMEM +10% FCS was added to each dish; 24 hours later cells were harvested and luciferase activity was measured. Results are shown in FIG. 31.

Example 22

Gene Transfer to Primary Airway Epithelial Cells Employing Molecular Conjugate Vectors Initial studies evaluating the feasibility of the use of gene transfer employing the molecular conjugate vectors of the invention for genetic correction of cystic fibrosis demonstrated that immortalized cell lines derived from human airway epithelium exhibited susceptibility to this gene transfer method. To exclude the possibility that this phenomenon was the result of immortalization-induced alterations of the airway epithelium, transferrin-polylysine molecular conjugates were also evaluated in human primary respiratory epithelium cells (1° AE).

1° AE cells were obtained from nasal polyp specimens of patients as described by Yankaskas, J. R. et at., 1987; the disclosure of which is fully incorporated by reference herein. Briefly, the tissues are rinsed in sterile saline, then in Joklik's Minimum Essential Medium (MEM) plus antibiotics (penicillin 50 U/ml, streptomycin 50 μg/ml, gentamicin 40 μg/ml) and transported to the laboratory at 4° C. Cartilage and excess submucosal tissue are dissected free, and the epithelial sheets are incubated in protease solution (Sigma, type 14, 0.1 mg/dl) in MEM at 4° C. for 16 to 48 hours (Wu, R, 1985). Fetal bovine serum (FBS, 10%) is added to neutralize the protease, and cells are detached by gentle agitation. The resulting suspension is filtered through 10 μm nylon mesh to remove debris, pelleted (150 x g, 5 min) and washed in F12+10% FBS.

The 1° AE cells were then treated with transferrin-polylysine conjugates (hTfpL) containing a luciferase encoding plasmid (pRSVL) as a reporter gene (L.U.). In this analysis, the primary cells did not exhibit the susceptibility to this vector exhibited by the corresponding immortalized cell lines (1° AE: background =429±41;+hTfpL=543±L.U.), likely indicating a relative paucity of transferrin receptors on 1° AE.

To exploit an alternative target receptor on 1° AE, conjugates were constructed that incorporated a replication-incompetent adenovirus as the ligand moiety (bAdpL; see Example 19 a) and 19 b) for the preparation of biotinylated adenovirus and streptavidin-polylysine conjugates; the luciferase encoding plasmid was used as the reporter gene). Human 1° AE treated with this conjugate exhibited levels of reporter gene expression significantly greater than background (+bAdpL =2585753±453585 L.U.). In addition, 1° AE derived from other species also exhibited a high level of susceptibility to gene transfer by this route (mouse= 3230244±343153; monkey=53498880±869481 L.U.). Thus, the ability to accomplish gene transfer to 1° AE establishes the potential utility of this approach to achieve the direct in vivo gene delivery.

Example 23

Gene Transfer to Hepatocytes with Molecular Conjugate Vectors a) Transfection of tissue culture cells Cells of the murine embryonic hepatocyte cell line BNL CL.2 (ATCC TIB 73) were grown as described in Example 6. HeLa cells and hepatocytes were grown in 6 cm plastic petri dishes. Transfection was carried out at a cell density of approximately $3\times10^5$ cells per dish. Prior to transfection, 1 ml of fresh medium containing 2% FCS replaced the standard culture medium.

b) Formation of binary complexes

Biotinylated adenoviruses (approx. $10^9$ PFUs; see Example 19 a) and 19 b)) were reacted with 800 ng streptavidinylated polylysine in 50 µl HBS. After 30 min at room temperature, 6 µg pCMVL-DNA in 170 µl HBS were added, incubated for 30 min and then 3 µg polylysine pL300 in 200 µl HBS was added and after further 30 min the solution used for transfection experiments.

c) Formation of Ternary complexes

Ternary DNA complexes containing adenovirus and transferrin were formed as follows: biotinylated adenoviruses (approx. $10^9$ viral particles) were mixed with 800 ng streptavidinylated polylysine. After 30 min at room temperature the solution was mixed with 6 µg plasmid DNA in 170 ml HBS, incubated for 30 min, then 10 µg transferrin-polylysine TfpL 190B (Wagner, E. et al., 1991b) in 200 µl HBS was added and after further 30 min the solution was used for transfection experiments.

d) β-galactosidase assay

BNL CL.2 cells were seeded on to cover slips and 24 h later the cells were transfected with the pCMV-β gal (Lim, K. and Chae, 1989) reporter gene. 48 h later, β-galactosidase was assayed according to Lim and Chae.

Binary transport complexes. Biotinylated adenovirus was combined with streptavidinylated polylysine. Alternatively adenovirus was linked covalently with polylysine through the action of transglutaminase. Adenovirus-polylysine conjugate was added to DNA allowing complex formation between DNA and polylysine, thus neutralizing a known fraction (ca. ¼) of the negative charges of the DNA. A calculated amount of polylysine was then added to neutralize the remainder of the charges. The complexes consisting of DNA bound to adenovirus-polylysine conjugate and to polylysine are referred to as binary transport complexes.

There are essentially two ways of assembling binary transfer complexes. DNA can be bound to streptavidinylated polylysine and then coupled to biotinylated adenovirus or the adenovirus is coupled to polylysine first and later complexed with DNA. The latter procedure quite clearly yields better results, especially at low DNA input, and therefore is the preferred method for assembling both binary and ternary complexes.

Ternary transport complexes containing transferrin. The adenovirus-polylysine conjugates were added to DNA allowing complex formation and neutralization of a fraction (approx. ¼) of the negative charges of the DNA. A calculated amount of transferrin-polylysine conjugates was then added to complex and neutralize the remainder of the DNA. Complexes consisting of DNA, adenovirus-polylysine and transferrin-polylysine are referred to as ternary complexes. In principle, such a ternary complex should have the capacity of being endocytosed by binding to either the cellular adenovirus receptors or to transferrin receptors.

Linkage between DNA condensates and adenovirus greatly enhances luciferase reporter gene expression. Physical linkage between adenovirus strain d1312 and polylysine can be brought about by either incubating the two components with transglutaminase or by biotinylation of the adenovirus and streptavidinylation on the polylysine. The effect of linkage on transfection efficiency is clearly demonstrated in FIG. 32 where hepatocytes were incubated with transferrin-polylysine DNA complexes (TfpL) in the presence of chloroquine or in the presence of adenovirus (AdenoV+TfpL). Transferrinfection (this term designates transferrin-mediated transfection) in the presence of free adenovirus is elevated showing the typical enhancement of release of transferrin-polylysine DNA complexes into the cells. In slot pLAdenoV/TpfL adenovirus was conjugated with polylysine by means of transglutaminase and was then reacted with DNA neutralizing part of the negative charges of the DNA. Later, transferrin-polylysine was added neutralizing the remainder of the charges. In this way, a ternary complex of adenovirus-polylysine/transferrin-polylysine/DNA was synthesized. As can be seen, an extraordinary high value of $1.5\times10^9$ luciferase light units was obtained (or approx. 5000 light units per cell). In slot adenoV+pL+TfpL, adenovirus and pL were mixed as for the transglutaminase treatment. However, to demonstrate the specificity of the transglutaminase mediated binding of polylysine to the virus, the enzyme was omitted. Then the virus preparation was completed to the same amount of DNA and TfpL as in pLAdenoV/TfpL. In this case, the transfection was moderate as in AdenoV+TfpL because in both experiments co-localization of virus and transferrin DNA is a stochastic process, in contrast to slot pLAdenoV/TfpL where co-internalization is assured by the physical linkage of virus and DNA in a ternary complex yield high level of transferrinfection.

Transfection of K562 cells reveals the endosomolytic properties of adenovirus. The human erythroleukemic cell line K562 contains ca. 150,000 transferrin receptors (Klausner, R. D. et al., 1983b). In the presence of chloroquine, as reported earlier (Cotten, M. et al., 1990), these cells can be transferrinfected at very high level with polylysine-transferrin reporter DNA complexes even in the absence of adenovirus (TfpL FIG. 33). The same complexes with added free adenovirus, but in the absence of chloroquine, yield relatively poor levels of reporter gene expression (AdenoV/TfpL) presumably because K562 cells like other blood cells (Silver, L. et al., 1988; Horvath, J. et al., 1988) have low levels of adenovirus receptors. When the adenovirus is linked to polylysine via biotin/streptavidin bridge and the reporter DNA fully condensed by addition of more polylysine to complete the binary complex (pLAdenoV/pL), adenovirus supported transfection reaches intermediate levels. Presumably, the few adenovirus receptors on K562 cells are used efficaciously. If however the coupled adenovirus-polylysine-reporter DNA is fully condensed and neutralized by addition of polylysine-transferrin to form a ternary complex pLAdenoV/TfpL and the numerous cellular transferrin receptors come into play, the transfection efficiency, owing to both efficient transferrin binding and to the endosomolytic properties of the virus, is increased by at least another 2 orders of magnitudes (FIG. 33).

Terry DNA complexes lead to the expression of the reporter gene in almost 100% of hepatocytes. The efficacy of the novel DNA transport complexes were also tested in mouse hepatocytes (BNL CL.2), determining the percentages of the cells which can be reached with our various transfection protocols. A β-galactosidase gene driven by a CMV promotor was used as a reporter gene. After fixation of the cells .-galactosidase activity was deed according to Lim and Chae, 1989.

Figures 34A, 34B, 34C:

FIG. 34 shows the β-galactosidase assay on mouse hepatocytes after a) transferrinfection in the presence of chloroquine; b) transferrinfection in the presence of free d1312 adenovirus and c) transfection with ternary, linked (d1312)

adenovirus-polylysine-transferrin-reporter DNA complexes. In the absence of adenovirus, after standard transferrinfection of the reporter DNA, only few cells express the reporter gene. The percentage of transfection is less than 0.1%. When chloroquine is included the percentage is increased to about 0.2% (FIG. 34a). With free adenovirus about 5–10% of the cells express the reporter gene (FIG. 34b) while the ternary complexes with transglutaminase modified virus lead to expression in most, if not all, cells (FIG. 34c). Because the ternary complexes can be used at high dilution, the toxic effect seen with high doses of free (inactivated) adenovirus does not usually arise. But it should be noted that where ternary complexes are deployed at high concentration in order to reach 100% of the tissue culture cells, a similar toxic effect becomes noticeable. The toxic effects may be caused by residual viral gene activity, the endosomolytic properties of the added virus or is simply a consequence of the very high level of expression of the transfected gene.

Expression of a transfected reporter gene is transient but lasts for weeks in non-dividing hepatocytes. Ternary sport complexes (pLAdenoV/TfpL) were made with d1312 polylysine adenovirus and d1312 modified adenovirus further inactivated by reacting the virus with psoralen. A 2/3 confluent hepatocyte cell culture was transfected as in FIG. 34b with the luciferase reporter gene CMVL and luciferase activity was determined at different time points. As can be seen from FIG. 35, luciferase activity was maximal after 3 days at which time the hepatocyte cell culture became confluent and the cells stopped dividing. Expression of the reporter gene persisted in the non-dividing cell culture without applying selection for the maintenance of the gene and lasted for at least 6 weeks, especially when psoralen inactivated adenovirus was used for the formation of the ternary transport complexes.

Example 24

The Use of the Chicken Adenovirus CELO to Augment DNA Delivery to Human Cells

In this example, the chicken adenovirus CELO was tested for its ability to augment DNA delivery into human HeLa cells in a fashion analogous to the above experiments employing the human adenovirus 5 experiments.

The chicken adenovirus CELO (Phelps strain, serotype FAV-1,7, chicken kidney cell passage) was used in these experiments. The virus (2 ml) was passed through a PD-10 gel filtration column equilibrated with 20 mM HEPES pH 7.3, 150 mM NaCl, (HBS)+10% glycerol and 2 ml of the eluent was reacted with 20 μl 1 mM NHS-LC-biotin (Pierce) for 3 hours at room temperature. The biotinylated virus was subsequently dialyzed against 3×300 ml of HBS +40% glycerol at 4° C. and subsequently stored in aliquots at −70° C.

HeLa cells (5×10$^5$ cells per 6 cm dish) were incubated in 2 ml of DMEM+2% FCS with 6 μg of the plasmid pCMVL complexed with polylysine (pLys) or transferrin-polylysine (TfpL) mixtures in 500 μl HBS (the complexes were pre-incubated for 30 minutes at room temperature). The samples were then added to the cells at 37° C. in the presence of the quantity of virus indicated in FIG. 36. With 33 the samples containing biotinylated CELO virus, the indicated quantity of virus was preincubated with the indicated quantity of streptavidin-polylysine (StrL) in 200 μl HBS for 30 minutes at room temperature before adding 6 μg of the plasmid pCLuc in 100 μl HBS. After a 30 minute zoom temperature incubation, the indicated quantity of TfpL material was added to the cells at 37° C. Two hours later, 5 ml of DMEM+10% FCS was added to the cells and 24 hours later the cells were harvested and processed for luciferase assay. The results are shown in FIG. 36.

As shown in FIG. 36, the CELO virus as a free entity augmented DNA delivery into HeLa cells (lanes 1–6. However, when the CELO virus was modified with biotin and included in a complex with streptavidin, either with or without additional transferrin-polylysine the virus was found to augment DNA delivery at a level that is comparable to when the human adenovirus d1312 is employed. The particular line of HeLa cells displays a high binding capacity for polylysine/DNA complexes in the absence of transferrin (compare the luciferase activity of samples 1 and 4 in FIG. 36), thus, inclusion of the CELO virus in a polylysine DNA complex is sufficient to trigger uptake of the virus.

Example 25

Transfection of Myoblasts a) Transfection of myoblasts and myotubes with DNA/transferrin-polylysine complexes in the presence of free adenovirus and in the presence of biotin/streptavidin-coupled adenovirus C2C12 myoblasts Blau et al., 1985; ATCC No.: CRL 1772) and G8 myoblasts (ATCC No.: CRL 1456) were grown in high glucose DMEM plus 10% FCS. Myoblast cultures were transfected at subconfluence with ca. 5×10$^5$ cells per 6 cm dish. Myotube cultures were prepared by plating myoblasts in 6 cm dishes (ca. 5×10$^5$ cells per dish) and changing the medium to high glucose DMEM plus 2% horse serum when the cells reach confluence (Barr and Leiden, 1991; Dhawan et al., 1991). Myotube transfections were performed 5–7 days later. The transfection complexes were prepared as described in Example 19 using the indicated quantities of TfpL, StrpL and biotinylated adenovirus d1312. The cells were harvested 20 hours post-transfection and processed for luciferase activity measurement. The FIG. 37 indicates the resulting luciferase activity, in light units, for the entire cell sample: both myoblast and myotube cultures could be transfected with high efficiency. Upon differentiation to myotubes there was less than one log decrease in transfection efficiencies (C2C12) or no significant decrease (G8). The participation in myotube formation occurred at a lower frequency with the G8 line which may partly account for the lack of a detectable decrease in efficiencies in the differentiated culture. The role of the transferrin/transferrin receptor interaction in the DNA delivery to this type of cell was not major. In all four cell preparations there was only weak delivery of DNA using TfpL/DNA complexes in the presence of free adenovirus d1312 (lanes 1,4,7,10). Transfection efficiencies were enhanced using the coupled virus system (lanes 2,3,5,6,8,9, 11,12). There was a less than 1 log increase in efficiencies comparing the delivery with combination complexes containing only virus and polylysine/StrpL condensed to complexes which include transferrin-polylysine (compare, for example, lanes 2, no transferrin, with lane 3, transferrin). The poor transfection with free virus and the high transfection with coupled virus complexes either in the presence of absence of transferrin-pL suggest that the adenovirus serves as the ligand in these cells and in the absence of coupling, the free virus may enter cells but the TfpL/DNA complex does not enter productively. (Me DNA used in this Example was pCMVL, designated pCluc in the Figure.)

b) Histochemical analysis of transfection frequencies in myotubes

C2C12 myotube cultures ($5\times10^5$ cells, as myoblasts, seeded per 6 cm dish and differentiated into myotubes) were prepared as in a). With the free virus samples, pCMVβ-gal DNA (6kg) was complexed with 8 µg TfpL in 500 µl HBS and supplied to the cells in the presence of 18 µl of adenovirus d1312 ($1\times10^{12}$ virus per ml) in 2 ml of DMEM/ 2% FCS. Coupled virus samples were prepared with pCM-VLacZ DNA (6 kg) complexed with 7 µg TfpL and 800 ng of StrpL plus 18 µl of biotinylated adenovirus d1312 ($1\times10^{12}$ virus per ml) in 500 µl HBS and supplied to cells in 2 ml of DMEM/2% FCS. After a 24 hour incubation cells were stained for beta-galactosidase activity, as described in Example 15.

The beta-galactosidase staining patterns were consistent with the results of transfections using luciferase as the reporter gene (see a). Very low gene expression was obtained in myotube cultures using the free virus while coupling the virus and DNA result in high level gene expression. The presence of blue-stained, multi-nucleated tubules indicated the successful transfer of a gene to these differentiated cells in the presence of free adenovirus.

c) Delivery of DNA to mouse primary myoblast and myotube cultures

The major skeletal muscles from the both hind legs of a 4 week-old male C57B1/6 mouse were sterilely isolated into PBS and minced into approximately 5 mm pieces. The tissue was suspended in 20 ml of PBS, allowed to settle for ca. 2 minutes and the supernatant was aspirated. This washing was repeated 3 times. The tissue was then mixed with 3.5 ml of PBS plus 0.5 ml of trypsin/EDTA, 0.5 ml of 1% (w/v) collagenase (type II, Sigma),and 0.5 ml of 1% BSA (fraction V, in 4 mM $CaCl_2$) and allowed to incubate at 37° C. for 30 minutes with frequent, gentle agitation At the end of the 30 minute incubation the remaining tissue was allowed to settle and the supernatant was removed and mixed with 5 ml of DMEM+20% FCS. The incubation with protease was repeated 3–4 times until the tissue was completely dispersed. The cell suspension was then passed through a cell strainer (Falcon) to remove any aggregates and tissue fragments, and centrifuged at 500 g for 15 minutes. The cell pellet was resuspended in 10 ml of DMEM+20% FCS and the fibroblasts were removed by plating the cells on a 15 cm diameter, uncoated tissue culture dish for 60 minutes. The unattached cells were then carefully removed and plated on 5 laminin-coated, 10 cm tissue culture dishes with 15 ml of DMEM+20% FCS per dish. Upon reaching confluence (approximately one week later) the cells were trypsinized and replated on laminin-coated, 6 cm dishes, approximately $1\times10^6$ cells per dish. To generate myotube cultures, approximately 5 days later (when the cells had reached confluence) the medium was changed to DMEM+2% horse serum and one week later transfections were performed. Myoblast cultures for transfection were transfected in 6 cm dishes at approximately 80% confluence.

Laminin-coated cell culture plates were prepared in the following manner. Cell culture dishes were coated with 0.025 mg/ml polylysine (MW 30,000–70,000, Sigma) in sterile water for 30 minutes at room temperature. The plates were rinsed 3 times with sterile water and air dried. The plates were then coated with 8 µg/ml laminin (EHS, Sigma) in water overnight at room temperature. Plates were then washed 3 times with sterile water before seeding cells.

The DNA complexes used for transfections were prepared by diluting the indicated quantity of psoralen/UV-inactivated biotinylated adenovirus d1312 (prepared as described in Example 19) in 150 µl of HBS and adding 1 µg of StrpL in 150 µl of HBS followed by a 30 minute, room temperature incubation. HBS (100 µl) containing 6 µg of pCMVL (designated pCluc in the Figure)was then added to each sample followed by another 30 minute room temperature incubation. Finally, 7 µg of TfpL in 100 µl of HBS was added to each sample, incubated for 30 minutes at room temperature and then supplied to either myoblast or myotube cultures in 6 cm dishes containing 2 ml of DMEM+2% FCS. After a 1 hour incubation, the medium was replaced with 5 µl of DMEM+20% FCS (myoblasts) or of DMEM+2% horse serum (myotubes) and the cells were harvested for luciferase analysis 48 hours later. The luciferase activity from the entire cell sample is displayed in FIG. 38.

Example 26

Improvement of CELO Virus Delivery to Myoblasts Using a Lectin Ligand a) Comparative analysis of Adenovirus d1312 and CELO virus in HeLa and C2C12 myoblasts Samples of either HeLa cells or C2C12 myoblasts ($5\times10^5$ cells per 6 cm dish) were transfected with 6 µg pCMVL (designated pCluc in the Figure) complexed with 1 µg StrpL/7µg TfpL plus 5 µl of biotinylated Adenovirus d1312 (see Example 19, $1\times10^{12}$ particles/ml) or 18 µl of biotinylated CELO virus (see Example 24, $0.3\times10^{12}$ particles per ml). After a 20 hour incubation the cells were harvested and processed for luciferase activity measurement. FIG. 39 indicates the resulting luciferase activity from each entire cell sample.

Transfection into HeLa cells could be performed with comparable efficiencies using either the human adenovirus d1312/StrpL/TfpL/DNA complexes, which can enter the cells by either the adenovirus receptor or the transferrin receptor or the CELO virus/StrpL/TfpL/DNA complexes which can enter via the transferrin receptor. However, while delivery of DNA into C2C12 myoblasts could be performed efficiently with adenovirus d1312 complexes, complexes containing the CELO virus functioned poorly in these cells. Previous examples have demonstrated that the transferrin receptor plays only a minor role in combination complex delivery to these cells; presumably the adenovirus receptor is the major site of entry. The poor activity of the CELO virus in myoblast might then be due to a poor binding of both the CELO virus and transferrin to the C2C12 myoblasts.

b) Improvement of CELO virus C2C12 myoblast transfection using wheat germ agglutinin as a ligand Due to the poor delivery obtained in a), a new ligand was selected to replace transferrin.

Biotinylated wheat germ agglutinin (24 moles biotin per mole of protein) was purchased from Boehringer Mannheim. Biotinylated CELO virus was prepared as previously described. Complexes containing 6 µg pCMVL plus the indicated quantities of StrpL, TfpL, biotinylated wheat germ agglutinin (WGA-B) and CELO virus were prepared in the following manner. Virus and WGA were diluted, together, in 150 µl HBS. StrpL was also diluted in 150 µl HBS and the two solutions were mixed and incubated at room temperature for 30 minutes. The DNA, diluted in 100 µl of HBS, was added to the StrpL/Virus/WGA solution followed by another 30 minute room temperature incubation. Finally, TfpL in 100 µl HBS was added to the mixture and again the sample was incubated at room temperature for 30 minutes. The complexes were supplied to C2C12 myoblasts ($5\times10^5$ cells per 6 cm dish) in 2 ml of DMEM plus 2%FCS. One hour later 5 ml of DMEM plus 10% FCS was added to the cells and 20 hours later the cells were processed for luciferase activity measurement. The activity (light units) in each entire cell sample is displayed in FIG. 40. (The DNA used in this Example was pCMVL, designated pCluc in the Figure.)

Very poor DNA delivery was obtained in the absence of virus either with or without the WGA (lanes 1,6). Moderate delivery was obtained with coupled CELO virus (lane 2) however a 16-fold increase in delivery was obtained if WGA-B is included in the complex. Increasing the quantity of WGA in the complex (from 1 µg to 5 µg) resulted in a slight decrease in delivery (compare lanes 3 and 4) while increasing the StrpL content of the complex (from 1 µg to 2 µg) enhanced the delivery slightly (compare lanes 3 and 5). These results clearly indicate that WGA-B as a ligand enhances CELO virus-mediated DNA delivery to C2C12 cells.

d) Expression of a full length factor VIII gene in C2C12 myoblast and myotube cultures C2C12 myoblast and myotubes cultures were prepared as described above. Transfections were performed using 6 µg of a plasmid encoding the full-length human factor VIII cDNA (Wood et al., 1984; Eaton et al., 1986) complexed with 5 or 15 µl of biotinylated adenovirus (as indie plus 0.5 or 1 µg StrpL, and 7 or 6 µg of TfpL in the standard complex formation protocol.

The DNA/virus complexes were supplied to cells in 2% FCS/DMEM. After a 4 hour incubation at 37° C., 3 ml of fresh DMEM+10% FCS was added to each dish. 18 hours later the medium was harvested and assayed for the presence of factor VIII using a COATEST, (KABI, Pharmacia) test system with an international standard as a reference. Factor VIII levels are plotted as mUnits generated per 24 hours, per $1 \times 10^6$ cells (FIG. 41).

Example 27

Use of Adenovirus Protein for DNA Delivery

Adenovirus wt300 was grown in HeLa cells, purified and biotinylated as described for adenovirus d1312. 1.2 ml of virus was dialyzed against 3 ×300 ml of 5 mM MES, 1 mM EDTA pH 6.25, 4° C., for 18 hours. The material was then centrifuged for 30 minutes at 27 K in an SW60 rotor. The supernatant was carefully removed, the pellet was resuspended in HBS/40% glycerol. HEPES, pH 7.4 and NaCl were added to the supernatant to 20 mM and 150 mM, and both the pellet (containing the viral core and the bulk of the hexon capsid, "core" in FIG. 42) and the supernatant fractions (containing the vertices, "vertices" in FIG. 42) were tested for DNA delivery activity into both Mov13 mouse fibroblasts (Strauss and Jaenisch, 1992) or HeLa cells.

Complex formation with DNA was performed in the following manner. The indicated quantities of each fraction, disrupted virus before centrifugation or intact, virus (expressed as µg protein as determined by a Bradford assay) were diluted in 300 µl HBS. Streptavidin-polylysine (3 µg in 50 µl HBS) was then added followed by a 30 minute room temperature incubation. 6 µg pCMVL (designated pCluc in the Figure) was diluted in 100 µl HBS and added to the first solution for a 30 minute incubation. Finally, 2 µg of TfpL in 100µl of HBS was added followed by another 30 minute incubation. In samples prepared with only TfpL, 8 µg of TfpL in 170 µl HBS was mixed with 6 µg of pCMVL in 330 µl of HBS for 30 minutes at room temperature. The indicated quantities of virus protein were diluted into 300 µl of HBS and then added to the TfpL/DNA complexes. All samples were then added to $5 \times 10^5$ cells in 6 cm dish, containing 2 ml of DMEM/10%FCS (either HeLa of Mov13 fibroblasts) for 1 hour. 5 ml of fresh medium containing 10% FCS was then added and the cells were processed for luciferase activity 20 hours later. The resulting luciferase activity (in light units) is displayed in FIG. 42 for both HeLa cells (panel A) or Mov13 fibroblasts panel B).

With both cell types there is a dose-dependent increase in DNA delivery activity associated with the vertex fraction (sample 4–6 in both panels). When the same quantity of biotinylated virus protein is included with TfpL/DNA complexes lacking streptavidin-polylysine DNA delivery close to background levels is observed (sample 3 in each panel).

Example 28

Enhanced Gene Transfer Using DNA Ternary Complexes Containing Galactose-ligand Conjugate a) Ternary complexes containing influenza peptide conjugate The presence of polylysine-conjugated peptides containing sequences derived from the N-terminus of influenza virus hemagglutinin HA-2 subunit in DNA/transferrin-polylysine complexes has been found to substantially augment the transferrin-polylysine mediated gene transfer (Examples 13 and 14).

Similar DNA combination complexes containing the tetra-antennary galactose ligand-polylysine conjugate and the polylysine-modified influenza peptide InflupL (prepared as described in Example 6 or 13, respectively) have been prepared by adding the ligand-polylysine conjugate to plasmid DNA pCMVL to neutralize half of the DNA charge, the remainder of the charge being used to load the complexes with influenza peptide-polylysine conjugate. The delivery of these DNA complexes, containing the synthetic ligand (gal) 4, to BNL CL2 hepatocytes (transfections were carried out as described in Example 6 g) resulted in a luciferase gene expression (FIG. 43) that was significantly higher than the expression obtained with transferrin as ligand. The expression was more than 500-fold higher than in control experiments obtained with DNA complexes lacking the influenza peptides, but containing the same amount of polylysine (FIG. 43). The activity obtained with the DNA combination complexes was also approx. 30-fold higher than with DNA/(gal)4 pL complexes incubated with cells in the presence of chloroquine.

b) Ternary complexes containing adenovirus conjugate

Complexes were prepared as follows: biotinylated adenovirus d1312 (prepared as in Example 19; 2 µl, 6 µl or 18 µl; $10^{12}$ particles/ml) in 50 µl HBS were mixed with streptavidin-polylysine (100 ng, 160 ng, or 480 ng) in 100 µl HBS; after a 30 min incubation, a solution of 6 µg pCMV-L in 200 µl HBS was added, and after further 30 min, a solution of 3.8 kg (gal)4 pL (prepared as in Example 6) or 7 µg TfpL in 150 µl HBS was added.

The DNA complex solutions were added to each 300,000 cells (ATCC TIB73, ATCC TIB74, ATCC TIB75, ATCC TIB76) grown in 6 cm plates in high glucose DMEM+ 2%FCS. Further cell culture procedures and luciferase assays were performed as described. Gene expression (after 24 h) as shown in FIG. 44.

Example 29

DNA Transfer With Transferrin-polylysine in the Presence of Flee and Conjugated Rhinovirus a) Rhinovirus HRV-2 preparations Rhinovirus HRV-2 was prepared and purified as described (Skern et at., 1984; the disclosure of which is fully incorporated by reference herein).

A 400 µl solution of rhinovirus (approx. 30 µg) in HBS (150 mM NaCl/5 mM HEPES, pH 7.9)/10% glycerol was treated with 10 nmol of NHS-LC-biotin (Pierce 21335). After incubation for 3 hrs at room temperature, the virus was separated from unincorporated biotin by extensive dialysis against HBS/40% glycerol at 4° C.

Light-sensitive rhinovirus, prepared by growing the virus in the presence of acridine orange, was inactivated as described (Madshus et al., 1984).

b) Preparation of DNA complexes and transfections i) Transferrin-polylysine I DNA complexes were prepared by mixing a solution of 6 µg of plasmid DNA pCMVL in 330 µl HBS (150 mM NaCl, 20 mM HEPES, pH 7.3) with a solution of 8 µg TfpL290 in 170 µl HBS.

Figure 45A:
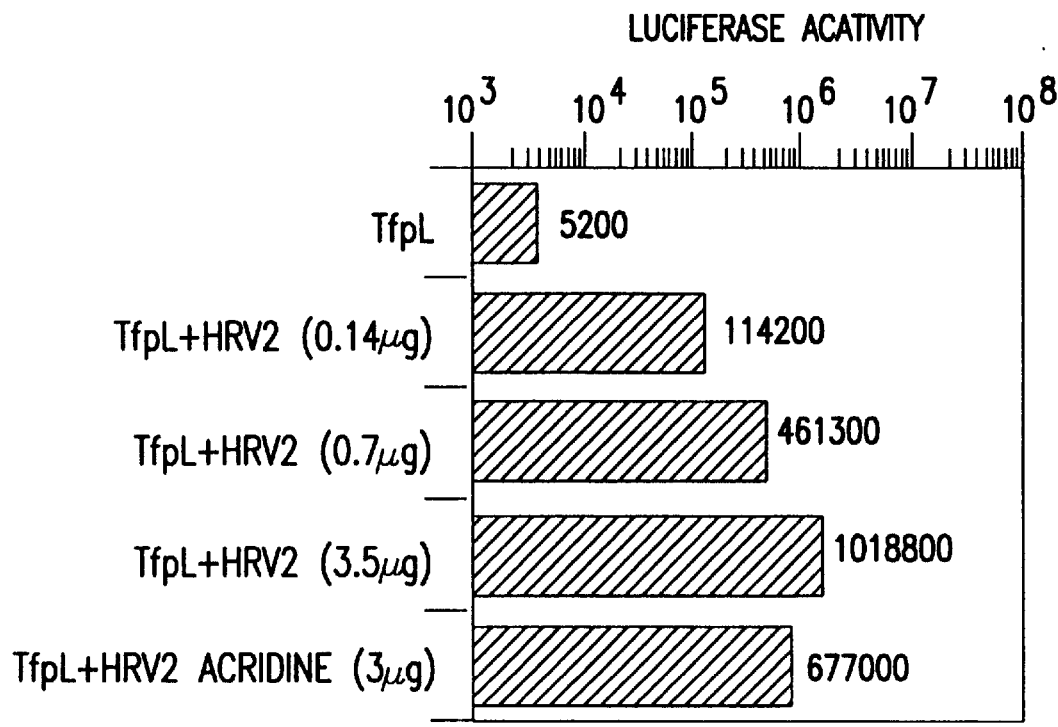

DNA complexes were mixed with 1.5 ml of medium (DMEM plus 2%FCS) and with 0.14 µg to 3.5 µg rhinovirus HRV-2 (or inactivated HRV-2). The mixture was added to NIH 3T3 cells (300,000 cells per 6 cm plate). Four hours later the transfection medium was replaced by fresh 4 ml of DMEM plus 10% FCS, Cells were harvested after 24 hrs and assayed for luciferase activity as previously described (FIG. 45A).

ii) DNA combination complexes containing transferrin-polylysine and rhinovirus-polylysine conjugates were prepared as follows: a 100 µl solution of biotinylated rhinovirus HRV-2 (3.5 µg) in HBS was mixed with 1 µg streptavidinylated polylysine in 100 µl HBS. (ale other virus concentrations were mixed with appropriate portions.) After 30 min at room temperature, the solution was mixed with 6 µg of plasmid DNA in 150 µl HBS, incubated for a further 30 min at room temperature, and subsequently mixed with 6 µg TfpL290 in 150 µµl HBS.

Figure 45B:
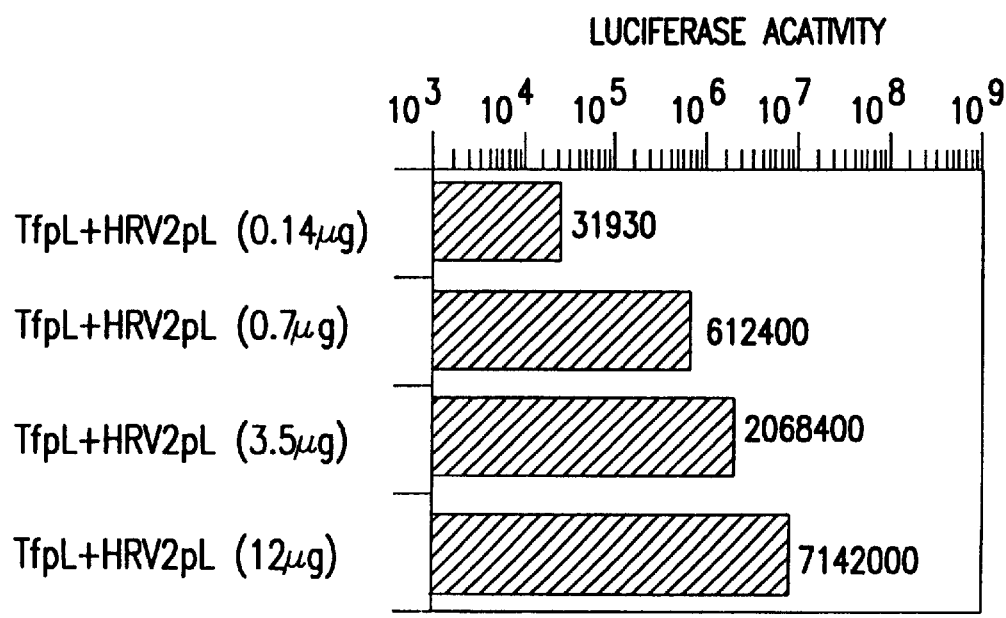

DNA complexes were mixed with 1.5 ml of medium (DMEM plus 2%FCS) and added to NIH 3 M cells (300,000 cells per 6 cm plate). Further treatment of the cultures and the assay for luciferase activity was performed as described in i) (FIG. 45B).

Example 30

Transfection of HeLa Cells With Combination Complexes Containing Ionically Bound Adenovirus Complex formation A) DNA complexes were prepared by first mixing 30 µl adenovirus d1312 (approx. $10^9$ PFUs) with 1 µg polylysine pLys450 (with an average chain length of 450 monomers) in 170 µl HBS and, after 30 min at room temperature, subsequent mixing with 6 µg of pCMVL-DNA in 170 µl HBS. After an incubation for another 30 min, complexes were mixed with 9 µg TfpL190 in 170 µl HBS. An aliquot of the complex mixture (10%=50 µl solution, 600 ng DNA; or 1%=5 µl solution 60 ng DNA) was diluted in 1.5 ml DMEM plus 2% FCS and added to 300000 HeLa cells. After 4 h, 2 ml of DMEM plus 20% FCS was added. Harvesting of cells 24 h after transfection and luciferase assay were performed as described. The luciferase activity corresponding to the total extract were 29115000 light units (in the case of 600 ng DNA) and 1090000 light units (in the case of 60 ng DNA).

Control experiment: Complex formation B) DNA complexes were prepared by first mixing 6 µg of pCMVL/DNA in 170 µl HBS with 1 µg polylysine pLys450 (with an average chain length of 450 monomers) in 170 µl HBS and, after 30 min at room temperature, subsequent mixing with 9 µg TfpL190 in 170 µl HBS. After an incubation for another 30 min, complexes were mixed with 30 µl adenovirus d1312 (approx. $10^9$ PFUs). An aliquot of the complex mixture (10%=50 µl solution, 600 ng DNA; or 1%=5 µl solution, 60 ng DNA) was diluted in 1.5 ml DMEM plus 2% FCS and added to 300000 HeLa cells. After 4 h, 2 ml of DMEM plus 20% FCS was added. Harvesting of cells 24 h after transfection and luciferase assay were performed as described as in the previous examples. The luciferase activity corresponding to the total extract were 405000 light units (in the case of 600 ng DNA) and 200 light units (in the case of 60 ng DNA).

Example 31

Local Application of DNA/adenovirus/transferrin-polylysine Conjugates Into Rat Liver a) Direct injection The complexes were prepared as described in Example 19. They comprised 200 µl biotinylated Adenovirus (d1312, 6.4 µg streptavidin-polylysine, 48 µg pCMVL and 48 µg TfpL290 in a total volume of 2000 µl HBS. A male Sprague-Dawley rat of 240 g was anesthetized with Avertin and a laparotomy of 4 cm performed. The complex solution was injected into the left lob of the liver. Then the wound was closed in layers. 48 hours after injection of the complexes the rat was sacrificed and the luciferase expression measured. In the area of injection 5615 light units/per mg protein of the liver homogenate were measured. Total luciferase activity at the injection site was 370,600 light units.

b) Application of conjugates to the liver via the bile draining system

The complexes were prepared as follows: 200 µµl biotinylated Adenovirus is d1312 diluted with 200 µl HBS were incubated with 6.4 µg streptavidin-modified polylysine in 400 µl HBS for 30 minutes at room temperature. Then 48 µg of pCMV-L in 800 µl HBS were added. After 30 minutes of incubation 48 µg of TfpL in 900 µµl HBS were further added. For application of the complexes male Sprague Dawley rats (250 g body weight) were anesthetize with Avertin and the abdomen opened with a median incision. The intestine was displaced to the left side of the body and a 27 G needle, which had been attached to a tube and a I ml syringe was inserted into the bile duct. The injection of the complexes was performed over a period of 4 minutes. Then the needle was retracted from the bile duct and the injection site sealed with a fibrin sealer (Immuno). The abdominal wound was closed With sutures and metal clips. After 30 hours the rat was killed and samples from different lobes of the river were assayed for luciferase gene expression. The pea activity of luciferase was 19000 light units/mg protein and the calculated overall expression in the total liver was in the range of $2.7 \times 10^6$ light units.

Example 32

Local Application of DNA/adenovirus/transferrin-polylysine Conjugates Into the Clamped Mouse Tail Vein The complexes were prepared as described in Example 19. They comprised 45 µl biotinylated Adenovirus d1312, 0.8 µg streptavidin-polylysine, 6 µg pCMVL and 24 µg TfpL290 in a total volume of 150 µl HBS. The complexes were injected into the tail vein of a male C3H/He mouse (two months old), which had been anesthetized with Avertin. Immediately after injection the tail vein was clamped for 20 minutes at the proximal and distal end of the tail such that the complex solution was restricted to the segment of the tail vein which had been injected and could not be flushed by the blood. 48 hours after injection the mouse was sacrificed and the tail vein prepared. Luciferase expression was measured in the homogenate of the tail vein segment. Expression resulted in 2,600 light units/3 cm tail vein.

Example 33

Transfection of Primary Human Melanoma Cells

Primary melanoma cells were isolated from a melanoma, which had been surgically removed from a patient, by mechanically disrupting the tumor in RPMI 1640 medium plus 5% FCS, 2mM glutamine, and antibiotics and pressing the tissue fragments through a steel sieve. The tumor cells were washed several times by centrifugation and subsequent resuspension and seeded into 725 cell culture flasks. 24 hours after isolation, the tumor cells were transfected with combination complexes comprising 3 µl, 9 µl or 27 µl biotinylated Adenovirus d1312 ($1 \times 10^{12}$ virus/ml), 0.5 µg streptavidin-polylysine, 6 µg pCMVL and 7 µg TfpL290 in a total volume of 500 µl HBS. 36 hours after transfection the cells were harvested and the expression of luciferase determined. Results are shown in FIG. 46.

Example 33B

Transfection of Primary Human Melamona Cells With LDL-polylysine Conjugates

Preparation of LDL polylysine 300 conjugates. A solution of 10 mg (14.3 µmole) LDL (Low Density Lipoprotein, Sigma, L-2139, molecular weight 3,500,000, particle size approx. 26 nm) in 2 ml HBS was mixed with 143 µl of a 10 mM ethanolic solution of SPDP (1.43 µmole; Pharmacia) and allowed to react for 2 h at room temperature. Gel filtration over a Sephadex G-25 column (14×140 mm) with HBS yielded 3.2 ml of a solution of approx. 10 mg LDL, modified with 0.70 µmole pyridyldithiopropionate residues. The solution was mixed with 1.2 ml 5 M NaCl in order to prevent precipitation that would otherwise occur upon addition of polylysine. Poly(L)lysine 300 was modified with SPDP as described and treated with dithiothreitol and subsequent gel filtration in order to obtain the mercapto modified form. The above modified LDL solution was mixed with a solution of 0.33 µmole polylysine 300, modified with 0.76 µmole mercapto groups, in 4 ml 2 M NaCl, 0.5 M HEPES pH 7.9, under argon and allowed to stand for 48 h at room temperature. The reaction solution was diluted to 32 ml with sterile water (NaCl concentration approx. 0.5 M) and separated by ion exchange chromatography (Biorad Macroprep S, 10×100 mm, 20 mM HEPES pH 7.3, gradient 0.2×3 M NaCl). The product fractions eluted at salt concentrations of 1.8 M–2.2 M and were pooled. After dialysis against HBS conjugates consisting of 2.35 mg (3.4 nmole) LDL, modified with 190 nmole polylysine (corresponding to 7.5 mg of free polylysine in its basic form) were obtained. This corresponds to an average modification of the LDL particles with approx. 55 polylysine chains.

Preparation of DNA complexes 18 µl biotinylated adenovirus d1312 preparation were diluted with HBS to 100 µl. 1.2 µg streptavidin-polylysine were adjusted with HBS to 100 µl and mixed with the above solution. After 30 min, 150 µl HBS containing 6 µg pCMVL were added. After further 30 min 300 µl HBS containing 4 µg LDLpL (content of polylysine: 20 µg) were added. The obtained solution was mixed with 1.5 ml DMEM +10% FCS and added to $3 \times 10^5$ primary melanoma cells in a 6 mm culture dish (designated HMM1 and HMM4) which were prepared as described in a).

The further cell culture procedure and the luciferase assay were performed as described. The results are given in FIG. 47."

Example 34

Transfection of Primary Human Fibroblasts

Human skin biopsies were put into a 6 cm petri dish containing DMEM, 2 mM glutamine, 20% FCS and antibiotics. Then the biopsies were thoroughly minced with a surgical knife and cultured in the presence of 3 ml medium for 5 days. Thereafter the cells were washed with fresh DMEM containing 2 mM glutamine 10% FCS and antibiotics and cultured for further 7 days. After this period of time the cells were trypsinized and subcultured into new petri dishes. When the cells were almost confluent, they were trypsinized again and stored frozen until transfection. For transfection the cells were thawed and seeded into 6 cm petri dishes and cultured in DMEM containing 2 mM glutamine 10% FCS and antibiotics. The transfection conjugates were prepared as follows: 3 µl, 10 µl, 20 µl and 30 µl of biotinylated adenovirus d1312 were incubated with 0.1 µg, 0.3 µg, 0.5 µg and 0.8 µg polylysine-modified streptavidin in 150 µl HBS for 30 minutes at room temperature. Then 6 µg of pCMV-βgal plasmid in 170 µl HBS were added and the mixture was incubated for further 30 minutes. In the final step 7.8 µg TfpL for the conjugates with 3 µl d1312, 7 µg TfpL for 10 µl d1312 and 6 µg TfpL for the conjugates with 20 µl and 30 µl d1312 in 170 µg HBS were added. After an incubation period of 30 minutes the conjugates were applied to the cells in 2 ml DMEM containing 2 mM glutamine, 2% FCS and antibiotics and the cells were incubated for 4 hours at 37° C. Then the medium was removed and culture was continued at 37° C. with DMEM containing 2 mM glutamine, 10% FCS and antibiotics. After 48 hours the expression of β-galactosidase was demonstrated as described in previous Examples.

In the transfection with 3 µl d1312 14% of the cells revealed production of ,β-galactosidase, with 10 µl d1312 32% positive cells were obtained, with 20 µl d1312 39% and with 30 µl d1312 64% of the cells were positive.

Example 35

Gene Transfer Using Non-viral Endosomolytic Agents a) Synthesis of membrane disrupting peptides i) Peptide synthesis:

Peptides were synthesized on an automatic synthesizer (ABI 431A) by the solid phase method using p-alkoxybenzylalcohol resin (0.97 mmol/g) as solid support and Fmoc-protected amino acids. The carboxy-terminal amino acid was coupled to the resin via the symmetric anhydride. Subsequent amino acids were coupled by the 1-hydroxybenzotriazole dicyclohexylcarbodiimide method. The following side chain protecting groups were used: (Trt)Asn, (Trt)Cys [(t-Bu)Cys in case of EALA and GLF], (t-Bu)Glu, (Trt)His, (t-Bu)Ser.

EALA: (SEQ ID NO:5) Tip Glu Ala Ala Leu Ala Glu Ala Leu Ala Glu Ala Leu Ala Glu His Leu Ala Glu Ala Leu Ala Glu Ala Leu Glu Ala Leu Ala Ala Gly Gly Ser Cys

GLF (SEQ ID NO:6) Gly Leu Phe Gly Ala Leu Ala Glu Ala Leu Ala Glu Ala Leu Ala Glu His Leu Ala Glu Ala Leu Ala Glu Ala Leu Glu Ala Leu Ala Ala Gly Gly Ser Cys

GLF-II (SEQ ID NO:7) Gly Leu Phe Gly Ala Leu Ala Glu Ala Leu Ala Glu Ala Leu Ala Glu Ala Leu Ala Glu Ala Leu Ala Glu Ala Leu Glu Ala Leu Ala Ala Gly Gly Ser Cys

GLF-delta (SEQ ID NO:8) Gly Leu Phe Glu Leu Ala Glu Ala Leu Ala Glu Ala Leu Ala Glu Ala Leu Ala Glu Ala Leu Ala Glu Ala Leu Glu Ala Leu Ala Ala Gly Gly Ser Cys EALA-Inf (SEQ ID NO:9) Gly Leu Phe Gly Ala Ile Ala Gly Phe Ile Glu Asn Gly Tip Glu Gly Au Ala Glu Ala Ala Ala Glu Ala Leu Glu Ala Leu Ala Ala Gly Gly Ser Cys EALA-P50 (SED ID NO: 10) Gly Leu Phe Glu Ala Ile Glu Gly Phe Ile Glu Asn Gly Tip Glu Gly Leu Ala Glu Ala Leu Ala Glu Ala Leu Glu Ala Leu Ala Ala Gly Gly Ser Cys P50 (SED ID NO:11) Gly Leu Phe Glu Ala Ile Glu Gly Phe Ile Glu Asn Gly Trp Glu Gly Met Ile Asp Gly Gly Gly Cys The peptides were cleaved from the resin and the side chain protecting groups were removed [except (t-Bu)Cys] by treatment of 100 mg peptide-loaded support with 3 ml of a mixture phenol/ethanedithiol/thioanisol/ water/ trifluoroacetic acid 0.75:0.25:0.5:0.5:10 for 1.5 h at room temperature. The crude peptides were precipitated in ether and washed two times. The S-t-Bu protected peptides EALA and GLF were dissolved in a small volume 1 M triethylammonium bicarbonate (TEAB) pH 8, diluted to 100 mM TEAB and further purified by reverse phase HPLC on a Nucleosil 500-5C4 column (0.1% TFA-acetonitrile gradient). Both peptides eluted at about 50% acetonitrile. The free Cys-SH form of the peptides was obtained by deprotecting Trt-Cys peptides in the same way as described above. The crude peptides (5 mg) were dissolved in 100 µl 100 mM TEAB, pH 8, containing 1 µl -mercaptoethanol and purified by gel filtration (Sephadex G-25, 100 mM TEAB, 0.5 mM EDTA) and freeze drying or ion-exchange chromatography (Mono Q Pharmacia, 20 mM Hepes, pH 7.3, gradient 0 to 3 M NaCl, the peptide elutes at 1.5 M NaCl).

ii) Modification with N-(hydroxyethyl)maleimide

The C-terminal SH group of the peptides GLFdelta, GLF-II, EALA-Inf, EALA-P50, P50 was blocked after gel filtration of the free SH form (Sephadex G-25, 20 mM Hepes, pH 7.3, 0.5 ml EDTA) by reaction with a 1.3- to 10-fold molar excess of N-(hydroxyethyl)maleimide (1 h, room temperature). Excess maleimide was removed by gel filtration (Sephadex G-25, 100 mM TEAB, pH 8) and the peptides (GLF-delta-mal, GLF-II-mal, EALA-Inf-mal, EALA-P50-mal, P50-mal) were obtained as triethylammonium salt upon freeze drying.

iii) Modification with 2,2'-dithiobispyridine:

The free SH peptides were reacted with 10 equivalents of 2,2'-dithiobispyridine (20 mM Hepes, pH 7.9, 0.5 mM EDTA) over night at room temperature. Excess reagent was removed by gel filtration (Sephadex G-25, 100 mM TEAB, pH 8) or ion-exchange chromatography (Mono Q Pharmacia, 20 mM Hepes, pH 7.3, gradient 0 to 3 M NaCl, the peptide elutes at 1.5 M NaCl) to obtain the (2-pyridylthio)-Cys peptides (GLF-delta-SSPy, GLF-II-SSPy, EALA-Inf-SSPy, 31EAIA-P50-SSPy, P50-SSPy).

iv) Dimerization of peptides:

The homodimer of P50 (P50 dim) was prepared by reacting equimolar amounts of P50Cys-(2-pyridylthio) and P50-Cys-SH in 20 mM Hepes, pH 7.3, over three days at room temperature. The reaction mixture was separated a Mono Q column (HR-515 Pharmacia; 20 mM Hepes, pH 7.3, gradient 0.09 M to 3 M NaCl, P50-dimer was eluted at 1.1 M NaCl). The heterodimer GLF-SS-P50 was prepared analogously by reaction of peptide P50, free mercapto form, with pyridylthio-modified peptide GLY.

b) Liposome leakage assay:

The ability of the synthetic peptides to disrupt liposomes was assayed by the release of fluorescent dye from liposomes loaded with a self-quenching concentration of calcein. Liposomes were prepared from egg phosphatidylcholine by reverse phase evaporation (Szola and Papahadjopoulos, 1978) with an aqueous phase of 100 mM calcein, 375 mM Na$^+$, 50 mM NaCl, pH 7.3 and extruded through a 100 nm polycarbonate filter (MacDonald et al., 1991) to obtain a uniform size distribution. The liposomes were separated from unincorporated material by gel filtration on Sephadex G25 with an iso-osmotic buffer (200 mM NaCl, 25 mM Hepes, pH 7.3). For the leakage assay at various pH values, the liposome stock solution was diluted (6 µl/ml) in 2 x assay buffer (400 mM NaCl, 40 mM Na citrate). An aliquot of 100 µl was added to 80 µl of a serial dilution of the peptide in water in a 96-well microtiter plate (final lipid concentration: 25 µM) and assayed for calcein fluorescence at 600 nm (excitation 490 nm) on a microtiterplate fluorescence photometer after 30 min of incubation at room temperature. The value for 100% leakage was obtained by addition of 1 µl of a 10% Triton X-100 solution. The leakage units were calculated as reciprocal value of the peptide concentration, where 50% leakage was observed (i.e. the volume (µl) of liposome solution which is lysed to 50% per µg of peptide). Values below 20 units are extrapolated. The results of the liposome leakage assay are shown in FIG. 48. GLF and EALA exhibited the highest pH specific activity.

c) Erythrocyte lysis assay:

Fresh human erythrocytes were washed with HBS several times and resuspended in 2 x assay buffer of the appropriate pH (300 mM NaCl, 30 mM Na citrate) at a concentration of 6.6 10$^7$/ml. An aliquot of 75 µl was added to 75 µl of a serial dilution of the peptide in water in a 96-well microtiter plate (cone type) and incubated for 1 h at 37° C. with constant shaking. After removing of the unlysed erythrocytes by centrifugation (1000 rcf, 5 min) 100 µl of the supernatant was transferred to a new microtiter plate and hemoglobin absorption was determined at 450 nm (background correction at 750 nm). 100% lysis was determined by adding 1 µl of a 10% Triton X-100 solution prior to centrifugation. The hemolytic units were calculated as reciprocal value of the peptide concentration, where 50% leakage was observed (i.e. the volume (µl) of erythrocyte solution which is lysed to 50% per µg of peptide). Values below 3 hemolytic units are extrapolated. The values are given in FIG. 49. As can be seen, P50 dim and EALA-P50 exhibited the highest pH specific activity with regard to lysis of cells and/or release of larger molecules such as hemoglobin. The P50 monomers P50mal and P50 SS-Py had lower activity. Melittin showed the highest activity, which was, however, not specific for acidic pH.

d) Preparation of DNA combination complexes:

DNA complexes were prepared by first mixing 6 µg of pCMVL-DNA in 150 µl HBS with 4 µg TfpL290 in 150 µl HBS and subsequent mixing with 4 to 20 µg of poly(L) lysine290 in 100 µl HBS after 30 min at room temperature; after further 30 min incubation at room temperature, 0.3 to 30 µg of peptide in 100 µl HBS was added and incubated for another 30 min. The optimal amount of endosomolyic agent was determined in preliminary titrations by assaying the resulting gene transfer efficiency (see Table 3 for gene transfer to BNL CL.2 cells). Simultaneous addition of pLys and endosomolytic agent as well as the use of larger volumes for the complex preparation (1.5 ml final volume) was shown to give comparable (or better) transfection efficiencies. In these experiments, the non-peptidic amphipathic substances desoxycholic acid and oleic acid were also shown to augment DNA delivery.

e) Transfection of cells:

Adherent cell lines (BNL CL.2 hepatocytes or NIH 3T3 cells, respectively) were grown in 6 cm dishes for 1 to 2 days prior to transfection (DMEM medium with 10% FCS; 300,000 cells per dish). The medium was removed and 1.5 ml of DMEM (2% FCS) and 500 µl of the DNA complexes were added. Alternatively, 0.5 ml DMEM 6% FCS and 1.5 ml of DNA complexes was used. After 4 h incubation 2 ml DMEM (18% FCS) was added. Alternatively, the transfection medium can be replaced by 4 ml of DMEM with 10% FCS. Harvesting of cells and luciferase assays were performed 24 h after transfection as described previously. The light unit values shown, represent the total luciferase activity of the transfected cells.

Transfection of BNL CL.2 hepatocytes is shown in FIG. 50:

FIG. 50A) DNA complexes were prepared by first mixing 6 µg of pCMVL-DNA in 250 µl HBS with 4 µg TfpL290 in 250 µl HBS and subsequent mixing with 20 µg of poly(L) lysinem90 in 750 µl HBS after 30 min at room temperature; after further 30 min incubation at room temperature, indicated amounts of peptides in 250 µl HBS were added. After an incubation for another 30 min, complexes were mixed with 0.5 ml DMEM plus 6% FCS and added to 450,000 cells.

FIG. 50B) DNA complexes were prepared as follows. A solution of 6 µg of pCMVL-DNA in 500 µl HBS was mixed with 4 µg TfpL290 in 250 µl HBS and left for 30 min at room temperature. A 500 µl solution of 20 µg of poly(L)lysine$_{290}$ in HBS with mixed with indicated amounts of peptides in 250 µl HBS and immediately added to the TfpL/DNA mixture. After further 30 min incubation at room temperature the complexes were mixed with 0.5 ml DMEM plus 6% FCS and added to 450,000 cells. Harvesting of cells 24 h after transfection and luciferase assays were performed as described previously.

The experiments carried out with NIH3T3 cells are shown in FIG. 51. The preparation of complexes according to A) and B) was the same as for the transfection of TIB 73.

In the cell culture experiments P50 dim and EALA-P50 exhibited the highest activity, EALA and GLF had medium activity, whereas P50 monomers and melittin had low activity.

Example 36

Gene Transfer Using a Synthetic Non-viral Peptide With an Oligolysine C-terminal Extension A peptide with the sequence (SEQ ID NO:4) Met Ala Gln Asp lie Ile Ser Thr Ile Gly Asp Leu Val Lys Tip Ile Ile Asp Thr Val Asn Lys Phe Thr Lys Lys Lys Lys Lys Lys Lys Lys Lys Lys Lys was synthesized and purified according to the method described in the previous Example. This peptide is derived from the δ-toxin of Staphylococcus aureus (SEQ ID NO:3) Met Ala Gln Asp He Ile Ser Thr Ile Gly Asp Leu Val Lys Tip Ile Ile Asp Thr Val Asn Lys Phe Thr Lys Lys, which is known to possess specificity for membrane disruption at acidic pH (Thiaudiere et al., 1991; Alouf et al., 1989), by extension by additional 10 lysine residues.

DNA complexes were prepared by first mixing 6 µg of pCMVL-DNA in 170 µl HBS with 4 µg TfpL290 in 170 µl HBS and subsequent mixing with approximately 3 µg of peptide in 170 µl HBS after 30 min at room temperature. After an incubation of another 30 min, complexes were mixed with 1.5 ml DMEM plus 2% FCS and added to 450,000 BNL CL.2 hepatocytes. After 2 h, 2 ml of DMEM plus 20% FCS were added. Harvesting of cells 24 h after transfection and measuring luciferase activity were performed as described in the previous Examples. The luciferase activity corresponding to the total extract was 481,000 light units.

Example 37

Transfection of Hepatocytes in the Presence of Melittin-peptides With a C-terminal Oligo-Lys-tail Peptides of the sequences (N to C terminus) (SEQ ID NO: 12) Gly Ile Gly Ala Val Leu Lys Val Leu Thr Thr Gly Leu Pro Ala Leu He Ser Trp Be Lys Arg Lys Arg Gln Gin Lys Lys Lys Lys Lys Lys Lys Lys Lys Lys (designated mel 1) and (SEQ ID NO: 13) Gly lie Gly Ala Val Leu Glu Val Leu Glu Thr Gly Leu Pro Ala Leu Ile Ser Trp lie Lys Arg Lys Arg Gln Gin Lys Lys Lys Lys Lys Lys Lys Lys Lys Lys (acidic mutant, designated mel 2) were synthesized as described in Example 36.

DNA complexes were prepared by first mixing 6 µg of pCMVL-DNA in 170 µl HBS with 4 µg TfpL290 in 170 µl HBS and subsequent mixing with approximately 3 µg of peptide mell or 5 µg of mel2 in 170 µl HBS after 30 min at room temperature. After an incubation for another 30 min, complexes were mixed with 1.5 ml DMEM plus 2% FCS and added to 450000 BNL CL.2 cells, cultivated as described in Example 36. After 4 h, 2 ml of DMEM plus 20% FCS was added. Harvesting of cells 24 h after transfection and luciferase assay were performed as described. The luciferase activity corresponding to the total extract were 9200 light units (in the case of mel1) and 9400 light units (in the case of mel2).

Example 38

Interferon Alpha Expression in HeLa Cells

HeLa cells (5×10$^5$ cells per 6 cm dish) were transfected with pAD-CMV1-IFN encoding human interferon alpha2c under the control of the CMV enhancer/promoter (described in DE 40 21 917 A. pAD-CMV1-IFN was obtained by recloning the HindIII-XbaI IFN- 2c insert into pAD-CMV1). Samples of 6 µg DNA in 330 µl HBS were mixed with 8 µg of TfpL in 330 µl HBS and allowed to assemble for 30 minutes at room temperature. Samples 6–10 contained only 4 µg of TfpL and after the first 30 minutes incubation an aliquot of P16pL (20 µg) in 160 µl of HBS was added to both samples 6 and 7 and an aliquot of pLys 290 (20 µg) was added to samples 8, 9 and 10. After an additional 30 minute incubation, aliquots of 160 µl of HBS containing 10 µl (sample 8) or 50 Al (sample 9 and 10) of free P16 were added (for synthesis of P16 and P16pL, see Example 13). After an additional 30 minute incubation, the samples were supplied to HeLa cells in 2 ml of DMEM/2%FCS in the presence of the following additional compounds. Sample 2, 7 and 10 contained 100 µM chloroquine, samples 3 and 4 contained 5 and 15 µl of adenovirus d1312, (1×10$^{12}$ particles/ml), sample 5 contained 15 µl of the same virus, psoralen-inactivated. As controls for adenovirus stimulation of endogenous interferon production, samples 11, 12 and 13 were treated with aliquots of virus equal to samples 3, 4 and 5). At 2 hours after transfection 5 ml of fresh DMEM+ 10%FCS were added to the cells. At 48 hours after transfection the medium was removed and replaced with 2 ml of fresh DMEM+10% FCS. This medium was harvested at 72 hours post transfection and an ELISA analysis for interferon alpha was performed as described in DE 40 21 917. The interferon alpha levels (in ng/ml) are displayed in FIG. 52.

TfpL functioned poorly to deliver IFN genes to these cells, consistent with the previous observations using luciferase or β-gal reporter genes. The presence of chloroquine generated a detectable signal (ca. 7 ng/ml, sample 2), but adenovirus dl312 stimulated DNA delivery in a dose dependent fashion (samples 3 and 4). Treating these cells with comparable quantities of virus in the absence of IFN DNA complexes did not result in a detectable interferon signal (samples 11 and 12). Transfection with the synthetic influenza derived endosomolytic peptide P16(see Example 13) as a conjugate (sample 6,7) or as a peptide ionically bound to the surface of TfpL/DNA complexes (samples 8, 9 and 10, for binding of peptides see Example 35) generated detectable levels of interferon production, which was enhanced with the peptide conjugate in the presence of chloroquine (sample 7).

Example 39

Gene Transfer Into B-lymphoblastoid Cells

Human-Ig polylysine conjugates and anti-human-Ig polylysine conjugates were prepared in the following manner (coupling was carried out with methods known in the literature (Jung et al., 1981) by introducing disulfide bridges after modification with succinimidyl-pyridyl dithiopropionate).

a) Preparation of anti-human-Ig/polylysine 300 conjugates.

A solution of 2 mg goat anti-human-Ig (Southern Biotechnology Associates, Inc., Birmingham, AL, USA) in HBS (150 mM NaCl, 20 mM HEPES, pH 8.7) was mixed with 14 μl of 5 mM ethanolic solution of SPDP (Pharmacia). After 10 h at room temperature, the solution was filtered on a Sephadex G 25 column ((eluted with 100 mM HEPES, pH 7.3), yielding 1.3 mg of anti-human-Ig, modified with 30 nmole pyridylthiopropionate residues. Poly(L)lysine 300 (Sigma; average degree of polymerization 300 lysine residues) was modified analogously and brought into the mercapto-modified form by treating with dithiothretol and subsequent gel filtration. A solution of 12 nmole polylysine 300, modified with 29 nmole mercapto groups in 0.3 ml HBS was mixed with the above anti-human-Ig under exclusion of oxygen and allowed to stand overnight at room temperature. By addition of 5 M NaCl, the reaction mixture was adjusted to 0.6 M NaCl. The conjugates were isolated by ion exchange chromatography Pharmacia, Mono S HR 515); after dialysis against 25 mM HEPES, pH 7.3, conjugates comprising 0.33 mg anti-human-Ig, modified with 4 nmole polylysine 300 (molar ratio 1:2) were obtained.

b) Preparation of human-IgG/polylysine 300 conjugates.

A solution of 19.5 mg (122 nmole) antibody (Sigma 14506) in 2 ml HBS was mixed with 39 μl of 10 mM ethanolic solution of SDP. After 2.5 h at room temperature, the solution was passed over a gel column (Sephadex G25; eluted with 100 mM HEPES, pH 7.9) yielding 19 mg (119 nmole) human-IgG modified with 252 nmole pyridyldithiopropionate residues. Polylysine 300 was treated analogously to a) in order to obtain the mercapto form. A solution of 119 nmole polylysine 300 modified with 282 nmole mercapto groups in 1 ml HBS was mixed with the above modified humanIgG under exclusion of oxygen and allowed to stand over night at room temperature. By addition of 5 M NaCl, the reaction mixture was adjusted to 0.6 M NaCl. The conjugates were isolated by ion exchange chromatography (Pharmacia, Mono S, 50 mM HEPES, pH 7.3; salt gradient 0.6 M to 3 M NaCl); : after dialysis against HBS , pH 7.3, conjugates comprising 9 mg (57 nmole) human-IgG, modified with 90 nmole polylysine 300 (molar ration 1:1.6) were obtained.

c) Complex formation and transfection of cells.

Complexes were prepared as follows: Biotinylated adenovirus dl312 (30 μl, $10^{12}$ particles/ml) in 50 μl HBS were mixed with streptavidin-polylysine (800 ng) in 100 μl HBS. After a 30 min incubation, a solution of μg pCMVL in 200 μl HBS was added and after a further 30 min, a solution of 5.1 μg polylysine 450, 10.2 μg TfpL, 12 μg human-Ig/polylysine conjugate or 10 μg anti-human-Ig/polylysine conjugate, in 150 μl HBS, were added. The DNA complex solutions were added to each $10^6$ B-lymphoblastoid cells (generated from human peripheral blood mononuclear cells by immortalizing with Epstein Barr virus as described by Wells and Crawford, 1989), grown in 24-well plates in ml of RPMI 1640+2% cell culture procedures and luciferase assays were performed as described. Gene expression after 48 h is shown in FIG. 53.

Example 40

Direct In Vivo Gene Transfer to Airway Epithelium Employing Adenovirus-polylysine-DNA Complexes In the present example, the direct in vivo gene transfer to the respiratory epithelium is accomplished in a rodent model using adenovirus-polylysine-DNA complexes. This establishes the feasibility of this approach as a method to accomplish transient gene expression in the respiratory epithelium. The capacity to achieve genetic modification of the airway epithelial cells in situ offers a potential strategy to accomplish gene therapy for disorders afflicting the airway epithelium.

The firefly luciferase reporter gene containing plasmid pCLuc4 was used to form conjugate-DNA complexes which were delivered to cotton rats via injection by the intratracheal route. The complexes (hTfpL/bAdpL) were formed with human transferrin-polylysine and adenovirus that had been inactivated by genomic deletion and treatment with psoralen plus UV-irradiation. This modification allows prolonged in vitro expression consequent to minimized adenoviral replication and/or gene expression. Lungs were harvested and lysates evaluated for luciferase gene expression at various time points post-injection.

FIG. 54 shows the time course of heterologous gene expression in cotton rat airway epithelium transduced with human transferrin-adenovirus-polylysine-DNA complexes. Ordinate represents luciferase gene expression as Light Units per 1250 μg total protein derived from lung lysates. Experiments were performed 3–4 times each and results expressed as mean+SEM. Maximum gene expression was noted at 24 hr post-administration. There was a rapid decrease of net gene expression such that levels diminished to background by day 7.

As shown in FIG. 54, the detectable in vivo gene expression mediated by the adenovirus-polylysine DNA complexes was of a transient nature. This closely parallels the expression pattern noted after lipofectin-mediated in vivo gene transfer to the respiratory epithelium (Hazinski et al., 1991). This result is not unanticipated as the delivered DNA would be present as a plasmid episome lacking replicative or integrative capacity (Wilson et al.). In the present design the conjugate system lacks a mechanism to mediate integration and thus the stable transduction frequency would be expected to be low. Alternatively, attrition of the modified cells could explain the extinction of gene transfer in the lung. In terms of the observed transduction frequency, it is hypothesized that the low percentage of cells transduced in vivo could represent a problem of initial binding of the vector to the target airway epithelial cell. In this regard, differentiated airway epithelium may present a vastly different cell surface receptor population than that characterizing immortalized airway epithelial cell lines or primary cultures of airway epithelial cells. Thus, vectors possessing a ligand with a high binding affinity to the differentiated airway epithelium may overcome this problem. In addition, various factors present in the environment of the airway epithelium may be deleterious to vector-mediated gene transfer. These factors include ciliary motion, the bronchial mucus, surfactant, and epithelial lining fluid proteases. To evaluate these possibilities, various maneuvers may be employed to modify the airway epithelial environment prior to vector delivery. These manipulations include: 1) the paralysis of ciliary motion by low temperature or topical anesthesia; 2) dispersal of bronchial mucus through the use of mucolytic agents such as N-acetyl cysteine; and 3) the delivery of inhibitors of proteases to the epithelial lining fluid such as $\alpha_1$-antitrypsin ($\alpha 1AT$) and bronchial protease inhibitor (BIP or SLIP). These various pre-delivery maneuvers can be non-invasively instituted to attempt to mitigate potential in situ barriers to in vivo airway epithelial gene transfer.

In terms of the time course of heterologous gene expression in the transduced animals, the rapid extinction observed could represent either: 1) loss of DNA from transduced cells or 2) loss of transduced cells secondary to vector-related toxicity. If vector toxicity is the basis of the limited gene expression noted in vivo, this may be addressed by the introduction of additional deletions into the genome of the adenovirus component of the vector.

Example 41

In Vivo Gene Transfer to Airway Epithelium Employing Molecular Conjugate Vectors Molecular conjugates with the capacity to bind selectively to the ciliated airway epithelial subset have been derived utilizing ligands with known specificity for this cellular target. The construction of these conjugate vectors entails: 1) the confirmation of the binding properties of the candidate ligands in the conjugate confirmation; and 2) the addition of components to enhance internalization after cell-specific binding. The candidate ligands include: 1) influenza virus; 2) the influenza hemagglutinin (HA) glycoprotein; and 3) the lectin SNA (see Piazza, et at., 1991; and Baum, et al., 1990). These agents have been demonstrated to bind selectively to ciliated airway epithelial cells. To evaluate the binding of the ligands in the conjugate confirmation, intact airway epithelial tissue was required as immortalized cell lines and primary airway epithelial cultures lacked the target surface markers characterizing the differentiated intact airway epithelium. Immunohistologic localization of binding to fixed human tracheal sections was employed to establish the cell-specific binding properties of the candidate ligands, and thus this assay system was used to evaluate the binding properties of the corresponding derivative conjugate vectors.

The ligand and polylysine components of the SNA-polylysine conjugates were complexed via a biotin-avidin bridge. Biotin SNA (3.7 µg) was diluted in 175 µl of HBS and combined with streptavidin-polylysine (1.8 µg), which had previously been diluted in 175 µl of HBS. The above mixture was incubated at room temperature for 30 min prior to the addition of 6 µg of pRSVL diluted in 150 µl of HBS followed by another 30 min incubation at room temperature to allow the complexes to form. Human transferrin-polylysine conjugates consisting of human transferrin covalently linked to poly(L)lysine, hTfpL, were prepared as described herein. Conjugate-DNA complexes were prepared by dilution of 6 µg of pRSVL in 350 µl HBS followed by addition of 8 µg of hTfpL diluted in 150 µl of HBS. Complexes were allowed to form by incubating for 30 min at room temperature. To form polylysine-DNA complexes, poly()lysine450, pL450, (3 µg) or pL295 (4 µg) was diluted in 150 µl of HBS, then added to 6 µg of pRSVL DNA diluted in 350 µl of HBS. The two components were incubated at room temperature for 30 min. To prepare a complex with two ligand moieties: SNA and hTf at a one-to-one ratio, the bSNA-StpL complex was first formed combining 1.9 µg of bSNA diluted in 175 µl of HBS and 0.9 µg of StpL diluted in 175 µl of HBS. The complex was allowed to form at room temperature for 30 min. pRSVL (6 µg) diluted in 150 µl of HBS was then followed by another 30 min incubation period. hTfpL (4 µg) diluted in 150 µl of HBS was added to further condense the DNA while incorporating the second ligand. This step was again followed by a 30 min incubation period at room temperature.

The basis of this assay was to administer conjugate-DNA complexes to tracheal sections, followed by detection of conjugate binding with a primary antibody. The primary antibody of choice was a monoclonal anti-transferrin antibody that was specific for the human transferrin ligand found in the conjugate-DNA complexes. The signal of the primary antibody was then amplified using an anti-mouse antibody containing horseradish peroxidase. Positive binding was observed as intense red staining. The assay was optimized using the SNApL-DNA complex Monoclonal anti-transferrin antibody was used to detect the human transferrin ligand. A series of conjugate-DNA complexes were formed to determine the binding specificity of the SNApL/hTfpL-DNA complex. Positive staining was observed in the ciliated subset of respiratory epithelial cells with the SNApL/hTfpL DNA complex using the monoclonal anti-transferrin antibody to determine binding specificity.

To validate this result, the following controls were executed: (1) Tracheal tissue that had only been treated with HRS, the conjugate buffer, showed no positive staining following incubation with primary and secondary antibodies. This result eliminated the possibility of cross-reactivity between either of the two antibodies and human tracheal tissue. (2) Following incubation with the SNApL/hTfpL-DNA complex, the tissue section was treated with an irrelevant antibody, an anti-neumaminidase monoclonal antibody (PY203), to determine whether or not the secondary antibody was binding directly to the conjugate-DNA complex and not the primary antibody. The lack of positive staining for this control eliminated this possibility. (3) Tracheal tissues are incubated with pL-DNA and treated with both primary and secondary antibodies to determine whether the primary antibody was binding to the polylysine component of the conjugate. No positive staining was observed, eliminating this possibility. (4) A tissue section was incubated with SNApL-DNA followed by treatment with primary and secondary antibodies. A negative result for this control eliminated the possibility of the primary antibody binding to the SNA component of the conjugate. (5) A tissue section was incubated with hTfpL-DNA to determine whether or not the SNApL/hTfpL-DNA complex was binding by virtue of the human transferrin ligand and/or the polylysine component. Red positive staining similar to that observed for the SNApL/hTfpL-DNA complex was observed (FIG. 55). These results indicate that the SNApL/hTfpL-DNA complex could be binding by virtue of the SNA ligand, the human transferrin ligand, or the polylysine component.

To determine whether or not the above conjugate is binding to ciliated airway epithelial cells by virtue of its polylysine component, an irrelevant ligand-polylysine complex was constructed. This irrelevant ligand was the antibody MP301, which possesses specificity for the Mycoplasma P1 protein.

Antibody-polylysine MP301pL (1.9 ng/ml; 5.5 µg in 150 µl HBS) was combined with a plasmid DNA pIB120 (6.0 µg in 350 µl HBS) and incubated 30 min at room temperature to form antibody-polylysine-DNA complexes. The complex (50 µl) was applied to hydrogen peroxide (3%) treated, fixed human trachea for 1 hr at °C. Blocking serum was added followed by the link antibody (biotinylated anti-mouse immunoglobulin) and incubated with peroxidase-labelled streptavidin. Staining was completed with AEC substrate. Intense red staining was noted in the apical region of ciliated airway epithelial cells. This pattern was not different from that noted with hTfpL and SNA/hTfpL complexes. It was concluded that nonspecific binding was occurring. This nonspecific binding was most likely due to polylysine interaction with the apical membrane glycocalyx constituents.

Bibliography:

Abrahamson, D. R. et al., 1981, J. Cell Biol., 91, 270–280.
Akopian, T. A. et al., 1991, Nucl. Acids Res. 19, 424.
Alouf J. E., Dufourcq J., Siffert O., Thiaudiere E. and Geoffroy Ch., 1989, Eur. J. Biochem. 183, 381–390.
Anderson, P. et al., 1982, J. Biol. Chem., 257, 11301–11304.
Andrews N. W., Abrams C. K., Slakin S. L. and Griffiths G., 1990, Cell 61, 1277–87.
Ansardi, D. C. et aL, 1991, J. Virology 65, 2088–2092.
Argiolas A. and Pisano J. J., 1985, J. Biol. Chem. 260, 1437–1444.
Armentano, D., Yu, S., Kantoff, P., von Ruden, T., Anderson, W. F. and Gilboa, E., 1987, J. Virol. 61, 1647–1650.
Armentano, D. et al., 1990, Proc. Natl. Acad. Sci. USA, 87, 6141–6145.
Asada-Kubota, M. et al., 1983, Exp. Pathol., 23, 95–101.
Ascoli, M. et al., 1978, J. Biol. Chem., 253, 7832–7838.
Ashwell, G. et al., 1982, Annu. Rev. Biochem., 51, 531–554.
Atherton, E., Gait, M. J., Sheppard, R. C. and Williams, B. J., 1979, Bioorg. Chem. 8, 351.
Barr, E. and Leiden, J., 1991, Science 254, 1507–1509.
Bartlett, G. R., 1959, J. Biol. Chem. 234, 466.
Baum and Paulson, 1990, Acta Histochem. Suppl. 40, 35–38.
Berkner, K. L., 1988, BioTechniques 6, 616–629.
Berns, K. I., 1990, Virology, 2nd Edition, Ed. by Fields, B. N., Knipe, D. M. d al., Raven Press Ltd., New York, 1743–1759.
Bhakdi S. and Tranum-Jensen J., 1991, Immunology today 12, 318–320.
Blau, H. et al., 1985, Science 230, 758–766.
Blobel C. P., Wolfsberg T. G., Turuck C. W., Myles D. G., Primakoff P. and White J. M., 1992, Nature 356, 248–252.
Blondelle S. E. and Houghten R. A., 1991, Biochemistry 30, 4671–4678.
Bondeson, J., WIkander, J. and Sundler, R., 1984, Biochim. Biophys. Acta 777, 21–27.
Boulanger, P. A. and Puvion, F., 1973, Eur. J. Biochem. 39, 37–42.
Bragg, R. R. et al., 1991, Onderstepoort J. Vet. Res. 58, 309–310.
Carpenter, G., 1984, Cell, 37, 357–358.
Chardonnet, Y. and Dales, S., 1970, Viology 40, 462–477.
Cheng, S-Y. et a4., 1980, Proc. Natl. Acad. Sci. USA, 77, 3425–3429.
Ciliberto, G., Dente, L, Cortese, R., 1985, Cell 41, 531–540.
Clarke, D. D., Mycek, M. J., Neidle, A. and Waelsch, H., 1959, Arch. Biochem. Biophys. 79, 338–354.
Clarke, et al., 1992, science 257, 1125–1128.
Collis, P., Antoniou, M. and Grosveld, F., 1990, EMBO J. 9, 233–240.
Cotten, M., Laengle-Rouault, F., Kirlappos., H., Wagner, E., Mechder, K., Zenke, M., Beug, H., and Birnstiel, M. L., 1990, Proc. Natl. Acad. Sci. USA 87, 4033–4037.
Davidson, D. and Hassell, J. A., 1987, J. Virol. 61, 1226–1239.
Davis, B. D. and Dulbecco, R., 1980, Microbiology, 3rd Edidon, Ed. by
Davis, B. D. et al., Harper & Row, Sterilization and Disinfection, 1263–1274.
Defer, C., Belin, M., Caillet-Boudin, M. and Boulanger, P., 1990, J. Virol. 64, 3661–3673.
Dempsey C. E., Bazzo R., Harvey T. S., Syperek I., Boheim G. and Campbell I. D., 1991, FEBS Lett. 281, 240–244.
DeWet, J., Wood, K., DeLuca, M., Helinsld, D. and Subramani, S., 1987, Mol. Cell. Biol. 7, 725–737.
Dhawan, J. et al., 1991, Science 254, 1509–1512.
Donti, E. et al., 1988, Cancer Genet. Cytogenet. 30, 225–231.
Dullccco, R., 1980,. Microbiology, 3rd Edition, Ed. by Davis, B. D. et al., Harper & Row, The Nature of Viruses, 853–884.
Eaton, D. L. et al., 1986, Biochemistry 25, 8343–8347.
Esser A. F., 1991, Immunology today 12, 316–318.
Fields, B. N. and Knipe, D. M., 1990, Virology, 2nd edition, Raven Press, Ltd., New York.
FitzGerald, D., Padmanhan, R., Pastn, I. and Willinglam, M., 1983, Cell 32, 607–617.
Folk, J. E., 1985, Methods Enyymol. 113, 358–375.
Franchini G., 1989, Science 244, 694–697.
Fricks C. E. and Hogle J. M., 1990, 3. Virol. 64, 1934–1945.
Fujiwara et al., 1981, J. Immunol. Meth. 45, 195.
Geoffroy C., Gaillard J.-L., Alouf J. E. and Berche P., 1987, Infection and Immunity 55, 1641–1646.
Gething M.J., White I. M. and Waterfield M. D., 1978, Proc. Natl. Acad. Sci. USA 75, 2737–2740.
Ginsberg, H. S., 1980, Microbiology, 3rd Edition, Ed. by Davis, B. D. et al., Harper & Row, Picornaviruses, 1095–1117.
Goldmacher, V. S., Blitfler, W. A., Iabert, J. M., McIntyre, G. and Steward, J., 1989, Molecular Pharmacology 36, 818–822.
Goldstein, J. L. et al., 1982, Clin. Res., 30, 417–426.
Goldstein, J. L et aL, 1979, Proc. Natl Acad. Sci. USA, 76, 333–337.

Goldstein, L. J. et al., 1980, Nature 285, 66.

Gong S., Lai C. and Esteban M., 1990, Virology 178, 81–91.

Green, M. et al., 1989, Cell 58, 215–223.

Hazinski, et al., 1991, Am. J Respir. Cell. Mol. Biol. 4, 206–209.

Hearst, J. E. and Thiry, L., 1977, Nucl. Acids Res. 4, 1339–1347.

Heldin, C-H. et al., 1982, J. Biol. Chem., 257, 4216–4221.

Herskowitz, I., 1987, Nature 329, 219.

Hizuka, N. et al., 1981, J. Biol. Chem., 256, 4591–4597.

Hoekstra D., 1990, J. Bioenerg. Biomembr. 22, 121–155.

Holland, J. J., 1990, Virology,2nd Edition, Ed. by Fields, B. N., Knipe, D. M. et al., Raven Press Ltd., New York, Defective Viral Genomes, 151–165.

Horvath, J. et al., 1988, J. Virol. 62, 341–345.

Horwitz, M. S., 1990, Virology, 2nd Edition, Ed. by Fields, B. N., Knipe, D. M. et al., Raven Press Ltd., New York, Adenoviridae and their replication, 1679–1721.

Hosang, M. et al., 1987, EMBO J., 6, 1197–1202.

Huang, A. S., 1987, The Molecular Basis of Viral Replication, Ed. by Bercoff, R. P., Plenum Press New York and London, The Role of Defective Interfering (DI) Particles in Viral Infection, 191–194.

Ikura T., Go N. and Inagaid F., 1991, Proteins 9, 81–89.

Imamura, K. et at., 1987, J. Immunol., 139, 2989–2992.

Iwanij, V., 1977, Eur. J. Biochem. 80, 359–368.

Jones, N. and Shenk, T., 1979, Proc.Nad.Acad.Sci. USA 76, 3665–3669.

Jung et al., 1981, Biochem. Res. Commun. 101, 599.

Kaplan, et al., 1979, J. Biol. Chem., 254, 7323–7328.

Kasid, A., Morecki, S., Aebersold, P., Cornetta, K., Culver, K., Freeman, S., Director, E., Lotze, M. T., Blaese, R. M., Anderson, W. F. and Rosenberg, S. A., 1990, Proc. Natl. Acad. Sci. USA 87, 473–477.

Kehoe M. A., Miller L., Walker J. A. and Boulnois G. J., 1987, Infect. Immun 55, 3228–3232.

Keller, G., Paige, C., Gilboa, E. andWagner, E. F., 1985, Nature318, 149–154.

Khang, C. and Nagaraji. K. V., 1989, Am. J. Vet Res. 50, 1466–1470.

Klausner, R. D. et al., 1983, J Biol. Chem., 258, 4715–4724.

Klausner, R. D. et al., 1983, Proc. Nad. Acad. Sci. USA 80, 2263–2266.

Kuhn, L. C. et al., 1982, Trends Biochem. Sci., 7, 299–302.

Kurachi, K., Davie, E. W., 1982, Proc. Natl. Acad. Sci USA 79, 6461–6464.

Laver, W. G. et al., 1971, vimrology 45, 598–614.

Lehrer R. I., Ganz T. and Selsted M. E., 1991, Cell 64, 229–230.

Leippe M., Ebel S., Schoenberger O. L., Horstmann R. D. and Muller-Ebeihard H. J., 1991, Proc. Nail. Acad. Sci. USA 88, 7659–7663.

Lim K. and Chae, C. B., 1989, BioTechniques 7, 576–579.

Luthmann, H. and Magnusson, G., 1983, Nucl. Acids Res. 11, 1295–1308.

MacDonald, R. C. et al., 1991, Biochim. Biophys. Acta 1061, 297–303.

Macgregor, G. and Caslkey, C. T., 1989, Nucl. Acids Res. 17, 2365.

Mackow E. R., Shaw R. D., Matsui S. M., Vo P. T., Dang M. N. and Greenberg H. B., 1988, Proc. Natl. Acad. Sci. USA 85, 645–649.

Madshus, I. H., Olsnes, S. and Sandvig, K., 1984, Virology 139, 346–357.

Malim, M. et al., 1989, Cell 58, 205–214.

MalMatis, T., Fritsch, E. F. and Sambrook, J. (1982) Molecular Cloning A Liboratory Manual. Cold Spring Harbor Laboratory, 474.

Marion D., Zasloff M. and Bax A., 1988, FEB 227, 21.

Marshall, S., 1985, J Biol. Chem., 250, 4133–4144.

Massague, J. et al. , 1986, J. Cell. Physiol., 128, 216–222.

McClure, M. O., Sommerfelt, M. A., Marsh, M. and Weiss, R. A., 1990, J. Geneml Virol. 71, 767–773.

Mellman, I. S. ed al., 1984, J. Cell Biol., 98, 1170–1177.

Mizel, S. B. ct al., 1987, 1987, J. Immunol., 138, 2906–2912.

Ojcius D. M. and Young J. D., 1991, TIBS 16, 225–229.

Oropeza-Werkerle R. L, Muller S., Briand J. P., Benz R., Schmid A. and Goebel W., 1992, Mol. Microbiol. 6, 115–121.

Otero, M. J. and Carso, L., 1987, Virology 160, 75–80.

Parente, R. A. et al., 1990, Biochemistry 29, 8720–8728.

Patek, P. Q., Collins, J. L. and Cohn, M. 1978, Nature 276, 510–511.

Piazza et al., 1991, J. Respir. Cell. Mol. Biol. 4, 83–87.

Ponder, J. P. et al., Proc. Natl. Acad. Sci. USA, 1991, 88, 1217–1221.

Posner, B. I. et al., 1982, J. Cell Biol., 93, 560–567.

Precious, B. and Russell, W. C., 1985, Virology, ed. Mahy, B. W. J., IRL Press, Oxford, Washington, DC, 193–205.

Rafalski, M., Lear, J. D. and DeGrado, W. F., 1990, Biochemistry 29, 7917–7922.

Reece, R. L. et al, 1987, AusL Vet J. 64, 365–367.

Riordan, J. R. et al., 1989, Science, 245, 1066–1073.

Rosenberg, S. A. et al., 1992, Human Gene Therapy 3, 75–90.

Ruysschaert J.-M. and Vandenbranden M., 1991, Biochem. Biophys. Res. Commun. 175, 872–879.

Schalch, D. S. et al., 1986, Endocrinology, 118, 1590–1597.

Sennett, C. et al., 1981, Annu. Rev. Biochem., 50, 1053–1086.

Seth, P., FitzGerald, D., Ginsberg, H., Willingham, M. and Pastan, I., 1984, Mol. Cell. Biol. 4, 1528–1533.

Severne, Y., Wieland, S., Schaffner, W. and Rusconi, S., 1988, EMBO J. 7, 2503–2508.

Shai Y., Bach D. and Yanovsky A., 1990, JBS 265, 20202–20209.

Sharon, N., 1987, Cell Separation: Methods and Selected Applications, Vol. 5, Academic Press Inc., pp.13–44.

Silver, L. et al., 1988, Virology 165, 377–387.

Sipe, D. M. et al., 1991, J. Biol. Chem. 256, 3469–3474.

Skern, T. et al., 1984, Virology 136, 125–132.

Slepushkin V. A., Andreev S. M., Siderova M. V., Melikyan G. B., Grigoriev V. B., Chumakov V. M., Grinfeldt A. E., Manukyan R. A. and Karamov E. V., 1992, AIDS Res. Human Retroviruses 8, 9–18.

Sly, W. et al., 1982, J. Cell Biochem., 18, 67–85.

Smith, K. A. et al., 1985, Proc. Natl. Acad. Sci. USA, 82, 864–867.

Stahl, P. D. et al., 1978, Proc. Natl. Acad. Sci. USA, 75, 1399–1403.

Straubinger, R. M. and Papahadjopoulos, D., 1983, Meth. Enzymol. 101, 512–527.

Strauss, W. and Jaenisch, R., 1992, EMBO J. 11, 417–422.

Subbarao, N. K. et al., 1987, Biochemistry 26, 2964–2972.
Sullenger, B. A. et al., 1990, Cell 63, 601–608.
Svensson, U., 1985, J.Virol., 55, 442–449.
Szoka, F. and Papahadjopoulos, D., 1978, Proc. Natl. Acad. Sci. USA 75, 4194–4198.
Takahashi S., 1990, Biochemistry 29, 6257–6264.
Takese, K. et al., 1990, Nippon Juigaki Zasshi 52, 207–215.
Thiaudiere E., Siffert O., Talbot J.-C., Bolard J., Alouf J. E. and Dufourcq J., 1991, Eur. J. Biochem. 195, 203–213.
Trono, D. et al., 1989, Cell 59, 113–120.
Uchida, Y., Tsukada, U. and Sugimori, T., 1977, J. Biochem. 82, 1425–1433.
Urakawa, T., et al., 1989, J. Gen. Virol. 70, 1453–1463.
Valerio, D., McIvor, R. S., Williams, S. R., Duyvesteyn, M. G. C., Van Ormondt, H., Van der Eb, A. J., Martin, D. W. Jr, 1984, Gene, 31, 147–153.
van Oostrum, J. and Burst, R. M., 1985, J. Virol. 56, 439–448.
Wagner, E., Zenke, M., Cotten, M., Beug, H. and Birnstiel, M. L., 1990, Proc. Natl. Acad. Sci. USA 87, 3410–3414.
Wagner, E., Cotten, M., Foisner, R. and Bimstiel, M. L., 1991a, Proc. Natl. Acad. Sci. USA 88, 4255–4259.
Wagner, E., Cotten, M., Mechdler, K., Kirlappos, H. and Birnstiel, M. L., 1991b, Bioconjugate Chemistry 2, 226–231.
Walker, F. et al., 1987, J. Cell Physiol., 130, 255–261.
Walker, R. D. et al., 1989, Proc. Nat. Acad. Sci. USA 86, 9514–9518.
Wells and Crawford, 1989, in "Lymphocytes, a practical approach," G. G. B. Klaus, Ed., IRL press, Oxford, pp. 149–162.
Wharton, S. A., Martin, S. R., Ruigrok, R. W. H., Skehel, J. J. and Wiley, D. C., 1988, J. Gen. Virol. 69, 1847–1857.
White J. M., 1990, Annu. Rev. Physiol 52, 675–697.
Wilchek, M. etal., 1988, Anal. Biochem. 171, 1.
Wilson, J. M., Danos, O., Grossman, M., Raulet, D. H. atid Mulligan, R. C., 1990, Proc. Natl. Acad. Sci. USA 87, 439–443.
Wilson et al., J. Biol. Chem. 267, 11483–11489.
Willumsen, N. J., Davis, C. W. and Boucher, R. C., 1989, Am. J. Physiol. 256 (Cell Physiol. 25), 1033–1044.
Wood, W. I., Capon, D. J., Simonsen, C. C., Eaton, D. L., Gitschier, J., Keyt, B., Seeburg, P. H., Smith, D. H., Hollinshead, P., Wion, K. L., Delwart, E., Tuddenham, E. G. D., Vehar, G. A., Lawn, R. M., 1984, Nature, 312, 330–337.
Wu, R., Y as J. R., Cheng, E., Knowles, M. R. and Boucher, R., 1985, Am. Rev. Respir. Dis. 132, 311–320.
Wu, G. Y. and Wu, C. H., 1987, J. Biol. Chem. 262, 4429–4432.
Wu, G. Y. and Wu, C. H., 1988, J. Biol. Chem. 263, 14621–14624.
Yankakas, J. R., Stutts, M. J., Cotton, C. U., Knowles, M. R., Gatzy, J. T. and Boucher, R. C., 1987, Genetics and Epithelial Cell Dysfunction in Cystic Fibrosis, Alan R. Liss, Inc., pp. 139–149.
Yankaskas, J. R., Haizlip, J. E., Conrad, M., Koval, D. Schlegel, R. and Boucher, R. C., 1991, Am. Rev. Respir. Dis. 143, A139.
Zamecnik, P. C., Goodchild, J., Taguchi, Y. and Sarin, P. S., 1986, Proc. Natl. Acad. Sci. USA 83, 4143–4146.
Zatloukal, K., Denk, H., Lackinger, E. and Rainer, I., 1989, Lab. Invest. 61, 603–608.
Zenke, M., Steinlein, P., Wagner, E., Cotten, M., Beug, H. and Birnstiel, M. L., 1990, Proc. Natl. Acad. Sci. USA 87, 3655–3659.
Zon, G., 1988, Pharmaceut. Research 5, No.9, 539–549.

TABLE 1A

| CELL TYPE Complex: | TfpL (A.) | TfpL + chloroquine (A.) | TfpL + free AdenoV (B.) | TfpL + coupled AdenoV (E.) | TfpL + Influ-pLys (F.) |
|---|---|---|---|---|---|
| Hepatocytes | | | | | |
| Hep G2 | – | +/– | +++ | | |
| BNL.C12 | – | +/– | ++++ | +++++ | +++ |
| primary | – | – | – | ++ | |
| Myoblasts/myotubes | | | | | |
| C2C12 | +/– | | +/– | +++++ | |
| G8 | +/– | | +/– | +++++ | |
| primary | | | +++ | | |
| Fibroblasts | | | | | |
| 3T3 | + | ++ | +++ | +++++ | ++ |
| Mov-13 | +/– | +/– | | +++++ | + |
| mouse L-cells | +/– | + | + | +++++ | ++ |
| primary | | | | ++++ | |
| Endothelial cells | | | | | |
| pig aorta | | +/– | + | +++ | +/– |
| Human neuroblastoma cell line | | | | | |
| GI-ME-N | +/– | +/– | +++ | ++++ | |
| HeLa cells | + | + | +++++ | +++++ | +++ |
| Mouse ES cells | | | | | |
| CCE | +/– | | + | ++ | |
| Bruce 4 | +/– | | ++ | +++ | |
| Erythroid cells | | | | | |
| K562 | – | ++++ | + | +++++ | + |
| chicken HD3 | ++ | ++++ | +++ | +++++ | |
| Bone marrow | | | | | |
| mouse | – | | – | ++ | |
| chicken | +/– | | + | +++ | |
| EBV-transformed human B-cells | – | – | – | +++ | + |
| Mouse plasma cell lines (MPC11.SP2/0) | | + | ++ | +++ | |

+/– Luciferase activity 1000–10,000 light units per $10^6$ cells
+ 10,000–1 million light units
++ 1–5 million light units
+++ 5–50 million light units
++++ 50–100 million light units
+++++ >100 million light units
TfpL transferrin-polylysine
AdenoV replication-defective adenovirus d1312
Influ-pLys influenza HA-2 N-terminal peptide-polylysine

TABLE 2A

| Membrane-active Proteins | | | | | |
|---|---|---|---|---|---|
| Viral fusion proteins | | | | | |
| N-terminal fusion sequence enveloped viruses | | | | | |
| influenza virus | myxoviridae | HA2 | | pH 5 | White, 1990 und Takahashi, 1990 |
| VSV | rhabdoviridae | G | | pH 5 | Hoekstra, 1990 |
| vaccinia virus | | 14 kDa | | pH 5 | Gong et al., 1990 |
| mendai virus | parainfluenzav. | F1 | | pH 7 | Hoekstra, 1990 und Gething et al., 1978 |
| measles virus | parainfluenzav. | F | | pH 7 | Hoekstra, 1990 |
| HIV | retroviridae | gp41 | | pH 7 | Slepushkin et al., 1992 |
| SIV | retroviridae | gp41 | | pH 7 | Ruyaschaert und Vandenbranden, 1991; Franchini, 1989 |
| unenveloped viruses | | | | | |
| polio virus | enteroviridae | vp1 | | pH 5 | Fricks und Hogie, 1990 |
| coxackie virus | enteroviridae | vp1 | | pH 5 | Gething et al., 1978 |
| rhino virus | | vp1 | | pH 5 | |
| internal fusion sequence enveloped viruses | | | | | |
| semliki forest v. | togaviridae | E1 | | pH 5 | White, 1990 |
| sindbis virus | | | | | White, 1990 |
| unenveloped viruses | | | | | |
| rhesus rotavirus | | vp5 | | | Mackow et al., 1988 |
| Toxins of microorganism | | | | | |
| streptolysin o | Streptococcus | 69 kDa | sulfhydryl activated, binds to cholesterol 20–80 mer, 15 nm pores | pH 7 | Kehoe et al., 1987 |
| listeriolysin o | L. monocytogenes | 60 kDa | sulfhydryl activated, binds to cholesterol related to C9 and streptolysin o | pH 5 | Geoffroy et al., 1987 |
| α-toxin | Staphylococcus | 34 kDa | amphipathic surface, β-sheet structure, hexamer lesions, 2 nm pores | pH 7 | |
| hemolysin | E. coli | 416 AA | 8 amphip. helixes | pH 7 | Oropeza-Werkerle et al., 1992 |
| hemolysin | Trypanosoma cruzi | 75 kDa | analogy to perforins, related to C9 | pH 5 | Andrews et al., 1990 |
| Vertebrate immunsystem | | | | | |
| perforin | cytotoxic T-cells | | $Ca^{2+}$ dependent membrane insertion | | Ojcius and Jung, 1991 |
| complement | C9 (MAC c5b-8, $9_{1-4}$) | | hollow protein cylinder, 10 nm channel, | | Shakdi und Tranum-Jensen, 1991; Easer, 1991 |
| | | | highly regulated activity | | |
| Sperm-egg fusion protein | | | | | |
| PH-30 | α-subunit of surface protein, internal fusion sequence | | | pH 7 | Blobel et al., 1992 |

| Membrane-active Peptides | | | | | |
|---|---|---|---|---|---|
| Defense toxins | | | | | |
| melittin Houghten, 1991: Ikura | bea venom | | 26AA | amph. α-helix | Pro-kinked | Blondelle und Dempsey et al., 1991: und Inagaki, 1991 |
| bombolitin 1985 | bumblebee venom | | 17AA | amph. α-helix | | Argiolas und Pisano, |
| mastoparan 1985 | wasp venom | | 14AA | amph. α-helix | | Argiolas und Pisano, |
| crabrolin 1985 | hornet venom | | 13AA | amph. α-helix | | Argiolas und Pisano, |
| pardaxin | moses sole fish (shark repellant) | | 33AA | amph. α-helix | Pro-kinked | Shai et al., 1990 |
| Antibacterial peptides | | | | | |
| sarcotoxin IA cecropins | flesh fly (in hemolymph) insects (humorel immune system, silk moth) | | 37AA | amph. α-helix | Pro-kinked | Easer, 1991 |
| maganin | skin Xenopus laevis | | 23AA | amph. α-helix | | Marion et al., 1998 |
| alameticin | fungus (Trichoderma viride) | | 15-24AA | amph. α-helix | α-aminobutyric acid | Easer, 1991 |
| Bacterial toxins | | | | | |
| d-toxin 1991: | Staphylococcus aureus | | 26AA | amph. α-helix | acid induced | Thiaudiere et al., Alouf et al., 1989 |
| amoebapore | Entamoeba histolytica | | 25AA | amph. α-helix | acid induced | Leippe et al., 1991 |

TABLE 2A-continued

Vertebrate immune system

| defensins | polynucleated neutrophils | | 29–34AA | SS-bridged β-sheet | Lehrer et al., 1991 |
|---|---|---|---|---|---|

TABLE 3

Transfection of BNL CL2 cells (6 μg pCMV-L DNA, 4 μg TfpL290)

| pLys | | 0 μg | 0.3 μg | 1 μg | 3 μg | 10 μg | 20 μg | 30 μg |
|---|---|---|---|---|---|---|---|---|
| 0 μg | P50 dim | 160 | 330 | 540 | 300 | | | |
|  | GLF | | 490 | 290 | 340 | | | |
|  | Melittin | | 0 | 0 | 0 | 70 | | 425 |
| 4 μg | P50 dim | 3100 | | 200 | 430 | 180 | 410 | |
|  | GLF | | 670 | 600 | 170 | | | |
|  | EALA | | 3140 | 150 | 560 | | | |
| 10 μg | P50 dim | 5700 | | | | 760 | 1330 | 3424800 |
|  | GLF | | 1950 | 16600 | 217000 | 215000 | 1980 | |
|  | EALA | | 2120 | 16800 | 179300 | 181700 | 76360 | |
| 20 μg | P50 dim | 3200 | | | 23300 | 185100 | 7054800 | 9344000 |
|  | GLF | | | | 418400 | 320600 | 294200 | |
|  | EALA | | | | 191000 | 181000 | 273600 | |
|  | Melittin | | | | 6545 | | | |
|  | Desoxy-cholic acid | | | 6730 | 34700 | 16000 | | |
|  | Oleic acid | | | 12200 | 11900 | 4100 | | |

What is claimed is:

1. A transfection kit, comprising a carrier means having in close confinement therein two or more container means, wherein a first container means contains a substance having an affinity for nucleic acid, which substance is optionally coupled with an internalizing factor for a higher eucaryotic cell; and a second container means contains an agent which has the ability per se of being internalized into a higher eucaryotic cell and of releasing the contents of the cell's endosome into the cell's cytoplasm.

2. A transfection kit, comprising a carrier means having in close confinement therein one or more container means, wherein a first container means contains a substance having an affinity for nucleic acid, which substance is optionally coupled with an internalizing factor for a higher eucaryotic cell, and wherein a second container means contains a substance having an affinity for a nucleic acid which is coupled to an agent which has the ability of being internalized into a higher eucalyotic cell as a component of a nucleic acid complex, and of releasing the contents of the cell's endosome, in which the complex is located after entering the cell, into the cell's cytoplasm.

3. A transfection kit of claim 2, characterized in that it contains a first container means containing a transglutaminasecoupled adenovirus-polylysine conjugate.

4. A transfection kit, comprising a carrier means having in close confinement therein one or more container means, wherein a first container means contains a biotin-modified endosomolytic agent and a second container means contains a streptavidin-modified substance having affinity for nucleic acid.

5. A transfection kit of claim 4, characterized in that said first container means contains biotinylated adenovirus and said second container means contains streptavidin-polylysine.

* * * * *

UNITED STATES PATENT AND TRADEMARK OFFICE
CERTIFICATE OF CORRECTION

PATENT NO. : 6,274,322 B1
DATED : August 14, 2001
INVENTOR(S) : Curiel et al.

It is certified that error appears in the above-identified patent and that said Letters Patent is hereby corrected as shown below:

Title page,
Item [60], after "Apr. 7, 1992," please insert therein -- now abandoned, --.

Column 1,
Line 12, please delete "1992, which" and insert therein -- 1992, now abandoned, which --.

Column 7,
Line 23, please delete "KS62" and insert therein -- K562 --.

Column 39,
Line 52, please delete "nihydrin" and insert therein -- ninhydrin --.

Column 62,
Line 55, please delete "Terry" and insert therein -- Ternary --.

Column 63,
Line 20, please delete "sport" and insert therein -- transport --.
Line 65, please delete "zoom" and insert therein -- room --.

Column 64,
Line 66, please delete "(Me" and insert therein -- (The --.

Column 67,
Line 66, please delete "(as indie" and insert therein -- (as indicated) --.

Column 70,
Line 23, please delete "lob" and insert therein -- lobe --.
Line 49, please delete "pea" and insert therein -- peak --.

Column 72,
Line 57, please delete "Tip" and insert therein -- Trp --.

Column 73,
Line 6, please delete "Tip" and insert therein -- Trp --.
Line 11, please delete "Tip" and insert therein -- Trp --.

UNITED STATES PATENT AND TRADEMARK OFFICE
CERTIFICATE OF CORRECTION

PATENT NO. : 6,274,322 B1
DATED : August 14, 2001
INVENTOR(S) : Curiel et al.

It is certified that error appears in the above-identified patent and that said Letters Patent is hereby corrected as shown below:

Column 75,
Line 53, please delete "lie" and insert therein -- Ile --.
Line 53, please delete "Tip" and insert therein -- Trp --.
Line 58, please delete "He" and insert therein -- Ile --.
Line 59, please delete "Tip" and insert therein -- Trp --.

Column 76,
Line 16, please delete "He" and insert therein -- Ile --.
Line 16, please delete "Be" and insert therein -- Ile --.
Line 16, please delete "Gin" and insert therein -- Gln --.
Line 18, please delete "lie" and insert therein -- Ile --.
Line 19, please delete "Gin" and insert therein -- Gln --.

Column 86,
Line 28, please delete "+++" entry for primary myoblasts/myotubes under the TfpL + free AdenoV (B.) Column, and insert -- +++ -- for primary myoblasts/myotubes under the TfpL + coupled AdenoV (E.) Column.

Column 97,
Line 9, please delete "eucarvotic" and insert therein -- eucaryotic --.
Line 19, please delete "eucalyotic" and insert therein -- eucaryotic --.

Signed and Sealed this

Thirtieth Day of April, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 23 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:1:

Gly Leu Phe Glu Ala Ile Ala Gly Phe Ile Glu Asn Gly Trp Glu Gly
1               5                   10                  15

Met Ile Asp Gly Gly Gly Cys
            20

(2) INFORMATION FOR SEQ ID NO:2:

(i) SEQUENCE CHARACTERISTICS:
        (A) LENGTH: 23 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:2:

Gly Leu Phe Gly Ala Ile Ala Gly Phe Ile Glu Asn Gly Trp Glu Gly
1               5                   10                  15

Met Ile Asp Gly Gly Gly Cys
            20

```
(2) INFORMATION FOR SEQ ID NO:3:

(i) SEQUENCE CHARACTERISTICS:
        (A) LENGTH: 26 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:3:

Met Ala Gln Asp Ile Ile Ser Thr Ile Gly Asp Leu Val Lys Trp Ile
1               5                   10                  15

Ile Asp Thr Val Asn Lys Phe Thr Lys Lys
            20                  25

(2) INFORMATION FOR SEQ ID NO:4:

(i) SEQUENCE CHARACTERISTICS:
        (A) LENGTH: 36 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:4:

Met Ala Gln Asp Ile Ile Ser Thr Ile Gly Asp Leu Val Lys Trp Ile
1               5                   10                  15

Ile Asp Thr Val Asn Lys Phe Thr Lys Lys Lys Lys Lys Lys Lys Lys
            20                  25                  30

Lys Lys Lys Lys
        35

(2) INFORMATION FOR SEQ ID NO:5:

(i) SEQUENCE CHARACTERISTICS:
        (A) LENGTH: 34 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:5:

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala Gly Gly
            20                  25                  30

Ser Cys (2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:6:

Gly Leu Phe Gly Ala Leu Ala Glu Ala Leu Ala Glu Ala Leu Ala Glu
1               5                   10                  15
```

```
His Leu Ala Glu Ala Leu Ala Glu Ala Leu Glu Ala Leu Ala Ala Gly
            20                  25                  30

Gly Ser Cys
        35

(2) INFORMATION FOR SEQ ID NO:7:

(i) SEQUENCE CHARACTERISTICS:
        (A) LENGTH: 35 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:7:

Gly Leu Phe Gly Ala Leu Ala Glu Ala Leu Ala Glu Ala Leu Ala Glu
1               5                   10                  15

Ala Leu Ala Glu Ala Leu Ala Glu Ala Leu Glu Ala Leu Ala Ala Gly
            20                  25                  30

Gly Ser Cys
        35

(2) INFORMATION FOR SEQ ID NO:8:

(i) SEQUENCE CHARACTERISTICS:
        (A) LENGTH: 34 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:8:

Gly Leu Phe Glu Leu Ala Glu Ala Leu Ala Glu Ala Leu Ala Glu Ala
1               5                   10                  15

Leu Ala Glu Ala Leu Ala Glu Ala Leu Glu Ala Leu Ala Ala Gly Gly
            20                  25                  30

Ser Cys (2) INFORMATION FOR SEQ ID NO:9:

(i) SEQUENCE CHARACTERISTICS:
        (A) LENGTH: 34 amino acids
        (B) TYPE: amino acid
        (C) STRANDEDNESS: single
        (D) TOPOLOGY: both (ii) MOLECULE TYPE: peptide (xi) SEQUENCE DESCRIPTION: SEQ ID NO:9:

Gly Leu Phe Gly Ala Ile Ala Gly Phe Ile Glu Asn Gly Trp Glu Gly
1               5                   10                  15

Leu Ala Glu Ala Leu Ala Glu Ala Leu Glu Ala Leu Ala Ala Gly Gly
            20                  25                  30

Ser Cys (2) INFORMATION FOR SEQ ID NO:10:

(i) SEQUENCE CHARACTERISTICS:
        (A) LENGTH: 34 amino acids
        (B) TYPE: amino acid
        (C) STRANDEDNESS: single
        (D) TOPOLOGY: both
```

(ii) MOLECULE TYPE: peptide (xi) SEQUENCE DESCRIPTION: SEQ ID NO:10:

Gly Leu Phe Glu Ala Ile Glu Gly Phe Ile Glu Asn Gly Trp Glu Gly
1               5                   10                  15

Leu Ala Glu Ala Leu Ala Glu Ala Leu Glu Ala Leu Ala Ala Gly Gly
                20                  25                  30

Ser Cys (2) INFORMATION FOR SEQ ID NO:11:

(i) SEQUENCE CHARACTERISTICS:
            (A) LENGTH: 23 amino acids
            (B) TYPE: amino acid
            (C) STRANDEDNESS: single
            (D) TOPOLOGY: both (ii) MOLECULE TYPE: peptide (xi) SEQUENCE DESCRIPTION: SEQ ID NO:11:

Gly Leu Phe Glu Ala Ile Glu Gly Phe Ile Glu Asn Gly Trp Glu Gly
1               5                   10                  15

Met Ile Asp Gly Gly Gly Cys
                20

(2) INFORMATION FOR SEQ ID NO:12:

(i) SEQUENCE CHARACTERISTICS:
            (A) LENGTH: 36 amino acids
            (B) TYPE: amino acid
            (C) STRANDEDNESS: single
            (D) TOPOLOGY: both (ii) MOLECULE TYPE: peptide (xi) SEQUENCE DESCRIPTION: SEQ ID NO:12:

Gly Ile Gly Ala Val Leu Lys Val Leu Thr Thr Gly Leu Pro Ala Leu
1               5                   10                  15

Ile Ser Trp Ile Lys Arg Lys Arg Gln Gln Lys Lys Lys Lys Lys Lys
                20                  25                  30

Lys Lys Lys Lys
        35

(2) INFORMATION FOR SEQ ID NO:13:

(i) SEQUENCE CHARACTERISTICS:
            (A) LENGTH: 36 amino acids
            (B) TYPE: amino acid
            (C) STRANDEDNESS: single
            (D) TOPOLOGY: both (ii) MOLECULE TYPE: peptide (xi) SEQUENCE DESCRIPTION: SEQ ID NO:13:

Gly Ile Gly Ala Val Leu Glu Val Leu Glu Thr Gly Leu Pro Ala Leu
1               5                   10                  15

Ile Ser Trp Ile Lys Arg Lys Arg Gln Gln Lys Lys Lys Lys Lys Lys
                20                  25                  30

Lys Lys Lys Lys
        35